(12) United States Patent
Hansjörg et al.

(10) Patent No.: US 8,129,552 B2
(45) Date of Patent: *Mar. 6, 2012

(54) PHOSPHOLIPIDS WITH UNSATURATED ALKYL AND ACYL CHAINS

(75) Inventors: Eibl Hansjörg, Bovenden-Eddigehausen (DE); Thomas Hottkowitz, Neustadt (DE)

(73) Assignee: Max-Planck-Gesellschaft zur Forderung der Wissenschaften E.v., Munich (DE)

( * ) Notice: Subject to any disclaimer, the term of this patent is extended or adjusted under 35 U.S.C. 154(b) by 404 days.

This patent is subject to a terminal disclaimer.

(21) Appl. No.: 11/847,118

(22) Filed: Aug. 29, 2007

(65) Prior Publication Data

US 2008/0214849 A1    Sep. 4, 2008

Related U.S. Application Data

(63) Continuation of application No. 09/762,006, filed as application No. PCT/EP99/05710 on Aug. 6, 1999, now abandoned.

(30) Foreign Application Priority Data

Aug. 6, 1998  (DE) .................................. 198 35 611

(51) Int. Cl.
  *C07F 9/02*  (2006.01)
(52) U.S. Cl. ........................................................ 554/78

(58) Field of Classification Search ..................... 554/78
See application file for complete search history.

(56) References Cited

U.S. PATENT DOCUMENTS 6,828,453 B2 * 12/2004 Eibl ................................ 554/82

FOREIGN PATENT DOCUMENTS

| DE | 34 27 093 A1 | 2/1985 |
| DE | 240020 | 10/1986 |
| DE | 36 19 883 A1 | 12/1986 |
| DE | 40 13 632 A1 | 10/1991 |
| EP | 0 071 019 A1 | 2/1983 |
| EP | 0 507 337 A2 | 10/1992 |
| EP | 0 534 445 A1 | 3/1993 |
| JP | 06228012 | 8/1994 |
| WO | 97/30058 A1 | 8/1997 |
| WO | 99/09037 A1 | 2/1999 |

OTHER PUBLICATIONS

Max-Planck's, 1992, CAS: 16:106694.*
Max-Planck's, 1993, CAS: 119:34313.*
An English translation of EP 534,445, Mar. 1993.
An English translation of AT 393505, Nov. 1991.
Theresa M. Allen, Journal of Liposome Research, vol. 2, No. 3, Jan. 1, 1992, pp. 289-305.
Maruyama et al., "Phosphatidyl Polyglycerols Prolong Liposome Circulation In Vivo," (1994), pp. 103-107.

* cited by examiner

*Primary Examiner* — Rei-tsang Shiao
(74) *Attorney, Agent, or Firm* — Rothwell, Figg, Ernst & Manbeck P.C.

(57) ABSTRACT

The invention relates to phospholipid-like compounds having defined apolar constituents and to the use of such compounds as liposomes, active ingredients, and solubilizers.

1 Claim, No Drawings

PHOSPHOLIPIDS WITH UNSATURATED ALKYL AND ACYL CHAINS

CROSS REFERENCE TO RELATED APPLICATIONS

This application is a Continuation of U.S. application Ser. No. 09/762,006, filed Feb. 1, 2001, which is a U.S.C. §371 National Phase Entry Application from PCT/EP99/05710, filed Aug. 6, 1999, which claims priority from German Application 198 35 611.0, filed Aug. 6, 1998.

The invention relates to phospholipid-like compounds of the formula (I) with defined apolar constituents, and to a process for the preparation thereof. The invention additionally relates to the use of the phospholipid-like compounds as liposomes, active ingredients and solubilizers.

Phospholipid-type compounds have many possible uses, for example as liposome constituents for transporting drugs or as gene transport vehicles, as solubilizers for drugs of low solubility in water, and themselves as active ingredients against diseases such as, for example, cancer or leishmaniosis.

Phospholipid-like compounds of this type consist of a polar and an apolar moiety. Glycerophospholipids comprise as essential constituent glycerol which is esterified in the sn-1 and sn-2 positions mainly with fatty acids (apolar moiety). If at least one of the two OH groups on the glycerol structure is etherified with an alcohol, the term used is ether phospholipids. The polarity of the compounds of the invention derives from the negatively charged phosphate group and from the esterified alcohol component, which contains a quaternary, positively charged nitrogen. This group may be present one or more times or else not present at all, resulting in each case in a negative or positive excess charge or else no charge.

The apolar portion is formed by alkyl or acyl chains, which may be in saturated or unsaturated form. The possible variations in the synthesis of the apolar region has to date been limited to the naturally occurring acyl radicals or alkyl chains. It is possible by specific modifications of the apolar region to change markedly and control specifically the physical, biochemical and biological properties of the phospholipid compounds.

Liposomes as transport vehicles or drug carriers are known. The frequently used phosphatidylcholines such as 1,2-dipalmitoyl-sn-glycero-3-phosphocholine (DPPC), 1,2-distearoyl-sn-glycero-3-phosphocholine (DSPC) or 1,2-dioleyl-sn-glycero-3-phosphocholine (DOPC) form on sonication with cholesterol in the ratio 60:40 liposomes of the order of 60 nm in size. However, it may often be advantageous to produce liposomes with a larger internal volume, because larger amounts of active ingredients can be transported therewith. However, the problem with this is that to produce liposomes with a diameter of more than 100 nm in size it is necessary to use processing techniques such as, for example, extrusion, which is associated with distinct disadvantages, for example due to the brittleness of the polycarbonate membrane or blockage of the pores. This makes it difficult in particular to prepare relatively large batches for pharmaceutical purposes. It is possible by extending the alkyl or acyl chains of the apolar moiety to achieve, because of steric factors, an arrangement of the molecules with less curvature on formation of vesicles. The result is the formation of larger liposomes, which can be achieved by ultrasound treatment without extrusion processes. In order to keep the phase transition temperature of phospholipids with extremely long fatty acids (with more than 22 C atoms) in a range which is favorable for liposome formation, fatty acids with a cis double bond located as near the middle as possible are used. Such extremely long-chain fatty acids occur in only small amounts in nature.

Phospholipid compounds can also be employed directly as active pharmaceutical ingredients. The antineoplastic and immunomodulatory effect of lysolecithins (which have only one instead of two fatty acids on the glycerol) and ether lysolecithins in cell culture experiments has been known for more than 30 years. The basic precondition for antineoplastic activity of lysophospholipids and analogs is accumulation in the diseased tissue. Lysophosphatidylcholines are readily metabolized by phospholipases or acryltransferases and are no longer available to the body, whereas ether lysolecithins can be detoxified by oxidative cleavage of the ether linkage or acylation of the sn-2 position. This is why substances which are less good substrates for phospholipid-metabolizing enzymes but still have a lysolecithin-like structure have been synthesized. The first phosphocholine with antitumor activity found was the ether lipid 1-O-octadecyl-2-O-methyl-rac-glycero-3-phosphocholine (ET18-OCH$_3$ also known as edelfosine). ET18-OCH$_3$ shows excellent antineoplastic activity in cell-culture experiments but proved to be virtually inactive in complex organisms.

Dispensing with glycerol as basis of the structure results in the metabolically more stable alkylphosphocholines (APC), substances which accumulate in membranes and have a marked effect in cell properties. Alkylphosphocholines do not occur in nature and are phosphocholine esters of long-chain alcohols which, because of their simplified structure, now have substrate properties only for phospholipase D. The best known representative to date of this class of substances is hexadecylphosphocholine (HePC), an alkylphosphocholine which was approved as medicine in 1992 under the name Miltex® (active ingredient: miltefosine) and has therefore also been intensively investigated. HePC is employed for the topical treatment of breast cancers and lymphomas with cutaneous metastases.

Alkylphosphocholines not only reduce tumors but also activate cytotoxic macrophages and inhibit the invasion of healthy tissue by neoplastic cells. Recent investigations have shown that APCs (and especially HePC) are potent active ingredients for controlling leishmaniosis and trypanosomiasis. Direct intravenous administration of an HePC solution causes thrombophlebitis in rats. In clinical studies, HePC shows toxicities in the gastrointestinal tract on oral administration and therefore cannot be administered in effective concentrations. One exception is HePC for controlling leishmaniosis: HePC acts in doses so low that the side effects described above do not occur.

The first intravenously injectable alkylphosphocholine to be found was erucylphosphocholine (ErPC), a phosphocholine with a C$_{22}$-alkyl chain and cis double bond in the ω-9-position. It has emerged that structural variations in the apolar region of unsaturated and thus intravenously administrable alkylphosphocholines, for example on shifting the double bond to the ω-12 or ω-6 position, lead to improved antitumor activity compared with erucylphosphocholine, the most effective compound to date (see table 2 in example 5).

Phospholipids are also used as solubilizers for drugs of low solubility in water. Once again, these solubilizing properties can be improved by modifying the apolar region.

To date it has been possible to modify specifically only the polar moiety in the synthesis of phospholipids of the above-mentioned classes. It has to date been possible to use for the apolar portion only commercially available fatty acids and naturally occurring fatty acids.

Phospholipids occurring in nature and specifically in mammals mainly comprise unbranched fatty acids with 8 to 24 C atoms which, owing to their biosynthesis, have almost exclusively an even number of carbon atoms. Unsaturated fatty acids usually have 1 to 4 double bonds, mainly in the cis configuration. Naturally occurring monounsaturated fatty acids usually have the double bond in the middle, i.e. in palmitoleic acid it is located at the ω-7 position or at the (z)-9 position in the preferred notation used in the examples herein. The higher fatty acids oleic, eicosenoic, erucic and nervonic acid each have the double bond at the ω-9 position in the carbon chain or, correspondingly, at the (Z)-9, (Z)-11, (Z)-13 and (Z)-15 position in the notation preferred herein.

In polyunsaturated fatty acids, the positions of the unsaturations are such that in each case there is only one $CH_2$ group between them. This is important for making the autoxidation of the fatty acids possible. However, it would be advantageous, precisely on use of phospholipids as drugs or liposomes, to prevent the autoxidation in order to obtain more stable compounds. This can be achieved only by compounds in which the unsaturations in the alkyl and acyl chains are more than one methylene group apart.

German patent application DE 197 35 776.8 discloses phospholipid-analogous compounds as liposome constituents, active pharmaceutical ingredients or solubilizers, which contain saturated or monounsaturated acyl or alkyl radicals, with the total of the carbon atoms in the acyl and alkyl being between 16 and 44.

It was therefore an object of the present invention to provide compounds which, owing to modifications in the apolar region, have improved properties for the aforementioned applications and, in addition, can be prepared on an industrial scale. It was a further object of the present invention to make it possible, by a novel process, to prepare unsaturated fatty acids in which the double bonds are at positions which do not occur in naturally occurring mono- and diunsaturated fatty acids, or to provide a process which makes it possible to prepare monounsaturated fatty acids which are difficult to obtain, for example nervonic acid, in industrial quantities.

This object is achieved according to the invention by a compound of the general formula (I)

in which B is a radical of the general formula (II)

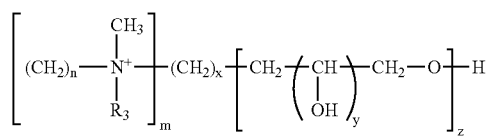

in which
n is an integer from 2 to 8;
m is 0, 1 or 2;
x is an integer from 0 to 8;
y is an integer from 1 to 4;
z is an integer from 0 to 5;
$R_3$ is an alkyl radical having 1 to 3 C atoms, which may be substituted by one or more hydroxyl groups;

and in which A is a radical selected from one of the formulae (III) to (IX):

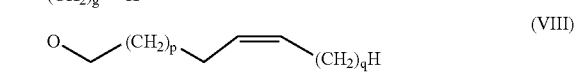

in which
g is an integer from 0 to 8;
p, q, r, s, t ≧ 0;
12 ≦ p+q ≦ 30 and
8 ≦ s+t+r ≦ 26;

where $R_1$ and $R_2$ are each independently hydrogen, a saturated or unsaturated acyl or alkyl radical or a radical selected from one of the formulae (X), (XI), (XII) and (XIII), and at least one of $R_1$ and $R_2$ is a radical selected from one of the formulae (X), (XI), (XII) and (XIII):

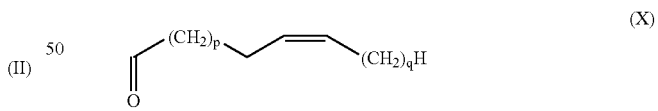

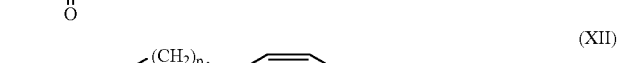

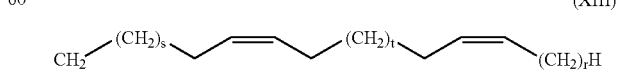

where q ≠ 8 for p+q=14, 16, 18 or 20, if neither of the radicals $R_1$ and $R_2$ is a radical of the formula (XI) or (XIII), or if A is a radical of the formula (VIII).

The structural elements used in the substances described herein can be varied as desired and tailored to suit the particular use. Particularly preferred monounsaturated acyl and alkyl radicals are those whose double bond is not in a natural position. Compounds in which both the radicals $R_1$ and $R_2$ are naturally occurring monounsaturated acyl or alkyl chains, such as, for example, those having the C=C bond in the ω-9 position, thus do not form part of the invention. The process of the invention makes it possible to choose the position of the double bond(s) without restriction, so that previously inaccessible alkyl/acyl chains can be prepared. As already explained above, the cis double bonds of natural diunsaturated alkyl and acyl chains are in each case separated by only one methylene group. Such compounds are unstable at room temperature in the presence of oxygen and must therefore be stored at low temperatures under nitrogen. The possibility of synthesizing (Z)-fatty acids and (Z)-alkenols with the alkyl or acyl chains of the formulae (IX), (XI) and (XIII) having 16 to 34 C atoms allows structural elements in which there are at least 2 methylene groups between the unsaturations to be provided. This results in a considerable stabilization of the fatty acids and alcohols and of the classes of compounds synthesized therefrom. Compounds of the invention can be stored without difficulty at room temperature without inert gas. The term (Z)-fatty acids or -alkenols as used herein encompasses both mono- and diunsaturated chains with one or two cis double bonds.

The advantage of the particularly preferred alkyl and acyl chains with two double bonds is that the physicochemical properties are favorable. Thus, for example, the diunsaturated fatty acids (Z,Z)-10,19-octacosadienoic acid, which is based on a 28 carbon chain, is liquid at room temperature, whereas monounsaturated fatty acids of this chain length occur only in the solid state at 20° C., irrespective of the position of the cis double bond. The incorporation of the structures of the invention into phospholipids makes it possible to transfer these favorable properties to the compounds of the invention, which is reflected inter alia in low phase transition temperatures. It is likewise possible, by extending the fatty acid chains, to more than double the vesicle diameter compared with liposomes prepared from conventional lecithins, which corresponds to the internal volume of ultrasound-prepared liposomes being eight times as large. It is thus possible to transport more than eight times as much active ingredient as is possible with conventional liposomes. In addition, preparations of large unilamellar vesicles (LUVs) in highly viscous solutions, for example sugar solutions, are possible, that is to say in a medium in which it is difficult to prepare liposomes by extrusion processes. The phase transition temperatures of the phospholipids with the extremely long fatty acids of the invention are, because of the cis double bond(s), in a region favorable for liposome preparations.

The compound of the general formula (I) has two variable components A and B, each of which can be modified individually. The compound of the invention of the formula (I) does not comprise a mixture of different molecules of indeterminate composition and chain length; on the contrary it is possible specifically to obtain a desired structure. This means that, if the desired product is an N,N-dimethyl-N-(2-hydroxypropyl-3,1-O,O-dihydroxypropyl)ammonium derivative, with y=1 and z=2 in formula (I), the compound is chemically defined and contains scarcely any contributions from y=1 and z=1 or y=1 and z=3 etc. Preference is given to the use of hydroxypropyl derivatives of a very particular chain length essentially free of other chain lengths.

The compound of the formula (I) is, according to the invention, a homogeneous compound of defined structure. The compound is preferably more than 99% homogeneous in relation to the value of z. However, it is also possible to provide the compound with a homogeneity of more than 99.9% in relation to the value of z.

For B in the compound of the formula (I), preference is given to m=1 with n=2 to 8. Particular preference is given to n=2 to 6, and even greater preference to 2 to 4. When z=0, x is preferably an integer from 1 to 3 and is even more preferably 1.

If z=1, y preferably has a value from 1 to 4, and if z=1 to 5, y is preferably 1. In the case where y>1, the radical —$CH_2$(CHOH)$_y$—$CH_2$—OH is preferably derived from sugar alcohols having four hydroxyl groups for y=2, five hydroxyl groups for y=3 and six hydroxyl groups for y=4. Examples of such radicals are mannitol derivatives for y=4, lyxitol derivatives for y=3 and threitol derivatives for y=2.

It is possible and also preferred for x to be 0. In this case, y is 2 to 4 for z=1. Or, in another preferred embodiment, z=1 to 5 for y=1.

It is possible and also preferred for m to be 0, in which case the compound of the formula (I) has a negative excess charge because of the negatively charged $PO^-_3$ group. For m=0, x is preferably 0, and y=1 for z=1 to 5, or, in a likewise preferred embodiment, y=2 to 4 for z=1.

The radical $R_3$ is preferably $CH_3$, $C_2H_5$ or 1,2-dihydroxypropyl.

The groups of the formulae (III) to (VII) are preferably in enantiopure form. However, they may also be racemates.

The compound of the formula (I) is according to the invention a compound of defined structure. Monounsaturated alkyl chains are preferably more than 97% homogeneous, but may also be provided with homogeneity of more than 99%. Diunsaturated alkyl chains are preferably more than 90% homogeneous, but may also in some cases be provided in purities of >97%.

The compound preferably comprises phospholipids with mono- or diunsaturated alkyl or acyl chains having 16-34 chain carbon atoms.

The compounds encompassed by the general formula (I) have excellent biological properties and are used as
1. liposome constituents for preparing liposomes for targeted accumulation of active ingredients or nucleic acids in target cells (alkyl/acyl chain length preferably 16-32 C atoms)
2. active ingredients against oncoses and protozoal infections (alkyl/acyl chain length preferably 16-26 C atoms) and
3. solubilizers for substances which are difficult to administer intravenously, such as, for example, Taxol (alkyl/acyl chain length preferably 16-30 C atoms).

Conventional liposomes have a residence time in serum of up to 5 hours but, especially on use of liposomes as carriers of active pharmaceutical ingredients, it is desirable for the residence time of liposomes in the bloodstream to be as long as possible, but especially in conjunction with uptake in selected target cells.

It has emerged from ultrasound preparations of liposomes that symmetrical lecithins with (Z)-fatty acids having up to 24 carbon atoms form liposomes when mixed with cholesterol, and the homogeneity of the vesicle population is crucially determined by the position of the double bond. The precondition for a narrow standard deviation of the vesicle size is a particular distance of the double bond from the carboxyl function. There is evidently, by comparison with conventional lecithins, a significant increase in the vesicle diameter, which is 125 nm for (Z)-15-tetra-cosenoic acid (nervonic acid). Mixed-chain phosphatidylcholines with a saturated acyl chain in the sn-1 position also form vesicles with very long-chain (Z)-fatty acids, and it is to be assumed that there is interdigitation of the fatty acid chains. The average hydrodynamic liposome diameter on esterification with (Z)-15-triacontenoic acid (30:1 $\Delta^{15}$) is 111 nm (stearic acid in the sn-1 position). A distinct enlargement of vesicles is also obtained by use of extremely long fatty acids in the case of phospholipids having a modified polar region, such as, for example, in the case of phosphatidyloligoglycerols, or in the case of phospholipids containing oligoglycerols linked via nitrogen atoms.

When the compound of the invention of general formula (I) is used as liposome constituent, the constituent A is preferably two-chain radical derived from glycerol, of the formulae (III) or (IV). In constituent B, these compounds preferably have an alkylammonium group, i.e. m is preferably equal to 1. The preferred parameters for compounds of the formula (I) used as liposome constituents are:

m=1, n=2-6, x=0, y=1, z=1-5 or
m=1, n=2-6, x=0, y=2-4, z=1 or
m=1, n=2-6, x=1, z=0 or
m=0, x=0, y=1, z=1-5, preferably 2-4 or
m=0, x=0, y=2-4, z=1.

$R_3$ is in this case preferably 1,2-dihydroxypropyl, $C_2H_5$ or even more preferably $CH_3$. The compound preferably comprises hydroxypropyl derivatives with 1 to 3 hydroxypropyl units, i.e. x=0 and z=1 to 3. Since y is preferably 1, these involve 1,3-linked linear oligoglycerol residues which are linked to the nitrogen atom via a 2-hydroxypropyl radical.

These compounds which are suitable as liposome constituents preferably have 2 radicals, that is to say $R_1$ and $R_2$. These may be in each case independently a radical of one of the formulae (X) to (XIII). If $R_1$ and $R_2$ are identical, they preferably have a maximum chain length of, in each case, 16 to 26 C atoms. In another preferred embodiment, one of the radicals is longer than 26 C atoms and may preferably have up to 32 C atoms. In this case, a methyl radical is preferably present on the nitrogen, i.e. when z=0, x is preferably 1. It is likewise preferred for at least of $R_1$ and $R_2$ to be a diunsaturated radical of the invention, and it is even more preferred for both $R_1$ and $R_2$ to be a diunsaturated radical of the invention.

One of the radicals $R_1$ and $R_2$ may also be a saturated acyl or alkyl radical. In this case, the other radical is a compound of one of the formulae (X) to (XIII), and is preferably a diunsaturated alkyl or acyl chain of the formula (XI) or (XIII).

In another preferred embodiment, the compound of the general formula (I) as liposome constituent may also have a negative excess charge. This is the case when m=0. Preference is given in this connection to glycero-glycerols and phosphatidyl-glycero-glycero-glycerols and phosphatidyl-glycero-glycero-glycero-glycerols (in these cases, x=0, y=1 and z=2 to 4). Additionally preferred in this connection are the previously mentioned compounds with y>1, i.e. the radical $CH_2-(-CHOH)_y-CH_2-OH$ is preferably derived from sugar alcohols having 4 hydroxyl groups for y=2, 5 hydroxyl groups for y=3 and 6 hydroxyl groups for y=4. Likewise preferred in this connection are phospho-sn-$G_1$ compounds.

Active ingredients of the invention are preferably compounds of the general formula (I) in which the structural parameter A is a radical of one of the formulae (VIII) or (IX). They are therefore unsaturated alkylphosphocholines.

The advantage of unsaturated chains in the apolar region is that such compounds can be administered intravenously. Active ingredients of the invention have better antitumor activity than erucylphosphochiline, the most effective compound to date. An increased cytostatic effect is obtained, for example, by shifting the cis double bond toward the phosphocholine group. Thus, even with the lowest dose, (Z)-10-docosenyl-1-phosphocholine (42 μmol/kg/week) shows a tumor reduction to 9% (T/C), whereas erucylphosphocholine with a dose which is more than twice as high (90 μmol/kg/week) shows a reduction only to 31% (T/C) (see example 5, table 1).

The preferred parameters for compounds of the formula (I) which are suitable as active ingredients are:
m=1, n=2-6, more preferably n=2-4, x=1, z=0.

Compounds of the general formula (I) are particularly suitable as active pharmaceutical ingredients when they have an alkylammonium radical (i.e. m=1) with which the distance between ammonium and phosphate is greater than or equal to 2, i.e. n is preferably 2, 3 or 4. In this case, $R_3$ is preferably a $CH_3$ or $C_2H_5$ group. It is likewise preferred for $R_3$ to be 1,2-dihydroxypropyl. These compounds are particularly active antitumor agents.

The most preferred compounds are those having an N,N,N-trimethylalkylammonium group, so that preference is given to z=0 and x=1.

It is preferred to dispense with a glycerol basic structure or a similar basic structure according to one of the formulae (III) to (VII) for active ingredients. The structural parameter A is thus preferably a compound of the formulae (VIII) or (IX). These are therefore preferably (z)-alkenylphosphocholines or (Z,Z)-alkadienylphosphocholines.

If a monounsaturated alkyl radical is present, this preferably has 16 to 23 carbon atoms. This is because it has emerged that compounds with chains having 24 C atoms or more are distinctly less suitable. With a diunsaturated alkyl radical, longer chains are suitable, preferably having about 19 to 26 C atoms. It has emerged that diunsaturated chains with 16 to 18 carbon atoms are inactive. It should be particularly emphasized in this connection that alkadienylphosphocholines with a terminal double bond (i.e. r=0) in formula (IX) have a marked antitumor effect even at very low dosage.

Compounds with a glycerol-like constituent also show antitumor activity, i.e. a compound according to one of the formulae (III) to (VII) may also be present on the phosphate residue. If in this case 2 radicals $R_1$ or $R_2$ are present, however, it is important that one R is a short chain. This short chain is preferably an alkyl radical having 1 to 4 C atoms. The other radical $R_1$ or $R_2$ is then preferably a radical of the formula XII or XIII. It is, in particular, a radical of the formula XIII.

Additionally preferred compounds are those in which both radicals $R_1$ and $R_2$ are each linked by an ether linkage to the glycerol residue, i.e. they are each independently a group of the formula (XII) or (XIII) Particular preference is also given to a compound where $R_1$ and $R_2$ are the same mono- or diunsaturated radical of the invention.

Mention should be made, as another preferred embodiment of the compound of the general formula (I), of compounds which are distinguished by a good solubilizing property. The preferred structural parameters for compounds of the formula (I) suitable as solubilizers are:
m=1, n=2-6, x=0, y=1, z=1-3, more preferably z=1,
m=1, n=2-6, x=0, y 2-4; z=1 or
m=1, n 2-6, x=1, z=0.

$R_3$ is preferably $CH_3$, $C_2H_5$ or 1,2-dihydroxypropyl.

Known compounds of this type encompass, for example, the erucyl ($C_{22}$) compounds. The compounds of the invention which are therefore preferred are those which have as structural parameter A a group according to one of the formulae (III) to (VII), where one of the radicals $R_1$ and $R_2$ is preferably a compound of the formulae (X) or (XI), i.e. one of the radicals $R_1$ or $R_2$ is preferably a diunsaturated chain according to the invention. Single-chain compounds are preferred for the solubilizers, i.e. when A is a group of the formulae (III) or (IV), and one of $R_1$ and $R_2$ is —OH or an alkyl having 1 to 4 C atoms.

When A is a radical according to one of the formulae (V) to (VII), i.e. when only one $R_1$ is present, $R_1$ is likewise preferably a diunsaturated chain. Solubilizers of the invention are preferably in the form of esters, i.e. chains of the formula (X) or (XI) are preferred. Very particular preference is given in this connection in turn to compounds with one or two diunsaturated alkadienyl radicals. Some compounds of the classes already mentioned previously are also suitable here too. One example are the single-chain glycero-phospho compounds not hydroxylated on the nitrogen, i.e. m=1, x=1 and z=0 in the structural parameter B.

Compounds particularly preferred as solubilizers are those having only one long-chain radical such as, for example, compounds based on lysolecithin which have an OH group on a C atom of the glycerol residue. Particularly preferred compounds are therefore those in which the structural parameter A is a radical according to one of the formulae (III) to (VII).

Some compounds with 2 radicals $R_1$ and $R_2$ also display particularly good solvent properties, however. Examples are those compounds in which $R_1$ and $R_2$ are two diunsaturated radicals having 16 to 24 C atoms.

The present invention further relates to a process for preparing unsaturated (Z)-fatty acids or (Z,Z)-fatty acids or (Z)-alkenols or (Z,Z)-alkenols having 16 to 34 carbon atoms, the process of the invention making available diunsaturated (Z,Z)-fatty acids and alkenols which have more than one $CH_2$ group between the cis double bonds. A lactone which may comprise 13 to 19 C atoms is used as starting material for this process.

The process comprises the following steps:
1) cleavage of the lactone ring with a trimethylsilyl halide to give the corresponding trimethylsilyl halo-carboxylate,
2) simultaneous or subsequent alcoholysis of the trimethylsilyl halo-carboxylate to give the corresponding halo-carboxylic ester,
3) reaction of the halo-carboxylic ester with triphenylphosphane to give the corresponding phosphonium salt,
4) reaction of the phosphonium salt with an aldehyde using a base and subsequent hydrolysis to give a corresponding (Z)-fatty acid salt,
5) liberation of the (Z)-fatty acid from the (z)-fatty acid salt, and
6) where appropriate conversion of the (Z)-fatty acid into the corresponding (Z)-alkenol using lithium aluminum hydride.

In step 1) there is preferably use of lactones of the formula (XIV)

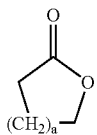

(XIV)

where a=10 to 16. The trimethylsilyl halides used to cleave the lactone ring are preferably trimethylsilyl iodide or trimethylsilyl chloride. The alcohol used for the alcoholysis in step 2) is preferably ethanol. The reaction of the phosphonium salt with an aldehyde is based on the procedure for a Witt-g reaction in the absence of lithium salts, which is also referred to as a salt-free Wittig reaction. The stereoselectivity of such reactions is generally elicited by sodium- or potassium-containing bases, and therefore preferred bases are, for example, $NaNH_2$, potassium tert-butoxide, NaHMDS or KHMDS. NaHMDS is particularly preferred. The hydrolysis and subsequent liberation and, where appropriate, the conversion of the fatty acids into an alkenol takes place by known processes.

A particularly preferred embodiment of the process of the present invention is the process for preparing nervonic acid ((Z)-15-tetracosenoic acid). This entails using cyclopentadecanolide as starting lactone and pelargonaldehyde as aldehyde in step 4. This process can be used to synthesize nervonic acid, which occurs only in small amounts in nature, even on an industrial scale.

The present invention further relates to liposomes comprising phospholipid-like compounds of the formula (I) as constituents of the liposome shell. These liposomes additionally contain phospholipids and/or alkylphospholipids and, where appropriate, cholesterol, the liposomes containing 1 to 50 mol % of a compound according to the invention of the formula (I) or salt thereof and, together with the phospholipids, the alkylphospholipids and the cholesterol, resulting in 100 mol % of the liposome shell.

The liposomes of the invention have a distinctly increased internal volume. They are thus able to transport a larger amount of active ingredient and/or nucleic acids. Preferred liposomes of the invention additionally comprise an active ingredient and, where appropriate, pharmaceutically acceptable diluents, excipients, carriers and fillers. The liposomes may comprise a nucleic acid in addition to the active ingredient or in place of the active ingredient. It is also possible according to the invention to use as active ingredients the active ingredients of the invention.

The present invention further relates to a pharmaceutical composition which comprises as active constituent a compound of the formula (I) which is suitable as active ingredient. The pharmaceutical composition may moreover additionally comprise pharmacologically acceptable diluents, excipients, carriers and fillers.

The present invention further relates to the use of the compounds of the invention as liposome constituents, as pharmacological active ingredients or as solubilizers. It has emerged that some of the compounds of the invention show a particularly good antitumor effect. Compounds of the invention can be employed not only as antitumor active ingredient but also against protozoal infections such as, for example, leishmaniosis or trypanosomiasis. They can likewise be used to promote the solubility of substances of low solubility in water, for example Taxol, so that these substances can also be administered intravenously in conjunction with the solubilizers of the invention.

The active ingredients which can be used are generally all active ingredients which can in fact be introduced by means of liposomes into the plasma. Preferred groups of active ingredients are, on the one hand, cytostatics, especially anthracycline antibiotics, such as, for example, doxorubicin, epirubicin or daunomycin, with doxorubicin being particularly preferred. Further preferred cytostatics are idarubicin, alkylphosphocholines in the structural variations described by us, 1-octadecyl-2-methyl-rac-glycero-3-phosphocholine and structural analogs derived therefrom, 5-fluorouracil, cis-platinum complexes such as carboplatin and Novantrone, and mitomycins.

Further preferred groups of active ingredients are immunomodulating substances such as, for example, cytokines, and among these in turn interferons and, in particular, α-interferon are particularly preferred, substances with antimycotic activity (for example amphotericin B) and active ingredients against protozoal infections (malaria, trypanosome and leishmania infections). Taxol is likewise preferred as active ingredient.

A further preferred group of active ingredients are lytic active ingredients as described in DE 41 32 345 A1. Miltefosine, edelfosine, ilmofosine and SRI62-834 are preferred. Alkylphosphocholines, also with extended alkyl chains, for example erucylphosphocholine and erucylphosphocholines with extended phospho-nitrogen distance, are particularly preferred.

The present invention further relates to the use of liposomes of the invention for producing an antitumor composition, where the active ingredient is particularly preferably doxorubicin.

The present invention additionally relates to the use of the liposomes of the invention for producing a composition for influencing the proliferation of cells, where the active ingredient is a cytokine, particularly preferably α-interferon.

The liposomes of the present invention can thus also be used as transport vehicles and specifically as gene transport vehicles.

The process and the compounds of the general formula (I) are illustrated in more detail in the following examples.

EXAMPLES

Example 1

Synthesis of ω-Substituted Phosphonium Salts

1a) Synthesis by Monobromination of α,ω-diols

The starting materials used for synthesizing olefinic alcohols are alkanediols, which are monobrominated with 48% strength hydrobromic acid to give ω-bromoalkan-1-ols. After acetylation of the remaining hydroxyl group, the compounds are fused with triphenylphosphane to give the triphenylphosphonium bromides substituted in the ω position. The latter are deprotonated with NaHMDS and then converted into olefins with unsubstituted aldehydes and subsequently hydrolyzed to (Z)-fatty alcohols.

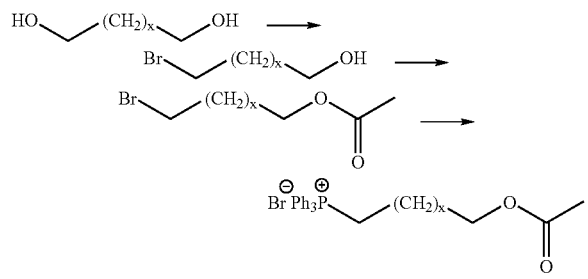

Synthesis of [ω(acetoxy)alkyl]triphenylphosphonium bromides by monobromination of α,ω-diols Monobromination 6-Bromo-1-hexanol 200.8 g (1.70 mol) of 1,6-hexanediol, 600 ml of 48% strength hydrobromic acid and 2 l of toluene were heated under reflux with vigorous stirring for 2 hours. After cooling to room temperature, the phases were separated. The organic phase was washed with 2×500 ml of saturated NaHCO$_3$ solution and 700 ml of water. Removal of the solvent resulted in 301.2 g (1.66 mol, 98%) of 6-bromo-1-hexanol.

MW=181.07 g/mol (C$_6$H$_{13}$BrO)
R$_f$ (precursor) 0.19 (diethyl ether)
R$_f$=0.59 (diethyl ether)

10-Bromo-1-decanol 87.8 g (0.50 mol) of 1,10-decanediol, 165.1 g of 48% strength hydrobromic acid and 2.5 l of high-boiling petroleum ether (b.p. 100-140° C.) were heated under reflux with vigorous stirring for 4 hours. A further 80.0 g of 48 strength hydrobromic acid were added, and the mixture was boiled for 5 hours. After cooling to 30° C., the phases were separated. The organic phase was washed first with a solution of 100 g of Na$_2$CO$_3$ in 500 ml of water and then with 2×500 ml of water. Removal of the solvent was followed by chromatography on 700 g of silica gel. The byproduct 1,10-dibromodecane was eluted with cyclohexane/diethyl ether (20:1). Chromatography with cyclohexane/diethyl ether (2:1) afforded 103.9 g (0.44 mol, 87%) of 10-bromo-1-decanol.

MW=237.18 g/mol (C$_{10}$H$_{21}$BrO)
R$_f$ 0.38 (diisopropyl ether)
$^1$H-NMR (300 MHz, CDCl$_3$): δ=1.30-1.43 (m, 12H, (CH$_2$)$_6$), 1.57 (m, 2H, CH$_2$CH$_2$OH), 1.85 (mc, 2H, CH$_2$CH$_2$Br), 2.22 (s, D$_2$O-exchangeable, 1H, OH), 3.41 (t, $^3$J=6.9 Hz, 2H, CH$_2$Br), 3.64 (t, $^3$J=6.7 Hz, 2H, CH$_2$OH)

Acetylation to give ω-bromoalkyl Acetates

Acetylation of the ω-bromoalkan-1-ols is carried out with acetic anhydride in THF with catalysis by DMAP. The esterifications take place rapidly at 30° C., irrespective of the chain length of the compound, and are complete only a few minutes after addition of the reactive anhydride.

6-Bromohexyl acetate 20.1 g (0.16 mol) of DMAP were added to 297.4 g (1.64 mol) of 6-bromo-1-hexanol in 1500 ml of THF. A solution of 184.4 g (1.81 mol) of acetic anhydride in 300 ml of THF was added dropwise in such a way that the reaction temperature did not exceed 30° C. After completion of the addition, the mixture was stirred for a further 30 minutes. The reaction mixture was mixed with 500 ml of diisopropyl ether and extracted successively with 700 ml each of water, 2× saturated NaHCO$_3$ solution and water. After drying over sodium sulfate, the solvent was removed in vacuo. 352.8 g (1.58 mol, 96%) of 6-bromohexyl acetate were obtained.

MW=223.11 g/mol (C$_8$H$_{15}$BrO$_2$)
R$_f$ 0.81 (diethyl ether)
$^1$H-NMR (300 MHz, CDCl$_3$) δ=1.33-1.53 (m, 4H, (CH$_2$)$_2$) 165 (mc, 2H, CH$_2$CH$_2$O), 1.87 (mc, 2H, CH$_2$CH$_2$Br), 2.04 (s, 3H, OOCCH$_3$), 3.41 (t, $^3$J=6.8 Hz, 2H, CH$_2$Br), 4.06 (t, $^3$J=6.7 Hz, 2H, CH$_2$O)
IR (film): ν[cm$^{-1}$]=2937 (s), 2859 (s), 1736 (s), 1460 (m), 1365 (m), 1240 (s), 1044 (m), 731 (w), 641 (w), 561 (w)

Quaternization to Give Phosphonium Bromides

[10-(Acetoxy)decyl]triphenylphosphonium bromide 117.3 g (0.42 mol) of the appropriate ω-substituted alkyl bromide/iodide and 110.2 g (0.4 mol) of triphenylphosphane were heated at 130° C. with stirring (glass stirrer) for 12 hours. The heating was removed and the mixture was allowed to cool to 90° C. 400 ml of THF were slowly added through the reflux condenser to the reaction mixture, which was stirred until a homogeneous phase was formed. It was allowed to cool to room temperature.

Addition of 2 l of diethyl ether was followed by vigorous stirring for 30 minutes. After standing for several days at −20° C., the supernatant solvent was decanted off from the solid phoshonium salt. The product was mixed with 800 ml of toluene and stirred at 60° C. for several hours. After phase separation, the phosphonium salt was taken up in 300 ml of dichloromethane. 3 l of diethyl ether were added and the mixture was left at −20° C. for several days. After renewed decantation off, the product was dissolved in dichloromethane and transferred into a flask. The phosphonium salt was dried in vacuo at 80° C. for 6 hours. 181.6 g (335 mmol, 80%) of [10-(acetoxy)-decyl]triphenylphosphonium bromide were obtained as a yellow, highly viscous oil.

MW=541.51 g/mol ($C_{30}H_{38}BrO_2P$)

$R_f$=0.23 (chloroform/methanol, 9:1)

| Analysis: | C | H | P |
|---|---|---|---|
| Calculated | 66.54 | 7.07 | 5.72 |
| Found | 66.67 | 7.06 | 5.55 |

1b) Synthesis Via ω-Halo Carboxylic Acids

Ethyl 11-bromoundecanoate 1000 g of 90% pure 11-bromoundecanoic acid (equivalent to 3.39 mol), 304.0 g (6.60 mol) of ethanol and 20.0 g of p-toluenesulfonic acid were introduced into 400 ml of chloroform in an experimental apparatus with water trap (for entrainers with higher specific gravity than water). The mixture was heated under reflux until water no longer separated out (about 6 hours). After the solution had cooled to room temperature it was washed successively with 1 l of water, 500 ml of saturated $NaHCO_3$ solution and 1 l of water. The solvent was removed in vacuo. Vacuum distillation (b.p. 131-133° C./1 mbar) resulted in 716.3 g (2.44 mol, 72%) of ethyl 11-bromoundecanoate.

MW 293.24 g/mol ($C_{13}H_{25}BrO_2$)

$R_f$=0.66 (cyclohexane/diisopropyl ether, 1:1)

| Analysis: | C | H |
|---|---|---|
| Calculated | 53.25 | 8.59 |
| Found | 53.22 | 8.57 |

$^1$H-NMR (300 MHz, $CDCl_3$): δ=1.23-1.42 (m, 15H, COO$CH_2CH_3$, 6×$CH_2$), 1.62 (mc, 2H, $CH_2CH_2$COO), 1.85 (mc, 2H, $CH_2CH_2$Br), 2.29 (t, $^3J$=7.5 Hz, 2H, $CH_2$COO); 3.41 (t, $^3J$=6.9 Hz, 2H, $CH_2$Br), 4.12 (quart, $^3J$=7.1 Hz, 2H, COO$CH_2$$CH_3$)

IR (film): ν[$cm^{-1}$]=2930 (s), 2854 (s), 1737 (s), 1464 (m), 1372 (m), 1179 (s), 1118 (m), 723 (w), 645 (w), 563 (w)

ω-Iodo-carboxylic Esters

Central intermediates in the synthesis of (Z)-15- and (Z)-16-olefins:

Lactone cleavage of cyclopentadecanolide and cyclohexadecanolide with trimethylsilyl iodide and subsequent alcoholysis results in the ethyl ω-iodo-carboxylates.

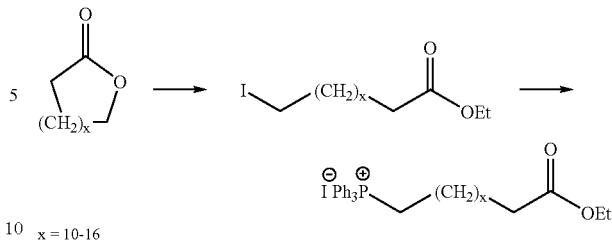

x = 10-16

Lactone Cleavage

Ethyl 15-iodopentadecanoate 150.3 g (0.63 mol) of cyclopentadecanolide were dissolved in 500 ml of acetonitrile under a nitrogen atmosphere, and 229.0 g (1.53 mol) of sodium iodide were added. 170 ml (1.34 mol) of trimethylsilyl chloride were added dropwise through a septum. The mixture was heated under reflux for 18 hours. 158.5 g (3.44 mol) of ethanol were cautiously added to the boiling reaction mixture, which was heated under reflux for a further 2 hours and then allowed to cool to room temperature. 500 ml of diethyl ether were added and the mixture was extracted three times with 500 ml of 1N sodium hydroxide solution each time. The aqueous phases were back-extracted with 300 ml of diethyl ether, and the solvent was removed from the combined organic phases in vacuo. The residue was crystallized from methanol twice at −20° C. Drying in vacuo for several days resulted in 202.3 g (0.51 mol, 81%) of ethyl 15-iodopentadecanoate. Although the product was obtained in good purity, it had an intense odor of precursor owing to very small amounts of lactone (perfumed!).

MW=396.35 g/mol ($C_{17}H_{33}IO_2$)

$R_f$ (intermediate)=0.15 (dichloromethane/diisopropyl ether, 50:1)

$R_f$=0.73 (dichloromethane/diisopropyl ether, 50:1)

| Analysis: | C | H |
|---|---|---|
| Calculated | 51.52 | 8.39 |
| Found | 51.40 | 8.24 |

Melting point: 31.4° C.

$^1$H-NMR (300 MHz, $CDCl_3$): δ 1.19-1.38 (m, 23H, COO$CH_2CH_3$, 10×$CH_2$), 1.61 (mc, 2H, $CH_2CH_2$COO), 1.82 (mc, 2H, $CH_2CH_2$I), 2.29 (t, $^3J$=7.6 Hz, 2H, $CH_2$COO), 3.19 (t, $^3J$=7.0 Hz, 2H, $CH_2$I), 4.12 (quart, $^3J$=7.1 Hz, 2H, COO$CH_2$$CH_3$)

IR (KBr): ν[$cm^{-1}$]=2916 (s), 2848 (s), 1735 (s), 1474 (w), 1464 (w), 1294 (w), 1248 (w), 1200 (m), 1166 (m), 720 (w)

Conversion into Phosphonium Salts

[14-(Ethoxycarbonyl)tetradecyl]triphenylphosphonium iodide 119.0 g (0.30 mol) of the appropriate ω-substituted alkyl bromide/iodide and 78.8 g (0.30 mol) of triphenylphosphane were heated at 130° C. with stirring (glass stirrer) for 12 hours. The heating was removed and the mixture was allowed to cool to 90° C. 400 ml of THF were slowly added through the reflux condenser to the reaction mixture, which was stirred until a homogeneous phase formed. It was allowed to cool to room temperature.

The product was precipitated by adding 2 l of diethyl ether at 0° C., and the resulting mixture was stirred at 4° C. for one day. It was then filtered with suction as quickly as possible through a large glass fiber filter, the residue was dissolved in dichloromethane and transferred into a flask. The solvent was removed in vacuo and then the phosphonium salt was dried in vacuo at 70° C. for 7 hours (in a rotary evaporator). 197.5 g (0.30 mol, 100%) of [14-(ethoxycarbonyl)tetradecyl]triphenylphosphonium iodide were obtained.

MW=658.64 g/mol ($C_{35}H_{48}IO_2P$)

$R_f$=0.53 (chloroform/methanol, 9:1)

| Analysis: | C | H | P |
|---|---|---|---|
| Calculated | 63.83 | 7.35 | 4.70 |
| Found | 64.00 | 7.42 | 4.61 |

$^1$H-NMR (300 MHz, CDCl$_3$): δ=1.19-1.28 (m, 25H, COOCH$_2$CH$_3$, 11×CH$_2$), 1.63 (m, 2H, CH$_2$CH$_2$COO), 2.28 (t, $^3$J=7.5 Hz, 2H, CH$_2$COO), 3.66 (m, 2H, CH$_2$P$^+$Ph$_3$I$^-$), 4.12 (quart, $^3$J=7.1 Hz, 2H, COOCH$_2$CH$_3$), 7.69-7.86 (m, 15H, aromatic-H)

Example 2

Synthesis of ω-Substituted Aldehydes

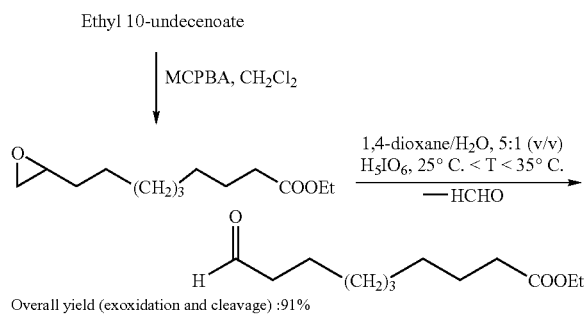

Ethyl 10-undecenoate

Overall yield (exoxidation and cleavage) :91%

Direct Epoxide Cleavage with Periodic Acid in Aqueous 1,4-dioxane

Ethyl 10,11-epoxyundecanoate 283.7 g (1.2 mol) of 73% pure m-chloroperoxybenzoic acid were added over the course of 1½ hours to 212.4 g (1.0 mol) of ethyl 10-undecenoate in 2 l of dichloromethane, maintaining the temperature below 20° C. After stirring at room temperature for 5 hours (glass stirrer) the reaction mixture was kept at −20° C. overnight. The precipitated m-chlorobenzoic acid was filtered off with suction and washed with 500 ml of cold pentane (−20° C.) The solvent was removed from the filtrate in vacuo, and the residue was taken up in 1 l of pentane. This solution was cautiously extracted with 2×500 ml of saturated NaHCO$_3$ solution and 500 ml of water. After drying over sodium sulfate, the solvent was removed in vacuo. The epoxide synthesized in this way still contained m-chlorobenzoic acid.

Crude yield: 259.5 g

MW 228.33 g/mol ($C_{13}H_{24}O_3$)

$R_f$=0.44 (dichloromethane/diisopropyl ether 50:1)

Oxidation of ω-halo Compounds Using Pyridine N-oxide

6-Acetoxyhexanal 29.0 g (130 mmol) of 6-bromohexyl acetate, 31.6 g (332 mmol) of pyridine N-oxide, 26.8 g (319 mmol) of NaHCO$_3$ and 200 ml of toluene were heated under reflux in an inert gas atmosphere for 18 hours. The reaction solution was washed with 400 ml of water, and the aqueous phase was back-extracted with 300 ml of toluene. After the solvent had been distilled out of the combined organic phases in vacuo, the crude product was filtered through a column of 300 g of silica gel (diisopropyl ether/cyclohexane, 1:1).

Yield: 12.5 g (79 mmol, 61%)

MW=158.20 g/mol ($C_8H_{14}O_3$)

$R_f$=0.44 (diisopropyl ether)

| Analysis: | C | H |
|---|---|---|
| Calculated | 60.74 | 8.92 |
| Found | 60.66 | 8.92 |

$^1$H-NMR (300 MHz, CDCl$_3$): δ=1.30-1.41 (m, 2H, 4-CH$_2$), 1.57-1.68 (m, 4H, CH$_2$CH$_2$CHO, CH$_2$CH$_2$O), 2.00 (s, 3H, OOCCH$_3$), 2.42 (dt, $^3$J$_{2,1}$=1.6 Hz, $^3$J$_{2,3}$=7.3 Hz, 2H, CH$_2$CHO), 4.02 (t $^3$J=6.6 Hz, 2H, CH$_2$O), 9.73 (t, $^3$J=1.6 Hz, 1H, CHO)

IR (film): ν[cm$^{-1}$]=2941 (s), 2865 (s), 2724 (m), 1736 (s), 1462 (m), 1389 (m), 1367 (s), 1241 (s), 1048 (s) 634 (m), 607 (m)

Example 3

The (Z)-alkenols and the monounsaturated (Z)-fatty acids are synthesized by stereoselective Wittig reaction of an ω-substituted aldehyde with an unsubstituted phosphonium salt and by reaction of an ω-substituted phosphonium salt with an unsubstituted aldehyde, respectively.

Unsubstituted aldehydes with a purity of more 97% are commercially available chemicals up to a chain length of 12 carbon atoms (dodecanal) and can be employed directly in the Wittig reaction. Longer-chain aldehydes can be obtained from purchasable fatty alcohols by Swern or Kornblum oxidation. Unsubstituted alkyl halides (mainly bromides and chlorides) are used to prepare simple phosphonium bromides, it being possible to purchase alkyl halides in a purity of more than 97%. Reference is made in example 1 and 2 to the synthesis of ω-substituted Wittig precursors. The generation of ylide solutions from phosphonium iodides is simpler because the deprotonation starts even at relatively low temperatures, and there is thus no need to heat the reaction mixture. The fatty acids can in some cases be obtained in good purity without chromatographic purification by precipitating their potassium salts.

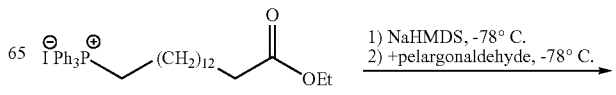

-continued

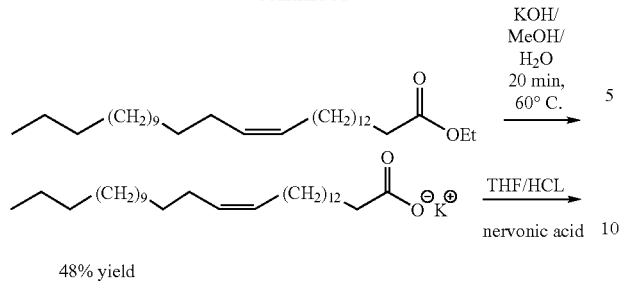

48% yield

Nervonic Acid Synthesis

Unsaturated fatty acids can be converted into the corresponding fatty alcohols using lithium aluminum hydride by processes described in the literature.

(Z)-Stereoselective Wittig Reaction of an ω-Substituted Phosphonium Bromide (Z)-10-Docosen-1-ol 86.7 g (160 mmol) of [10-(acetoxy)decyl]triphenylphosphonium bromide were introduced into 400 ml of dry THF. Under an argon atmosphere, 200 ml of sodium bis(trimethylsilyl)amide (1M in THF) were slowly injected into the reaction solution. Stirring (glass stirrer) at room temperature for 30 minutes was followed by heating under reflux for one hour. The ylide solution was then cooled firstly to 10° C. and then to −78° C. and, after stirring at this temperature for 30 minutes, 30.0 g (163 mmol) of lauraldehyde in 50 ml of THF were slowly added dropwise. The mixture was stirred for a further 30 minutes and then allowed to warm to room temperature overnight.
Workup The reaction mixture was mixed with 600 ml of water and 200 ml of diethyl ether, the phases were separated, and the solvent was removed from the organic phase in vacuo. For the hydrolysis, a solution of 25 g of potassium hydroxide in 10 ml of water/200 ml of methanol was added, and the mixture was stirred at 60° C. for 20 minutes. The reaction solution was mixed with 600 ml of water and extracted with 300 ml of diethyl ether. After the organic phase had been washed with 500 ml of saturated $NaHCO_3$ solution and 500 ml of water, the solvent was distilled off in vacuo. The crude product was purified by column chromatography (cyclohexane/diisopropyl ether: gradual increase in the polarity from 19:1 to 1:1) on 550 g of silica gel. The compound was precipitated from acetone at −20° C. Drying in a desiccator for several days resulted in 26.8 g (82.6 mmol, 52%) of the long-chain fatty alcohol.

$^1$H-NMR (300 MHz, $CDCl_3$): δ=0.88 (t, $^3J$=6.6 Hz, 3H, alkyl-$CH_3$), 1.23-1.30 (m, 30H, —$CH_2$—), 1.56 (mc, 2H, C $H_2CH_2OH$), 2.00 (m, 4H, allyl-H), 3.64 (t, $^3J$=6.2 Hz, 2H, C $H_2OH$), 5.35 (t, $^3J_{cis}$=3.8 Hz, 2H, —CH=CH-cis)

IR (KBr): ν[$cm^{-1}$]=3366 (m), 2998 (m), 2918 (s), 2848 (s), 1459 (m), 1366 (w), 1067 (m), 724 (m), 688 (w), 580 (w)

MW ($C_{22}H_{44}O$)=324.59 g/mol

| Analysis: | C | H |
|---|---|---|
| Calculated | 81.41 | 13.66 |
| Found | 81.56 | 13.72 |

Stereoselective Witting Reaction of an ω-Substituted Phosphonium Iodide (Z)-15-Tetracosenoic Acid (Nervonic Acid)

197.4 g (300 mmol) of the appropriate phosphonium salt were introduced into 1100 ml of dry THF under an inert gas atmosphere. After cooling to −78° C., 360 ml of sodium bis(trimethylsilyl)amide (1M in THF) were slowly added dropwise to the reaction solution while stirring (glass stirrer). After stirring at this temperature for 30 minutes, a solution of 47.0 g (330 mmol) of pelargonaldehyde in 50 ml of THF was added dropwise over a period of 40 minutes; after stirring vigorously for 30 minutes, the mixture was allowed to warm to room temperature overnight.
Workup 50 ml of water were added to the reaction mixture, and then the solvent was removed in vacuo. A solution of 25 g of potassium hydroxide in 10 ml of water/200 ml of methanol was added, and the reaction solution was stirred at 60° C. for 20 minutes. Azeotropic drying was then carried out with addition of toluene and distillation in vacuo. The residue was heated with 1.5 l of acetone while stirring vigorously at 60° C. for 10 minutes. The potassium salt which precipitated during this was filtered off with suction and washed several times with acetone. The product was dissolved off the filter using a solution of 600 ml of THF/150 ml of concentrated hydrochloric acid. The resulting two-phase mixture was mixed with 500 ml of diisopropyl ether and the phases were separated. The organic phase was washed three times with 500 ml of water each time and dried over sodium sulfate, and the solvent was distilled off in vacuo.

The crude product was purified by column chromatography on 1100 g of silica gel. The apolar impurity was eluted first with cyclohexane/diisopropyl ether (19:1). Chromatography with cyclohexane/diisopropyl ether (1:1) afforded the product.

The acid was dissolved in acetone with heating, and crystallized at −20° C. In the dry state, 52.5 g (142 mmol, 48%) of fatty acid were obtained as a white crystalline powder.

MW=366.63 g/mol ($C_{24}H_{46}O_2$)

| Analysis: | C | H |
|---|---|---|
| Calculated | 78.63 | 12.65 |
| Found | 78.77 | 12.52 |

Melting point: 41.1° C. (Lit. 42-43° C.)

It is also possible to prepare monounsaturated (Z)-alkenols and (Z)-fatty acids by reacting ω-substituted aldehydes with saturated phosphonium salts by the processes described above Terminally unsaturated alkadienecarboxylic acids are obtained by (Z)-selective Wittig reaction of a terminally unsaturated aldehyde with an ω-substituted phosphonium salt (for example 10-undecenal).

Example 4

Reaction of α,ω-dibromoalkanes at both ends with triphenylphosphane results in α,ω-bis(triphenylphosphonio)alkane dibromides. After conversion into the bisphosphorane, stereospecific conversion into an olefin takes place under salt-free conditions with a solution of a substituted and an unsubstituted aldehyde. Alkaline hydrolysis of the resulting ester affords, depending on the aldehyde used, (Z,Z)-alkadienols or (Z,Z)-fatty acids.

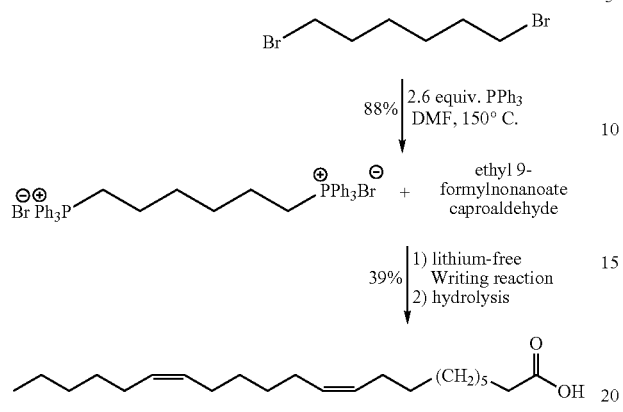

Lithium salt-free crossed Wittig reaction of a bisphosphonium salt with an unsubstituted and with an ω-substituted aldehyde: synthesis of (Z,Z)-10,16-docosadien-1-ol Synthesis of an α,ω-bis(triphenylphosphonio)alkane dibromide 1,6-Bis(triphenylphosphonio)hexane dibromide (62)

122.2 g (0.50 mol) of 1,6-dibromohexane were dissolved together with 341.7 g (1.30 mol) of triphenylphosphane in 1500 ml of DMF. The reaction mixture was heated under reflux with stirring (glass stirrer) for 4 hours. It was allowed to cool to room temperature. The product was filtered off with suction and washed with 2×250 ml of acetone and 200 ml of diethyl ether. Drying in vacuo for several days resulted in 336.5 g (0.44 mol, 88%) of the crystalline bisphoshonium salt.

MW=768.55 g/mol ($C_{42}H_{42}Br_2P_2$)
$R_f$=0.26 (chloroform/methanol, 9:1)

| Analysis: | C | H | P |
|---|---|---|---|
| Calculated | 66.64 | 5.51 | 8.06 |
| Found | 65.77 | 5.59 | 7.98 |

Crossed Wittig Reaction (Z,Z)-10,16-Docosadienoic acid 76.9 g (100 mmol) of 1,6-bis(triphenylphosphonio)hexane dibromide were suspended in 500 ml of THF. 240 ml (240 mmol) of sodium bis(trimethylsilyl)amide (1M in THF) were injected through a septum under an inert gas atmosphere. The ylide solution was stirred at room temperature for 30 minutes and then under reflux for 1 hour. After it had been cooled to −78° C., a solution of 21.5 g (100 mmol) of ethyl 9-formylnonanoate and 10.1 g (101 mmol) of caproaldehyde in 50 ml of THF was added dropwise over the course of 30 minutes. The mixture was stirred for a further 30 minutes and then allowed to warm to room temperature overnight.

50 ml of water were added to the reaction mixture, and then the solvent was removed in vacuo. A solution of 25 g of potassium hydroxide in 10 ml of water/200 ml of methanol were added, and the reaction solution was stirred at 60° C. for 20 minutes. It was then dried azeotropically by addition of toluene and distillation in vacuo. The residue was heated with 1.5 l of acetone while stirring vigorously at 60° C. for 10 minutes. The potassium salt which precipitated during this was filtered off with suction and washed several times with acetone. The product was dissolved off the filter using a solution of 600 ml of THF/150 ml of concentrated hydrochloric acid. The resulting two-phase mixture was mixed with 500 ml of diisopropyl ether, and the phases were separated. The organic phase was washed three times with 500 ml of water each time and dried over sodium sulfate, and the solvent was distilleed off in vacuo.

The crude product was purified by column chromatography (cyclohexane/diisopropyl ether; gradual increase in the polarity from 4:1 to 1:1) on 400 g of silica gel. 13.0 g (38.6 mmol, 39%) of the diunsaturated fatty acid were obtained.

MW=336.56 g/mol ($C_{22}H_{40}O_2$)
$R_f$=0.35 (cyclohexane/diisopropyl ether, 1:1)

| Analysis: | C | H |
|---|---|---|
| Calculated | 78.51 | 11.98 |
| Found | 78.30 | 11.92 |

$^1$H-NMR (300 MHz, CDCl$_3$): δ=0.89 (t, $^3$J=6.8 Hz, 3H, —CH$_3$), 1.30-1.43 (m, 20H, 10×CH$_2$), 1.63 (mc, 2H, C H$_2$CH$_2$COOH), 2.03 (bs, 8H, allyl-H), 2.35 (t, $^3$J=7.5 Hz, 2H, CH$_2$COOH), 5.34 (mc, 4H, —CH=CH-cis)

Example 5

Comparison of the Known Antitumor Active Ingredient Erucylphosphocholine with Active Ingredients of the Invention Comparison of a compound not of the invention (erucylphosphocholine) with two active ingredients of the invention is shown in Table 1.

TABLE 1

| Alkylphosphocholine | Weekly dose [μmol/kg] | T/C [%]* |
|---|---|---|
| Erucylphosphocholine (data taken from Kaufmann-Kolle et al. 1996) | 90 | 31 |
| | 180 | 6 |
| | 360 | <0.1 |
| (Z)-10-Docosenyl-1-PC | 42 | 9 |
| | 170 | 0.5 |
| | 256 | 0.2 |
| (Z)-11,21-Docosadienyl-1-PC | 42 | 8 |
| | 170 | 2 |

Table 1: *Quotient of the median tumor volume in the treated and the control group × 100. Evaluation after therapy for 5 weeks.

After the lack of activity of a (Z,Z)-alkadienylphosphocholine with methylene-interrupted double bonds and based on the C$_{18}$ chain had been demonstrated, it was possible to restore the activity of the class of substances by extending the alkadienyl chain and isolating the double bonds more markedly from one another (table 2).

TABLE 2

| Unsaturated alkylphosphocholine | Dose [μmol/kg] | Median tumor volume [cm³] | |
|---|---|---|---|
| | | End of therapy | 2 weeks later |
| (Z)-12-Heneicosenyl-1-phosphocholine | 42 | 3.4 | 4.5 |
| | 84 | 0.3 | 1.2 |
| | 170 | 0.1 | 0.1 |
| | 256 | 0.2 | 0.8 |
| (Z)-10-Docosenyl-1-phosphocholine (double bond in ω-12 position) | 42 | 4.0 | 4.5 |
| | 84 | 1.2 | 3.4 |
| | 170 | 0.2 | 0.2 |
| | 256 | 0.1 | 0.2 |
| (Z)-16-Docosenyl-1-phosphocholine (double bond in ω-6 position) | 42 | 26.9 | — |
| | 84 | 2.5 | 7.6 |
| | 170 | 0.2 | 0.4 |
| (Z,Z)-6,12-Eicosadienyl-1-PC | 42 | 10 | 13.9 |
| | 84 | 3.2 | 13.9 |
| | 170 | 0.4 | 1.9 |
| | 256 | 0 | 0 |
| (Z)-11,21-Docosadienyl-1-PC | 42 | 1.5 | 2.5 |
| | 84 | 0.9 | 2.9 |
| | 170 | 0.4 | 0.5 |
| (Z,Z)-10,16-Docosadienyl-1-PC | 42 | 7.5 | 11.4 |
| | 84 | 0.6 | 0.6 |
| | 170 | 0.5 | 0.7 |

Example 6

Exemplary Compounds

The Rf values of the exemplary compounds were determined in the system CHCl₃/CH₃OH/glacial acetic acid/H₂O: 100/60/20/5 (proportions by volume). They are grouped very closely together, specifically as follows:

| Rf | Compounds Nos. |
|---|---|
| 0.10-0.15 | 1454-1496 |
| 0.15-0.20 | 1399-1453; 1543-1555 |
| 0.20-0.25 | 1320-1398; 1523-1542; 1752-1812 |
| 0.25-0.30 | 1497-1522; 1691-1751 |
| 0.30-0.35 | 1083-1319; 1556-1568; 1630-1690 |
| 0.35-0.40 | 1569-1629 |
| 0.40-0.45 | 1813-1839 |
| 0.30-0.40 | 1-1082 |

1. Examples of (Z)-alkenylphosphocholines

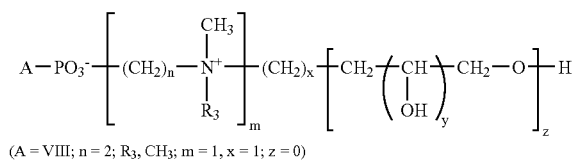

(A = VIII; n = 2; R₃, CH₃; m = 1, x = 1; z = 0)

where A is a monounsaturated alkyl chain of the following structure (p, q ≧ 0; 12 ≦ p+q ≦ 30):

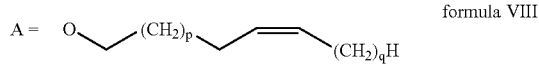

formula VIII

16 Chain Carbon Atoms
$C_{21}H_{44}NO_4P$ (405.56)
1. (Z)-3-hexadecenyl-1-phosphocholine
2. (Z)-4-hexadecenyl-1-phosphocholine
3. (Z)-5-hexadecenyl-1-phosphocholine
4. (Z)-6-hexadecenyl-1-phosphocholine
5. (z)-8-hexadecenyl-1-phosphocholine
6. (Z)-9-hexadecenyl-1-phosphocholine
7. (Z)-10-hexadecenyl-1-phosphocholine
8. (z)-11-hexadecenyl-1-phosphocholine
9. (Z)-12-hexadecenyl-1-phosphocholine
10. (Z)-13-hexadecenyl-1-phosphocholine
11. (z)-14-hexadecenyl-1-phosphocholine
12. 15-hexadecenyl-1-phosphocholine 17 Chain Carbon Atoms
$C_{22}H_{46}NO_4P$ (419.59)
13. (Z)-3-heptadecenyl-1-phosphocholine
14. (Z)-4-heptadecenyl-1-phosphocholine
15. (Z)-5-heptadecenyl-1-phosphocholine
16. (Z)-6-heptadecenyl-1-phosphocholine
17. (Z)-7-heptadecenyl-1-phosphocholine
18. (Z)-8-heptadecenyl-1-phosphocholine
19. (Z)-9-heptadecenyl-1-phosphocholine
20. (Z)-10-heptadecenyl-1-phosphocholine
21. (Z)-11-heptadecenyl-1-phosphocholine
22. (Z)-12-heptadecenyl-1-phosphocholine
23. (Z)-13-heptadecenyl-1-phosphocholine
24. (Z)-14-heptadecenyl-1-phosphocholine
25. (Z)-15-heptadecenyl-1-phosphocholine
26. 16-heptadecenyl-1-phosphocholine 18 Chain Carbon Atoms
$C_{23}H_{48}NO_4P$ (433.61)
27. (Z)-3-octadecenyl-1-phosphocholine
28. (Z)-4-octadecenyl-1-phosphocholine
29. (Z)-5-octadecenyl-1-phosphocholine
30. (Z)-6-octadecenyl-1-phosphocholine
31. (Z)-7-octadecenyl-1-phosphocholine
32. (Z)-8-octadecenyl-1-phosphocholine
33. (z)-10-octadecenyl-1-phosphocholine
34. (Z)-11-octadecenyl-1-phosphocholine
35. (Z)-12-octadecenyl-1-phosphocholine
36. (Z)-13-octadecenyl-1-phosphocholine
37. (Z)-14-octadecenyl-1-phosphocholine
38. (Z)-15-octadecenyl-1-phosphocholine
39. (Z)-16-octadecenyl-1-phosphocholine
40. 17-octadecenyl-1-phosphocholine 19 Chain Carbon Atoms
$C_{24}H_{50}NO_4P$ (447.64)
41. (z)-3-nonadecenyl-1-phosphocholine
42. (Z)-4-nonadecenyl-1-phosphocholine
43. (Z)-5-nonadecenyl-1-phosphocholine
44. (z)-6-nonadecenyl-1-phosphocholine
45. (z)-7-nonadecenyl-1-phosphocholine
46. (z)-8-nonadecenyl-1-phosphocholine
47. (z)-9-nonadecenyl-1-phosphocholine
48. (Z)-10-nonadecenyl-1-phosphocholine
49. (Z)-11-nonadecenyl-1-phosphocholine
50. (Z)-12-nonadecenyl-1-phosphocholine
51. (Z)-13-nonadecenyl-1-phosphocholine
52. (Z)-14-nonadecenyl-1-phosphocholine,
53. (Z)-15-nonadecenyl-1-phosphocholine
54. (Z)-16-nonadecenyl-1-phosphocholine
55. (Z)-17-nonadecenyl-1-phosphocholine
56. 18-nonadecenyl-1-phosphocholine 20 Chain Carbon Atoms
$C_{25}H_{52}NO_4P$ (461.67)
57. (Z)-3-eicosenyl-1-phosphocholine 58. (Z)-4-eicosenyl-1-phosphocholine
59. (Z)-5-eicosenyl-1-phosphocholine
60. (z)-6-eicosenyl-1-phosphocholine
61. (Z)-7-eicosenyl-1-phosphocholine
62. (Z)-8-eicosenyl-1-phosphocholine
63. (Z)-9-eicosenyl-1-phosphocholine
64. (Z)-10-eicosenyl-1-phosphocholine
65. (Z)-12-eicosenyl-1-phosphocholine
66. (Z)-13-eicosenyl-1-phosphocholine
67. (Z)-14-eicosenyl-1-phosphocholine
68. (Z)-15-eicosenyl-1-phosphocholine
69. (Z)-16-eicosenyl-1-phosphocholine
70. (Z)-17-eicosenyl-1-phosphocholine
71. (Z)-18-eicosenyl-1-phosphocholine
72. 19-eicosenyl-1-phosphocholine 21 Chain Carbon Atoms
$C_{26}H_{54}NO_4P$ (475.69)
73. (Z)-3-heneicosenyl-1-phosphocholine
74. (Z)-4-heneicosenyl-1-phosphocholine
75. (Z)-5-heneicosenyl-1-phosphocholine
76. (Z)-6-heneicosenyl-1-phosphocholine
77. (Z)-7-heneicosenyl-1-phosphocholine
78. (Z)-8-heneicosenyl-1-phosphocholine
79. (Z)-9-heneicosenyl-1-phosphocholine
80. (Z)-10-heneicosenyl-1-phosphocholine
81. (Z)-1'-heneicosenyl-1-phosphocholine
82. (Z)-12-heneicosenyl-1-phosphocholine
83. (Z)-13-heneicosenyl-1-phosphocholine
84. (Z)-14-heneicosenyl-1-phosphocholine
85. (Z)-15-heneicosenyl-1-phosphocholine
86. (Z)-16-heneicosenyl-1-phosphocholine
87. (Z)-17-heneicosenyl-1-phosphocholine
88. (Z)-18-heneicosenyl-1-phosphocholine
89. (Z)-19-heneicosenyl-1-phosphocholine
90. 20-heneicosenyl-1-phosphocholine 22 Chain Carbon Atoms
$C_{27}H_{56}NO_4P$ (489.72)
91. (Z)-3-docosenyl-1-phosphocholine
92. (Z)-4-docosenyl-1-phosphocholine
93. (Z)-5-docosenyl-1-phosphocholine
94. (Z)-6-docosenyl-1-phosphocholine
95. (Z)-7-docosenyl-1-phosphocholine
96. (Z)-8-docosenyl-1-phosphocholine
97. (Z)-9-docosenyl-1-phosphocholine
98. (Z)-10-docosenyl-1-phosphocholine
99. (z)-1'-docosenyl-1-phosphocholine
100. (Z)-12-docosenyl-1-phosphocholine
101. (Z)-14-docosenyl-1-phosphocholine
102. (Z)-15-docosenyl-1-phosphocholine
103. (Z)-16-docosenyl-1-phosphocholine
104. (Z)-17-docosenyl-1-phosphocholine
105. (Z)-18-docosenyl-1-phosphocholine
106. (Z)-19-docosenyl-1-phosphocholine
107. (Z)-20-docosenyl-1-phosphocholine
108. 21-docosenyl-1-phosphocholine 23 Chain Carbon Atoms
$C_{28}H_{58}NO_4P$ (503.75)
109. (Z)-3-tricosenyl-1-phosphocholine
110. (Z)-4-tricosenyl-1-phosphocholine
111. (Z)-5-tricosenyl-1-phosphocholine
112. (Z)-6-tricosenyl-1-phosphocholine
113. (Z)-7-tricosenyl-1-phosphocholine
114. (Z)-8-tricosenyl-1-phosphocholine
115. (Z)-9-tricosenyl-1-phosphocholine
116. (Z)-10-tricosenyl-1-phosphocholine
117. (Z)-11-tricosenyl-1-phosphocholine
118. (Z)-12-tricosenyl-1-phosphocholine
119. (z)-13-tricosenyl-1-phosphocholine
120. (Z)-14-tricosenyl-1-phosphocholine
121. (Z)-15-tricosenyl-1-phosphocholine
122. (Z)-16-tricosenyl-1-phosphocholine
123. (Z)-17-tricosenyl-1-phosphocholine
124. (Z)-18-tricosenyl-1-phosphocholine
125. (Z)-19-tricosenyl-1-phosphocholine
126. (Z)-20-tricosenyl-1-phosphocholine
127. (Z)-21-tricosenyl-1-phosphocholine
128. 22-tricosenyl-1-phosphocholine 24 Chain Carbon Atoms
$C_{29}H_{60}NO_4P$ (517.77)
129. (Z)-3-tetracosenyl-1-phosphocholine
130. (Z)-4-tetracosenyl-1-phosphocholine
131. (Z)-5-tetracosenyl-1-phosphocholine
132 (Z)-6-tetracosenyl-1-phosphocholine
133. (Z)-7-tetracosenyl-1-phosphocholine
134. (Z)-8-tetracosenyl-1-phosphocholine
135. (Z)-9-tetracosenyl-1-phosphocholine
136. (Z)-10-tetracosenyl-1-phosphocholine
137. (Z)-11-tetracosenyl-1-phosphocholine
138. (Z)-12-tetracosenyl-1-phosphocholine
139. (Z)-13-tetracosenyl-1-phosphocholine
140. (Z)-14-tetracosenyl-1-phosphocholine
141. (Z)-16-tetracosenyl-1-phosphocholine
142. (Z)-17-tetracosenyl-1-phosphocholine
143. (Z)-18-tetracosenyl-1-phosphocholine 2. Examples of
(Z)-alkenyl-1-phospho-N,N,N-trimethyl-propyl
ammonium compounds

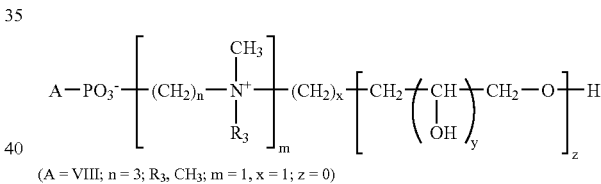

(A = VIII; n = 3; $R_3$, $CH_3$; m = 1, x = 1; z = 0)

where A is a monounsaturated alkyl chain of the following structure (p, q≧0; 12≦p+q≦30):

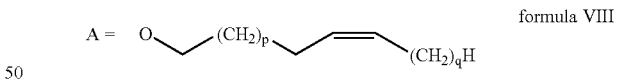

formula VIII

16 Chain Carbon Atoms
$C_{22}H_{46}NO_4P$ (419.59)
144. (Z)-3-hexadecenyl-1-phospho-N,N,N-trimethylpropylammonium
145. (Z)-4-hexadecenyl-1-phospho-N,N,N-trimethylpropylammonium
146. (Z)-5-hexadecenyl-1-phospho-N,N,N-trimethylpropylammonium
147. (Z)-6-hexadecenyl-1-phospho-N,N,N-trimethylpropylammonium
148. (Z)-7-hexadecenyl-1-phospho-N,N,N-trimethylpropylammonium
149. (Z)-8-hexadecenyl-1-phospho-N,N,N-trimethylpropylammonium
150. (Z)-9-hexadecenyl-1-phospho-N,N,N-trimethylpropylammonium 151. (Z)-10-hexadecenyl-1-phospho-N,N,N-trimethylpropylammonium
152. (Z)-11-hexadecenyl-1-phospho-N,N,N-trimethylpropylammonium
153. (Z)-12-hexadecenyl-1-phospho-N,N,N-trimethylpropylammonium
154. (Z)-13-hexadecenyl-1-phospho-N,N,N-trimethylpropylammonium
155. (Z)-14-hexadecenyl-1-phospho-N,N,N-trimethylpropylammonium
156. 15-hexadecenyl-1-phospho-N,N,N-trimethylpropylammonium 17 Chain Carbon Atoms
$C_{23}H_{48}NO_4P$ (433.61)

157. (Z)-3-heptadecenyl-1-phospho-N,N,N-trimethylpropylammonium
158. (Z)-4-heptadecenyl-1-phospho-N,N,N-trimethylpropylammonium
159. (Z)-5-heptadecenyl-1-phospho-N,N,N-trimethylpropylammonium
160. (Z)-6-heptadecenyl-1-phospho-N,N,N-trimethylpropylammonium
161. (Z)-7-heptadecenyl-1-phospho-N,N,N-trimethylpropylammonium
162. (Z)-8-heptadecenyl-1-phospho-N,N,N-trimethylpropylammonium
163. (Z)-9-heptadecenyl-1-phospho-N,N,N-trimethylpropylammonium
164. (Z)-10-heptadecenyl-1-phospho-N,N,N-trimethylpropylammonium
165. (Z)-11-heptadecenyl-1-phospho-N,N,N-trimethylpropylammonium
166. (Z)-12-heptadecenyl-1-phospho-N,N,N-trimethylpropylammonium
167. (Z)-13-heptadecenyl-1-phospho-N,N,N-trimethylpropylammonium
168. (Z)-14-heptadecenyl-1-phospho-N,N,N-trimethylpropylammonium
169. (Z)-15-heptadecenyl-1-phospho-N,N,N-trimethylpropylammonium
170. 16-heptadecenyl-1-phospho-N,N,N-trimethylpropylammonium 18 Chain Carbon Atoms
$C_{24}H_{50}NO_4P$ (447.64)

171. (Z)-3-octadecenyl-1-phospho-N,N,N-trimethylpropylammonium
172. (Z)-4-octadecenyl-1-phospho-N,N,N-trimethylpropylammonium
173. (Z)-5-octadecenyl-1-phospho-N,N,N-trimethylpropylammonium
174. (Z)-6-octadecenyl-1-phospho-N,N,N-trimethylpropylammonium
175. (Z)-7-octadecenyl-1-phospho-N,N,N-trimethylpropylammonium
176. (Z)-8-octadecenyl-1-phospho-N,N,N-trimethylpropylammonium
177. (Z)-10-octadecenyl-1-phospho-N,N,N-trimethylpropylammonium
178. (Z)-11-octadecenyl-1-phospho-N,N,N-trimethylpropylammonium
179. (Z)-12-octadecenyl-1-phospho-N,N,N-trimethylpropylammonium
180. (Z)-13-octadecenyl-1-phospho-N,N,N-trimethylpropylammonium
181. (Z)-14-octadecenyl-1-phospho-N,N,N-trimethylpropylammonium
182. (Z)-15-octadecenyl-1-phospho-N,N,N-trimethylpropylammonium
183. (Z)-16-octadecenyl-1-phospho-N,N,N-trimethylpropylammonium
184. 17-octadecenyl-1-phospho-N,N,N-trimethylpropylammonium 19 Chain Carbon Atoms
$C_{25}H_{52}NO_4P$ (461.67)

185. (Z)-3-nonadecenyl-1-phospho-N,N,N-trimethylpropylammonium
186. (Z)-4-nonadecenyl-1-phospho-N,N,N-trimethylpropylammonium
187. (Z)-5-nonadecenyl-1-phospho-N,N,N-trimethylpropylammonium
188. (Z)-6-nonadecenyl-1-phospho-N,N,N-trimethylpropylammonium
189. (Z)-7-nonadecenyl-1-phospho-N,N,N-trimethylpropylammonium
190. (Z)-8-nonadecenyl-1-phospho-N,N,N-trimethylpropylammonium
191. (Z)-9-nonadecenyl-1-phospho-N,N,N-trimethylpropylammonium
192. (Z)-10-nonadecenyl-1-phospho-N,N,N-trimethylpropylammonium
193. (Z)-11-nonadecenyl-1-phospho-N,N,N-trimethylpropylammonium
194. (Z)-12-nonadecenyl-1-phospho-N,N,N-trimethylpropylammonium
195. (Z)-13-nonadecenyl-1-phospho-N,N,N-trimethylpropylammonium
196. (Z)-14-nonadecenyl-1-phospho-N,N,N-trimethylpropylammonium
197. (Z)-15-nonadecenyl-1-phospho-N,N,N-trimethylpropylammonium
198. (Z)-16-nonadecenyl-1-phospho-N,N,N-trimethylpropylammonium
199. (Z)-17-nonadecenyl-1-phospho-N,N,N-trimethylpropylammonium
200. 18-nonadecenyl-1-phospho-N,N,N-trimethylpropylammonium 20 Chain Carbon Atoms
$C_{26}H_{54}NO_4P$ (475.69)

201. (Z)-3-eicosenyl-1-phospho-N,N,N-trimethylpropylammonium
202. (Z)-4-eicosenyl-1-phospho-N,N,N-trimethylpropylammonium
203. (Z)-5-eicosenyl-1-phospho-N,N,N-trimethylpropylammonium
204. (Z)-6-eicosenyl-1-phospho-N,N,N-trimethylpropylammonium
205. (Z)-7-eicosenyl-1-phospho-N,N,N-trimethylpropylammonium
206. (Z)-8-eicosenyl-1-phospho-N,N,N-trimethylpropylammonium
207. (Z)-9-eicosenyl-1-phospho-N,N,N-trimethylpropylammonium
208. (Z)-10-eicosenyl-1-phospho-N,N,N-trimethylpropylammonium
209. (Z)-12-eicosenyl-1-phospho-N,N,N-trimethylpropylammonium
210. (Z)-13-eicosenyl-1-phospho-N,N,N-trimethylpropylammonium
211. (Z)-14-eicosenyl-1-phospho-N,N,N-trimethylpropylammonium
212. (Z)-15-eicosenyl-1-phospho-N,N,N-trimethylpropylammonium 213. (Z)-16-eicosenyl-1-phospho-N,N,N-trimethylpropylammonium
214. (z)-17-eicosenyl-1-phospho-N,N,N-trimethylpropylammonium
215. (z)-18-eicosenyl-1-phospho-N,N,N-trimethylpropylammonium
216. 19-eicosenyl-1-phospho-N,N,N-trimethylpropylammonium 21 Chain Carbon Atoms
$C_{27}H_{56}NO_4P$ (489.72)

217. (Z)-3-heneicosenyl-1-phospho-N,N,N-trimethylpropylammonium
218. (Z)-4-heneicosenyl-1-phospho-N,N,N-trimethylpropylammonium
219. (Z)-5-heneicosenyl-1-phospho-N,N,N-trimethylpropylammonium
220. (Z)-6-heneicosenyl-1-phospho-N,N,N-trimethylpropylammonium
221. (Z)-7-heneicosenyl-1-phospho-N,N,N-trimethylpropylammonium
222. (Z)-8-heneicosenyl-1-phospho-N,N,N-trimethylpropylammonium
223. (Z)-9-heneicosenyl-1-phospho-N,N,N-trimethylpropylammonium
224. (Z)-10-heneicosenyl-1-phospho-N,N,N-trimethylpropylammonium
225. (Z)-11-heneicosenyl-1-phospho-N,N,N-trimethylpropylammonium
226. (Z)-12-heneicosenyl-1-phospho-N,N,N-trimethylpropylammonium
227. (Z)-13-heneicosenyl-1-phospho-N,N,N-trimethylpropylammonium
228. (Z)-14-heneicosenyl-1-phospho-N,N,N-trimethylpropylammonium
229. (Z)-15-heneicosenyl-1-phospho-N,N,N-trimethylpropylammonium
230. (Z)-16-heneicosenyl-1-phospho-N,N,N-trimethylpropylammonium
231. (Z)-17-heneicosenyl-1-phospho-N,N,N-trimethylpropylammonium
232. (z)-18-heneicosenyl-1-phospho-N,N,N-trimethylpropylammonium
233. (Z)-19-heneicosenyl-1-phospho-N,N,N-trimethylpropylammonium
234. 20-heneicosenyl-1-phospho-N,N,N-trimethylpropylammonium 22 Chain Carbon Atoms
$C_{21}H_{58}NO_4P$ (503.75)

235. (Z)-3-docosenyl-1-phospho-N,N,N-trimethylpropylammonium
236. (Z)-4-docosenyl-1-phospho-N,N,N-trimethylpropylammonium
237. (Z)-5-docosenyl-1-phospho-N,N,N-trimethylpropylammonium
238. (Z)-6-docosenyl-1-phospho-N,N,N-trimethylpropylammonium
239. (Z)-7-docosenyl-1-phospho-N,N,N-trimethylpropylammonium
240. (Z)-8-docosenyl-1-phospho-N,N,N-trimethylpropylammonium
241. (Z)-9-docosenyl-1-phospho-N,N,N-trimethylpropylammonium
242. (Z)-10-docosenyl-1-phospho-N,N,N-trimethylpropylammonium
243. (Z)-11-docosenyl-1-phospho-N,N,N-trimethylpropylammonium
244. (Z)-12-docosenyl-1-phospho-N,N,N-trimethylpropylammonium
245. (Z)-14-docosenyl-1-phospho-N,N,N-trimethylpropylammonium
246. (Z)-15-docosenyl-1-phospho-N,N,N-trimethylpropylammonium
247. (Z)-16-docosenyl-1-phospho-N,N,N-trimethylpropylammonium
248. (Z)-17-docosenyl-1-phospho-N,N,N-trimethylpropylammonium
249. (Z)-18-docosenyl-1-phospho-N,N,N-trimethylpropylammonium
250. (Z)-19-docosenyl-1-phospho-N,N,N-trimethylpropylammonium
251. (Z)-20-docosenyl-1-phospho-N,N,N-trimethylpropylammonium
252. 21-docosenyl-1-phospho-N,N,N-trimethylpropylammonium 23 Chain Carbon Atoms
$C_{29}H_{60}NO_4P$ (517.77)

253. (Z)-3-tricosenyl-1-phospho-N,N,N-trimethylpropylammonium
254. (Z)-4-tricosenyl-1-phospho-N,N,N-trimethylpropylammonium
255. (Z)-5-tricosenyl-1-phospho-N,N,N-trimethylpropylammonium
256. (Z)-6-tricosenyl-1-phospho-N,N,N-trimethylpropylammonium
257. (Z)-7-tricosenyl-1-phospho-N,N,N-trimethylpropylammonium
258. (Z)-8-tricosenyl-1-phospho-N,N,N-trimethylpropylammonium
259. (Z)-9-tricosenyl-1-phospho-N,N,N-trimethylpropylammonium
260. (Z)-10-tricosenyl-1-phospho-N,N,N-trimethylpropylammonium
261. (Z)-11-tricosenyl-1-phospho-N,N,N-trimethylpropylammonium
262. (Z)-12-tricosenyl-1-phospho-N,N,N-trimethylpropylammonium
263. (Z)-13-tricosenyl-1-phospho-N,N,N-trimethylpropylammonium
264. (Z)-14-tricosenyl-1-phospho-N,N,N-trimethylpropylammonium
265. (Z)-15-tricosenyl-1-phospho-N,N,N-trimethylpropylammonium
266. (Z)-16-tricosenyl-1-phospho-N,N,N-trimethylpropylammonium
267. (Z)-17-tricosenyl-1-phospho-N,N,N-trimethylpropylammonium
268. (Z)-18-tricosenyl-1-phospho-N,N,N-trimethylpropylammonium
269. (Z)-19-tricosenyl-1-phospho-N,N,N-trimethylpropylammonium
270. (Z)-20-tricosenyl-1-phospho-N,N,N-trimethylpropylammonium
271. (Z)-21-tricosenyl-1-phospho-N,N,N-trimethylpropylammonium
272. 22-tricosenyl-1-phospho-N,N,N-trimethylpropylammonium 24 Chain Carbon Atoms
$C_{30}H_{62}NO_4P$ (531.80)

273. (Z)-3-tetracosenyl-1-phospho-N,N,N-trimethylpropylammonium
274. (Z)-4-tetracosenyl-1-phospho-N,N,N-trimethylpropylammonium 275. (Z)-5-tetracosenyl-1-phospho-N,N,N-trimethylpropylammonium
276. (Z)-6-tetracosenyl-1-phospho-N,N,N-trimethylpropylammonium
277. (Z)-7-tetracosenyl-1-phospho-N,N,N-trimethylpropylammonium
278. (Z)-8-tetracosenyl-1-phospho-N,N,N-trimethylpropylammonium
279. (Z)-9-tetracosenyl-1-phospho-N,N,N-trimethylpropylammonium
280. (Z)-10-tetracosenyl-1-phospho-N,N,N-trimethylpropylammonium
281. (Z)-11-tetracosenyl-1-phospho-N,N,N-trimethylpropylammonium
282. (Z)-12-tetracosenyl-1-phospho-N,N,N-trimethylpropylammonium
283. (Z)-13-tetracosenyl-1-phospho-N,N,N-trimethylpropylammonium
284. (Z)-14-tetracosenyl-1-phospho-N,N,N-trimethylpropylammonium
285. (Z)-15-tetracosenyl-1-phospho-N,N,N-trimethylpropylammonium
286. (Z)-16-tetracosenyl-1-phospho-N,N,N-trimethylpropylammonium
287. (Z)-17-tetracosenyl-1-phospho-N,N,N-trimethylpropylammonium
288. (Z)-18-tetracosenyl-1-phospho-N,N,N-trimethylpropylammonium 3. Examples of (Z)-alkenyl-1-phospho-N,N,N-trimethylbutylammonium Compounds

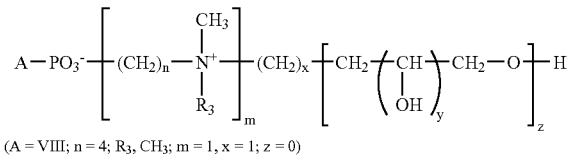

(A = VIII; n = 4; $R_3$, $CH_3$; m = 1, x = 1; z = 0)

where A is a monounsaturated alkyl chain of the following structure (p, q $\geqq$ 0; 12 $\leqq$ p+q $\leqq$ 30):

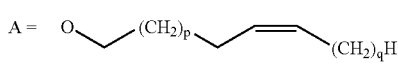

formula VIII

16 Chain Carbon Atoms
$C_{23}H_{48}NO_4P$ (433.61)
289. (Z)-3-hexadecenyl-1-phospho-N,N,N-trimethylbutylammonium
290. (Z)-4-hexadecenyl-1-phospho-N,N,N-trimethylbutylammonium
291. (Z)-5-hexadecenyl-1-phospho-N,N,N-trimethylbutylammonium
292. (Z)-6-hexadecenyl-1-phospho-N,N,N-trimethylbutylammonium
293. (Z)-7-hexadecenyl-1-phospho-N,N,N-trimethylbutylammonium
294. (Z)-8-hexadecenyl-1-phospho-N,N,N-trimethylbutylammonium
295. (Z)-9-hexadecenyl-1-phospho-N,N,N-trimethylbutylammonium
296. (Z)-10-hexadecenyl-1-phospho-N,N,N-trimethylbutylammonium
297. (Z)-11-hexadecenyl-1-phospho-N,N,N-trimethylbutylammonium
298. (Z)-12-hexadecenyl-1-phospho-N,N,N-trimethylbutylammonium
299. (Z)-13-hexadecenyl-1-phospho-N,N,N-trimethylbutylammonium
300. (Z)-14-hexadecenyl-1-phospho-N,N,N-trimethylbutylammonium
301. 15-hexadecenyl-1-phospho-N,N,N-trimethylbutylammonium 17 Chain Carbon Atoms
$C_{24}H_{50}NO_4P$ (447.64)
302. (Z)-3-heptadecenyl-1-phospho-N,N,N-trimethylbutylammonium
303. (Z)-4-heptadecenyl-1-phospho-N,N,N-trimethylbutylammonium
304. (Z)-5-heptadecenyl-1-phospho-N,N,N-trimethylbutylammonium
305. (Z)-6-heptadecenyl-1-phospho-N,N,N-trimethylbutylammonium
306. (Z)-7-heptadecenyl-1-phospho-N,N,N-trimethylbutylammonium
307. (Z)-8-heptadecenyl-1-phospho-N,N,N-trimethylbutylammonium
308. (Z)-9-heptadecenyl-1-phospho-N,N,N-trimethylbutylammonium
309. (z)-10-heptadecenyl-1-phospho-N,N,N-trimethylbutylammonium
310. (Z)-11-heptadecenyl-1-phospho-N,N,N-trimethylbutylammonium
311. (Z)-12-heptadecenyl-1-phospho-N,N,N-trimethylbutylammonium
312. (Z)-13-heptadecenyl-1-phospho-N,N,N-trimethylbutylammonium
313. (Z)-14-heptadecenyl-1-phospho-N,N,N-trimethylbutylammonium
314. (Z)-15-heptadecenyl-1-phospho-N,N,N-trimethylbutylammonium
315. 16-heptadecenyl-1-phospho-N,N,N-trimethylbutylammonium 18 Chain Carbon Atoms
$C_{25}H_{52}NO_4P$ (461.67)
316. (Z)-3-octadecenyl-1-phospho-N,N,N-trimethylbutylammonium
317. (Z)-4-octadecenyl-1-phospho-N,N,N-trimethylbutylammonium
318. (Z)-5-octadecenyl-1-phospho-N,N,N-trimethylbutylammonium
319. (Z)-6-octadecenyl-1-phospho-N,N,N-trimethylbutylammonium
320. (Z)-7-octadecenyl-1-phospho-N,N,N-trimethylbutylammonium
321. (Z)-8-octadecenyl-1-phospho-N,N,N-trimethylbutylammonium
322. (Z)-10-octadecenyl-1-phospho-N,N,N-trimethylbutylammonium
323. (Z)-11-octadecenyl-1-phospho-N,N,N-trimethylbutylammonium
324. (Z)-12-octadecenyl-1-phospho-N,N,N-trimethylbutylammonium
325. (Z)-13-octadecenyl-1-phospho-N,N,N-trimethylbutylammonium
326. (Z)-14-octadecenyl-1-phospho-N,N,N-trimethylbutylammonium 327. (Z)-15-octadecenyl-1-phospho-N,N,N-trimethylbutylammonium
328. (Z)-16-octadecenyl-1-phospho-N,N,N-trimethylbutylammonium
329. 17-octadecenyl-1-phospho-N,N,N-trimethylbutylammonium 19 Chain Carbon Atoms
$C_{26}H_{54}NO_4P$ (475.69)

330. (Z)-3-nonadecenyl-1-phospho-N,N,N-trimethylbutylammonium
331. (Z)-4-nonadecenyl-1-phospho-N,N,N-trimethylbutylammonium
332. (Z)-5-nonadecenyl-1-phospho-N,N,N-trimethylbutylammonium
333. (Z)-6-nonadecenyl-1-phospho-N,N,N-trimethylbutylammonium
334. (Z)-7-nonadecenyl-1-phospho-N,N,N-trimethylbutylammonium
335. (Z)-8-nonadecenyl-1-phospho-N,N,N-trimethylbutylammonium
336. (Z)-9-nonadecenyl-1-phospho-N,N,N-trimethylbutylammonium
337. (Z)-10-nonadecenyl-1-phospho-N,N,N-trimethylbutylammonium
338. (Z)-11-nonadecenyl-1-phospho-N,N,N-trimethylbutylammonium
339. (Z)-12-nonadecenyl-1-phospho-N,N,N-trimethylbutylammonium
340. (Z)-13-nonadecenyl-1-phospho-N,N,N-trimethylbutylammonium
341. (Z)-14-nonadecenyl-1-phospho-N,N,N-trimethylbutylammonium
342. (Z)-15-nonadecenyl-1-phospho-N,N,N-trimethylbutylammonium
343. (Z)-16-nonadecenyl-1-phospho-N,N,N-trimethylbutylammonium
344. (Z)-17-nonadecenyl-1-phospho-N,N,N-trimethylbutylammonium
345. 18-nonadecenyl-1-phospho-N,N,N-trimethylbutylammonium 20 Chain Carbon Atoms
$C_{27}H_{56}NO_4P$ (489.72)

346. (Z)-3-eicosenyl-1-phospho-N,N,N-trimethylbutylammonium
347. (Z)-4-eicosenyl-1-phospho-N,N,N-trimethylbutylammonium
348. (Z)-5-eicosenyl-1-phospho-N,N,N-trimethylbutylammonium
349. (Z)-6-eicosenyl-1-phospho-N,N,N-trimethylbutylammonium
350. (Z)-7-eicosenyl-1-phospho-N,N,N-trimethylbutylammonium
351. (Z)-8-eicosenyl-1-phospho-N,N,N-trimethylbutylammonium
352. (Z)-9-eicosenyl-1-phospho-N,N,N-trimethylbutylammonium
353. (Z)-10-eicosenyl-1-phospho-N,N,N-trimethylbutylammonium
354. (Z)-11-eicosenyl-1-phospho-N,N,N-trimethylbutylammonium
355. (Z)-12-eicosenyl-1-phospho-N,N,N-trimethylbutylammonium
356. (Z)-13-eicosenyl-1-phospho-N,N,N-trimethylbutylammonium
357. (Z)-14-eicosenyl-1-phospho-N,N,N-trimethylbutylammonium
358. (Z)-15-eicosenyl-1-phospho-N,N,N-trimethylbutylammonium
359. (Z)-16-eicosenyl-1-phospho-N,N,N-trimethylbutylammonium
360. (Z)-17-eicosenyl-1-phospho-N,N,N-trimethylbutylammonium
361. (Z)-18-eicosenyl-1-phospho-N,N,N-trimethylbutylammonium
362. 19-eicosenyl-1-phospho-N,N,N-trimethylbutylammonium 21 Chain Carbon Atoms
$C_{28}H_{58}NO_4P$ (503.75)

363. (Z)-3-heneicosenyl-1-phospho-N,N,N-trimethylbutylammonium
364. (Z)-4-heneicosenyl-1-phospho-N,N,N-trimethylbutylammonium
365. (Z)-5-heneicosenyl-1-phospho-N,N,N-trimethylbutylammonium
366. (Z)-6-heneicosenyl-1-phospho-N,N,N-trimethylbutylammonium
367. (Z)-7-heneicosenyl-1-phospho-N,N,N-trimethylbutylammonium
368. (Z)-8-heneicosenyl-1-phospho-N,N,N-trimethylbutylammonium
369. (Z)-9-heneicosenyl-1-phospho-N,N,N-trimethylbutylammonium
370. (Z)-10-heneicosenyl-1-phospho-N,N,N-trimethylbutylammonium
371. (Z)-11-heneicosenyl-1-phospho-N,N,N-trimethylbutylammonium
372. (Z)-12-heneicosenyl-1-phospho-N,N,N-trimethylbutylammonium
373. (Z)-13-heneicosenyl-1-phospho-N,N,N-trimethylbutylammonium
374. (Z)-14-heneicosenyl-1-phospho-N,N,N-trimethylbutylammonium
375. (Z)-15-heneicosenyl-1-phospho-N,N,N-trimethylbutylammonium
376. (Z)-16-heneicosenyl-1-phospho-N,N,N-trimethylbutylammonium
377. (Z)-17-heneicosenyl-1-phospho-N,N,N-trimethylbutylammonium
378. (Z)-18-heneicosenyl-1-phospho-N,N,N-trimethylbutylammonium
379. (Z)-19-heneicosenyl-1-phospho-N,N,N-trimethylbutylammonium
380. 20-heneicosenyl-1-phospho-N,N,N-trimethylbutylammonium 22 Chain Carbon Atoms
$C_{29}H_{60}NO_4P$ (517.77)

381. (Z)-3-docosenyl-1-phospho-N,N,N-trimethylbutylammonium
382. (Z)-4-docosenyl-1-phospho-N,N,N-trimethylbutylammonium
383. (Z)-5-docosenyl-1-phospho-N,N,N-trimethylbutylammonium
384. (Z)-6-docosenyl-1-phospho-N,N,N-trimethylbutylammonium
385. (Z)-7-docosenyl-1-phospho-N,N,N-trimethylbutylammonium
386. (Z)-8-docosenyl-1-phospho-N,N,N-trimethylbutylammonium
387. (Z)-9-docosenyl-1-phospho-N,N,N-trimethylbutylammonium
388. (Z)-10-docosenyl-1-phospho-N,N,N-trimethylbutylammonium 389. (Z)-11-docosenyl-1-phospho-N,N,N-trimethylbutylammonium
390. (Z)-12-docosenyl-1-phospho-N,N,N-trimethylbutylammonium
391. (Z)-14-docosenyl-1-phospho-N,N,N-trimethylbutylammonium
392. (Z)-15-docosenyl-1-phospho-N,N,N-trimethylbutylammonium
393. (Z)-16-docosenyl-1-phospho-N,N,N-trimethylbutylammonium
394. (Z)-17-docosenyl-1-phospho-N,N,N-trimethylbutylammonium
395. (Z)-18-docosenyl-1-phospho-N,N,N-trimethylbutylammonium
396. (Z)-19-docosenyl-1-phospho-N,N,N-trimethylbutylammonium
397. (Z)-20-docosenyl-1-phospho-N,N,N-trimethylbutylammonium
398. 21-docosenyl-1-phospho-N,N,N-trimethylbutylammonium 23 Chain Carbon Atoms
$C_{30}H_{62}NO_4P$ (531.80)
399. (Z)-3-tricosenyl-1-phospho-N,N,N-trimethylbutylammonium
400. (Z)-4-tricosenyl-1-phospho-N,N,N-trimethylbutylammonium
401. (Z)-5-tricosenyl-1-phospho-N,N,N-trimethylbutylammonium
402. (Z)-6-tricosenyl-1-phospho-N,N,N-trimethylbutylammonium
403. (Z)-7-tricosenyl-1-phospho-N,N,N-trimethylbutylammonium
404. (Z)-8-tricosenyl-1-phospho-N,N,N-trimethylbutylammonium
405. (Z)-9-tricosenyl-1-phospho-N,N,N-trimethylbutylammonium
406. (Z)-10-tricosenyl-1-phospho-N,N,N-trimethylbutylammonium
407. (Z)-11-tricosenyl-1-phospho-N,N,N-trimethylbutylammonium
408. (Z)-12-tricosenyl-1-phospho-N,N,N-trimethylbutylammonium
409. (Z)-13-tricosenyl-1-phospho-N,N,N-trimethylbutylammonium
410. (Z)-14-tricosenyl-1-phospho-N,N,N-trimethylbutylammonium
411. (Z)-15-tricosenyl-1-phospho-N,N,N-trimethylbutylammonium
412. (Z)-16-tricosenyl-1-phospho-N,N,N-trimethylbutylammonium
413. (Z)-17-tricosenyl-1-phospho-N,N,N-trimethylbutylammonium
414. (Z)-18-tricosenyl-1-phospho-N,N,N-trimethylbutylammonium
415. (z)-19-tricosenyl-1-phospho-N,N,N-trimethylbutylammonium
416. (Z)-20-tricosenyl-1-phospho-N,N,N-trimethylbutylammonium
417. (Z)-21-tricosenyl-1-phospho-N,N,N-trimethylbutylammonium
418. 22-tricosenyl-1-phospho-N,N,N-trimethylbutylammonium 24 Chain Carbon Atoms
$C_{31}H_{64}NO_4P$ (545.83)
419. (Z)-3-tetracosenyl-1-phospho-N,N,N-trimethylbutylammonium
420. (Z)-4-tetracosenyl-1-phospho-N,N,N-trimethylbutylammonium
421. (Z)-5-tetracosenyl-1-phospho-N,N,N-trimethylbutylammonium
422. (Z)-6-tetracosenyl-1-phospho-N,N,N-trimethylbutylammonium
423. (Z)-7-tetracosenyl-1-phospho-N,N,N-trimethylbutylammonium
424. (Z)-8-tetracosenyl-1-phospho-N,N,N-trimethylbutylammonium
425. (Z)-9-tetracosenyl-1-phospho-N,N,N-trimethylbutylammonium
426. (Z)-10-tetracosenyl-1-phospho-N,N,N-trimethylbutylammonium
427. (Z)-11-tetracosenyl-1-phospho-N,N,N-trimethylbutylammonium
428. (Z)-12-tetracosenyl-1-phospho-N,N,N-trimethylbutylammonium
429. (Z)-13-tetracosenyl-1-phospho-N,N,N-trimethylbutylammonium
430. (Z)-14-tetracosenyl-1-phospho-N,N,N-trimethylbutylammonium
431. (Z)-15-tetracosenyl-1-phospho-N,N,N-trimethylbutylammonium
432. (Z)-16-tetracosenyl-1-phospho-N,N,N-trimethylbutylammonium
433. (Z)-17-tetracosenyl-1-phospho-N,N,N-trimethylbutylammonium
434. (Z)-18-tetracosenyl-1-phospho-N,N,N-trimethylbutylammonium 4. Examples of (Z,Z)-alkadienylphosphocholines

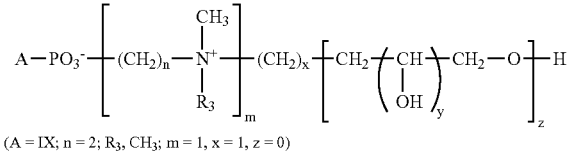

(A = IX; n = 2; R₃, CH₃; m = 1, x = 1, z = 0)

where A is a diunsaturated alkyl chain of the following structure (s, t, r ≧ 0; 8 ≦ s+t+r ≦ 26):

formula IX

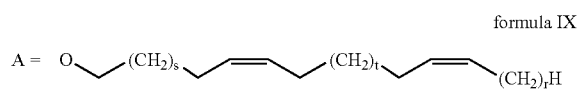

16 Chain Carbon Atoms
$C_{21}H_{42}NO_4P$ (403.54)
435. (Z,Z)-3,7-hexadecadienyl-1-phosphocholine
436. (Z,Z)-4,8-hexadecadienyl-1-phosphocholine
437. (Z,Z)-5,9-hexadecadienyl-1-phosphocholine
438. (Z,Z)-6,10-hexadecadienyl-1-phosphocholine
439. (Z,Z)-7,11-hexadecadienyl-1-phosphocholine
440. (Z,Z)-8,12-hexadecadienyl-1-phosphocholine
441. (Z,Z)-9,13-hexadecadienyl-1-phosphocholine
442. (Z,Z)-3,8-hexadecadienyl-1-phosphocholine
443. (Z,Z)-4,9-hexadecadienyl-1-phosphocholine
444. (Z,Z)-5,10-hexadecadienyl-1-phosphocholine
445. (Z,Z)-6,11-hexadecadienyl-1-phosphocholine
446. (Z,Z)-7,12-hexadecadienyl-1-phosphocholine
447. (Z,Z)-8,13-hexadecadienyl-1-phosphocholine 448. (Z,Z)-3,9-hexadecadienyl-1-phosphocholine
449. (Z,Z)-4,10-hexadecadienyl-1-phosphocholine
450. (Z,Z)-5,11-hexadecadienyl-1-phosphocholine
451. (Z,Z)-6,12-hexadecadienyl-1-phosphocholine
452. (Z,Z)-7,13-hexadecadienyl-1-phosphocholine
453. (Z,Z)-3,10-hexadecadienyl-1-phosphocholine
454. (Z,Z)-4,11-hexadecadienyl-1-phosphocholine
455. (Z,Z)-5,12-hexadecadienyl-1-phosphocholine
456. (Z,Z)-6,13-hexadecadienyl-1-phosphocholine
457. (Z,Z)-3,11-hexadecadienyl-1-phosphocholine
458. (Z,Z)-4,12-hexadecadienyl-1-phosphocholine
459. (Z,Z)-5,13-hexadecadienyl-1-phosphocholine
460. (Z,Z)-3,12-hexadecadienyl-1-phosphocholine
461. (Z,Z)-4,13-hexadecadienyl-1-phosphocholine
462. (Z,Z)-3,13-hexadecadienyl-1-phosphocholine
17 Chain Carbon Atoms
$C_{22}H_{44}NO_4P$ (417.57)
463. (Z,Z)-3,7-heptadecadienyl-1-phosphocholine
464. (Z,Z)-4,8-heptadecadienyl-1-phosphocholine
465. (Z,Z)-5,9-heptadecadienyl-1-phosphocholine
466. (Z,Z)-6,10-heptadecadienyl-1-phosphocholine
467. (Z,Z)-7,11-heptadecadienyl-1-phosphocholine
468. (Z,Z)-8,12-heptadecadienyl-1-phosphocholine
469. (Z,Z)-9,13-heptadecadienyl-1-phosphocholine
470. (Z,Z)-10,14-heptadecadienyl-1-phosphocholine
471. (Z,Z)-3,8-heptadecadienyl-1-phosphocholine
472. (Z,Z)-4,9-heptadecadienyl-1-phosphocholine
473. (Z,Z)-5,10-heptadecadienyl-1-phosphocholine
474. (Z,Z)-6,11-heptadecadienyl-1-phosphocholine
475. (Z,Z)-7,12-heptadecadienyl-1-phosphocholine
476. (Z,Z)-8,13-heptadecadienyl-1-phosphocholine
477. (Z,Z)-9,14-heptadecadienyl-1-phosphocholine
478. (Z,Z)-3,9-heptadecadienyl-1-phosphocholine
479. (Z,Z)-4,10-heptadecadienyl-1-phosphocholine
480. (Z,Z)-5,11-heptadecadienyl-1-phosphocholine
481. (Z,Z)-6,12-heptadecadienyl-1-phosphocholine
482. (Z,Z)-7,13-heptadecadienyl-1-phosphocholine
483. (Z,Z)-8,14-heptadecadienyl-1-phosphocholine
484. (Z,Z)-3,10-heptadecadienyl-1-phosphocholine
485. (Z,Z)-4,11-heptadecadienyl-1-phosphocholine
486. (Z,Z)-5,12-heptadecadienyl-1-phosphocholine
487. (Z,Z)-6,13-heptadecadienyl-1-phosphocholine
488. (Z,Z)-7,14-heptadecadienyl-1-phosphocholine
489. (Z,Z)-3,11-heptadecadienyl-1-phosphocholine
490. (Z,Z)-4,12-heptadecadienyl-1-phosphocholine
491. (Z,Z)-5,13-heptadecadienyl-1-phosphocholine
492. (Z,Z)-6,14-heptadecadienyl-1-phosphocholine
493. (Z,Z)-3,12-heptadecadienyl-1-phosphocholine
494. (Z,Z)-4,13-heptadecadienyl-1-phosphocholine
495. (Z,Z)-5,14-heptadecadienyl-1-phosphocholine
496. (Z,Z)-3,13-heptadecadienyl-1-phosphocholine
497. (Z,Z)-4,14-heptadecadienyl-1-phosphocholine
498. (Z,Z)-3,14-heptadecadienyl-1-phosphocholine
18 Chain Carbon Atoms
$C_{23}H_{46}NO_4P$ (431.60)
499. (Z,Z)-3,7-octadecadienyl-1-phosphocholine
500. (Z,Z)-4,8-octadecadienyl-1-phosphocholine
501. (Z,Z)-5,9-octadecadienyl-1-phosphocholine
502. (Z,Z)-6,10-octadecadienyl-1-phosphocholine
503. (Z,Z)-7,11-octadecadienyl-1-phosphocholine
504. (Z,Z)-8,12-octadecadienyl-1-phosphocholine
505. (Z,Z)-9,13-octadecadienyl-1-phosphocholine
506. (Z,Z)-10,14-octadecadienyl-1-phosphocholine
507. (Z,Z)-11,15-octadecadienyl-1-phosphocholine
508. (Z,Z)-3,8-octadecadienyl-1-phosphocholine
509. (Z,Z)-4,9-octadecadienyl-1-phosphocholine
510. (Z,Z)-5,10-octadecadienyl-1-phosphocholine
511. (Z,Z)-6,11-octadecadienyl-1-phosphocholine
512. (Z,Z)-7,12-octadecadienyl-1-phosphocholine
513. (Z,Z)-8,13-octadecadienyl-1-phosphocholine
514. (Z,Z)-9,14-octadecadienyl-1-phosphocholine
515. (Z,Z)-10,15-octadecadienyl-1-phosphocholine
516. (Z,Z)-3,9-octadecadienyl-1-phosphocholine
517. (Z,Z)-4,10-octadecadienyl-1-phosphocholine
518. (Z,Z)-5,11-octadecadienyl-1-phosphocholine
519. (Z,Z)-6,12-octadecadienyl-1-phosphocholine
520. (Z,Z)-7,13-octadecadienyl-1-phosphocholine
521. (Z,Z)-8,14-octadecadienyl-1-phosphocholine
522. (Z,Z)-9,15-octadecadienyl-1-phosphocholine
523. (Z,Z)-3,10-octadecadienyl-1-phosphocholine
524. (Z,Z)-4,11-octadecadienyl-1-phosphocholine
525. (Z,Z)-5,12-octadecadienyl-1-phosphocholine
526. (Z,Z)-6,13-octadecadienyl-1-phosphocholine
527. (Z,Z)-7,14-octadecadienyl-1-phosphocholine
528. (Z,Z)-8,15-octadecadienyl-1-phosphocholine
529. (Z,Z)-3,11-octadecadienyl-1-phosphocholine
530. (Z,Z)-4,12-octadecadienyl-1-phosphocholine
531. (Z,Z)-5,13-octadecadienyl-1-phosphocholine
532. (Z,Z)-6,14-octadecadienyl-1-phosphocholine
533. (Z,Z)-7,15-octadecadienyl-1-phosphocholine
534 (Z,Z)-3,12-octadecadienyl-1-phosphocholine
535. (Z,Z)-4,13-octadecadienyl-1-phosphocholine
536. (Z,Z)-5,14-octadecadienyl-1-phosphocholine
537. (Z,Z)-6,15-octadecadienyl-1-phosphocholine
538. (Z,Z)-3,13-octadecadienyl-1-phosphocholine
539. (Z,Z)-4,14-octadecadienyl-1-phosphocholine
540. (Z,Z)-5,15-octadecadienyl-1-phosphocholine
541. (Z,Z)-3,14-octadecadienyl-1-phosphocholine
542. (Z,Z)-4,15-octadecadienyl-1-phosphocholine
543. (Z,Z)-3,15-octadecadienyl-1-phosphocholine
19 Chain Carbon Atoms
$C_{24}H_{48}NO_4P$ (445.62)
544. (Z,Z)-3,7-nonadecadienyl-1-phosphocholine
545. (Z,Z)-4,8-nonadecadienyl-1-phosphocholine
546. (Z,Z)-5,9-nonadecadienyl-1-phosphocholine
547. (Z,Z)-6,10-nonadecadienyl-1-phosphocholine
548. (Z,Z)-7,11-nonadecadienyl-1-phosphocholine
549. (Z,Z)-8,12-nonadecadienyl-1-phosphocholine
550. (Z,Z)-9,13-nonadecadienyl-1-phosphocholine
551. (Z,Z)-10,14-nonadecadienyl-1-phosphocholine
552. (Z,Z)-11,15-nonadecadienyl-1-phosphocholine
553. (Z,Z)-12,16-nonadecadienyl-1-phosphocholine
554. (Z,Z)-3,8-nonadecadienyl-1-phosphocholine
555. (Z,Z)-4,9-nonadecadienyl-1-phosphocholine
556. (Z,Z)-5,10-nonadecadienyl-1-phosphocholine
557. (Z,Z)-6,11-nonadecadienyl-1-phosphocholine
558. (Z,Z)-7,12-nonadecadienyl-1-phosphocholine
559. (Z,Z)-8,13-nonadecadienyl-1-phosphocholine
560. (Z,Z)-9,14-nonadecadienyl-1-phosphocholine
561. (Z,Z)-10,15-nonadecadienyl-1-phosphocholine
562. (Z,Z)-11,16-nonadecadienyl-1-phosphocholine
563. (Z,Z)-3,9-nonadecadienyl-1-phosphocholine
564. (Z,Z)-4,10-nonadecadienyl-1-phosphocholine
565. (Z,Z)-5,11-nonadecadienyl-1-phosphocholine
566. (Z,Z)-6,12-nonadecadienyl-1-phosphocholine
567. (Z,Z)-7,13-nonadecadienyl-1-phosphocholine
568. (Z,Z)-8,14-nonadecadienyl-1-phosphocholine
569. (Z,Z)-9,15-nonadecadienyl-1-phosphocholine
570. (Z,Z)-10,16-nonadecadienyl-1-phosphocholine
571. (Z,Z)-3,10-nonadecadienyl-1-phosphocholine
572. (Z,Z)-4,11-nonadecadienyl-1-phosphocholine
573. (Z,Z)-5,12-nonadecadienyl-1-phosphocholine
574. (Z,Z)-6,13-nonadecadienyl-1-phosphocholine
575. (Z,Z)-7,14-nonadecadienyl-1-phosphocholine 576. (Z,Z)-8,15-nonadecadienyl-1-phosphocholine
577. (Z,Z)-9,16-nonadecadienyl-1-phosphocholine
578. (Z,Z)-3,11-nonadecadienyl-1-phosphocholine
579. (Z,Z)-4,12-nonadecadienyl-1-phosphocholine
580. (Z,Z)-5,13-nonadecadienyl-1-phosphocholine
581. (Z,Z)-6,14-nonadecadienyl-1-phosphocholine
582. (Z,Z)-7,15-nonadecadienyl-1-phosphocholine
583. (Z,Z)-8,16-nonadecadienyl-1-phosphocholine
584. (Z,Z)-3,12-nonadecadienyl-1-phosphocholine
585. (Z,Z)-4,13-nonadecadienyl-1-phosphocholine
586. (Z,Z)-5,14-nonadecadienyl-1-phosphocholine
587. (Z,Z)-6,15-nonadecadienyl-1-phosphocholine
588. (Z,Z)-7,16-nonadecadienyl-1-phosphocholine
589. (Z,Z)-3,13-nonadecadienyl-1-phosphocholine
590. (Z,Z)-4,14-nonadecadienyl-1-phosphocholine
591. (Z,Z)-5,15-nonadecadienyl-1-phosphocholine
592. (Z,Z)-6,16-nonadecadienyl-1-phosphocholine
593. (Z,Z)-3,14-nonadecadienyl-1-phosphocholine
594. (Z,Z)-4,15-nonadecadienyl-1-phosphocholine
595. (Z,Z)-5,16-nonadecadienyl-1-phosphocholine
596. (Z,Z)-3,15-nonadecadienyl-1-phosphocholine
597. (Z,Z)-4,16-nonadecadienyl-1-phosphocholine
20 Chain Carbon Atoms
$C_{25}H_{50}NO_4P$ (459.65)
598. (Z,Z)-3,7-eicosadienyl-1-phosphocholine
599. (Z,Z)-4,8-eicosadienyl-1-phosphocholine
600. (Z,Z)-5,9-eicosadienyl-1-phosphocholine
601. (Z,Z)-6,10-eicosadienyl-1-phosphocholine
602. (Z,Z)-7,11-eicosadienyl-1-phosphocholine
603. (Z,Z)-8,12-eicosadienyl-1-phosphocholine
604. (Z,Z)-9,13-eicosadienyl-1-phosphocholine
605. (Z,Z)-10,14-eicosadienyl-1-phosphocholine
606. (Z,Z)-11,15-eicosadienyl-1-phosphocholine
607. (Z,Z)-12,16-eicosadienyl-1-phosphocholine
608. (Z,Z)-13,17-eicosadienyl-1-phosphocholine
609. (Z,Z)-3,8-eicosadienyl-1-phosphocholine
610. (Z,Z)-4,9-eicosadienyl-1-phosphocholine
611. (Z,Z)-5,10-eicosadienyl-1-phosphocholine
612. (Z,Z)-6,11-eicosadienyl-1-phosphocholine
613. (Z,Z)-7,12-eicosadienyl-1-phosphocholine
614. (Z,Z)-8,13-eicosadienyl-1-phosphocholine
615. (Z,Z)-9,14-eicosadienyl-1-phosphocholine
616. (Z,Z)-10,15-eicosadienyl-1-phosphocholine
617. (Z,Z)-11,16-eicosadienyl-1-phosphocholine
618. (Z,Z)-12,17-eicosadienyl-1-phosphocholine
619. (Z,Z)-3,9-eicosadienyl-1-phosphocholine
620. (Z,Z)-4,10-eicosadienyl-1-phosphocholine
621. (Z,Z)-5,11-eicosadienyl-1-phosphocholine
622. (Z,Z)-6,12-eicosadienyl-1-phosphocholine
623. (Z,Z)-7,13-eicosadienyl-1-phosphocholine
624. (Z,Z)-8,14-eicosadienyl-1-phosphocholine
625. (Z,Z)-9,15-eicosadienyl-1-phosphocholine
626. (Z,Z)-10,16-eicosadienyl-1-phosphocholine
627. (Z,Z)-11,17-eicosadienyl-1-phosphocholine
628. (Z,Z)-3,10-eicosadienyl-1-phosphocholine
629. (Z,Z)-4,11-eicosadienyl-1-phosphocholine
630. (Z,Z)-5,12-eicosadienyl-1-phosphocholine
631. (Z,Z)-6,13-eicosadienyl-1-phosphocholine
632. (Z,Z)-7,14-eicosadienyl-1-phosphocholine
633. (Z,Z)-8,15-eicosadienyl-1-phosphocholine
634. (Z,Z)-9,16-eicosadienyl-1-phosphocholine
635. (Z,Z)-10,17-eicosadienyl-1-phosphocholine
636. (Z,Z)-3,11-eicosadienyl-1-phosphocholine
637. (Z,Z)-4,12-eicosadienyl-1-phosphocholine
638. (Z,Z)-5,13-eicosadienyl-1-phosphocholine
639. (Z,Z)-6,14-eicosadienyl-1-phosphocholine
640. (Z,Z)-7,15-eicosadienyl-1-phosphocholine
641. (Z,Z)-8,16-eicosadienyl-1-phosphocholine
642. (Z,Z)-9,17-eicosadienyl-1-phosphocholine
643. (Z,Z)-3,12-eicosadienyl-1-phosphocholine
644. (Z,Z)-4,13-eicosadienyl-1-phosphocholine
645. (Z,Z)-5,14-eicosadienyl-1-phosphocholine
646. (Z,Z)-6,15-eicosadienyl-1-phosphocholine
647. (Z,Z)-7,16-eicosadienyl-1-phosphocholine
648. (Z,Z)-8,17-eicosadienyl-1-phosphocholine
649. (Z,Z)-3,13-eicosadienyl-1-phosphocholine
650. (Z,Z)-4,14-eicosadienyl-1-phosphocholine
651. (Z,Z)-5,15-eicosadienyl-1-phosphocholine
652. (Z,Z)-6,16-eicosadienyl-1-phosphocholine
653. (Z,Z)-7,17-eicosadienyl-1-phosphocholine
654. (Z,Z)-3,14-eicosadienyl-1-phosphocholine
655. (Z,Z)-4,15-eicosadienyl-1-phosphocholine
656. (Z,Z)-5,16-eicosadienyl-1-phosphocholine
657. (Z,Z)-6,17-eicosadienyl-1-phosphocholine
658. (Z,Z)-3,15-eicosadienyl-1-phosphocholine
659. (Z,Z)-4,16-eicosadienyl-1-phosphocholine
660. (Z,Z)-5,17-eicosadienyl-1-phosphocholine
661. (Z,Z)-3,17-eicosadienyl-1-phosphocholine
21 Chain Carbon Atoms
$C_{26}H_{52}NO_4P$ (473.68)
662. (Z,Z)-3,7-heneicosadienyl-1-phosphocholine
663. (Z,Z)-4,8-heneicosadienyl-1-phosphocholine
664. (Z,Z)-5,9-heneicosadienyl-1-phosphocholine
665. (Z,Z)-6,10-heneicosadienyl-1-phosphocholine
666. (Z,Z)-7,11-heneicosadienyl-1-phosphocholine
667. (Z,Z)-8,12-heneicosadienyl-1-phosphocholine
668. (Z,Z)-9,13-heneicosadienyl-1-phosphocholine
669. (Z,Z)-10,14-heneicosadienyl-1-phosphocholine
670. (Z,Z)-11,15-heneicosadienyl-1-phosphocholine
671. (Z,Z)-12,16-heneicosadienyl-1-phosphocholine
672. (Z,Z)-13,17-heneicosadienyl-1-phosphocholine
673. (Z,Z)-14,18-heneicosadienyl-1-phosphocholine
674. (Z,Z)-3,8-heneicosadienyl-1-phosphocholine
675. (Z,Z)-4,9-heneicosadienyl-1-phosphocholine
676. (Z,Z)-5,10-heneicosadienyl-1-phosphocholine
677. (Z,Z)-6,11-heneicosadienyl-1-phosphocholine
678. (Z,Z)-7,12-heneicosadienyl-1-phosphocholine
679. (Z,Z)-8,13-heneicosadienyl-1-phosphocholine
680. (Z,Z)-9,14-heneicosadienyl-1-phosphocholine
681. (Z,Z)-10,15-heneicosadienyl-1-phosphocholine
682. (Z,Z)-11,16-heneicosadienyl-1-phosphocholine
683. (Z,Z)-12,17-heneicosadienyl-1-phosphocholine
684. (Z,Z)-13,18-heneicosadienyl-1-phosphocholine
685. (Z,Z)-3,9-heneicosadienyl-1-phosphocholine
686. (Z,Z)-4,10-heneicosadienyl-1-phosphocholine
687. (Z,Z)-5,11-heneicosadienyl-1-phosphocholine
688. (Z,Z)-6,12-heneicosadienyl-1-phosphocholine
689. (Z,Z)-7,13-heneicosadienyl-1-phosphocholine
690. (Z,Z)-8,14-heneicosadienyl-1-phosphocholine
691. (Z,Z)-9,15-heneicosadienyl-1-phosphocholine
692. (Z,Z)-10,16-heneicosadienyl-1-phosphocholine
693. (Z,Z)-11,17-heneicosadienyl-1-phosphocholine
694. (Z,Z)-12,18-heneicosadienyl-1-phosphocholine
695. (Z,Z)-3,1'-heneicosadienyl-1-phosphocholine
696. (Z,Z)-4,11-heneicosadienyl-1-phosphocholine
697. (Z,Z)-5,12-heneicosadienyl-1-phosphocholine
698. (Z,Z)-6,13-heneicosadienyl-1-phosphocholine
699. (Z,Z)-7,14-heneicosadienyl-1-phosphocholine
700. (Z,Z)-8,15-heneicosadienyl-1-phosphocholine
701. (Z,Z)-9,16-heneicosadienyl-1-phosphocholine
702. (Z,Z)-10,17-heneicosadienyl-1-phosphocholine
703. (Z,Z)-11,18-heneicosadienyl-1-phosphocholine
704. (Z,Z)-3,11-heneicosadienyl-1-phosphocholine
705. (Z,Z)-4,12-heneicosadienyl-1-phosphocholine 706. (Z,Z)-5,13-heneicosadienyl-1-phosphocholine
707. (Z,Z)-6,14-heneicosadienyl-1-phosphocholine
708. (Z,Z)-7,15-heneicosadienyl-1-phosphocholine
709. (Z,Z)-8,16-heneicosadienyl-1-phosphocholine
710. (Z,Z)-9,17-heneicosadienyl-1-phosphocholine
711. (Z,Z)-10,18-heneicosadienyl-1-phosphocholine
712. (Z,Z)-3,12-heneicosadienyl-1-phosphocholine
713. (Z,Z)-4,13-heneicosadienyl-1-phosphocholine
714. (Z,Z)-5,14-heneicosadienyl-1-phosphocholine
715. (Z,Z)-6,15-heneicosadienyl-1-phosphocholine
716. (Z,Z)-7,16-heneicosadienyl-1-phosphocholine
717. (Z,Z)-8,17-heneicosadienyl-1-phosphocholine
718. (Z,Z)-9,18-heneicosadienyl-1-phosphocholine
719. (Z,Z)-3,13-heneicosadienyl-1-phosphocholine
720. (Z,Z)-4,14-heneicosadienyl-1-phosphocholine
721. (Z,Z)-5,15-heneicosadienyl-1-phosphocholine
722. (Z,Z)-6,16-heneicosadienyl-1-phosphocholine
723. (Z,Z)-7,17-heneicosadienyl-1-phosphocholine
724. (Z,Z)-8,18-heneicosadienyl-1-phosphocholine
725. (Z,Z)-3,14-heneicosadienyl-1-phosphocholine
726. (Z,Z)-4,15-heneicosadienyl-1-phosphocholine
727. (Z,Z)-5,16-heneicosadienyl-1-phosphocholine
728. (Z,Z)-6,17-heneicosadienyl-1-phosphocholine
729. (Z,Z)-7,18-heneicosadienyl-1-phosphocholine
730. (Z,Z)-3,15-heneicosadienyl-1-phosphocholine
731. (Z,Z)-4,16-heneicosadienyl-1-phosphocholine
732. (Z,Z)-5,17-heneicosadienyl-1-phosphocholine
733. (Z,Z)-6,18-heneicosadienyl-1-phosphocholine
734. (Z,Z)-3,17-heneicosadienyl-1-phosphocholine
735. (Z,Z)-4,18-heneicosadienyl-1-phosphocholine 22 Chain Carbon Atoms
$C_{27}H_{54}NO_4P$ (487.70)

736. (Z,Z)-3,7-docosadienyl-1-phosphocholine
737. (Z,Z)-4,8-docosadienyl-1-phosphocholine
738. (Z,Z)-5,9-docosadienyl-1-phosphocholine
739. (Z,Z)-6,10-docosadienyl-1-phosphocholine
740. (Z,Z)-7,11-docosadienyl-1-phosphocholine
741. (Z,Z)-8,12-docosadienyl-1-phosphocholine
742. (Z,Z)-9,13-docosadienyl-1-phosphocholine
743. (Z,Z)-10,14-docosadienyl-1-phosphocholine
744. (Z,Z)-11,15-docosadienyl-1-phosphocholine
745. (Z,Z)-12,16-docosadienyl-1-phosphocholine
746. (Z,Z)-13,17-docosadienyl-1-phosphocholine
747. (Z,Z)-14,18-docosadienyl-1-phosphocholine
748. (Z,Z)-15,19-docosadienyl-1-phosphocholine
749. (Z,Z)-3,8-docosadienyl-1-phosphocholine
750. (Z,Z)-4,9-docosadienyl-1-phosphocholine
751. (Z,Z)-5,10-docosadienyl-1-phosphocholine
752. (Z,Z)-6,11-docosadienyl-1-phosphocholine
753. (Z,Z)-7,12-docosadienyl-1-phosphocholine
754. (Z,Z)-8,13-docosadienyl-1-phosphocholine
755 (Z,Z)-9,14-docosadienyl-1-phosphocholine
756. (Z,Z)-10,15-docosadienyl-1-phosphocholine
757. (Z,Z)-11,16-docosadienyl-1-phosphocholine
758. (Z,Z)-12,17-docosadienyl-1-phosphocholine
759. (Z,Z)-13,18-docosadienyl-1-phosphocholine
760. (Z,Z)-14,19-docosadienyl-1-phosphocholine
761. (Z,Z)-3,9-docosadienyl-1-phosphocholine
762. (Z,Z)-4,10-docosadienyl-1-phosphocholine
763. (Z,Z)-5,11-docosadienyl-1-phosphocholine
764. (Z,Z)-6,12-docosadienyl-1-phosphocholine
765. (Z,Z)-7,13-docosadienyl-1-phosphocholine
766. (Z,Z)-8,14-docosadienyl-1-phosphocholine
767. (Z,Z)-9,15-docosadienyl-1-phosphocholine
768. (Z,Z)-10,16-docosadienyl-1-phosphocholine
769. (Z,Z)-11,17-docosadienyl-1-phosphocholine
770. (Z,Z)-12,18-docosadienyl-1-phosphocholine
771. (Z,Z)-13,19-docosadienyl-1-phosphocholine
772. (Z,Z)-3,10-docosadienyl-1-phosphocholine
773. (Z,Z)-4,11-docosadienyl-1-phosphocholine
774. (Z,Z)-5,12-docosadienyl-1-phosphocholine
775. (Z,Z)-6,13-docosadienyl-1-phosphocholine
776. (Z,Z)-7,14-docosadienyl-1-phosphocholine
777. (Z,Z)-8,15-docosadienyl-1-phosphocholine
778. (Z,Z)-9,16-docosadienyl-1-phosphocholine
779. (Z,Z)-10,17-docosadienyl-1-phosphocholine
780. (Z,Z)-11,18-docosadienyl-1-phosphocholine
781. (Z,Z)-12,19-docosadienyl-1-phosphocholine
782. (Z,Z)-3,11-docosadienyl-1-phosphocholine
783. (Z,Z)-4,12-docosadienyl-1-phosphocholine
784. (Z,Z)-5,13-docosadienyl-1-phosphocholine
785. (Z,Z)-6,14-docosadienyl-1-phosphocholine
786. (Z,Z)-7,15-docosadienyl-1-phosphocholine
787. (Z,Z)-8,16-docosadienyl-1-phosphocholine
788. (Z,Z)-9,17-docosadienyl-1-phosphocholine
789. (Z,Z)-10,18-docosadienyl-1-phosphocholine
790. (Z,Z)-11,19-docosadienyl-1-phosphocholine
791. (Z,Z)-3,12-docosadienyl-1-phosphocholine
792. (Z,Z)-4,13-docosadienyl-1-phosphocholine
793. (Z,Z)-5,14-docosadienyl-1-phosphocholine
794. (Z,Z)-6,15-docosadienyl-1-phosphocholine
795. (Z,Z)-7,16-docosadienyl-1-phosphocholine
796. (Z,Z)-8,17-docosadienyl-1-phosphocholine
797. (Z,Z)-9,18-docosadienyl-1-phosphocholine
798. (Z,Z)-10,19-docosadienyl-1-phosphocholine
799. (Z,Z)-3,13-docosadienyl-1-phosphocholine
800. (Z,Z)-4,14-docosadienyl-1-phosphocholine
801. (Z,Z)-5,15-docosadienyl-1-phosphocholine
802. (Z,Z)-6,16-docosadienyl-1-phosphocholine
803. (Z,Z)-7,17-docosadienyl-1-phosphocholine
804. (Z,Z)-8,18-docosadienyl-1-phosphocholine
805. (Z,Z)-9,19-docosadienyl-1-phosphocholine
806. (Z,Z)-3,14-docosadienyl-1-phosphocholine
807. (Z,Z)-4,15-docosadienyl-1-phosphocholine
808. (Z,Z)-5,16-docosadienyl-1-phosphocholine
809. (Z,Z)-6,17-docosadienyl-1-phosphocholine
810. (Z,Z)-7,18-docosadienyl-1-phosphocholine
811. (Z,Z)-8,19-docosadienyl-1-phosphocholine
812. (Z,Z)-3,15-docosadienyl-1-phosphocholine
813. (Z,Z)-4,16-docosadienyl-1-phosphocholine
814. (Z,Z)-5,17-docosadienyl-1-phosphocholine
815. (Z,Z)-6,18-docosadienyl-1-phosphocholine
816. (Z,Z)-7,19-docosadienyl-1-phosphocholine
817. (Z,Z)-3,17-docosadienyl-1-phosphocholine
818. (Z,Z)-4,18-docosadienyl-1-phosphocholine
819. (Z,Z)-5,19-docosadienyl-1-phosphocholine
820. (Z,Z)-3,19-docosadienyl-1-phosphocholine 23 Chain Carbon Atoms
$C_{28}H_{56}NO_4P$ (501.73)

821. (Z,Z)-3,7-tricosadienyl-1-phosphocholine
822. (Z,Z)-4,8-tricosadienyl-1-phosphocholine
823. (Z,Z)-5,9-tricosadienyl-1-phosphocholine
824. (Z,Z)-6,10-tricosadienyl-1-phosphocholine
825. (Z,Z)-7,11-tricosadienyl-1-phosphocholine
826. (Z,Z)-8,12-tricosadienyl-1-phosphocholine
827. (Z,Z)-9,13-tricosadienyl-1-phosphocholine
828. (Z,Z)-10,14-tricosadienyl-1-phosphocholine
829. (Z,Z)-11,15-tricosadienyl-1-phosphocholine
830. (Z,Z)-12,16-tricosadienyl-1-phosphocholine
831. (Z,Z)-13,17-tricosadienyl-1-phosphocholine
832. (Z,Z)-14,18-tricosadienyl-1-phosphocholine
833 (Z,Z)-15,19-tricosadienyl-1-phosphocholine
834. (Z,Z)-16,20-tricosadienyl-1-phosphocholine
835. (Z,Z)-3,8-tricosadienyl-1-phosphocholine 836. (Z,Z)-4,9-tricosadienyl-1-phosphocholine
837. (Z,Z)-5,10-tricosadienyl-1-phosphocholine
838. (Z,Z)-6,11-tricosadienyl-1-phosphocholine
839. (Z,Z)-7,12-tricosadienyl-1-phosphocholine
840. (Z,Z)-8,13-tricosadienyl-1-phosphocholine
841. (Z,Z)-9,14-tricosadienyl-1-phosphocholine
842. (Z,Z)-10,15-tricosadienyl-1-phosphocholine
843. (Z,Z)-11,16-tricosadienyl-1-phosphocholine
844. (Z,Z)-12,17-tricosadienyl-1-phosphocholine
845. (Z,Z)-13,18-tricosadienyl-1-phosphocholine
846. (Z,Z)-14,19-tricosadienyl-1-phosphocholine
847. (Z,Z)-15,20-tricosadienyl-1-phosphocholine
848. (Z,Z)-3,9-tricosadienyl-1-phosphocholine
849. (Z,Z)-4,10-tricosadienyl-1-phosphocholine
850. (Z,Z)-5,11-tricosadienyl-1-phosphocholine
851. (Z,Z)-6,12-tricosadienyl-1-phosphocholine
852. (Z,Z)-7,13-tricosadienyl-1-phosphocholine
853. (Z,Z)-8,14-tricosadienyl-1-phosphocholine
854. (Z,Z)-9,15-tricosadienyl-1-phosphocholine
855. (Z,Z)-10,16-tricosadienyl-1-phosphocholine
856. (Z,Z)-11,17-tricosadienyl-1-phosphocholine
857. (Z,Z)-12,18-tricosadienyl-1-phosphocholine
858. (Z,Z)-13,19-tricosadienyl-1-phosphocholine
859. (Z,Z)-14,20-tricosadienyl-1-phosphocholine
860. (Z,Z)-3,10-tricosadienyl-1-phosphocholine
861. (Z,Z)-4,11-tricosadienyl-1-phosphocholine
862. (Z,Z)-5,12-tricosadienyl-1-phosphocholine
863. (Z,Z)-6,13-tricosadienyl-1-phosphocholine
864. (Z,Z)-7,14-tricosadienyl-1-phosphocholine
865. (Z,Z)-8,15-tricosadienyl-1-phosphocholine
866. (Z,Z)-9,16-tricosadienyl-1-phosphocholine
867. (Z,Z)-10,17-tricosadienyl-1-phosphocholine
868. (Z,Z)-11,18-tricosadienyl-1-phosphocholine
869. (Z,Z)-12,19-tricosadienyl-1-phosphocholine
870. (Z,Z)-13,20-tricosadienyl-1-phosphocholine
871. (Z,Z)-3,11-tricosadienyl-1-phosphocholine
872. (Z,Z)-4,12-tricosadienyl-1-phosphocholine
873. (Z,Z)-5,13-tricosadienyl-1-phosphocholine
874. (Z,Z)-6,14-tricosadienyl-1-phosphocholine
875. (Z,Z)-7,15-tricosadienyl-1-phosphocholine
876. (Z,Z)-8,16-tricosadienyl-1-phosphocholine
877. (Z,Z)-9,17-tricosadienyl-1-phosphocholine
878. (Z,Z)-10,18-tricosadienyl-1-phosphocholine
879. (Z,Z)-11,19-tricosadienyl-1-phosphocholine
880. (Z,Z)-12,20-tricosadienyl-1-phosphocholine
881. (Z,Z)-3,12-tricosadienyl-1-phosphocholine
882. (Z,Z)-4,13-tricosadienyl-1-phosphocholine
883. (Z,Z)-5,14-tricosadienyl-1-phosphocholine
884. (Z,Z)-6,15-tricosadienyl-1-phosphocholine
885. (Z,Z)-7,16-tricosadienyl-1-phosphocholine
886. (Z,Z)-8,17-tricosadienyl-1-phosphocholine
887. (Z,Z)-9,18-tricosadienyl-1-phosphocholine
888. (Z,Z)-10,19-tricosadienyl-1-phosphocholine
889. (Z,Z)-11,20-tricosadienyl-1-phosphocholine
890. (Z,Z)-3,13-tricosadienyl-1-phosphocholine
891. (Z,Z)-4,14-tricosadienyl-1-phosphocholine
892. (Z,Z)-5,15-tricosadienyl-1-phosphocholine
893. (Z,Z)-6,16-tricosadienyl-1-phosphocholine
894. (Z,Z)-7,17-tricosadienyl-1-phosphocholine
895. (Z,Z)-8,18-tricosadienyl-1-phosphocholine
896. (Z,Z)-9,19-tricosadienyl-1-phosphocholine
897. (Z,Z)-10,20-tricosadienyl-1-phosphocholine
898. (Z,Z)-3,14-tricosadienyl-1-phosphocholine
899. (Z,Z)-4,15-tricosadienyl-1-phosphocholine
900. (Z,Z)-5,16-tricosadienyl-1-phosphocholine
901. (Z,Z)-6,17-tricosadienyl-1-phosphocholine
902. (Z,Z)-7,18-tricosadienyl-1-phosphocholine
903. (Z,Z)-8,19-tricosadienyl-1-phosphocholine
904. (Z,Z)-9,20-tricosadienyl-1-phosphocholine
905. (Z,Z)-3,15-tricosadienyl-1-phosphocholine
906. (Z,Z)-4,16-tricosadienyl-1-phosphocholine
907. (Z,Z)-5,17-tricosadienyl-1-phosphocholine
908. (Z,Z)-6,18-tricosadienyl-1-phosphocholine
909. (Z,Z)-7,19-tricosadienyl-1-phosphocholine
910. (Z,Z)-8,20-tricosadienyl-1-phosphocholine
911. (Z,Z)-3,17-tricosadienyl-1-phosphocholine
912. (Z,Z)-4,18-tricosadienyl-1-phosphocholine
913. (Z,Z)-5,19-tricosadienyl-1-phosphocholine
914. (Z,Z)-6,20-tricosadienyl-1-phosphocholine
915. (Z,Z)-3,19-tricosadienyl-1-phosphocholine
916. (Z,Z)-4,20-tricosadienyl-1-phosphocholine 24 Chain Carbon Atoms
$C_{29}H_{58}NO_4P$ (515.76)

917. (Z,Z)-3,7-tetracosadienyl-1-phosphocholine
918. (Z,Z)-4,8-tetracosadienyl-1-phosphocholine
919. (Z,Z)-5,9-tetracosadienyl-1-phosphocholine
920. (Z,Z)-6,10-tetracosadienyl-1-phosphocholine
921. (Z,Z)-7,11-tetracosadienyl-1-phosphocholine
922. (Z,Z)-8,12-tetracosadienyl-1-phosphocholine
923. (Z,Z)-9,13-tetracosadienyl-1-phosphocholine
924. (Z,Z)-10,14-tetracosadienyl-1-phosphocholine
925. (Z,Z)-11,15-tetracosadienyl-1-phosphocholine
926. (Z,Z)-12,16-tetracosadienyl-1-phosphocholine
927. (Z,Z)-13,17-tetracosadienyl-1-phosphocholine
928. (Z,Z)-14,18-tetracosadienyl-1-phosphocholine
929. (Z,Z)-15,19-tetracosadienyl-1-phosphocholine
930. (Z,Z)-16,20-tetracosadienyl-1-phosphocholine
931. (Z,Z)-17,21-tetracosadienyl-1-phosphocholine
932. (Z,Z)-3,8-tetracosadienyl-1-phosphocholine
933. (Z,Z)-4,9-tetracosadienyl-1-phosphocholine
934. (Z,Z)-5,10-tetracosadienyl-1-phosphocholine
935. (Z,Z)-6,11-tetracosadienyl-1-phosphocholine
936. (Z,Z)-7,12-tetracosadienyl-1-phosphocholine
937. (Z,Z)-8,13-tetracosadienyl-1-phosphocholine
938. (Z,Z)-9,14-tetracosadienyl-1-phosphocholine
939. (Z,Z)-10,15-tetracosadienyl-1-phosphocholine
940. (Z,Z)-11,16-tetracosadienyl-1-phosphocholine
941. (Z,Z)-12,17-tetracosadienyl-1-phosphocholine
942. (Z,Z)-13,18-tetracosadienyl-1-phosphocholine
943. (Z,Z)-14,19-tetracosadienyl-1-phosphocholine
944. (Z,Z)-15,20-tetracosadienyl-1-phosphocholine
945. (Z,Z)-16,21-tetracosadienyl-1-phosphocholine
946. (Z,Z)-3,9-tetracosadienyl-1-phosphocholine
947. (Z,Z)-4,10-tetracosadienyl-1-phosphocholine
948. (Z,Z)-5,11-tetracosadienyl-1-phosphocholine
949. (Z,Z)-6,12-tetracosadienyl-1-phosphocholine
950. (Z,Z)-7,13-tetracosadienyl-1-phosphocholine
951. (Z,Z)-8,14-tetracosadienyl-1-phosphocholine
952. (Z,Z)-9,15-tetracosadienyl-1-phosphocholine
953. (Z,Z)-10,16-tetracosadienyl-1-phosphocholine
954. (Z,Z)-11,17-tetracosadienyl-1-phosphocholine
955. (Z,Z)-12,18-tetracosadienyl-1-phosphocholine
956. (Z,Z)-13,19-tetracosadienyl-1-phosphocholine
957. (Z,Z)-14,20-tetracosadienyl-1-phosphocholine
958. (Z,Z)-15,21-tetracosadienyl-1-phosphocholine
959. (Z,Z)-3,10-tetracosadienyl-1-phosphocholine
960. (Z,Z)-4,11-tetracosadienyl-1-phosphocholine
961. (Z,Z)-5,12-tetracosadienyl-1-phosphocholine
962. (Z,Z)-6,13-tetracosadienyl-1-phosphocholine
963. (Z,Z)-7,14-tetracosadienyl-1-phosphocholine
964. (Z,Z)-8,15-tetracosadienyl-1-phosphocholine
965. (Z,Z)-9,16-tetracosadienyl-1-phosphocholine
966. (Z,Z)-10,17-tetracosadienyl-1-phosphocholine
967. (Z,Z)-11,18-tetracosadienyl-1-phosphocholine 968. (Z,Z)-12,19-tetracosadienyl-1-phosphocholine
969. (Z,Z)-13,20-tetracosadienyl-1-phosphocholine
970. (Z,Z)-14,21-tetracosadienyl-1-phosphocholine
971. (Z,Z)-3,11-tetracosadienyl-1-phosphocholine
972. (Z,Z)-4,12-tetracosadienyl-1-phosphocholine
973. (Z,Z)-5,13-tetracosadienyl-1-phosphocholine
974. (Z,Z)-6,14-tetracosadienyl-1-phosphocholine
975. (Z,Z)-7,15-tetracosadienyl-1-phosphocholine
976 (Z,Z)-8,16-tetracosadienyl-1-phosphocholine
977. (Z,Z)-9,17-tetracosadienyl-1-phosphocholine
978. (Z,Z)-10,18-tetracosadienyl-1-phosphocholine
979. (Z,Z)-11,19-tetracosadienyl-1-phosphocholine
980. (Z,Z)-12,20-tetracosadienyl-1-phosphocholine
981. (Z,Z)-13,21-tetracosadienyl-1-phosphocholine
982. (Z,Z)-3,12-tetracosadienyl-1-phosphocholine
983. (Z,Z)-4,13-tetracosadienyl-1-phosphocholine
984. (Z,Z)-5,14-tetracosadienyl-1-phosphocholine
985. (Z,Z)-6,15-tetracosadienyl-1-phosphocholine
986. (Z,Z)-7,16-tetracosadienyl-1-phosphocholine
987. (Z,Z)-8,17-tetracosadienyl-1-phosphocholine
988. (Z,Z)-9,18-tetracosadienyl-1-phosphocholine
989. (Z,Z)-10,19-tetracosadienyl-1-phosphocholine
990. (Z,Z)-11,20-tetracosadienyl-1-phosphocholine
991. (Z,Z)-12,21-tetracosadienyl-1-phosphocholine
992. (Z,Z)-3,13-tetracosadienyl-1-phosphocholine
993. (Z,Z)-4,14-tetracosadienyl-1-phosphocholine
994. (Z,Z)-5,15-tetracosadienyl-1-phosphocholine
995. (Z,Z)-6,16-tetracosadienyl-1-phosphocholine
996. (Z,Z)-7,17-tetracosadienyl-1-phosphocholine
997. (Z,Z)-8,18-tetracosadienyl-1-phosphocholine
998. (Z,Z)-9,19-tetracosadienyl-1-phosphocholine
999. (Z,Z)-10,20-tetracosadienyl-1-phosphocholine
1000. (Z,Z)-11,21-tetracosadienyl-1-phosphocholine
1001. (Z,Z)-3,14-tetracosadienyl-1-phosphocholine
1002. (Z,Z)-4,15-tetracosadienyl-1-phosphocholine
1003. (Z,Z)-5,16-tetracosadienyl-1-phosphocholine
1004. (Z,Z)-6,17-tetracosadienyl-1-phosphocholine
1005. (Z,Z)-7,18-tetracosadienyl-1-phosphocholine
1006. (Z,Z)-8,19-tetracosadienyl-1-phosphocholine
1007. (Z,Z)-9,20-tetracosadienyl-1-phosphocholine
1008. (Z,Z)-10,21-tetracosadienyl-1-phosphocholine
1009. (Z,Z)-3,15-tetracosadienyl-1-phosphocholine
1010. (Z,Z)-4,16-tetracosadienyl-1-phosphocholine
1011. (Z,Z)-5,17-tetracosadienyl-1-phosphocholine
1012. (Z,Z)-6,18-tetracosadienyl-1-phosphocholine
1013. (Z,Z)-7,19-tetracosadienyl-1-phosphocholine
1014. (Z,Z)-8,20-tetracosadienyl-1-phosphocholine
1015. (Z,Z)-9,21-tetracosadienyl-1-phosphocholine
1016. (Z,Z)-3,17-tetracosadienyl-1-phosphocholine
1017. (Z,Z)-4,18-tetracosadienyl-1-phosphocholine
1018. (Z,Z)-5,19-tetracosadienyl-1-phosphocholine
1019. (Z,Z)-6,20-tetracosadienyl-1-phosphocholine
1020 (Z,Z)-7,21-tetracosadienyl-1-phosphocholine
1021. (Z,Z)-3,19-tetracosadienyl-1-phosphocholine
1022. (Z,Z)-4,20-tetracosadienyl-1-phosphocholine
1023. (Z,Z)-5,21-tetracosadienyl-1-phosphocholine 25 Chain Carbon Atoms
$C_{30}H_{60}NO_4P$ (529.78)
1024. (Z,Z)-6,12-pentacosadienyl-1-phosphocholine
1025. (Z,Z)-9,15-pentacosadienyl-1-phosphocholine
1026. (Z,Z)-6,16-pentacosadienyl-1-phosphocholine
1027. (Z,Z)-9,18-pentacosadienyl-1-phosphocholine
1028. (Z,Z)-10,20-pentacosadienyl-1-phosphocholine
1029. (Z,Z)-13,20-pentacosadienyl-1-phosphocholine 26 Chain Carbon Atoms
$C_{31}H_{62}NO_4P$ (543.81)
1030. (Z,Z)-6,12-hexacosadienyl-1-phosphocholine
1031. (Z,Z)-9,15-hexacosadienyl-1-phosphocholine
1032. (Z,Z)-6,16-hexacosadienyl-1-phosphocholine
1033. (Z,Z)-9,18-hexacosadienyl-1-phosphocholine
1034. (Z,Z)-6,20-hexacosadienyl-1-phosphocholine 5. Examples of (Z,Z)-alkadienyl-1-phospho-N,N,N-trimethylpropylammonium Compounds

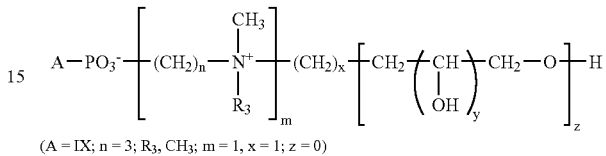

(A = IX; n = 3; $R_3$, $CH_3$; m = 1, x = 1; z = 0)

where A is a diunsaturated alkyl chain of the following structure (s,t,r≧0; 8≦s+t+r≦26)

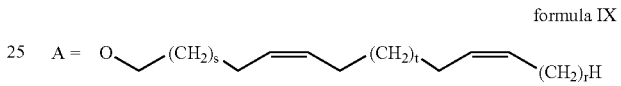

formula IX

1035.) (Z,Z)-5,11-hexadecadienyl-1-phospho-N,N,N-trimethylpropylammonium
$C_{22}H_{44}NO_4P$ (417.57)
1036.) (Z,Z)-5,11-heptadecadienyl-1-phospho-N,N,N-trimethylpropylammonium
$C_{23}H_{46}NO_4P$ (431.60)
1037.) (Z,Z)-5,11-octadecadienyl-1-phospho-N,N,N-trimethylpropylammonium
$C_{24}H_{48}NO_4P$ (445.62)
1038.) (Z,Z)-6,12-nonadecadienyl-1-phospho-N,N,N-trimethylpropylammonium
$C_{25}H_{50}NO_4P$ (459.65)
1039.) (Z,Z)-10,16-eicosadienyl-1-phospho-N,N,N-trimethylpropylammonium
$C_{26}H_{52}NO_4P$ (473.68)
1040.) (Z,Z)-10,16-heneicosadienyl-1-phospho-N,N,N-trimethylpropylammonium
$C_{27}H_{54}NO_4P$ (487.70)
1041.) (Z,Z)-10,16-docosadienyl-1-phospho-N,N,N-trimethylpropylammonium
$C_{28}H_{56}NO_4P$ (501.73)
1042.) (Z,Z)-10,16-tricosadienyl-1-phospho-N,N,N-trimethylpropylammonium
$C_{29}H_{58}NO_4P$ (515.76)
1043.) (Z,Z)-6,18-tetracosadienyl-1-phospho-N,N,N-trimethylpropylammonium
$C_{30}H_{60}NO_4P$ (529.78)

6. Examples of (Z,Z)-alkadienyl-1-phospho-N,N,N-trimethylbutylammonium Compounds

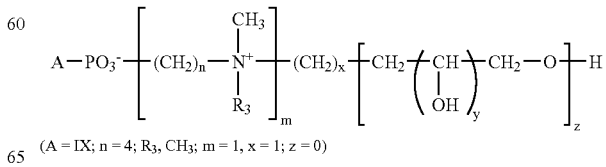

(A = IX; n = 4; $R_3$, $CH_3$; m = 1, x = 1; z = 0)

where A is a diunsaturated alkyl chain of the following structure (s,t,r≧0; 8≦s+t+r≦26):

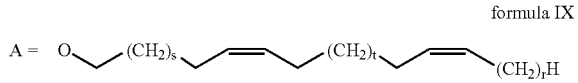

formula IX

1044.) (Z,Z)-5,11-hexadecadienyl-1-phospho-N,N,N-trimethylbutylammonium
$C_{23}H_{46}NO_4P$ (431.60)
1045.) (Z,Z)-5,11-heptadecadienyl-1-phospho-N,N,N-trimethylbutylammonium
$C_{24}H_{48}NO_4P$ (445.62)
1046.) (Z,Z)-5,11-octadecadienyl-1-phospho-N,N,N-trimethylbutylammonium
$C_{25}H_{50}NO_4P$ (459.65)
1047.) (Z,Z)-6,12-nonadecadienyl-1-phospho-N,N,N-trimethylbutylammonium
$C_{26}H_{52}NO_4P$ (473.68)
1048.) (Z,Z)-10,16-eicosadienyl-1-phospho-N,N,N-trimethylbutylammonium
$C_{27}H_{54}NO_4P$ (487.70)
1049.) (Z,Z)-10,16-heneicosadienyl-1-phospho-N,N,N-trimethylbutylammonium
$C_{28}H_{56}NO_4P$ (501.73)
1050.) (Z,Z)-10,16-docosadienyl-1-phospho-N,N,N-trimethylbutylammonium
$C_{29}H_{58}NO_4P$ (515.76)
1051.) (Z,Z)-10,16-tricosadienyl-1-phospho-N,N,N-trimethylbutylammonium
$C_{30}H_{60}NO_4P$ (529.78)
1052.) (Z,Z)-6,18-tetracosadienyl-1-phospho-N,N,N-trimethylbutylammonium
$C_{31}H_{62}NO_4P$ (543.81)

7. Examples of Terminally Unsaturated alkadienylphosphocholines

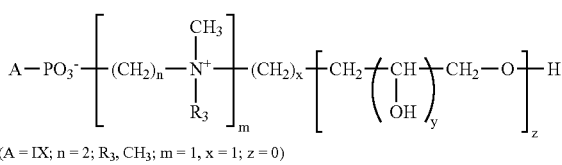

(A = IX; n = 2; $R_3$, $CH_3$; m = 1, x = 1; z = 0)

where A is a diunsaturated alkyl chain of the following structure (s,t≧0; r=0; 8≦s+t+r≦26):

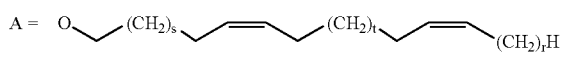

formula IX

1053.) (Z)-11,15-hexadecadienyl-1-phosphocholine
$C_{21}H_{42}NO_4P$ (403.54)
1054.) (Z)-11,16-heptadecadienyl-1-phosphocholine
$C_{22}H_{44}NO_4P$ (417.57)
1055.) (Z)-11,17-octadecadienyl-1-phosphocholine
$C_{23}H_{46}NO_4P$ (431.60)
1056.) (Z)-11,18-nonadecadienyl-1-phosphocholine
$C_{24}H_{48}NO_4P$ (445.62)
1057.) (z)-11,19-eicosadienyl-1-phosphocholine
$C_{25}H_{50}NO_4P$ (459.65)
1058.) (Z)-11,20-heneicosadienyl-1-phosphocholine
$C_{26}H_{52}NO_4P$ (473.68)
1059.) (Z)-11,21-docosadienyl-1-phosphocholine
$C_{27}H_{54}NO_4P$ (487.70)
1060.) (Z)-11,22-tricosadienyl-1-phosphocholine
$C_{28}H_{56}NO_4P$ (501.73)
1061.) (Z)-11,23-tetracosadienyl-1-phosphocholine
$C_{29}H_{58}NO_4P$ (515.76)
1062.) (Z)-11,24-pentacosadienyl-1-phosphocholine
$C_{30}H_{60}NO_4P$ (529.78)

8. Examples of Terminally Unsaturated alkadienyl-1-phospho-N,N,N-ttrimethylpropylammonium compounds

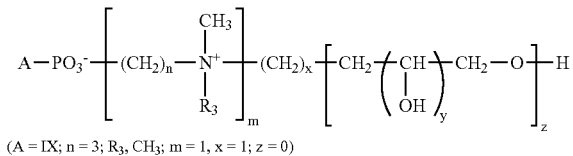

(A = IX; n = 3; $R_3$, $CH_3$; m = 1, x = 1; z = 0)

where A is a diunsaturated alkyl chain of the following structure (s,t≧0; r=0; 8≦s+t+r≦26):

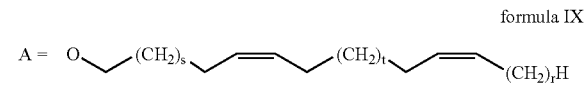

formula IX

1063.) (Z)-11,15-hexadecadienyl-1-phospho-N,N,N-trimethylpropylammonium
$C_{22}H_{44}NO_4P$ (417.57)
1064.) (Z)-11,16-heptadecadienyl-1-phospho-N,N,N-trimethylpropylammonium
$C_{23}H_{46}NO_4P$ (431.60)
1065.) (Z)-11,17-octadecadienyl-1-phospho-N,N,N-trimethylpropylammonium
$C_{24}H_{48}NO_4P$ (445.62)
1066.) (Z)-11,18-nonadecadienyl-1-phospho-N,N,N-trimethylpropylammonium
$C_{25}H_{50}NO_4P$ (459.65)
1067.) (Z)-11,19-eicosadienyl-1-phospho-N,N,N-trimethylpropylammonium
$C_{26}H_{52}NO_4P$ (473.68)
1068.) (Z)-11,20-heneicosadienyl-1-phospho-N,N,N-trimethylpropylammonium
$C_{27}H_{54}NO_4P$ (487.70)
1069.) (Z)-11,21-docosadienyl-1-phospho-N,N,N-trimethylpropylammonium
$C_{28}H_{56}NO_4P$ (501.73)
1070.) (Z)-11,22-tricosadienyl-1-phospho-N,N,N-trimethylpropylammonium
$C_{29}H_{58}NO_4P$ (515.76)
1071.) (Z)-11,23-tetracosadienyl-1-phospho-N,N,N-trimethylpropylammonium
$C_{30}H_{60}NO_4P$ (529.78)
1072.) (Z)-11,24-pentacosadienyl-1-phospho-N,N,N-trimethylpropylanmonium
$C_{31}H_{62}NO_4P$ (543.81)

9. Examples of Terminally Unsaturated alkadienyl-1-phospho-N,N,N-trimethylbutylammonium Compounds

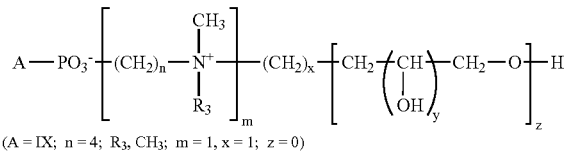

(A = IX; n = 4; $R_3$, $CH_3$; m = 1, x = 1; z = 0)

where A is a diunsaturated alkyl chain of the following structure (s,t≧0; r=0; 8≦s+t+r≦26):

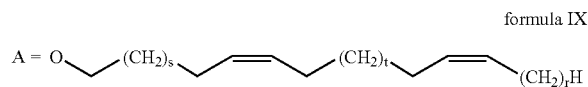

formula IX

1073.) (Z)-11,15-hexadecadienyl-1-phospho-N,N,N-trimethylbutylammonium
$C_{23}H_{46}NO_4P$ (431.60)
1074.) (Z)-11,16-heptadecadienyl-1-phospho-N,N,N-trimethylbutylammonium
$C_{24}H_{48}NO_4P$ (445.62)
1075.) (Z)-11,17-octadecadienyl-1-phospho-N,N,N-trimethylbutylammonium
$C_{25}H_{50}NO_4P$ (459.65)
1076.) (Z)-11,18-nonadecadienyl-1-phospho-N,N,N-trimethylbutylammonium
$C_{26}H_{52}NO_4P$ (473.68)
1077.) (Z)-11,19-eicosadienyl-1-phospho-N,N,N-trimethylbutylammonium
$C_{27}H_{54}NO_4P$ (487.70)
1078.) (Z)-11,20-heneicosadienyl-1-phospho-N,N,N-trimethylbutylammonium
$C_{28}H_{56}NO_4P$ (501.73)
1079.) (Z)-11,21-docosadienyl-1-phospho-N,N,N-trimethylbutylammonium
$C_{29}H_{58}NO_4P$ (515.76)
1080.) (Z)-11,22-tricosadienyl-1-phospho-N,N,N-trimethylbutylammonium
$C_{30}H_{60}NO_4P$ (529.78)
1081.) (Z)-11,23-tetracosadienyl-1-phospho-N,N,N-trimethylbutylammonium
$C_{31}H_{62}NO_4P$ (543.81)
1082.) (Z)-11,24-pentacosadienyl-1-phospho-N,N,N-trimethylbutylammonium
$C_{32}H_{64}NO_4P$ (557.84)

10. Active Ingredients Based on alkylated (ether)lysolecithins—Monounsaturated Compounds

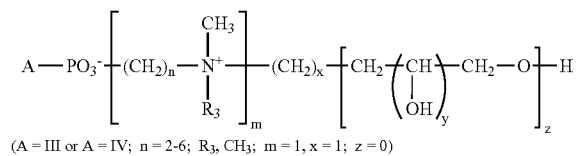

(A = III or A = IV; n = 2-6; $R_3$, $CH_3$; m = 1, x = 1; z = 0)

1083.) 1-O—(Z)-6-octadecenyl-2-O-methyl-sn-glycero-3-phosphocholine (n=2)
$C_{27}H_{56}NO_6P$ (521.72)
1084.) 1-O—(Z)-10-octadecenyl-2-O-methyl-sn-glycero-3-phosphocholine (n=2)
$C_{27}H_{56}NO_6P$ (521.72)
1085.) 1-O—(Z)-12-octadecenyl-2-O-methyl-sn-glycero-3-phosphocholine (n=2)
$C_{27}H_{56}NO_6P$ (521.72)
1086.) 1-O—(Z)-6-nonadecenyl-2-O-methyl-sn-glycero-3-phosphocholine (n=2)
$C_{28}H_{58}NO_6P$ (535.75)
1087.) 1-O—(Z)-10-nonadecenyl-2-O-methyl-sn-glycero-3-phosphocholine (n=2)
$C_{28}H_{58}NO_6P$ (535.75)
1088.) 1-O—(Z)-12-nonadecenyl-2-O-methyl-sn-glycero-3-phosphocholine (n=2)
$C_{28}H_{58}NO_6P$ (535.75)
1089.) 1-O-(z)-6-eicosenyl-2-O-methyl-sn-glycero-3-phosphocholine (n=2)
$C_{29}H_{60}NO_6P$ (549.77)
1090.) 1-O—(Z)-10-eicosenyl-2-O-methyl-sn-glycero-3-phosphocholine (n=2)
$C_{29}H_{60}NO_6P$ (549.77)
1091.) 1-O—(Z)-12-eicosenyl-2-O-methyl-sn-glycero-3-phosphocholine (n=2)
$C_{29}H_{60}NO_6P$ (549.77)
1092.) 1-O—(Z)-6-heneicosenyl-2-O-methyl-sn-glycero-3-phosphocholine (n=2)
$C_{30}H_{62}NO_6P$ (563.80)
1093.) 1-O—(Z)-10-heneicosenyl-2-O-methyl-sn-glycero-3-phosphocholine (n=2)
$C_{30}H_{62}NO_6P$ (563.80)
1094.) 1-O—(Z)-12-heneicosenyl-2-O-methyl-sn-glycero-3-phosphocholine (n=2)
$C_{30}H_{62}NO_6P$ (563.80)
1095.) 1-O—(Z)-6-docosenyl-2-O-methyl-sn-glycero-3-phosphocholine (n=2)
$C_{31}H_{64}NO_6P$ (577.83)
1096.) 1-O—(Z)-10-docosenyl-2-O-methyl-sn-glycero-3-phosphocholine (n=2)
$C_{31}H_{64}NO_6P$ (577.83)
1097.) 1-O—(Z)-12-docosenyl-2-O-methyl-sn-glycero-3-phosphocholine (n=2)
$C_{31}H_{64}NO_6P$ (577.83)
1098.) 1-O—(Z)-6-tricosenyl-2-O-methyl-sn-glycero-3-phosphocholine (n=2)
$C_{32}H_{66}NO_6P$ (591.86)
1099.) 1-O—(Z)-10-tricosenyl-2-O-methyl-sn-glycero-3-phosphocholine (n=2)
$C_{32}H_{66}NO_6P$ (591.86)
1100.) 1-O—(Z)-12-tricosenyl-2-O-methyl-sn-glycero-3-phosphocholine (n=2)
$C_{32}H_{66}NO_6P$ (591.86)
1101.) 1-O—(Z)-6-tetracosenyl-2-O-methyl-sn-glycero-3-phosphocholine (n=2)
$C_{33}H_{68}NO_6P$ (605.89)
1102.) 1-O—(Z)-10-tetracosenyl-2-O-methyl-sn-glycero-3-phosphocholine (n=2)
$C_{33}H_{68}NO_6P$ (605.89)
1103.) 1-O—(Z)-12-tetracosenyl-2-O-methyl-sn-glycero-3-phosphocholine (n=2)
$C_{33}H_{68}NO_6P$ (605.89)
1104.) 1-O—(Z)-6-octadecenyl-2-O-methyl-sn-glycero-3-phospho-N,N,N-trimethylpropylammonium (n=3)
$C_{28}H_{58}NO_6P$ (535.75)

1105.) 1-O—(Z)-10-octadecenyl-2-O-methyl-sn-glycero-3-phospho-N,N,N-trimethylpropylammonium (n=3) $C_{26}H_{58}NO_6P$ (535.75)

1106.) 1-O—(Z)-12-octadecenyl-2-O-methyl-sn-glycero-3-phospho-N,N,N-trimethylpropylammonium (n=3) $C_{28}H_{58}NO_6P$ (535.75)

1107.) 1-O—(Z)-6-nonadecenyl-2-O-methyl-sn-glycero-3-phospho-N,N,N-trimethylpropylammonium (n=3) $C_{29}H_{60}NO_6P$ (549.77)

1108.) 1-O—(Z)-10-nonadecenyl-2-O-methyl-sn-glycero-3-phospho-N,N,N-trimethylpropylammonium (n=3) $C_{29}H_{60}NO_6P$ (549.77)

1109.) 1-O—(Z)-12-nonadecenyl-2-O-methyl-sn-glycero-3-phospho-N,N,N-trimethylpropylammonium (n=3) $C_{29}H_{10}NO_6P$ (549.77)

1110.) 1-O—(Z)-6-eicosenyl-2-O-methyl-sn-glycero-3-phospho-N,N,N-trimethylpropylammonium (n=3) $C_{30}H_{62}NO_6P$ (563.80)

1111.) 1-O—(Z)-10-eicosenyl-2-O-methyl-sn-glycero-3-phospho-N,N,N-trimethylpropylammonium (n=3) $C_{30}H_{62}NO_6P$ (563.80)

1112.) 1-O—(Z)-12-eicosenyl-2-O-methyl-sn-glycero-3-phospho-N,N,N-trimethylpropylammonium (n=3) $C_{30}H_{62}NO_6P$ (563.80)

1113.) 1-O—(Z)-6-heneicosenyl-2-O-methyl-sn-glycero-3-phospho-N,N,N-trimethylpropylammonium (n=3) $C_{31}H_{64}NO_6P$ (577.83)

1114.) 1-O—(Z)-10-heneicosenyl-2-O-methyl-sn-glycero-3-phospho-N,N,N-trimethylpropylammonium (n=3) $C_{31}H_{64}NO_6P$ (577.83)

1115.) 1-O—(Z)-12-heneicosenyl-2-O-methyl-sn-glycero-3-phospho-N,N,N-trimethylpropylammonium (n=3) $C_{31}H_{64}NO_6P$ (577.83)

1116.) 1-O-(z)-6-docosenyl-2-O-methyl-sn-glycero-3-phospho-N,N,N-trimethylpropylammonium (n=3) $C_{32}H_6NO_6P$ (591.86)

1117.) 1-O—(Z)-10-docosenyl-2-O-methyl-sn-glycero-3-phospho-N,N,N-trimethylpropylammonium (n=3) $C_{32}H_{66}NO_6P$ (591.86)

1118.) 1-O—(Z)-12-docosenyl-2-O-methyl-sn-glycero-3-phospho-N,N,N-trimethylpropylammonium (n=3) $C_{32}H_{66}NO_6P$ (591.86)

1119.) 1-O—(Z)-6-tricosenyl-2-O-methyl-sn-glycero-3-phospho-N,N,N-trimethylpropylammonium (n=3) $C_{33}H_{68}NO_6P$ (605.89)

1120.) 1-O—(Z)-10-tricosenyl-2-O-methyl-sn-glycero-3-phospho-N,N,N-trimethylpropylammonium (n=3) $C_{33}H_{68}NO_6P$ (605.89)

1121.) 1-O—(Z)-12-tricosenyl-2-O-methyl-sn-glycero-3-phospho-N,N,N-trimethylpropylammonium (n=3) $C_{33}H_{68}NO_6P$ (605.89)

1122.) 1-O—(Z)-6-tetracosenyl-2-O-methyl-sn-glycero-3-phospho-N,N,N-trimethylpropylammonium (n=3) $C_{34}H_{70}NO_6P$ (619.91)

1123.) 1-O—(Z)-10-tetracosenyl-2-O-methyl-sn-glycero-3-phospho-N,N,N-trimethylpropylammonium (n=3) $C_{34}H_{10}NO_6P$ (619.91)

1124.) 1-O—(Z)-12-tetracosenyl-2-O-methyl-sn-glycero-3-phospho-N,N,N-trimethylpropylammonium (n=3) $C_{34}H_{70}NO_6P$ (619.91)

1125.) 1-O—(Z)-6-octadecenyl-2-O-methyl-sn-glycero-3-phospho-N,N,N-trimethylbutylammonium (n=4) $C_{29}H_{60}NO_6P$ (549.77)

1126.) 1-O—(Z)-10-octadecenyl-2-O-methyl-sn-glycero-3-phospho-N,N,N-trimethylbutylammonium (n=4) $C_{29}H_{60}NO_6P$ (549.77)

1127.) 1-O—(Z)-12-octadecenyl-2-O-methyl-sn-glycero-3-phospho-N,N,N-trimethylbutylammonium (n=4) $C_{29}H_{60}NO_6P$ (549.77)

1128.) 1-O—(Z)-6-nonadecenyl-2-O-methyl-sn-glycero-3-phospho-N,N,N-trimethylbutylammonium (n=4) $C_{30}H_{62}NO_6P$ (563.80)

1129.) 1-O—(Z)-10-nonadecenyl-2-O-methyl-sn-glycero-3-phospho-N,N,N-trimethylbutylammonium (n=4) $C_{30}H_{62}NO_6P$ (563.80)

1130.) 1-O—(Z)-12-nonadecenyl-2-O-methyl-sn-glycero-3-phospho-N,N,N-trimethylbutylammonium (n=4) $C_{30}H_{62}NO_6P$ (563.80)

1131.) 1-O—(Z)-6-eicosenyl-2-O-methyl-sn-glycero-3-phospho-N,N,N-trimethylbutylammonium (n=4) $C_{31}H_{64}NO_6P$ (577.83)

1132.) 1-O—(Z)-10-eicosenyl-2-O-methyl-sn-glycero-3-phospho-N,N,N-trimethylbutylammonium (n=4) $C_{31}H_{64}NO_6P$ (577.83)

1133.) 1-O—(Z)-12-eicosenyl-2-O-methyl-sn-glycero-3-phospho-N,N,N-trimethylbutylammonium (n=4) $C_{31}H_{64}NO_6P$ (577.83)

1134.) 1-O—(Z)-6-heneicosenyl-2-O-methyl-sn-glycero-3-phospho-N,N,N-trimethylbutylammonium (n=4) $C_{32}H_{66}NO_6P$ (591.86)

1135.) 1-O—(Z)-10-heneicosenyl-2-O-methyl-sn-glycero-3-phospho-N,N,N-trimethylbutylammonium (n=4) $C_{32}H_{66}NO_6P$ (591.86)

1136.) 1-O—(Z)-12-heneicosenyl-2-O-methyl-sn-glycero-3-phospho-N,N,N-trimethylbutylammonium (n=4) $C_{32}H_{66}NO_6P$ (591.86)

1137.) 1-O—(Z)-6-docosenyl-2-O-methyl-sn-glycero-3-phospho-N,N,N-trimethylbutylammonium (n=4) $C_{33}H_{68}NO_6P$ (605.89)

1138.) 1-O—(Z)-10-docosenyl-2-O-methyl-sn-glycero-3-phospho-N,N,N-trimethylbutylammonium (n=4) $C_{33}H_{68}NO_6P$ (605.89)

1139.) 1-O—(Z)-12-docosenyl-2-O-methyl-sn-glycero-3-phospho-N,N,N-trimethylbutylammonium (n=4) $C_{33}H_{68}NO_6P$ (605.89)

1140.) 1-O—(Z)-6-tricosenyl-2-O-methyl-sn-glycero-3-phospho-N,N,N-trimethylbutylammonium (n=4) $C_{34}H_{70}NO_6P$ (619.91)

1141.) 1-O—(Z)-10-tricosenyl-2-O-methyl-sn-glycero-3-phospho-N,N,N-trimethylbutylammonium (n=4) $C_{34}H_{70}NO_6P$ (619.91)

1142.) 1-O—(Z)-12-tricosenyl-2-O-methyl-sn-glycero-3-phospho-N,N,N-trimethylbutylammonium (n=4) $C_{34}H_{70}NO_6P$ (619.91)

1143.) 1-O—(Z)-6-tetracosenyl-2-O-methyl-sn-glycero-3-phospho-N,N,N-trimethylbutylammonium (n=4) $C_{35}H_{72}NO_6P$ (633.93)

1144.) 1-O—(Z)-10-tetracosenyl-2-O-methyl-sn-glycero-3-phospho-N,N,N-trimethylbutylammonium (n=4) $C_{35}H_{72}NO_6P$ (633.93)

1145.) 1-O-(z)-12-tetracosenyl-2-O-methyl-sn-glycero-3-phospho-N,N,N-trimethylbutylammonium (n=4) $C_{35}H_{72}NO_6P$ (633.93)

1146.) 1-O—(Z)-10-octadecenyl-3-O-methyl-sn-glycero-2-phosphocholine (n=2) $C_{27}H_{56}NO_6P$ (521.72)

1147.) 1-O—(Z)-6-nonadecenyl-3-O-methyl-sn-glycero-2-phosphocholine (n=2) $C_{28}H_{58}NO_6P$ (535.75)

1148.) 1-O—(Z)-12-eicosenyl-3-O-methyl-sn-glycero-2-phosphocholine (n=2) $C_{29}H_{60}NO_6P$ (549.77)

1149.) 1-O—(Z)-10-heneicosenyl-3-O-methyl-sn-glycero-2-phosphocholine (n=2)
$C_{30}H_{62}NO_6P$ (563.80)

1150.) 1-O-(z)-10-docosenyl-3-O-methyl-sn-glycero-2-phosphocholine (n=2)
$C_{31}H_{64}NO_6P$ (577.83)

1151.) 1-O—(Z)-12-docosenyl-3-O-methyl-sn-glycero-2-phosphocholine (n=2)
$C_{31}H_{64}NO_6P$ (577.83)

1152.) 1-O—(Z)-10-tricosenyl-3-O-methyl-sn-glycero-2-phosphocholine (n=2)
$C_{32}H_{66}NO_6P$ (591.86)

1153.) 1-O—(Z)-10-tetracosenyl-3-O-methyl-sn-glycero-2-phosphocholine (n=2)
$C_{33}H_{68}NO_6P$ (605.89)

1154.) 1-O—(Z)-10-octadecenyl-3-O-methyl-sn-glycero-2-phospho-N,N,N-trimethylpropylammonium (n=3)
$C_{28}H_{58}NO_6P$ (535.75)

1155.) 1-O—(Z)-6-nonadecenyl-3-O-methyl-sn-glycero-2-phospho-N,N,N-trimethylpropylammonium (n=3)
$C_{29}H_{60}NO_6P$ (549.77)

1156.) 1-O—(Z)-12-eicosenyl-3-O-methyl-sn-glycero-2-phospho-N,N,N-trimethylpropylammonium (n=3)
$C_{30}H_{62}NO_6P$ (563.80)

1157.) 1-O—(Z)-10-heneicosenyl-3-O-methyl-sn-glycero-2-phospho-N,N,N-trimethylpropylammonium (n=3)
$C_{31}H_{64}NO_6P$ (577.83)

1158.) 1-O—(Z)-10-docosenyl-3-O-methyl-sn-glycero-2-phospho-N,N,N-trimethylpropylammonium (n=3)
$C_{32}H_{66}NO_6P$ (591.86)

1159.) 1-O—(Z)-12-docosenyl-3-O-methyl-sn-glycero-2-phospho-N,N,N-trimethylpropylammonium (n=3)
$C_{32}H_{66}NO_6P$ (591.86)

1160.) 1-O—(Z)-10-tricosenyl-3-O-methyl-sn-glycero-2-phospho-N,N,N-trimethylpropylammonium (n=3)
$C_{33}H_{68}NO_6P$ (605.89)

1161.) 1-O—(Z)-10-tetracosenyl-3-O-methyl-sn-glycero-2-phospho-N,N,N-trimethylpropylammonium (n=3)
$C_{34}H_{70}NO_6P$ (619.91)

1162.) 1-O—(Z)-10-octadecenyl-2-O-tert-butyl-sn-glycero-3-phosphocholine (n=2)
$C_{30}H_{62}NO_6P$ (563.80)

1163.) 1-O-(z)-6-nonadecenyl-2-O-tert-butyl-sn-glycero-3-phosphocholine (n=2)
$C_{31}H_{64}NO_6P$ (577.82)

1164.) 1-O—(Z)-12-eicosenyl-2-O-tert-butyl-sn-glycero-3-phosphocholine (n=2)
$C_{32}H_{66}NO_6P$ (591.85)

1165.) 1-O—(Z)-10-heneicosenyl-2-O-tert-butyl-sn-glycero-3-phosphocholine (n=2)
$C_{33}H_{68}NO_6P$ (605.88)

1166.) 1-O—(Z)-10-docosenyl-2-O-tert-butyl-sn-glycero-3-phosphocholine (n=2)
$C_{34}H_{70}NO_6P$ (619.91)

1167.) 1-O—(Z)-12-docosenyl-2-O-tert-butyl-sn-glycero-3-phosphocholine (n=2)
$C_{34}H_{70}NO_6P$ (619.91)

1168.) 1-O—(Z)-10-tricosenyl-2-O-tert-butyl-sn-glycero-3-phosphocholine (n=2)
$C_{35}H_{72}NO_6P$ (633.94)

1169.) 1-O—(Z)-10-tetracosenyl-2-O-tert-butyl-sn-glycero-3-phosphocholine (n=2)
$C_{36}H_{74}NO_6P$ (647.97)

1170.) 1-O—(Z)-10-octadecenyl-2-O-tert-butyl-sn-glycero-3-phospho-N,N,N-trimethylpropylammonium (n=3)
$C_{31}H_{64}NO_6P$ (577.82)

1171.) 1-O—(Z)-6-nonadecenyl-2-O-tert-butyl-sn-glycero-3-phospho-N,N,N-trimethylpropylammonium (n=3)
$C_{32}H_{66}NO_6P$ (591.85)

1172.) 1-O—(Z)-12-eicosenyl-2-O-tert-butyl-sn-glycero-3-phospho-N,N,N-trimethylpropylammonium (n=3)
$C_{33}H_{68}NO_6P$ (605.88)

1173.) 1-O—(Z)-10-heneicosenyl-2-O-tert-butyl-sn-glycero-3-phospho-N,N,N-trimethylpropylammonium (n=3)
$C_{34}H_{70}NO_6P$ (619.91)

1174.) 1-O—(Z)-10-docosenyl-2-O-tert-butyl-sn-glycero-3-phospho-N,N,N-trimethylpropylammonium (n=3)
$C_{35}H_{72}NO_6P$ (633.94)

1175.) 1-O—(Z)-12-docosenyl-2-O-tert-butyl-sn-glycero-3-phospho-N,N,N-trimethylpropylammonium (n=3)
$C_{35}H_{72}NO_6P$ (633.94)

1176.) 1-O—(Z)-10-tricosenyl-2-O-tert-butyl-sn-glycero-3-phospho-N,N,N-trimethylpropylammonium (n=3)
$C_{36}H_{74}NO_6P$ (647.97)

1177.) 1-O—(Z)-10-tetracosenyl-2-O-tert-butyl-sn-glycero-3-phospho-N,N,N-trimethylpropylammonium (n=3)
$C_{37}H_{76}NO_6P$ (661.99)

11. Active Ingredients Based on alkylated (ether) lysolecithins—Diunsaturated Compounds $$A-PO_3^- -(CH_2)_n - \overset{CH_3}{\underset{R_3}{N^+}} - (CH_2)_x - \left[CH_2 - \left(\overset{CH}{\underset{OH}{|}}\right)_y - CH_2 - O\right]_z - H$$

(A = III or A = IV; n = 2-6; $R_3$, $CH_3$; m = 1, x = 1; z = 0)

1-O—(Z,Z)-Alkadienyl-2-O-methyl-sn-glycero-3-phosphocholines

1178.) 1-O—(Z,Z)-6,12-hexadecadienyl-2-O-methyl-sn-glycero-3-phosphocholine (n=2)
$C_{25}H_{50}NO_6P$ (491.65)

1179.) 1-O—(Z,Z)-6,12-heptadecadienyl-2-O-methyl-sn-glycero-3-phosphocholine (n=2)
$C_{26}H_{52}NO_6P$ (505.68)

1180.) 1-O—(Z,Z)-6,12-octadecadienyl-2-O-methyl-sn-glycero-3-phosphocholine (n=2)
$C_{27}H_{54}NO_6P$ (519.71)

1181.) 1-O—(Z,Z)-6,12-nonadecadienyl-2-O-methyl-sn-glycero-3-phosphocholine (n=2)
$C_{28}H_{56}NO_6P$ (533.74)

1182.) 1-O—(Z,Z)-9,15-eicosadienyl-2-O-methyl-sn-glycero-3-phosphocholine (n=2)
$C_{29}H_{58}NO_6P$ (547.77)

1183.) 1-O—(Z,Z)-9,15-heneicosadienyl-2-O-methyl-sn-glycero-3-phosphocholine (n=2)
$C_{30}H_{60}NO_6P$ (561.8)

1184.) 1-O—(Z,Z)-5,17-docosadienyl-2-O-methyl-sn-glycero-3-phosphocholine (n=2)
$C_{31}H_{62}NO_6P$ (575.83)

1185.) 1-O—(Z,Z)-6,18-tricosadienyl-2-O-methyl-sn-glycero-3-phosphocholine (n=2)
$C_{32}H_{64}NO_6P$ (589.86)

1186.) 1-O—(Z,Z)-6,18-tetracosadienyl-2-O-methyl-sn-glycero-3-phosphocholine (n=2)
$C_{33}H_{66}NO_6P$ (603.89)

1187.) 1-O—(Z,Z)-6,18-pentacosadienyl-2-O-methyl-sn-glycero-3-phosphocholine (n=2)
$C_{34}H_{68}NO_6P$ (617.92)

1-O—(Z,Z)-Alkadienyl-2-O-methyl-sn-glycero-3-phospho-N,N,N-trimethylpropylammonium compounds 1188.) 1-O—(Z,Z)-6,12-hexadecadienyl-2-O-methyl-sn-glycero-3-phospho-N,N,N-trimethylpropylammonium (n=3)
$C_{26}H_{52}NO_6P$ (505.68)
1189.) 1-O—(Z,Z)-6,12-heptadecadienyl-2-O-methyl-sn-glycero-3-phospho-N,N,N-trimethylpropylammonium (n=3)
$C_{27}H_{54}NO_6P$ (519.71)
1190.) 1-O—(Z,Z)-6,12-octadecadienyl-2-O-methyl-sn-glycero-3-phospho-N,N,N-trimethylpropylammonium (n=3)
$C_{28}H_{56}NO_6P$ (533.74)
1191.) 1-O—(Z,Z)-6,12-nonadecadienyl-2-O-methyl-sn-glycero-3-phospho-N,N,N-trimethylpropylammonium (n=3)
$C_{29}H_{58}NO_6P$ (547.77)
1192.) 1-O—(Z,Z)-9,15-eicosadienyl-2-O-methyl-sn-glycero-3-phospho-N,N,N-trimethylpropylammonium (n=3)
$C_{30}H_{60}NO_6P$ (561.8)
1193.) 1-O—(Z,Z)-9,15-heneicosadienyl-2-O-methyl-sn-glycero-3-phospho-N,N,N-trimethylpropylammonium (n=3)
$C_{31}H_{62}NO_6P$ (575.83)
1194.) 1-O—(Z,Z)-5,17-docosadienyl-2-O-methyl-sn-glycero-3-phospho-N,N,N-trimethylpropylammonium (n=3)
$C_{32}H_{64}NO_6P$ (589.86)
1195.) 1-O—(Z,Z)-6,18-tricosadienyl-2-O-methyl-sn-glycero-3-phospho-N,N,N-trimethylpropylammonium (n=3)
$C_{33}H_{66}NO_6P$ (603.89)
1196.) 1-O—(Z,Z)-6,18-tetracosadienyl-2-O-methyl-sn-glycero-3-phospho-N,N,N-trimethylpropylammonium (n=3)
$C_{34}H_{68}NO_6P$ (617.92)
1197.) 1-O—(Z,Z)-6,18-pentacosadienyl-2-O-methyl-sn-glycero-3-phospho-N,N,N-trimethylpropylammonium (n=3)
$C_{35}H_{70}NO_6P$ (631.95)

1-O—(Z,Z)-Alkadienyl-2-O-methyl-sn-glycero-3-phospho-N,N,N-trimethylbutylammonium Compounds 1198.) 1-O—(Z,Z)-6,12-hexadecadienyl-2-O-methyl-sn-glycero-3-phospho-N,N,N-trimethylbutylammonium (n=4)
$C_{27}H_{54}NO_6P$ (519.71)
1199.) 1-O—(Z,Z)-6,12-heptadecadienyl-2-O-methyl-sn-glycero-3-phospho-N,N,N-trimethylbutylammonium (n=4)
$C_{28}H_{56}NO_6P$ (533.74)
1200.) 1-O—(Z,Z)-6,12-octadecadienyl-2-O-methyl-sn-glycero-3-phospho-N,N,N-trimethylbutylammonium (n=4)
$C_{29}H_{58}NO_6P$ (547.77)
1201.) 1-O—(Z,Z)-6,12-nonadecadienyl-2-O-methyl-sn-glycero-3-phospho-N,N,N-trimethylbutylammonium (n=4)
$C_{30}H_{60}NO_6P$ (561.8)
1202.) 1-O—(Z,Z)-9,15-eicosadienyl-2-O-methyl-sn-glycero-3-phospho-N,N,N-trimethylbutylammonium (n=4)
$C_{31}H_{62}NO_6P$ (575.83)
1203.) 1-O—(Z,Z)-9,15-heneicosadienyl-2-O-methyl-sn-glycero-3-phospho-N,N,N-trimethylbutylammonium (n=4)
$C_{32}H_{64}NO_6P$ (589.86)
1204.) 1-O—(Z,Z)-5,17-docosadienyl-2-O-methyl-sn-glycero-3-phospho-N,N,N-trimethylbutylammonium (n=4)
$C_{33}H_{66}NO_6P$ (603.89)
1205.) 1-O—(Z,Z)-6,18-tricosadienyl-2-O-methyl-sn-glycero-3-phospho-N,N,N-trimethylbutylammonium (n=4)
$C_{34}H_{68}NO_6P$ (617.92)
1206.) 1-O—(Z,Z)-6,18-tetracosadienyl-2-O-methyl-sn-glycero-3-phospho-N,N,N-trimethylbutylammonium (n=4)
$C_{35}H_{70}NO_6P$ (631.95)
1207.) 1-O—(Z,Z)-6,18-pentacosadienyl-2-O-methyl-sn-glycero-3-phospho-N,N,N-trimethylbutylammonium (n=4)
$C_{36}H_{72}NO_6P$ (645.94)

1-O—(Z,Z)-Alkadienyl-3-O-methyl-sn-glycero-2-phosphocholine (n=2)

1208.) 1-O—(Z,Z)-6,12-hexadecadienyl-3-O-methyl-sn-glycero-2-phosphocholine (n=2)
$C_{25}H_{50}NO_6P$ (491.65)
1209.) 1-O—(Z,Z)-6,12-heptadecadienyl-3-O-methyl-sn-glycero-2-phosphocholine (n=2)
$C_{26}H_{52}NO_6P$ (505.68)
1210.) 1-O—(Z,Z)-6,12-octadecadienyl-3-O-methyl-sn-glycero-2-phosphocholine (n=2)
$C_{27}H_{54}NO_6P$ (519.71)
1211.) 1-O—(Z,Z)-6,12-nonadecadienyl-3-O-methyl-sn-glycero-2-phosphocholine (n=2)
$C_{28}H_{56}NO_6P$ (533.74)
1212.) 1-O—(Z,Z)-9,15-eicosadienyl-3-O-methyl-sn-glycero-2-phosphocholine (n=2)
$C_{29}H_{58}NO_6P$ (547.77)
1213.) 1-O—(Z,Z)-9,15-heneicosadienyl-3-O-methyl-sn-glycero-2-phosphocholine (n=2)
$C_{30}H_{60}NO_6P$ (561.8)
1214.) 1-O—(Z,Z)-5,17-docosadienyl-3-O-methyl-sn-glycero-2-phosphocholine (n=2)
$C_{31}H_{62}NO_6P$ (575.83)
1215.) 1-O—(Z,Z)-6,18-tricosadienyl-3-O-methyl-sn-glycero-2-phosphocholine (n=2)
$C_{32}H_{64}NO_6P$ (589.86)
1216.) 1-O—(Z,Z)-6,18-tetracosadienyl-3-O-methyl-sn-glycero-2-phosphocholine (n=2)
$C_{29}H_{58}NO_4P$ (515.76)
1217.) 1-O—(Z,Z)-6,18-pentacosadienyl-3-O-methyl-sn-glycero-2-phosphocholine (n=2)
$C_{34}H_{68}NO_6P$ (617.92)

1-O—(Z,Z-Alkadienyl-3-O-methyl-sn-glycero-2-phospho-N,N,N-trimethylpropylammonium Compounds 1218.) 1-O—(Z,Z)-6,12-hexadecadienyl-3-O-methyl-sn-glycero-2-phospho-N,N,N-trimethylpropylammonium (n=3)
$C_{26}H_{52}NO_6P$ (505.68)
1219.) 1-O—(Z,Z)-6,12-heptadecadienyl-3-O-methyl-sn-glycero-2-phospho-N,N,N-trimethylpropylammonium (n=3)
$C_{27}H_{54}NO_6P$ (519.71)

1220.) 1-O—(Z,Z)-6,12-octadecadienyl-3-O-methyl-sn-glycero-2-phospho-N,N,N-trimethylpropylammonium (n=3)
$C_{28}H_{56}NO_6P$ (533.74)
1221.) 1-O—(Z,Z)-6,12-nonadecadienyl-3-O-methyl-sn-glycero-2-phospho-N,N,N-trimethylpropylammonium (n=3)
$C_{29}H_{58}NO_6P$ (547.77)
1222.) 1-O—(Z,Z)-9,15-eicosadienyl-3-O-methyl-sn-glycero-2-phospho-N,N,N-trimethylpropylammonium (n=3)
$C_{30}H_{60}NO_6P$ (561.8)
1223.) 1-O—(Z,Z)-9,15-heneicosadienyl-3-O-methyl-sn-glycero-2-phospho-N,N,N-trimethylpropylammonium (n=3)
$C_{31}H_{62}NO_6P$ (575.83)
1224.) 1-O—(Z,Z)-5,17-docosadienyl-3-O-methyl-sn-glycero-2-phospho-N,N,N-trimethylpropylammonium (n=3)
$C_{32}H_{64}NO_6P$ (589.86)
1225.) 1-O—(Z,Z)-6,18-tricosadienyl-3-O-methyl-sn-glycero-2-phospho-N,N,N-trimethylpropylammonium (n=3)
$C_{33}H_{66}NO_6P$ (603.89)
1226.) 1-O—(Z,Z)-6,18-tetracosadienyl-3-O-methyl-sn-glycero-2-phospho-N,N,N-trimethylpropylammonium (n=3)
$C_{34}H_{68}NO_6P$ (617.92)
1227.) 1-O—(Z,Z)-6,18-pentacosadienyl-3-O-methyl-sn-glycero-2-phospho-N,N,N-trimethylpropylammonium (n=3)
$C_{35}H_{70}NO_6P$ (631.95)

1-O—(Z,Z)-Alkadienyl-2-O-tert-butyl-sn-glycero-3-phosphocholine (n=2)

1228.) 1-O—(Z,Z)-6,12-hexadecadienyl-2-O-tert-butyl-sn-glycero-3-phosphocholine (n=2)
$C_{28}H_{56}NO_6P$ (533.73)
1229.) 1-O—(Z,Z)-6,12-heptadecadienyl-2-O-tert-butyl-sn-glycero-3-phosphocholine (n=2)
$C_{29}H_{58}NO_6P$ (547.76)
1230.) 1-O—(Z,Z)-6,12-octadecadienyl-2-O-tert-butyl-sn-glycero-3-phosphocholine (n=2)
$C_{30}H_{60}NO_6P$ (561.78)
1231.) 1-O—(Z,Z)-6,12-nonadecadienyl-2-O-tert-butyl-sn-glycero-3-phosphocholine (n=2)
$C_{31}H_{62}NO_6P$ (575.81)
1232.) 1-O—(Z,Z)-9,15-eicosadienyl-2-O-tert-butyl-sn-glycero-3-phosphocholine (n=2)
$C_{32}H_{64}NO_6P$ (589.84)
1233.) 1-O—(Z,Z)-9,15-heneicosadienyl-2-O-tert-butyl-sn-glycero-3-phosphocholine (n=2)
$C_{33}H_{66}NO_6P$ (603.87)
1234.) 1-O—(Z,Z)-5,17-docosadienyl-2-O-tert-butyl-sn-glycero-3-phosphocholine (n=2)
$C_{34}H_{68}NO_6P$ (617.9)
1235.) 1-O—(Z,Z)-6,18-tricosadienyl-2-O-tert-butyl-sn-glycero-3-phosphocholine (n=2)
$C_{35}H_{70}NO_6P$ (631.93)
1236.) 1-O—(Z,Z)-6,18-tetracosadienyl-2-O-tert-butyl-sn-glycero-3-phosphocholine (n=2)
$C_{36}H_{72}NO_6P$ (645.96)
1237.) 1-O—(Z,Z)-6,18-pentacosadienyl-2-O-tert-butyl-sn-glycero-3-phosphocholine (n=2)
$C_{37}H_{74}NO_6P$ (660.03)

1-O—(Z,Z)-Alkadienyl-2-O-tert-butyl-sn-glycero-3-phospho-N,N,N-trimethylpropylammonium compounds 1238.) 1-O—(Z,Z)-6,12-hexadecadienyl-2-O-tert-butyl-sn-glycero-3-phospho-N,N,N-trimethylpropylammonium (n=3)
$C_{29}H_{58}NO_6P$ (547.76)
1239.) 1-O—(Z,Z)-6,12-heptadecadienyl-2-O-tert-butyl-sn-glycero-3-phospho-N,N,N-trimethylpropylammonium (n=3)
$C_{30}H_{60}NO_6P$ (561.78)
1240.) 1-O—(Z,Z)-6,12-octadecadienyl-2-O-tert-butyl-sn-glycero-3-phospho-N,N,N-trimethylpropylammonium (n=3)
$C_{31}H_{62}NO_6P$ (575.81)
1241.) 1-O—(Z,Z)-6,12-nonadecadienyl-2-O-tert-butyl-sn-glycero-3-phospho-N,N,N-trimethylpropylammonium (n=3)
$C_{32}H_{64}NO_6P$ (589.84)
1242.) 1-O—(Z,Z)-9,15-eicosadienyl-2-O-tert-butyl-sn-glycero-3-phospho-N,N,N-trimethylpropylammonium (n=3)
$C_{33}H_{66}NO_6P$ (603.87)
1243.) 1-O—(Z,Z)-9,15-heneicosadienyl-2-O-tert-butyl-sn-glycero-3-phospho-N,N,N-trimethylpropylammonium (n=3)
$C_{34}H_{68}NO_6P$ (617.9)
1244.) 1-O—(Z,Z)-5,17-docosadienyl-2-O-tert-butyl-sn-glycero-3-phospho-N,N,N-trimethylpropylammonium (n=3)
$C_{35}H_{70}NO_6P$ (631.93)
1245.) 1-O—(Z,Z)-6,18-tricosadienyl-2-O-tert-butyl-sn-glycero-3-phospho-N,N,N-trimethylpropylammonium (n=3)
$C_{36}H_{72}NO_6P$ (645.96)
1246.) 1-O—(Z,Z)-6,18-tetracosadienyl-2-O-tert-butyl-sn-glycero-3-phospho-N,N,N-trimethylpropylammonium (n=3)
$C_{37}H_{74}NO_6P$ (660.03)
1247.) 1-O—(Z,Z)-6,18-pentacosadienyl-2-O-tert-butyl-sn-glycero-3-phospho-N,N,N-trimethylpropylammonium (n=3)
$C_{38}H_{76}NO_6P$ (674.03)

12. Active Ingredients Based on alkanediol-phospho Compounds—Monounsaturated Compounds

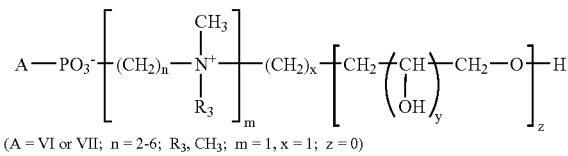

(A = VI or VII; n = 2-6; $R_3$, $CH_3$; m = 1, x = 1; z = 0)

1-O—(Z)-Alkenylpropanediol-(1,2)-phosphocholines

1248.) 1-O—(Z)-10-octadecenylpropanediol-(1,2)-phosphocholine
$C_{26}H_{54}NO_5P$ (491.68)
1249.) 1-O—(Z)-6-nonadecenylpropanediol-(1,2)-phosphocholine
$C_{27}H_{16}NO_5P$ (505.71)

1250.) 1-O—(Z)-12-eicosenylpropanediol-(1,2)-phosphocholine
$C_{28}H_{58}NO_5P$ (519.74)
1251.) 1-O—(Z)-10-heneicosenylpropanediol-(1,2)-phosphocholine
$C_{29}H_{60}NO_5P$ (533.77)
1252.) 1-O—(Z)-10-docosenylpropanediol-(1,2)-phosphocholine
$C_{30}H_{12}NO_5P$ (547.80)
1253.) 1-O—(Z)-12-docosenylpropanediol-(1,2)-phosphocholine
$C_{30}H_{62}NO_5P$ (547.80)
1254.) 1-O—(Z)-10-tricosenylpropanediol-(1,2)-phosphocholine
$C_{31}H_{64}NO_5P$ (561.83)
1255.) 1-O—(Z)-10-tetracosenylpropanediol-(1,2)-phosphocholine
$C_{32}H_{66}NO_5P$ (575.86)

1-O—(Z)-Alkenylpropanediol-(1,2)-phospho-N,N,N-trimethylpropylammonium compounds 1256.) 1-O—(Z)-10-octadecenylpropanediol-(1,2)-phospho-N,N,N-trimethylpropylammonium
$C_{27}H_{56}NO_5P$ (505.71)
1257.) 1-O—(Z)-6-nonadecenylpropanediol-(1,2)-phospho-N,N,N-trimethylpropylammonium
$C_{28}H_{58}NO_5P$ (519.74)
1258.) 1-O—(Z)-12-eicosenylpropanediol-(1,2)-phospho-N,N,N-trimethylpropylammonium
$C_{29}H_{10}NO_5P$ (533.77)
1259.) 1-O—(Z)-10-heneicosenylpropanediol-(1,2)-phospho-N,N,N-trimethylpropylammonium
$C_{30}H_{62}NO_5P$ (547.80)
1260.) 1-O—(Z)-10-docosenylpropanediol-(1,2)-phospho-N,N,N-trimethylpropylammonium
$C_{31}H_{64}NO_5P$ (561.83)
1261.) 1-O—(Z)-12-docosenylpropanediol-(1,2)-phospho-N,N,N-trimethylpropylammonium
$C_{31}H_{64}NO_5P$ (561.83)
1262.) 1-O—(Z)-10-tricosenylpropanediol-(1,2)-phospho-N,N,N-trimethylpropylammonium
$C_{32}H_{66}NO_5P$ (575.86)
1263.) 1-O—(Z)-10-tetracosenylpropanediol-(1,2)-phospho-N,N,N-trimethylpropylammonium
$C_{33}H_{68}N_5P$ (589.89)

2-O—(Z)-Alkenylpropanediol-(1,2)-phosphocholines

1264.) 2-O—(Z)-10-octadecenylpropanediol-(1,2)-phosphocholine
$C_{26}H_{54}NO_4P$ (491.68)
1265.) 2-O—(Z)-6-nonadecenylpropanediol-(1,2)-phosphocholine
$C_{27}H_{56}NO_5P$ (505.71)
1266.) 2-O—(Z)-12-eicosenylpropanediol-(1,2)-phosphocholine
$C_{28}H_{58}NO_5P$ (519.74)
1267.) 2-O—(Z)-10-heneicosenylpropanediol-(1,2)-phosphocholine
$C_{29}H_{60}NO_5P$ (533.77)
1268.) 2-O—(Z)-10-docosenylpropanediol-(1,2)-phosphocholine
$C_{30}H_{62}NO_5P$ (547.80)
1269.) 2-O—(Z)-12-docosenylpropanediol-(1,2)-phosphocholine
$C_{30}H_{62}NO_5P$ (547.80)
1270.) 2-O—(Z)-10-tricosenylpropanediol-(1,2)-phosphocholine
$C_{31}H_{64}NO_6P$ (561.83)
1271.) 2-O—(Z)-10-tetracosenylpropanediol-(1,2)-phosphocholine
$C_{32}H_{66}NO_5P$ (575.86)

2-O—(Z)-Alkenylpropanediol-(1,2)-phospho-N,N,N-trimethylpropylammonium compounds 1272.) 2-O—(Z)-10-octadecenylpropanediol-(1,2)-phospho-N,N,N-trimethylpropylammonium
$C_{27}H_{56}NO_5P$ (505.71)
1273.) 2-O—(Z)-6-nonadecenylpropanediol-(1,2)-phospho-N,N,N-trimethylpropylammonium
$C_{28}H_{58}NO_5P$ (519.74)
1274.) 2-O—(Z)-12-eicosenylpropanediol-(1,2)-phospho-N,N,N-trimethylpropylammonium
$C_{29}H_{60}NO_5P$ (533.77)
1275.) 2-O—(Z)-10-heneicosenylpropanediol-(1,2)-phospho-N,N,N-trimethylpropylammonium
$C_{30}H_{62}NO_5P$ (547.80)
1276.) 2-O-(z)-10-docosenylpropanediol-(1,2)-phospho-N,N,N-trimethylpropylammonium
$C_{31}H_{64}NO_6P$ (561.83)
1277.) 2-O—(Z)-12-docosenylpropanediol-(1,2)-phospho-N,N,N-trimethylpropylammonium
$C_{31}H_{64}NO_5P$ (561.83)
1278.) 2-O-(z)-10-tricosenylpropanediol-(1,2)-phospho-N,N,N-trimethylpropylammonium
$C_{32}H_{66}NO_5P$ (575.86)
1279.) 2-O—(Z)-10-tetracosenylpropanediol-(1,2)-phospho-N,N,N-trimethylpropylammonium
$C_{33}H_{68}NO_5P$ (589.89)

13. Active Ingredients Based on alkanediol-phospho Compounds—Diunsaturated Compounds

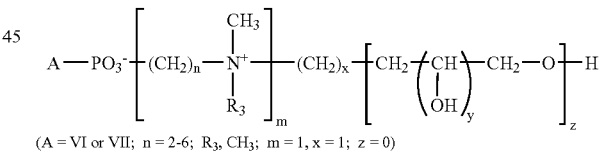
(A = VI or VII; n = 2-6; $R_3$, $CH_3$; m = 1, x = 1; z = 0)

1-O—(Z,Z)-Alkadienylpropanediol-(1,2)-phosphocholines

1280.) 1-O—(Z,Z)-6,12-hexadecadienylpropanediol-(1,2)-phosphocholine
$C_{24}H_{48}NO_5P$ (461.62)
1281.) 1-O—(Z,Z)-6,12-heptadecadienylpropanediol-(1,2)-phosphocholine
$C_{25}H_{50}NO_5P$ (475.65)
1282.) 1-O—(Z,Z)-6,12-octadecadienylpropanediol-(1,2)-phosphocholine
$C_{26}H_{52}NO_5P$ (489.68)
1283.) 1-O—(Z,Z)-6,12-nonadecadienyipropanediol-(1,2)-phosphocholine
$C_{27}H_{54}NO_5P$ (503.71)

1284.) 1-O—(Z,Z)-9,15-eicosadienylpropanediol-(1,2)-phosphocholine
$C_{28}H_{56}NO_5P$ (517.74)
1285.) 1-O—(Z,Z)-9,15-heneicosadienylpropanediol-(1,2)-phosphocholine
$C_{29}H_{58}NO_5P$ (531.77)
1286.) 1-O—(Z,Z)-5,17-docosadienylpropanediol-(1,2)-phosphocholine
$C_{30}H_{60}NO_5P$ (545.8)
1287.) 1-O—(Z,Z)-6,18-tricosadienylpropanediol-(1,2)-phosphocholine
$C_{31}H_{62}NO_5P$ (559.83)
1288.) 1-O—(Z,Z)-6,18-tetracosadienylpropanediol-(1,2)-phosphocholine
$C_{32}H_{64}NO_5P$ (573.86)
1289.) 1-O—(Z,Z)-6,18-pentacosadienylpropanediol-(1,2)-phosphocholine
$C_{33}H_{66}NO_5P$ (587.89)

1-O—(Z,Z)-Alkadienylpropanediol-(1,2)-phospho-N,N,N-trimethylpropylammonium Compounds 1290.) 1-O—(Z,Z)-6,12-hexadecadienylpropanediol-(1,2)-phospho-N,N,N-trimethylpropylammonium
$C_{25}H_{50}NO_5P$ (475.65)
1291.) 1-O—(Z,Z)-6,12-heptadecadienylpropanediol-(1,2)-phospho-N,N,N-trimethylpropylammonium
$C_{26}H_{52}NO_5P$ (489.68)
1292.) 1-O—(Z,Z)-6,12-octadecadienylpropanediol-(1,2)-phospho-N,N,N-trimethylpropylammonium
$C_{27}H_{54}NO_5P$ (503.71)
1293.) 1-O—(Z,Z)-6,12-nonadecadienylpropanediol-(1,2)-phospho-N,N,N-trimethylpropylammonium
$C_{28}H_{56}NO_5P$ (517.74)
1294.) 1-O—(Z,Z)-9,15-eicosadienylpropanediol-(1,2)-phospho-N,N,N-trimethylpropylammonium
$C_{29}H_{58}NO_5P$ (531.77)
1295.) 1-O—(Z,Z)-9,15-heneicosadienylpropanediol-(1,2)-phospho-N,N,N-trimethylpropylammonium
$C_{30}H_{60}NO_5P$ (545.8)
1296.) 1-O—(Z,Z)-5,17-docosadienylpropanediol-(1,2)-phospho-N,N,N-trimethylpropylammoniurn
$C_{31}H_{62}NO_5P$ (559.83)
1297.) 1-O—(Z,Z)-6,18-tricosadienylpropanediol-(1,2)-phospho-N,N,N-trimethylpropylammonium
$C_{32}H_{64}NO_5P$ (573.86)
1298.) 1-O—(Z,Z)-6,18-tetracosadienylpropanediol-(1,2)-phospho-N,N,N-trimethylpropylammonium
$C_{33}H_{66}NO_5P$ (587.89)
1299.) 1-O—(Z,Z)-6,18-pentacosadienylpropanediol-(1,2)-phospho-N,N,N-trimethylpropylammonium.
$C_{34}H_{68}NO_5P$ (601.92)

2-O—(Z,Z)-Alkadienylpropanediol-(1,2)-phosphocholines

1300.) 2-O—(Z,Z)-6,12-hexadecadienylpropanediol-(1,2)-phosphocholine
$C_{24}H_{48}NO_5P$ (461.62)
1301.) 2-O—(Z,Z)-6,12-heptadecadienylpropanediol-(1,2)-phosphocholine
$C_{25}H_{50}NO_5P$ (475.65)
1302.) 2-O—(Z,Z)-6,12-octadecadienylpropanediol-(1,2)-phosphocholine
$C_{26}H_{52}NO_5P$ (489.68)
1303.) 2-O—(Z,Z)-6,12-nonadecadienylpropanediol-(1,2)-phosphocholine
$C_{27}H_{54}NO_5P$ (503.71)
1304.) 2-O—(Z,Z)-9,15-eicosadienylpropanediol-(1,2)-phosphocholine
$C_{28}H_{56}NO_5P$ (517.74)
1305.) 2-O—(Z,Z)-9,15-heneicosadienylpropanediol-(1,2)-phosphocholine
$C_{29}H_{58}NO_5P$ (531.77)
1306.) 2-O—(Z,Z)-5,17-docosadienylpropanediol-(1,2)-phosphocholine
$C_{30}H_{60}NO_5P$ (545.8)
1307.) 2-O—(Z,Z)-6,18-tricosadienylpropanediol-(1,2)-phosphocholine
$C_{31}H_{62}NO_5P$ (559.83)
1308.) 2-O—(Z,Z)-6,18-tetracosadienylpropanediol-(1,2)-phosphocholine
$C_{32}H_{64}NO_5P$ (573.86)
1309.) 2-O—(Z,Z)-6,18-pentacosadienylpropanediol-(1,2)-phosphocholine
$C_{33}H_{66}NO_5P$ (587.89)

2-O—(Z,Z)-Alkadienylpropanediol-(1,2)-phospho-N,N,N-trimethylpropylammonium Compounds 1310.) 2-O—(Z,Z)-6,12-hexadecadienylpropanediol-(1,2)-phospho-N,N,N-trimethylpropylammonium
$C_{25}H_{50}NO_5P$ (475.65)
1311.) 2-O—(Z,Z)-6,12-heptadecadienylpropanediol-(1,2)-phospho-N,N,N-trimethylpropylammonium
$C_{26}H_{52}NO_5P$ (489.68)
1312.) 2-O—(Z,Z)-6,12-octadecadienylpropanediol-(1,2)-phospho-N,N,N-trimethylpropylammonium
$C_{27}H_{54}NO_5P$ (503.71)
1313.) 2-O—(Z,Z)-6,12-nonadecadienylpropanediol-(1,2)-phospho-N,N,N-trimethylpropylammonium
$C_{28}H_{56}NO_5P$ (517.74)
1314.) 2-O—(Z,Z)-9,15-eicosadienylpropanediol-(1,2)-phospho-N,N,N-trimethylpropylammonium
$C_{29}H_{58}NO_5P$ (531.77)
1315.) 2-O—(Z,Z)-9,15-heneicosadienylpropanediol-(1,2)-phospho-N,N,N-trimethylpropylammonium
$C_{30}H_{60}NO_5P$ (545.8)
1316.) 2-O—(Z,Z)-5,17-docosadienylpropanediol-(1,2)-phospho-N,N,N-trimethylpropylammonium
$C_{31}H_{62}NO_5P$ (559.83)
1317.) 2-O—(Z,Z)-6,18-tricosadienylpropanediol-(1,2)-phospho-N,N,N-trimethylpropylammonium
$C_{32}H_{64}NO_5P$ (573.86)
1318.) 2-O—(Z,Z)-6,18-tetracosadienylpropanediol-(1,2)-phospho-N,N,N-trimethylpropylammonium
$C_{33}H_{66}NO_5P$ (587.89)
1319.) 2-O—(Z,Z)-6,18-pentacosadienylpropanediol-(1,2)-phospho-N,N,N-trimethylpropylammonium
$C_{34}H_{68}NO_5P$ (601.92)

Solubilizers

1. Examples of Single-Chain glycero-phospho-N,N-dimethyl-N-dihydroxypropylalkylammonium Compounds

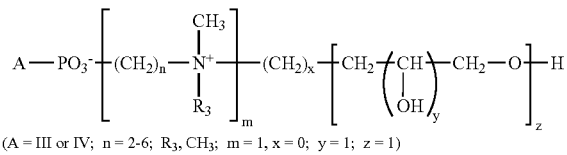

(A = III or IV; n = 2-6; $R_3$, $CH_3$; m = 1, x = 0; y = 1; z = 1)

n=2

1320.) 1-(Z)-6-hexadecenoyl-sn-glycero-3-phospho-N,N-dimethyl-N-dihydroxypropylethylammonium (n=2)
$C_{26}H_{52}NO_9P$ (553.67)

1321.) 1-(Z)-10-heptadecenoyl-sn-glycero-3-phospho-N,N-dimethyl-N-dihydroxypropylethylammonium (n=2)
$C_{27}H_{54}NO_9P$ (567.70)

1322.) 1-(Z)-6-octadecenoyl-sn-glycero-3-phospho-N,N-dimethyl-N-dihydroxypropylethylammonium (n=2)
$C_{28}H_{56}NO_9P$ (581.73)

1323.) 1-(Z)-6-nonadecenoyl-sn-glycero-3-phospho-N,N-dimethyl-N-dihydroxypropylethylammonium (n=2)
$C_{29}H_{58}NO_9P$ (595.75)

1324.) 1-(Z)-12-eicosenoyl-sn-glycero-3-phospho-N,N-dimethyl-N-dihydroxypropylethylammonium (n=2)
$C_{30}H_{60}NO_9P$ (609.78)

1325.) 1-(z)-10-heneicosenoyl-sn-glycero-3-phospho-N,N-dimethyl-N-dihydroxypropylethylammonium (n=2)
$C_{31}H_{62}NO_9P$ (623.81)

1326.) 1-(Z)-10-docosenoyl-sn-glycero-3-phospho-N,N-dimethyl-N-dihydroxypropylethylammonium (n=2)
$C_{32}H_{64}NO_9P$ (637.84)

1327.) 1-(z)-12-docosenoyl-sn-glycero-3-phospho-N,N-dimethyl-N-dihydroxypropylethylammonium (n=2)
$C_{32}H_{64}NO_9P$ (637.84)

1328.) 1-(Z)-10-tricosenoyl-sn-glycero-3-phospho-N,N-dimethyl-N-dihydroxypropylethylammonium (n=2)
$C_{33}H_{66}NO_9P$ (651.86)

1329.) 1-(Z)-10-tetracosenoyl-sn-glycero-3-phospho-N,N-dimethyl-N-dihydroxypropylethylammonium (n=2)
$C_{34}H_{68}NO_9P$ (665.89)

1330.) 1-(Z)-15-pentacosenoyl-sn-glycero-3-phospho-N,N-dimethyl-N-dihydroxypropylethylammonium (n=2)
$C_3H_{70}NO_9P$ (679.92)

1331.) 1-(Z)-16-hexacosenoyl-sn-glycero-3-phospho-N,N-dimethyl-N-dihydroxypropylethylammonium (n=2)
$C_{36}H_{72}NO_9P$ (693.94)

1332.) 1-(Z,Z)-5,11-hexadecadienoyl-sn-glycero-3-phospho-N,N-dimethyl-N-dihydroxypropylethylammonium (n=2)
$C_{26}H_{50}NO_9P$ (551.66)

1333.) 1-(Z,Z)-5,11-heptadecadienoyl-sn-glycero-3-phospho-N,N-dimethyl-N-dihydroxypropylethylammonium (n=2)
$C_{27}H_{52}NO_9P$ (565.68)

1334.) 1-(Z,Z)-5,11-octadecadienoyl-sn-glycero-3-phospho-N,N-dimethyl-N-dihydroxypropylethylammonium (n=2)
$C_{28}H_{54}NO_9P$ (579.71)

1335.) 1-(Z,Z)-6,12-nonadecadienoyl-sn-glycero-3-phospho-N,N-dimethyl-N-dihydroxypropylethylammonium (n=2)
$C_{29}H_{56}NO_9P$ (593.74)

1336.) 1-(Z,Z)-10,16-eicosadienoyl-sn-glycero-3-phospho-N,N-dimethyl-N-dihydroxypropylethyl ammonium (n=2)
$C_{30}H_{58}NO_9P$ (607.77)

1337.) 1-(Z,Z)-10,16-heneicosadienoyl-sn-glycero-3-phospho-N,N-dimethyl-N-dihydroxypropylethylammonium (n=2)
$C_{31}H_{60}NO_9P$ (621.79)

1338.) 1-(Z,Z)-10,16-docosadienoyl-sn-glycero-3-phospho-N,N-dimethyl-N-dihydroxypropylethylammonium (n=2)
$C_{32}H_{62}NO_9P$ (635.82)

1339.) 1-(Z,Z)-10,16-tricosadienoyl-sn-glycero-3-phospho-N,N-dimethyl-N-dihydroxypropylethylammonium (n=2)
$C_{33}H_{64}NO_9P$ (649.85)

1340.) 1-(Z,Z)-6,18-tetracosadienoyl-sn-glycero-3-phospho-N,N-dimethyl-N-dihydroxypropylethylammonium (n=2)
$C_{34}H_{66}NO_9P$ (663.87)

1341.) 1-(Z,Z)-10,16-pentacosadienoyl-sn-glycero-3-phospho-N,N-dimethyl-N-dihydroxypropylethylammonium (n=2)
$C_{35}H_{68}NO_9P$ (677.90)

1342.) 1-(Z,Z)-6,18-hexacosadienoyl-sn-glycero-3-phospho-N,N-dimethyl-N-dihydroxypropylethylammonium (n=2)
$C_{36}H_{70}NO_9P$ (691.93)

Alkenyl

1343.) 1-O—(Z)-6-hexadecenyl-sn-glycero-3-phospho-N,N-dimethyl-N-dihydroxypropylethylammonium (n=2)
$C_{26}H_{54}NO_8P$ (539.69)

1344.) 1-O—(Z)-6-octadecenyl-sn-glycero-3-phospho-N,N-dimethyl-N-dihydroxypropylethylammonium (n=2)
$C_{28}H_{58}NO_8P$ (567.74)

1345.) 1-O—(Z)-12-eicosenyl-sn-glycero-3-phospho-N,N-dimethyl-N-dihydroxypropylethylammonium (n=2)
$C_{30}H_{62}NO_8P$ (595.80)

1346.) 1-O—(Z)-10-docosenyl-sn-glycero-3-phospho-N,N-dimethyl-N-dihydroxypropylethylammonium (n=2)
$C_{32}H_{66}NO_8P$ (623.85)

1347.) 1-O—(Z)-10-tetracosenyl-sn-glycero-3-phospho-N,N-dimethyl-N-dihydroxypropylethylammonium (n=2)
$C_{34}H_{70}NO_8P$ (651.91)

1348.) 1-O—(Z)-16-hexacosenyl-sn-glycero-3-phospho-N,N-dimethyl-N-dihydroxypropylethylammonium (n=2)
$C_{36}H_{74}NO_8P$ (679.96)

1349.) 1-O—(Z,Z)-5,11-hexadecadienyl-sn-glycero-3-phospho-N,N-dimethyl-N-dihydroxypropylethylammonium (n=2)
$C_{26}H_{52}NO_8P$ (537.67)

1350.) 1-O—(Z,Z)-5,11-octadecadienyl-sn-glycero-3-phospho-N,N-dimethyl-N-dihydroxypropylethylammonium (n=2)
$C_{28}H_{56}NO_8P$ (565.73)

1351.) 1-O—(Z,Z)-10,16-eicosadienyl-sn-glycero-3-phospho-N,N-dimethyl-N-dihydroxypropylethylammonium (n=2)
$C_{30}H_{60}NO_8P$ (593-78)

1352.) 1-O—(Z,Z)-10,16-docosadienyl-sn-glycero-3-phospho-N,N-dimethyl-N-dihydroxypropylethylammonium (n=2)
$C_{32}H_{64}NO_8P$ (621.84)

1353.) 1-O—(Z,Z)-6,18-tetracosadienyl-sn-glycero-3-phospho-N,N-dimethyl-N-dihydroxypropylethylammonium (n=2)
$C_{34}H_{68}NO_8P$ (649.89)

1354.) 1-O—(Z,Z)-6,18-hexacosadienyl-sn-glycero-3-phospho-N,N-dimethyl-N-dihydroxypropylethylammonium (n=2)
$C_{36}H_{72}NO_6P$ (677.94)
n=3
1355.) 1-(z)-6-hexadecenoyl-sn-glycero-3-phospho-N,N-dimethyl-N-dihydroxypropylpropylammonium (n=3)
$C_{27}H_{54}NO_9P$ (567.70)
1356.) 1-(Z)-10-heptadecenoyl-sn-glycero-3-phospho-N,N-dimethyl-N-dihydroxypropylpropylammonium (n=3)
$C_{28}H_{56}NO_9P$ (581.73)
1357.) 1-(z)-6-octadecenoyl-sn-glycero-3-phospho-N,N-dimethyl-N-dihydroxypropylpropylammonium (n=3)
$C_{29}H_{58}NO_9P$ (595.75)
1358.) 1-(Z)-12-eicosenoyl-sn-glycero-3-phospho-N,N-dimethyl-N-dihydroxypropylpropylammonium (n=3)
$C_{31}H_{62}NO_9P$ (623.81)
1359.) 1-(z)-10-docosenoyl-sn-glycero-3-phospho-N,N-dimethyl-N-dihydroxypropylpropylammonium (n=3)
$C_{33}H_{66}NO_9P$ (651.86)
1360.) 1-(Z)-12-docosenoyl-sn-glycero-3-phospho-N,N-dimethyl-N-dihydroxypropylpropylammonium (n=3)
$C_{33}H_{66}NO_9P$ (651.86)
1361.) 1-(Z)-10-tricosenoyl-sn-glycero-3-phospho-N,N-dimethyl-N-dihydroxypropylpropylammonium (n=3)
$C_{34}H_{68}NO_9P$ (665.89)
1362.) 1-(Z)-10-tetracosenoyl-sn-glycero-3-phospho-N,N-dimethyl-N-dihydroxypropylpropylammonium (n=3)
$C_{35}H_{70}NO_9P$ (679.92)
1363.) 1-(Z,Z)-5,11-hexadecadienoyl-sn-glycero-3-phospho-N,N-dimethyl-N-dihydroxypropylpropylammonium (n=3)
$C_{27}H_{52}NO_9P$ (565.68)
1364.) 1-(Z,Z)-5,11-octadecadienoyl-sn-glycero-3-phospho-N,N-dimethyl-N-dihydroxypropylpropylammonium (n=3)
$C_{29}H_{56}NO_9P$ (593.74)
1365.) 1-(Z,Z)-10,16-eicosadienoyl-sn-glycero-3-phospho-N,N-dimethyl-N-dihydroxypropylpropylammonium (n=3)
$C_{31}H_{60}NO_9P$ (621.79)
1366.) 1-(Z,Z)-10,16-heneicosadienoyl-sn-glycero-3-phospho-N,N-dimethyl-N-dihydroxypropylpropylammonium (n=3)
$C_{32}H_{62}NO_9P$ (635.82)
1367.) 1-(Z,Z)-10,16-docosadienoyl-sn-glycero-3-phospho-N,N-dimethyl-N-dihydroxypropylpropylammonium (n=3)
$C_{33}H_{64}NO_9P$ (649.85)
1368.) 1-(Z,Z)-6,18-tetracosadienoyl-sn-glycero-3-phospho-N,N-dimethyl-N-dihydroxypropylpropylammonium (n=3)
$C_{35}H_{68}NO_9P$ (677.90)
1369.) 1-(Z,Z)-6,18-hexacosadienoyl-sn-glycero-3-phospho-N,N-dimethyl-N-dihydroxypropylpropylammonium (n=3)
$C_{37}H_{72}NO_9P$ (705.95)
1370.) 1-O—(Z)-6-hexadecenyl-sn-glycero-3-phospho-N,N-dimethyl-N-dihydroxypropylpropylammonium (n=3)
$C_{27}H_{56}NO_8P$ (553.72)
1371.) 1-O—(Z)-6-octadecenyl-sn-glycero-3-phospho-N,N-dimethyl-N-dihydroxypropylpropylammonium (n=3)
$C_{29}H_{60}NO_8P$ (581.77)
1372.) 1-O—(Z)-12-eicosenyl-sn-glycero-3-phospho-N,N-dimethyl-N-dihydroxypropylpropylammonium (n=3)
$C_{31}H_{64}NO_8P$ (609.83)
1373.) 1-O—(Z)-10-docosenyl-sn-glycero-3-phospho-N,N-dimethyl-N-dihydroxypropylpropylammonium (n=3)
$C_{33}H_{68}NO_8P$ (637.88)
1374.) 1-O—(Z)-10-tetracosenyl-sn-glycero-3-phospho-N,N-dimethyl-N-dihydroxypropylpropylammonium (n=3)
$C_{35}H_{72}NO_8P$ (665.94)
1375.) 1-O—(Z,Z)-5,11-hexadecadienyl-sn-glycero-3-phospho-N,N-dimethyl-N-dihydroxypropylpropylammonium (n=3)
$C_{27}H_{54}NO_8P$ (551.7)
1376.) 1-O—(Z,Z)-5,11-octadecadienyl-sn-glycero-3-phospho-N,N-dimethyl-N-dihydroxypropylpropylammonium (n=3)
$C_{29}H_{58}NO_8P$ (579.76)
1377.) 1-O—(Z,Z)-10,16-eicosadienyl-sn-glycero-3-phospho-N,N-dimethyl-N-dihydroxypropylpropylammonium (n=3)
$C_{31}H_{62}NO_8P$ (607.81)
1378.) 1-O—(Z,Z)-10,16-docosadienyl-sn-glycero-3-phospho-N,N-dimethyl-N-dihydroxypropylpropylammonium (n=3)
$C_{33}H_{66}NO_8P$ (635.87)
1379.) 1-O—(Z,Z)-6,18-tetracosadienyl-sn-glycero-3-phospho-N,N-dimethyl-N-dihydroxypropylpropylammonium (n=3)
$C_{35}H_{70}NO_8P$ (663.92)
1380.) 1-O—(Z,Z)-6,18-hexacosadienyl-sn-glycero-3-phospho-N,N-dimethyl-N-dihydroxypropylpropylammonium (n=3)
$C_{37}H_{74}NO_8P$ (691.97)
n=4
1381.) 1-(Z)-6-octadecenoyl-sn-glycero-3-phospho-N,N-dimethyl-N-dihydroxypropylbutylammonium (n=4)
$C_{30}H_{60}NO_9P$ (609.78)
1382.) 1-(Z)-10-docosenoyl-sn-glycero-3-phospho-N,N-dimethyl-N-dihydroxypropylbutylammonium (n=4)
$C_{34}H_{68}NO_9P$ (665.89)
1383.) 1-(Z,Z)-5,11-hexadecadienoyl-sn-glycero-3-phospho-N,N-dimethyl-N-dihydroxypropylbutylammonium (n=4)
$C_{28}H_{54}NO_9P$ (579.71)
1384.) 1-(Z,Z)-10,16-docosadienoyl-sn-glycero-3-phospho-N,N-dimethyl-N-dihydroxypropylbutylammonium (n=4)
$C_{34}H_{66}NO_9P$ (663.88)
1385.) 1-(Z,Z)-6,18-hexacosadienoyl-sn-glycero-3-phospho-N,N-dimethyl-N-dihydroxypropylbutylammonium (n=4)
$C_{38}H_{74}NO_9P$ (719.98)
1386.) 1-O—(Z)-6-octadecenyl-sn-glycero-3-phospho-N,N-dimethyl-N-dihydroxypropylbutylammonium (n=4)
$C_{30}H_{62}NO_8P$ (595.80)
1387.) 1-O—(Z)-10-docosenyl-sn-glycero-3-phospho-N,N-dimethyl-N-dihydroxypropylbutylammonium (n=4)
$C_{34}H_{70}NO_8P$ (651.91)
1388.) 1-O—(Z,Z)-5,11-octadecadienyl-sn-glycero-3-phospho-N,N-dimethyl-N-dihydroxypropylbutylammonium (n=4)
$C_{30}H_{60}NO_8P$ (593.78)
1389.) 1-O—(Z)-12-eicosenyl-sn-glycero-3-phospho-N,N-dimethyl-N-dihydroxypropylbutylammonium (n=4)
$C_{32}H_{66}NO_8P$ (623.85)
n=6
1390.) 1-(Z)-6-octadecenoyl-sn-glycero-3-phospho-N,N-dimethyl-N-dihydroxypropylhexylammonium (n=6)
$C_{32}H_{64}NO_9P$ (637.84)

1391.) 1-(Z)-10-docosenoyl-sn-glycero-3-phospho-N,N-dimethyl-N-dihydroxypropylhexylammonium (n=6)
$C_{36}H_{72}NO_9P$ (693.94)

1392.) 1-(Z,Z)-5-hexadecadienoyl-sn-glycero-3-phospho-N,N-dimethyl-N-dihydroxypropylhexylammonium (n=6)
$C_{30}H_{58}NO_9P$ (607.77)

1393.) 1-(Z,Z)-10,16-docosadienoyl-sn-glycero-3-phospho-N,N-dimethyl-N-dihydroxypropylhexylammonium (n=6)
$C_{36}H_{70}NO_9P$ (691.93)

1394.) 1-(Z,Z)-6,18-hexacosadienoyl-sn-glycero-3-phospho-N,N-dimethyl-N-dihydroxypropylhexylammonium (n=6)
$C_{40}H_{78}NO_9P$ (748.03)

1395.) 1-O—(Z)-6-octadecenyl-sn-glycero-3-phospho-N,N-dimethyl-N-dihydroxypropylhexylammonium (n=6)
$C_{32}H_{66}NO_8P$ (623.85)

1396.) 1-O—(Z)-10-docosenyl-sn-glycero-3-phospho-N,N-dimethyl-N-dihydroxypropylhexylammonium (n=6)
$C_{36}H_{74}NO_8P$ (679.96)

1397.) 1-O—(Z,Z)-5,11-octadecadienyl-sn-glycero-3-phospho-N,N-dimethyl-N-dihydroxypropylhexylammonium (n=6)
$C_{32}H_{64}NO_8P$ (621.84)

1398.) 1-O—(Z)-12-eicosenyl-sn-glycero-3-phospho-N,N-dimethyl-N-dihydroxypropylhexylammonium (n=6)
$C_{34}H_{70}NO_8P$ (651.91)

2. Examples of Single-Chain glycero-phospho-N,N-dimethyl-N-(2-hydroxypropyl-3,1-O,O-dihydroxypropyl)alkylammonium Compounds

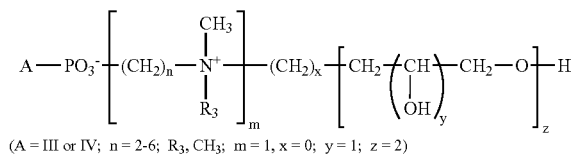

(A = III or IV; n = 2-6; $R_3$, $CH_3$; m = 1, x = 0; y = 1; z = 2)

n=2
1399.) 1-(z)-6-hexadecenoyl-sn-glycero-3-phospho-N,N-dimethyl-N-(2-hydroxypropyl-3,1-O,O-dihydroxypropyl)ethylammonium (n=2)
$C_{28}H_{58}NO_{11}P$ (627.75)

1400.) 1-(Z)-6-nonadecenoyl-sn-glycero-3-phospho-N,N-dimethyl-N-(2-hydroxypropyl-3,1-O,O-dihydroxypropyl)ethylammonium (n=2)
$C_{32}H_{64}NO_{11}P$ (669.83)

1401.) 1-(Z)-10-docosenoyl-sn-glycero-3-phospho-N,N-dimethyl-N-(2-hydroxypropyl-3,1-O,O-dihydroxypropyl)ethylammonium (n=2)
$C_{35}H_{70}NO_{11}P$ (711.91)

1402.) 1-(Z)-12-docosenoyl-sn-glycero-3-phospho-N,N-dimethyl-N-(2-hydroxypropyl-3,1-O,O-dihydroxypropyl)ethylammonium (n=2)
$C_{35}H_{70}NO_{11}P$ (711.91)

1403.) 1-(Z)-10-tetracosenoyl-sn-glycero-3-phospho-N,N-dimethyl-N-(2-hydroxypropyl-3,1-O,O-dihydroxypropyl)ethylammonium (n=2)
$C_{37}H_{74}NO_{11}P$ (739.97)

1404.) 1-(Z)-16-hexacosenoyl-sn-glycero-3-phospho-N,N-dimethyl-N-(2-hydroxypropyl-3,1-O,O-dihydroxypropyl)ethylammonium (n=2)
$C_{39}H_{78}NO_{11}P$ (768.02)

1405.) 1-(Z,Z)-5,11-hexadecadienoyl-sn-glycero-3-phospho-N,N-dimethyl-N-(2-hydroxypropyl-3,1-O,O-dihydroxypropyl)ethylammonium (n=2)
$C_{29}H_{56}NO_{11}P$ (625.74)

1406.) 1-(Z,Z)-5,11-octadecadienoyl-sn-glycero-3-phospho-N,N-dimethyl-N-(2-hydroxypropyl-3,1-O,O-dihydroxypropyl)ethylammonium (n=2)
$C_{31}H_{60}NO_{11}P$ (653.79)

1407.) 1-(Z,Z)-10,16-heneicosadienoyl-sn-glycero-3-phospho-N,N-dimethyl-N-(2-hydroxypropyl-3,1-O,O-dihydroxypropyl)ethylammonium (n=2)
$C_{34}H_{66}NO_{11}P$ (695.87)

1408.) 1-(Z,Z)-10,16-docosadienoyl-sn-glycero-3-phospho-N,N-dimethyl-N-(2-hydroxypropyl-3,1-O,O-dihydroxypropyl)ethylammonium (n=2)
$C_{35}H_{68}NO_{11}P$ (709.90)

1409.) 1-(Z,Z)-6,18-hexacosadienoyl-sn-glycero-3-phospho-N,N-dimethyl-N-(2-hydroxypropyl-3,1-O,O-dihydroxypropyl)ethylammonium (n=2)
$C_{39}H_{76}NO_{11}P$ (766.01)

Alkenyl
1410.) 1-O-(z)-6-octadecenyl-sn-glycero-3-phospho-N,N-dimethyl-N-(2-hydroxypropyl-3,1-O,O-dihydroxypropyl)ethylammonium (n=2)
$C_{31}H_{64}NO_{10}P$ (641.82)

1411.) 1-O—(Z)-12-eicosenyl-sn-glycero-3-phospho-N,N-dimethyl-N-(2-hydroxypropyl-3,1-O,O-dihydroxypropyl)ethylammonium (n=2)
$C_{33}H_{68}NO_{10}P$ (669.88)

1412.) 1-O—(Z)-10-docosenyl-sn-glycero-3-phospho-N,N-dimethyl-N-(2-hydroxypropyl-3,1-O,O-dihydroxypropyl)ethylammonium (n=2)
$C_{35}H_{72}N_{10}P$ (697.93)

1413.) 1-O—(Z)-10-tetracosenyl-sn-glycero-3-phospho-N,N-dimethyl-N-(2-hydroxypropyl-3,1-O,O-dihydroxypropyl)ethylammonium (n=2)
$C_{37}H_{76}N_{10}P$ (725.98)

1414.) 1-O-(z)-16-hexacosenyl-sn-glycero-3-phospho-N,N-dimethyl-N-(2-hydroxypropyl-3,1-O,O-dihydroxypropyl)ethylammonium (n=2)
$C_{39}H_{80}NO_{10}P$ (754.04)

1415.) 1-O—(Z,Z)-5,1-octadecadienyl-sn-glycero-3-phospho-N,N-dimethyl-N-(2-hydroxypropyl-3,1-O,O-dihydroxypropyl)ethylammonium (n=2)
$C_{31}H_{62}NO_{10}P$ (639.81)

1416.) 1-O—(Z,Z)-6,18-tetracosadienyl-sn-glycero-3-phospho-N,N-dimethyl-N-(2-hydroxypropyl-3,1-O,O-dihydroxypropyl)ethylammonium (n=2)
$C_{37}H_{74}NO_{10}P$ (723.97)

1417.) 1-O—(Z,Z)-6,18-hexacosadienyl-sn-glycero-3-phospho-N,N-dimethyl-N-(2-hydroxypropyl-3,1-O,O-dihydroxypropyl)ethylammonium (n=2)
$C_{39}H_{78}NO_{10}P$ (752.04)

n=3
1418.) 1-(Z)-6-octadecenoyl-sn-glycero-3-phospho-N,N-dimethyl-N-(2-hydroxypropyl-3,1-O,O-dihydroxypropyl)propylammonium (n=3)
$C_{32}H_{64}NO_{11}P$ (669.83)

1419.) 1-(Z)-12-eicosenoyl-sn-glycero-3-phospho-N,N-dimethyl-N-(2-hydroxypropyl-3,1-O,O-dihydroxypropyl)propylammonium (n=3)
$C_{34}H_{68}NO_{11}P$ (697.89)

1420.) 1-(Z)-10-docosenoyl-sn-glycero-3-phospho-N,N-dimethyl-N-(2-hydroxypropyl-3,1-O,O-dihydroxypropyl)propylammonium (n=3)
$C_{36}H_{72}NO_{11}P$ (725.94)

1421.) 1-(Z)-12-docosenoyl-sn-glycero-3-phospho-N,N-dimethyl-N-(2-hydroxypropyl-3,1-O,O-dihydroxypropyl)propylammonium (n=3)
$C_{36}H_{72}NO_{11}P$ (725.94)

1422.) 1-(Z)-10-tetracosenoyl-sn-glycero-3-phospho-N,N-dimethyl-N-(2-hydroxypropyl-3,1-O,O-dihydroxypropyl)propylammonium (n=3)
$C_{38}H_{76}NO_{11}P$ (754.0)

1423.) 1-(Z,Z)-5,11-octadecadienoyl-sn-glycero-3-phospho-N,N-dimethyl-N-(2-hydroxypropyl-3,1-O,O-dihydroxypropyl)propylammonium (n=3)
$C_{32}H_{62}NO_{11}P$ (667.83)

1424.) 1-(Z,Z)-10,16-eicosadienoyl-sn-glycero-3-phospho-N,N-dimethyl-N-(2-hydroxypropyl-3,1-O,O-dihydroxypropyl)propylammonium (n=3)
$C_{34}H_{66}NO_{11}P$ (695.89)

1425.) 1-(Z,Z)-10,16-docosadienoyl-sn-glycero-3-phospho-N,N-dimethyl-N-(2-hydroxypropyl-3,1-O,O-dihydroxypropyl)propylammonium (n=3)
$C_{36}H_{70}NO_{11}P$ (723.94)

1426.) 1-(Z,Z)-6,18-tetracosadienoyl-sn-glycero-3-phospho-N,N-dimethyl-N-(2-hydroxypropyl-3,1-O,O-dihydroxypropyl)propylammonium (n=3)
$C_{38}H_{74}NO_{11}P$ (751.98)

1427.) 1-(Z,Z)-6,18-hexacosadienoyl-sn-glycero-3-phospho-N,N-dimethyl-N-(2-hydroxypropyl-3,1-O,O-dihydroxypropyl)propylammonium (n=3)
$C_{40}H_{78}NO_{11}P$ (780.03)

1428.) 1-O-(z)-6-hexadecenyl-sn-glycero-3-phospho-N,N-dimethyl-N-(2-hydroxypropyl-3,1-O,O-dihydroxypropyl)propylammonium (n=3)
$C_{30}H_{62}NO_{10}P$ (627.80)

1429.) 1-O-(z)-10-docosenyl-sn-glycero-3-phospho-N,N-dimethyl-N-(2-hydroxypropyl-3,1-O,O-dihydroxypropyl)propylammonium (n=3)
$C_{36}H_{74}NO_{10}P$ (711.96)

1430.) 1-O—(Z)-10-tetracosenyl-sn-glycero-3-phospho-N,N-dimethyl-N-(2-hydroxypropyl-3,1-O,O-dihydroxypropyl)propylammonium (n=3)
$C_{38}H_{78}NO_{10}P$ (740.01)

1431.) 1-O—(Z,Z)-5,11-hexadecadienyl-sn-glycero-3-phospho-N,N-dimethyl-N-(2-hydroxypropyl-3,1-O,O-dihydroxypropyl)propylammonium (n=3)
$C_{30}H_{60}NO_{10}P$ (625.78)

1432.) 1-O—(Z,Z)-5,11-octadecadienyl-sn-glycero-3-phospho-N,N-dimethyl-N-(2-hydroxypropyl-3,1-O,O-dihydroxypropyl)propylammonium (n=3)
$C_{32}H_{64}NO_{10}P$ (653.83)

1433.) 1-O—(Z,Z)-10,16-eicosadienyl-sn-glycero-3-phospho-N,N-dimethyl-N-(2-hydroxypropyl-3,1-O,O-dihydroxypropyl)propylammonium (n=3)
$C_{34}H_{68}NO_{10}P$ (681.89)

1434.) 1-O—(Z,Z)-6,18-tetracosadienyl-sn-glycero-3-phospho-N,N-dimethyl-N-(2-hydroxypropyl-3,1-O,O-dihydroxypropyl)propylammonium (n=3)
$C_{38}H_{76}NO_{10}P$ (738.0)

1435.) 1-O—(Z,Z)-6,18-hexacosadienyl-sn-glycero-3-phospho-N,N-dimethyl-N-(2-hydroxypropyl-3,1-O,O-dihydroxypropyl)propylammonium (n=3)
$C_{40}H_{80}NO_{10}P$ (766.05)

n=4
1436.) 1-(Z)-6-octadecenoyl-sn-glycero-3-phospho-N,N-dimethyl-N-(2-hydroxypropyl-3,1-O,O-dihydroxypropyl)butylammonium (n=4)
$C_{33}H_{66}NO_{11}P$ (683.86)

1437.) 1-(Z)-6-docosenoyl-sn-glycero-3-phospho-N,N-dimethyl-N-(2-hydroxypropyl-3,1-O,O-dihydroxypropyl)butylammonium (n=4)
$C_{37}H_{74}NO_{11}P$ (739.97)

1438.) 1-(Z,Z)-5,11-hexadecadienoyl-sn-glycero-3-phospho-N,N-dimethyl-N-(2-hydroxypropyl-3,1-O,O-dihydroxypropyl)butylammonium (n=4)
$C_{31}H_{60}NO_{11}P$ (653.79)

1439.) 1-(Z,Z)-10,16-docosadienoyl-sn-glycero-3-phospho-N,N-dimethyl-N-(2-hydroxypropyl-3,1-O,O-dihydroxypropyl)butylammonium (n=4)
$C_{37}H_{72}NO_{11}P$ (737.95)

1440.) 1-(Z,Z)-6,18-hexacosadienoyl-sn-glycero-3-phospho-N,N-dimethyl-N-(2-hydroxypropyl-3,1-O,O-dihydroxypropyl)butylammonium (n=4)
$C_{41}H_{80}NO_{11}P$ (794.06)

1441.) 1-O—(Z)-6-octadecenyl-sn-glycero-3-phospho-N,N-dimethyl-N-(2-hydroxypropyl-3,1-O,O-dihydroxypropyl)butylammonium (n=4)
$C_{33}H_{68}NO_{10}P$ (669.88)

1442.) 1-O—(Z)-10-docosenyl-sn-glycero-3-phospho-N,N-dimethyl-N-(2-hydroxypropyl-3,1-O,O-dihydroxypropyl)butylammonium (n=4)
$C_{37}H_{76}NO_{10}P$ (725.98)

1443.) 1-O—(Z,Z)-5,11-octadecadienyl-sn-glycero-3-phospho-N,N-dimethyl-N-(2-hydroxypropyl-3,1-O,O-dihydroxypropyl)butylammonium (n=4)
$C_{33}H_{66}NO_{10}P$ (667.86)

1444.) 1-O—(Z)-12-eicosenyl-sn-glycero-3-phospho-N,N-dimethyl-N-(2-hydroxypropyl-3,1-O,O-dihydroxypropyl)butylammonium (n=4)
$C_{35}H_{72}NO_{10}P$ (697.93)

n=6
1445.) 1-(z)-6-octadecenoyl-sn-glycero-3-phospho-N,N-dimethyl-N-(2-hydroxypropyl-3,1-O,O-dihydroxypropyl)hexylammonium (n=6)
$C_{35}H_{70}NO_{11}P$ (711.91)

1446.) 1-(z)-10-docosenoyl-sn-glycero-3-phospho-N,N-dimethyl-N-(2-hydroxypropyl-3,1-O,O-dihydroxypropyl)hexylammonium (n=6)
$C_{39}H_{78}NO_{11}P$ (768.02)

1447.) 1-(Z,Z)-5,11-hexadecadienoyl-sn-glycero-3-phospho-N,N-dimethyl-N-(2-hydroxypropyl-3,1-O,O-dihydroxypropyl)hexylammonium (n=6)
$C_{33}H_{64}NO_{11}P$ (681.85)

1448.) 1-(Z,Z)-10,16-docosadienoyl-sn-glycero-3-phospho-N,N-dimethyl-N-(2-hydroxypropyl-3,1-O,O-dihydroxypropyl)hexylammonium (n=6)
$C_{39}H_{76}NO_{11}P$ (766.01)

1449.) 1-(Z,Z)-6,18-hexacosadienoyl-sn-glycero-3-phospho-N,N-dimethyl-N-(2-hydroxypropyl-3,1-O,O-dihydroxypropyl)hexylammonium (n=6)
$C_{43}H_{84}NO_{11}P$ (822.11)

1450.) 1-O—(Z)-6-octadecenyl-sn-glycero-3-phospho-N,N-dimethyl-N-(2-hydroxypropyl-3,1-O,O-dihydroxypropyl)hexylammonium (n=6)
$C_{35}H_{72}NO_{10}P$ (697.93)

1451.) 1-O—(Z)-10-docosenyl-sn-glycero-3-phospho-N,N-dimethyl-N-(2-hydroxypropyl-3,1-O,O-dihydroxypropyl)hexylammonium (n=6)
$C_{39}H_{80}NO_{10}P$ (754.04)

1452.) 1-O—(Z,Z)-5,11-octadecadienyl-sn-glycero-3-phospho-N,N-dimethyl-N-(2-hydroxypropyl-3,1-O,O-dihydroxypropyl)hexylammonium (n=6)
$C_{35}H_{70}NO_{10}P$ (695.92)

1453.) 1-O—(Z)-12-eicosenyl-sn-glycero-3-phospho-N,N-dimethyl-N-(2-hydroxypropyl-3,1-O,O-dihydroxypropyl)hexylammonium (n=6)
$C_{37}H_{76}NO_{10}P$ (725.98)

3. Examples of Single-Chain glycero-phospho-N,N-dimethyl-N-(2-hydroxypropyl-3,1-O,O-2-hydroxypropyl-3,1-O,O-dihydroxypropyl)alkylammonium Compounds

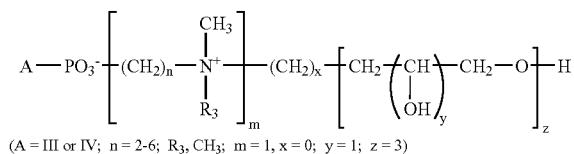

(A = III or IV; n = 2-6; $R_3$, $CH_3$; m = 1, x = 0; y = 1; z = 3)

In the following text, N-(2-hydroxypropyl-3,1-O,O-2-hydroxypropyl-3,1-O,O-dihydroxypropyl) is abbreviated to N—($HP_1$—$HP_2$-di$HP_3$)

n=2

1454.) 1-(Z)-6-hexadecenoyl-sn-glycero-3-phospho-N,N-dimethyl-N—($HP_1$—$HP_2$-di$HP_3$)ethylammonium (n=2)
$C_{32}H_{64}NO_{13}P$ (701.83)

1455.) 1-(Z)-6-nonadecenoyl-sn-glycero-3-phospho-N,N-dimethyl-N—($HP_1$—$HP_2$-di$HP_3$)ethylammonium (n=2)
$C_{35}H_{70}NO_{13}P$ (743.91)

1456.) 1-(Z)-10-docosenoyl-sn-glycero-3-phospho-N,N-dimethyl-N—($HP_1$—$HP_2$-di$HP_3$)ethylammonium (n=2)
$C_{38}H_{76}NO_{13}P$ (785.99)

1457.) 1-(Z)-12-docosenoyl-sn-glycero-3-phospho-N,N-dimethyl-N—($HP_1$—$HP_2$-di$HP_3$)ethylammonium (n=2)
$C_{38}H_{76}NO_{13}P$ (785.99)

1458.) 1-(Z)-16-hexacosenoyl-sn-glycero-3-phospho-N,N-dimethyl-N—($HP_1$—$HP_2$-di$HP_3$)ethylammonium (n=2)
$C_{42}H_{84}NO_{13}P$ (842.10)

1459.) 1-(Z,Z)-5,11-hexadecadienoyl-sn-glycero-3-phospho-N,N-dimethyl-N—($HP_1$—$HP_2$-di$HP_3$) ethylammonium (n=2)
$C_{32}H_{62}NO_{13}P$ (699.82)

1460.) 1-(Z,Z)-5,11-octadecadienoyl-sn-glycero-3-phospho-N,N-dimethyl-N—($HP_1$—$HP_2$-di$HP_3$) ethylammonium (n=2)
$C_{34}H_{66}NO_{13}P$ (727.87)

1461.) 1-(Z,Z)-10,16-docosadienoyl-sn-glycero-3-phospho-N,N-dimethyl-N—($HP_1$—$HP_2$-di$HP_3$) ethylammonium (n=2)
$C_{38}H_{74}NO_{13}P$ (783.98)

1462.) 1-(Z,Z)-6,18-hexacosadienoyl-sn-glycero-3-phospho-N,N-dimethyl-N—($HP_1$—$HP_2$-di$HP_3$) ethylammonium (n=2)
$C_{42}H_{82}NO_{13}P$ (840.09)

Alkenyl

1463.) 1-O—(Z)-6-octadecenyl-sn-glycero-3-phospho-N,N-dimethyl-N—($HP_1$—$HP_2$-di$HP_3$)ethylammonium (n=2)
$C_{34}H_{70}NO_{12}P$ (715.90)

1464.) 1-O—(Z)-12-eicosenyl-sn-glycero-3-phospho-N,N-dimethyl-N—($HP_1$—$HP_2$-di$HP_3$)ethylammonium (n=2)
$C_{36}H_{74}NO_{12}P$ (743.96)

1465.) 1-O—(Z)-10-docosenyl-sn-glycero-3-phospho-N,N-dimethyl-N—($HP_1$—$HP_2$-di$HP_3$)ethylammonium (n=2)
$C_{38}H_{78}NO_{12}P$ (772.01)

1466.) 1-O—(Z)-16-hexacosenyl-sn-glycero-3-phospho-N,N-dimethyl-N—($HP_1$—$HP_2$-di$HP_3$) ethylammonium (n=2)
$C_{42}H_{86}NO_{12}P$ (828.12)

1467.) 1-O—(Z,Z)-5,11-octadecadienyl-sn-glycero-3-phospho-N,N-dimethyl-N—($HP_1$—$HP_2$-di$HP_3$) ethylammonium (n=2)
$C_{34}H_{68}NO_{12}P$ (713.89)

1468.) 1-O—(Z,Z)-6,18-hexacosadienyl-sn-glycero-3-phospho-N,N-dimethyl-N—($HP_1$—$HP_2$-di$HP_3$) ethylammonium (n=2)
$C_{42}H_{84}NO_{12}P$ (826.10)

n=3

1469.) 1-(Z)-6-octadecenoyl-sn-glycero-3-phospho-N,N-dimethyl-N—($HP_1$—$HP_2$-di$HP_3$)propylammonium (n=3)
$C_{35}H_{70}NO_{13}P$ (743.91)

1470.) 1-(Z)-10-docosenoyl-sn-glycero-3-phospho-N,N-dimethyl-N—($HP_1$—$HP_2$-di$HP_3$)propylammonium (n=3)
$C_{39}H_{78}NO_{13}P$ (800.02)

1471.) 1-(Z)-10-tetracosenoyl-sn-glycero-3-phospho-N,N-dimethyl-N—($HP_1$—$HP_2$-di$HP_3$)propylammonium (n=3)
$C_{41}H_{82}NO_{13}P$ (828.07)

1472.) 1-(Z,Z)-5,11-octadecadienoyl-sn-glycero-3-phospho-N,N-dimethyl-N—($HP_1$—$HP_2$-di$HP_3$)propylammonium (n=3)
$C_{35}H_{68}NO_{13}P$ (741.90)

1473.) 1-(Z,Z)-10,16-eicosadienoyl-sn-glycero-3-phospho-N,N-dimethyl-N—($HP_1$—$HP_2$-di$HP_3$)propylammonium (n=3)
$C_{37}H_{72}NO_{13}P$ (769.95)

1474.) 1-(Z,Z)-10,16-docosadienoyl-sn-glycero-3-phospho-N,N-dimethyl-N—($HP_1$—$HP_2$-di$HP_3$) propylammonium (n=3)
$C_{39}H_{76}NO_{13}P$ (798.01)

1475.) 1-(Z,Z)-6,18-hexacosadienoyl-sn-glycero-3-phospho-N,N-dimethyl-N—($HP_1$—$HP_2$-di$HP_3$)propylammonium (n=3)
$C_{43}H_{84}NO_{13}P$ (854.11)

1476.) 1-O—(Z)-10-docosenyl-sn-glycero-3-phospho-N,N-dimethyl-N—($HP_1$—$HP_2$-di$HP_3$)propylammonium (n=3)
$C_{39}H_{80}NO_{12}P$ (786.04)

1477.) 1-O-(z)-10-tetracosenyl-sn-glycero-3-phospho-N,N-dimethyl-N—($HP_1$—$HP_2$-di$HP_3$) propylammonium (n=3)
$C_{41}H_{84}NO_{12}P$ (814.09)

1478.) 1-O—(Z,Z)-10,16-eicosadienyl-sn-glycero-3-phospho-N,N-dimethyl-N—($HP_1$—$HP_2$-di$HP_3$)propylammonium (n=3)
$C_{37}H_{74}NO_{12}P$ (812.08)

1479.) 1-O—(Z,Z)-6,18-tetracosadienyl-sn-glycero-3-phospho-N,N-dimethyl-N—($HP_1$—$HP_2$-di$HP_3$) propylammonium (n=3)
$C_{41}H_{82}NO_{12}P$ (812.08)

1480.) 1-O—(Z,Z)-6,18-hexacosadienyl-sn-glycero-3-phospho-N,N-dimethyl-N—($HP_1$—$HP_2$-di$HP_3$)propyl-1-ammonium (n=3)
$C_{43}H_{86}NO_{12}P$ (840.13)

n=4

1481.) 1-(Z)-10-docosenoyl-sn-glycero-3-phospho-N,N-dimethyl-N—($HP_1$—$HP_2$-di$HP_3$)butylammonium (n=4)
$C_{40}H_{80}NO_{13}P$ (814.05)

1482.) 1-(Z,Z)-10,16-docosadienoyl-sn-glycero-3-phospho-N,N-dimethyl-N—($HP_1$—$HP_2$-di$HP_3$) butylammonium (n=4)
$C_{40}H_{78}NO_{13}P$ (812.03)

1483.) 1-(Z,Z)-6,18-hexacosadienoyl-sn-glycero-3-phospho-N,N-dimethyl-N—(HP$_1$—HP$_2$-diHP$_3$) butylammonium (n=4)
$C_{44}H_{86}NO_{13}P$ (868.14)

1484.) 1-O—(Z)-6-octadecenyl-sn-glycero-3-phospho-N,N-dimethyl-N—(HP$_1$—HP$_2$-diHP$_3$)butylammonium (n=4)
$C_{36}H_{74}NO_{12}P$ (743.96)

1485.) 1-O—(Z)-10-docosenyl-sn-glycero-3-phospho-N,N-dimethyl-N—(HP$_1$—HP$_2$-diHP$_3$)butylammonium (n=4)
$C_{40}H_{82}NO_{12}P$ (800.06)

1486.) 1-O—(Z,Z)-5,11-octadecadienyl-sn-glycero-3-phospho-N,N-dimethyl-N—(HP$_1$—HP$_2$-diHP$_3$) butylammonium (n=4)
$C_{36}H_{72}NO_{12}P$ (741.94)

1487.) 1-O—(Z)-12-eicosenyl-sn-glycero-3-phospho-N,N-dimethyl-N—(HP$_1$—HP$_2$-diHP$_3$)butylammonium (n=4)
$C_{38}H_{78}NO_{12}P$ (772.01)

n=6

1488.) 1-(Z)-6-octadecenoyl-sn-glycero-3-phospho-N,N-dimethyl-N—(HP$_1$—HP$_2$-diHP$_3$)hexylammonium (n=6)
$C_{38}H_{76}NO_{13}P$ (785.99)

1489.) 1-(Z)-10-docosenoyl-sn-glycero-3-phospho-N,N-dimethyl-N—(HP$_1$—HP$_2$-diHP$_3$)hexylammonium (n=6)
$C_{42}H_{84}NO_{13}P$ (842.10)

1490.) 1-(Z,Z)-5,11-hexadecadienoyl-sn-glycero-3-phospho-N,N-dimethyl-N—(HP$_1$—HP$_2$-diHP$_3$)hexylammonium (n=6)
$C_{36}H_{70}NO_{13}P$ (755.92)

1491.) 1-(Z,Z)-10,16-docosadienoyl-sn-glycero-3-phospho-N,N-dimethyl-N—(HP$_1$—HP$_2$-diHP$_3$) hexylammonium (n=6)
$C_{42}H_{82}NO_{13}P$ (840.09)

1492.) 1-(Z,Z)-6,18-hexacosadienoyl-sn-glycero-3-phospho-N,N-dimethyl-N—(HP$_1$—HP$_2$-diHP$_3$)hexylammonium (n=6)
$C_{46}H_{90}NO_{13}P$ (896.19)

1493.) 1-O—(Z)-6-octadecenyl-sn-glycero-3-phospho-N,N-dimethyl-N—(HP$_1$—HP$_2$-diHP$_3$)hexylammonium (n=6)
$C_{38}H_{78}NO_{12}P$ (772.01)

1494.) 1-O—(Z)-10-docosenyl-sn-glycero-3-phospho-N,N-dimethyl-N—(HP$_1$—HP$_2$-diHP$_3$)hexylammonium (n=6)
$C_{42}H_{86}NO_{12}P$ (828.12)

1495.) 1-O—(Z,Z)-5,11-octadecadienyl-sn-glycero-3-phospho-N,N-dimethyl-N—(HP$_1$—HP$_2$-diHP$_3$)hexylammonium (n=6)
$C_{38}H_{76}NO_{12}P$ (769.99)

1496.) 1-O-(z)-12-eicosenyl-sn-glycero-3-phospho-N,N-dimethyl-N—(HP$_1$—HP$_2$-diHP$_3$)hexylammonium (n=6)
$C_{40}H_{82}NO_{12}P$ (800.06)

4. Examples of Single-Chain glycero-phospho Compounds not Hydroxylated on the Nitrogen $$A-PO_3^- \left[ (CH_2)_n - \underset{R_3}{\underset{|}{\overset{CH_3}{\overset{|}{N^+}}}} \right]_m (CH_2)_x \left[ CH_2 \underset{y}{\left(\underset{OH}{\overset{|}{CH}}\right)} CH_2 - O \right]_z H$$

(A = III; n = 2-6; R$_3$, CH$_3$; m = 1, x = 1; z = 0)

1497.) 1-(Z)-6-octadecenoyl-sn-glycero-3-phospho-N,N,N-trimethylpropylammonium (n=3)
$C_{27}H_{54}NO_7P$ (535.70)

1498.) 1-(Z)-10-docosenoyl-sn-glycero-3-phospho-N,N,N-trimethylpropylammonium (n=3)
$C_{31}H_{62}NO_7P$ (591.81)

1499.) 1-(Z)-10-tetracosenoyl-sn-glycero-3-phospho-N,N,N-trimethylpropylammonium (n=3)
$C_{33}H_{66}NO_7P$ (619.86)

1500). 1-(Z,Z)-5,11-octadecadienoyl-sn-glycero-3-phospho-N,N,N-trimethylpropylammonium (n=3)
$C_{27}H_{52}NO_7P$ (533.69)

1501). 1-(Z,Z)-10,16-eicosadienoyl-sn-glycero-3-phospho-N,N,N-trimethylpropylammonium (n=3)
$C_{29}H_{56}NO_7P$ (561.74)

1502). 1-(Z,Z)-10,16-docosadienoyl-sn-glycero-3-phospho-N,N,N-trimethylpropylammonium (n=3)
$C_{31}H_{60}NO_7P$ (589.79)

1503). 1-(Z,Z)-6,18-hexacosadienoyl-sn-glycero-3-phospho-N,N,N-trimethylpropylammonium (n=3)
$C_{35}H_{68}NO_7P$ (645.90)

1504.) 1-O—(Z)-10-docosenyl-sn-glycero-3-phospho-N,N,N-trimethylpropylammonium (n=3)
$C_{31}H_{64}NO_6P$ (577.83)

1505.) 1-O-(z)-10-tetracosenyl-sn-glycero-3-phospho-N,N,N-trimethylpropylammonium (n=3)
$C_{33}H_{68}NO_6P$ (605.88)

1506.) 1-O—(Z,Z)-10,16-eicosadienyl-sn-glycero-3-phospho-N,N,N-trimethylpropylammonium (n=3)
$C_{29}H_{58}NO_6P$ (547.76)

1507.) 1-O—(Z,Z)-6,18-tetracosadienyl-sn-glycero-3-phospho-N,N,N-trimethylpropylammonium (n=3)
$C_{33}H_{66}NO_6P$ (603.86)

1508.) 1-O—(Z,Z)-6,18-hexacosadienyl-sn-glycero-3-phospho-N,N,N-trimethylpropylammonium (n=3)
$C_{35}H_{70}NO_6P$ (631.92)

5. Examples of ω,ω'-alkanediol-phospho-N,N-dimethyl-N-dihydroxypropylalkylammonium Compounds

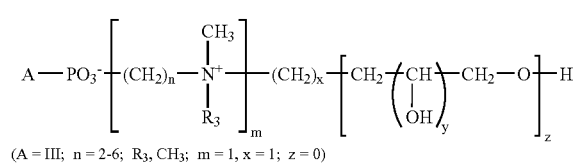

(A = V; n = 2-6; R$_3$, CH$_3$; m = 1, x = 0; y = 1; z = 1)

1509.) 1-(Z)-10-docosenoyl-ethyleneglycol-phospho-N,N-dimethyl-N-dihydroxypropylethylammonium (n=2)
$C_{31}H_{62}NO_8P$ (607.81)

1510.) 1-(Z)-6-octadecenoyl-propanediol-(1,3)-phospho-N,N-dimethyl-N-dihydroxypropylethylammonium (n=2)
$C_{28}H_{56}NO_8P$ (565.73)

1511.) 1-(Z)-10-docosenoyl-propanediol-(1,3)-phospho-N,N-dimethyl-N-dihydroxypropylethylammonium (n=2)
$C_{32}H_{64}NO_8P$ (621.84)

1512.) 1-(Z)-10-tetracosenoyl-propanediol-(1,3)-phospho-N,N-dimethyl-N-dihydroxypropylethylammonium (n=2)
$C_{34}H_{68}NO_8P$ (649.89)

1513.) 1-(Z,Z)-5,11-octadecadienoyl-propanediol-(1,3)-phospho-N,N-dimethyl-N-dihydroxypropylethylammonium (n=2)
$C_{28}H_{54}NO_8P$ (563.71)

1514.) 1-(Z,Z)-10,16-eicosadienoyl-propanediol-(1,3)-phospho-N,N-dimethyl-N-dihydroxypropylethylammonium (n=2)
$C_{30}H_{58}NO_8P$ (591.77)

1515.) 1-(Z,Z)-10,16-docosadienoyl-propanediol-(1,3)-phospho-N,N-dimethyl-N-dihydroxypropylethylammonium (n=2)
$C_{32}H_{62}NO_8P$ (619.82)
1516.) 1-(Z,Z)-6,18-hexacosadienoyl-propanediol-(1,3)-phospho-N,N-dimethyl-N-dihydroxypropylethylammonium (n=2)
$C_{36}H_{70}NO_8P$ (675.93)
1517.) 1-(Z)-10-docosenoyl-propanediol-(1,3)-phospho-N,N-dimethyl-N-dihydroxypropylpropylammonium (n=3)
$C_{33}H_{66}NO_8P$ (635.86)
1518.) 1-(Z)-10-docosenoyl-propanediol-(1,3)-phospho-N,N-dimethyl-N-dihydroxypropylbutylammonium (n=4)
$C_{34}H_{68}NO_8P$ (649.89)

6. Examples of alkanediol-(1,2)-phospho-N,N-dimethyl-N-dihydroxypropylalkylammonium Compounds

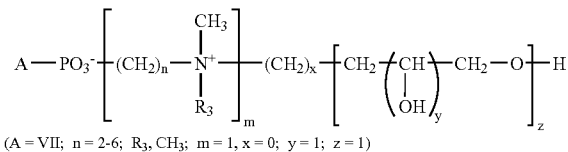

(A = VII; n = 2-6; $R_3$, $CH_3$; m = 1, x = 0; y = 1; z = 1)

1519.) 2-(Z)-10-docosenoyl-propanediol-(1,2)-phospho-N,N-dimethyl-N-dihydroxypropylethylammonium (n=2)
$C_{32}H_{64}NO_8P$ (621.84)
1520.) 1-(Z)-10-docosenoyl-propanediol-(1,2)-phospho-N,N-dimethyl-N-dihydroxypropylethylammonium (n=2)
$C_{32}H_{64}NO_8P$ (621.84)
1521.) 2-(Z)-10-docosenoyl-propanediol-(1,2)-phospho-N,N-dimethyl-N-dihydroxypropylpropylammonium (n=3)
$C_{33}H_{66}NO_8P$ (635.86)
1522.) 1-(Z)-10-docosenoyl-propanediol-(1,2)-phospho-N,N-dimethyl-N-dihydroxypropylbutylammonium (n=4)
$C_{34}H_{68}NO_7P$ (649.89)

7. Examples of ω,ω-alkanediol-phospho-N,N-dimethyl-N-(2-hydroxypropyl-3,1-O,O-dihydroxypropyl)alkylammonium Compounds A—PO$_3^-$—[(CH$_2$)$_n$—N$^+$(CH$_3$)(R$_3$)—]$_m$(CH$_2$)$_x$—[CH$_2$—CH(OH)—CH$_2$—O]$_y$—H]$_z$ (A = V; n = 2-6; $R_3$, $CH_3$; m = 1, x = 0; y = 1; z = 2)

1523.) 1-(Z)-10-docosenoyl-ethyleneglycol-phospho-N,N-dimethyl-N-(2-hydroxypropyl-3,1-O,O-dihydroxypropyl)ethylammonium (n=2)
$C_{34}H_{68}NO_{10}P$ (681.89)
1524.) 1-(Z)-6-octadecenoyl-propanediol-(1,3)-phospho-N,N-dimethyl-N-(2-hydroxypropyl-3,1-O,O-dihydroxypropyl)ethylammonium (n=2)
$C_{31}H_{62}NO_{10}P$ (639.81)
1525.) 1-(Z)-10-docosenoyl-propanediol-(1,3)-phospho-N,N-dimethyl-N-(2-hydroxypropyl-3,1-O,O-dihydroxypropyl)ethylammonium (n=2)
$C_{35}H_{70}NO_{10}P$ (695.92)
1526.) 1-(Z)-10-tetracosenoyl-propanediol-(1,3)-phospho-N,N-dimethyl-N-(2-hydroxypropyl-3,1-O,O-dihydroxypropyl)ethylammonium (n=2)
$C_{37}H_{74}NO_{10}P$ (723.97)
1527.) 1-(Z,Z)-5,11-octadecadienoyl-propanediol-(1,3)-phospho-N,N-dimethyl-N-(2-hydroxypropyl-3,1-O,O-dihydroxypropyl)ethylammonium (n=2)
$C_{31}H_{60}NO_{10}P$ (637.79)
1528.) 1-(Z,Z)-10,16-eicosadienoyl-propanediol-(1,3)-phospho-N,N-dimethyl-N-(2-hydroxypropyl-3,1-O,O-dihydroxypropyl)ethylammonium (n=2)
$C_{33}H_{64}NO_{10}P$ (665.85)
1529.) 1-(Z,Z)-10,16-docosadienoyl-propanediol-(1,3)-phospho-N,N-dimethyl-N-(2-hydroxypropyl-3,1-O,O-dihydroxypropyl)ethylammonium (n=2)
$C_{35}H_{68}NO_{10}P$ (693.90)
1530.) 1-(Z,Z)-6,18-hexacosadienoyl-propanediol-(1,3)-phospho-N,N-dimethyl-N-(2-hydroxypropyl-3,1-O,O-dihydroxypropyl)ethylammonium (n=2)
$C_{39}H_{76}NO_{10}P$ (750.01)
1531.) 1-(Z)-10-docosenoyl-propanediol-(1,3)-phospho-N,N-dimethyl-N-(2-hydroxypropyl-3,1-O,O-dihydroxypropyl)propylammonium (n=3)
$C_{36}H_{72}NO_{10}P$ (709.94)
1532.) 1-(Z)-10-docosenoyl-propanediol-(1,3)-phospho-N,N-dimethyl-N-(2-hydroxypropyl-3,1-O,O-dihydroxypropyl)butylammonium (n=4)
$C_{37}H_{74}NO_{10}P$ (723.96)
1533.) 1-(Z)-10-docosenoyl-butanediol-(1,4)-phospho-N,N-dimethyl-N-(2-hydroxypropyl-3,1-O,O-dihydroxypropyl)propylammonium (n=3)
$C_{37}H_{74}NO_{10}P$ (723.96)
1534.) 1-(Z)-10-docosenoyl-hexanediol-(1,6)-phospho-N,N-dimethyl-N-(2-hydroxypropyl-3,1-O,O-dihydroxypropyl)propylammonium (n=3)
$C_{39}H_{78}NO_{10}P$ (752.02)
1535.) 1-(Z)-10-docosenoyl-octanediol-(1,8)-phospho-N,N-dimethyl-N-(2-hydroxypropyl-3,1-O,O-dihydroxypropyl)propylammonium (n=3)
$C_{41}H_{82}NO_{10}P$ (780.07)

8. Examples of alkanediol-(1,2)-phospho-N,N-dimethyl-N-(2-hydroxypropyl-3,1-O,O-dihydroxypropyl)alkylammonium Compounds A—PO$_3^-$—[(CH$_2$)$_n$—N$^+$(CH$_3$)(R$_3$)—]$_m$(CH$_2$)$_x$—[CH$_2$—CH(OH)—CH$_2$—O]$_y$—H]$_z$ (A = VII; n = 2-6; $R_3$, $CH_3$; m = 1, x = 0; y = 1; z = 2)

1536.) 2-(Z)-10-docosenoyl-propanediol-(1,2)-phospho-N,N-dimethyl-N-(2-hydroxypropyl-3,1-O,O-dihydroxypropyl)ethylammonium (n=2)
$C_{35}H_{70}NO_{10}P$ (695.91)
1537.) 1-(Z)-10-docosenoyl-propanediol-(1,2)-phospho-N,N-dimethyl-N-(2-hydroxypropyl-3,1-O,O-dihydroxypropyl)ethylammonium (n=2)
$C_{35}H_{70}NO_{10}P$ (695.91)
1538.) 2-(Z)-10-docosenoyl-propanediol-(1,2)-phospho-N,N-dimethyl-N-(2-hydroxypropyl-3,1-O,O-dihydroxypropyl)propylammonium (n=3)
$C_{36}H_{72}NO_{10}P$ (709.94)

1539.) 1-(Z)-10-docosenoyl-propanediol-(1,2)-phospho-N,N-dimethyl-N-(2-hydroxypropyl-3,1-O,O-dihydroxypropyl)butylammonium (n=4)
$C_{37}H_{74}NO_{10}P$ (723.97)

1540.) 1-(Z)-10-docosenoyl-butanediol-(1,2)-phospho-N,N-dimethyl-N-(2-hydroxypropyl-3,1-O,O-dihydroxypropyl)propylammonium (n=3)
$C_{37}H_{74}NO_{10}P$ (723.97)

1541.) 1-(Z)-10-docosenoyl-hexanediol-(1,2)-phospho-N,N-dimethyl-N-(2-hydroxypropyl-3,1-O,O-dihydroxypropyl)propylammonium (n=3)
$C_{39}H_{74}NO_{10}P$ (752.02)

1542.) 1-(Z)-10-docosenoyl-octanediol-(1,2)-phospho-N,N-dimethyl-N-(2-hydroxypropyl-3,1-O,O-dihydroxypropyl)propylammonium (n=3)
$C_{41}H_{82}NO_{10}P$ (780.07)

9. Examples of ω,ω'-alkanediol-phospho-N,N-dimethyl-N-(2-hydroxypropyl-3,1-O,O-2-hydroxypropyl-3,1-O,O-dihydroxypropyl)alkylammonium Compounds

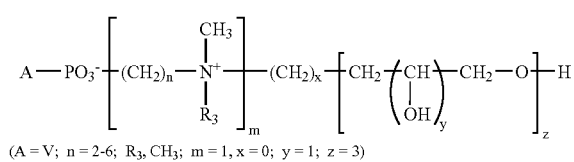

(A = V; n = 2-6; $R_3$, $CH_3$; m = 1, x = 0; y = 1; z = 3)

1543.) 1-(Z)-10-docosenoyl-ethyleneglycol-phospho-N,N-dimethyl-N—($HP_1$—$HP_2$-di$HP_3$)ethylammonium (n=2)
$C_{37}H_{74}NO_{12}P$ (755.97)

1544.) 1-(Z)-6-octadecenoyl-propanediol-(1,3)-phospho-N,N-dimethyl-N—($HP_1$—$HP_2$-di$HP_3$) ethylammonium (n=2)
$C_{34}H_{68}NO_{12}P$ (713.89)

1545.) 1-(Z)-10-docosenoyl-propanediol-(1,3)-phospho-N,N-dimethyl-N—($HP_1$—$HP_2$-di$HP_3$) ethylammonium (n=2)
$C_{38}H_{76}NO_{12}P$ (769.99)

1546.) 1-(Z)-10-tetracosenoyl-propanediol-(1,3)-phospho-N,N-dimethyl-N—($HP_1$—$HP_2$-di$HP_3$) ethylammonium (n=2)
$C_{40}H_{80}NO_{12}P$ (798.05)

1547.) 1-(Z,Z)-5,11-octadecadienoyl-propanediol-(1,3)-phospho-N,N-dimethyl-N—($HP_1$—$HP_2$-di$HP_3$)ethylammonium (n=2)
$C_{34}H_{66}NO_{12}P$ (711.89)

1548.) 1-(Z,Z)-10,16-eicosadienoyl-propanediol-(1,3)-phospho-N,N-dimethyl-N—($HP_1$—$HP_2$-di$HP_3$) ethylammonium (n=2)
$C_{36}H_{70}NO_{12}P$ (739.93)

1549.) 1-(Z,Z)-10,16-docosadienoyl-propanediol-(1,3)-phospho-N,N-dimethyl-N—($HP_1$—$HP_2$-di$HP_3$) ethylammonium (n=2)
$C_{38}H_{74}NO_{12}P$ (767.98)

1550.) 1-(Z,Z)-6,18-hexacosadienoyl-propanediol-(1,3)-phospho-N,N-dimethyl-N—($HP_1$—$HP_2$-di$HP_3$) ethylammonium (n=2)
$C_{42}H_{82}NO_{12}P$ (824.09)

1551.) 1-(Z)-10-docosenoyl-propanediol-(1,3)-phospho-N,N-dimethyl-N—($HP_1$—$HP_2$-di$HP_3$) propylammonium (n=3)
$C_{39}H_{78}NO_{12}P$ (784.01)

1552.) 1-(Z)-10-docosenoyl-propanediol-(1,3)-phospho-N,N-dimethyl-N—($HP_1$—$HP_2$-di$HP_3$) butylammonium (n=4)
$C_{40}H_{80}NO_{12}P$ (798.04)

1553.) 1-(Z)-10-docosenoyl-butanediol-(1,4)-phospho-N,N-dimethyl-N—($HP_1$—$HP_2$-di$HP_3$) propylammonium (n=3)
$C_{40}H_{80}NO_{12}P$ (798.04)

1554.) 1-(Z)-10-docosenoyl-hexanediol-(1,6)-phospho-N,N-dimethyl-N—($HP_1$—$HP_2$-di$HP_3$) propylammonium (n=3)
$C_{42}H_{84}NO_{12}P$ (826.10)

1555.) 1-(z)-10-docosenoyl-octanediol-(1,8)-phospho-N,N-dimethyl-N—($HP_1$—$HP_2$-di$HP_3$) propylammonium (n=3)
$C_{44}H_{88}NO_{12}P$ (854.16)

10. Examples of alkanediol-phospho Compounds not Hydroxylated on the Nitrogen

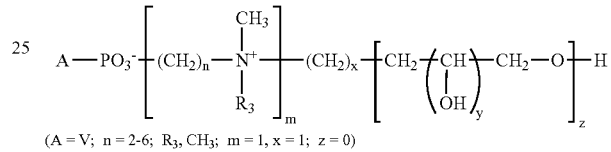

(A = V; n = 2-6; $R_3$, $CH_3$; m = 1, x = 1; z = 0)

1556.) 1-(Z)-10-docosenoyl-ethyleneglycol-phospho-N,N,N-trimethylpropylammonium (n=3)
$C_{30}H_{60}NO_6P$ (561.78)

1557.) 1-(Z)-6-octadecenoyl-propanediol-(1,3)-phospho-N,N,N-trimethylethylammonium (n=2)
$C_{26}H_{52}NO_6P$ (505.68)

1558.) 1-(Z)-10-docosenoyl-propanediol-(1,3)-phospho-N,N,N-trimethylethylammonium (n=2)
$C_{30}H_{60}NO_6P$ (561.78)

1559.) 1-(Z)-10-tetracosenoyl-propanediol-(1,3)-phospho-N,N,N-trimethylpropylammonium (n=3)
$C_{33}H_{66}NO_6P$ (603.86)

1560.) 1-(Z,Z)-5,11-octadecadienoyl-propanediol-(1,3)-phospho-N,N,N-trimethylpropylammonium (n=3)
$C_{27}H_{52}NO_6P$ (517.69)

1561.) 1-(Z,Z)-10,16-eicosadienoyl-propanediol-(1,3)-phospho-N,N,N-trimethylpropylammonium (n=3)
$C_{29}H_{56}NO_6P$ (545.74)

1562.) 1-(Z,Z)-10,16-docosadienoyl-propanediol-(1,3)-phospho-N,N,N-trimethylpropylammonium (n=3)
$C_{31}H_{60}NO_6P$ (573.79)

1563.) 1-(Z,Z)-6,18-hexacosadienoyl-propanediol-(1,3)-phospho-N,N,N-trimethylpropylammonium (n=3)
$C_{31}H_{68}NO_6P$ (629.90)

1564.) 1-(Z)-10-docosenoyl-propanediol-(1,3)-phospho-N,N,N-trimethylpropylammonium (n=3)
$C_{31}H_{62}NO_6P$ (575.81)

1565.) 1-(Z)-10-docosenoyl-propanediol-(1,3)-phospho-N,N,N-trimethylbutylammonium (n=4)
$C_{32}H_{64}NO_6P$ (589.84)

1566.) 1-(Z)-10-docosenoyl-butanediol-(1,4)-phospho-N,N,N-trimethylpropylammonium (n=3)
$C_{32}H_{64}NO_6P$ (589.84)

1567.) 1-(Z)-10-docosenoyl-hexanediol-(1,6)-phospho-N,N,N-trimethylpropylammonium (n=3)
$C_{34}H_{68}NO_6P$ (617.89)

1568.) 1-(Z)-10-docosenoyl-octanediol-(1,8)-phospho-N,N,N-trimethylpropylammonium (n=3)
$C_{36}H_{72}NO_6P$ (645.94)

Liposome Constituents

Neutral Phospholipids

1. Examples of Two-Chain glycero-phospho-N,N-dimethyl-N-dihydroxypropylalkylammonium Compounds

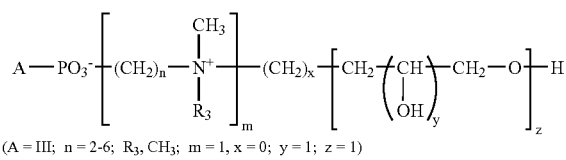

(A = III; n = 2-6; $R_3$, $CH_3$; m = 1, x = 0; y = 1; z = 1)

n=2

1569.) 1,2-di-(Z)-6-hexadecenoyl-sn-glycero-3-phospho-N,N-dimethyl-N-dihydroxypropylethylammonium (n=2)
$C_{42}H_{80}NO_{10}P$ (790.07)
1570.) 1,2-di-(Z)-10-heptadecenoyl-sn-glycero-3-phospho-N,N-dimethyl-N-dihydroxypropylethylammonium (n=2)
$C_{44}H_{84}NO_{10}P$ (818.13)
1571.) 1,2-di-(Z)-6-octadecenoyl-sn-glycero-3-phospho-N,N-dimethyl-N-dihydroxypropylethylammonium (n=2)
$C_{46}H_{88}NO_{10}P$ (846.18)
1572.) 1,2-di-(Z)-6-nonadecenoyl-sn-glycero-3-phospho-N,N-dimethyl-N-dihydroxypropylethylammonium (n=2)
$C_{48}H_{92}NO_{10}P$ (874.23)
1573.) 1,2-di-(Z)-12-eicosenoyl-sn-glycero-3-phospho-N,N-dimethyl-N-dihydroxypropylethylammonium (n=2)
$C_{50}H_{96}NO_{10}P$ (902.29)
1574.) 1,2-di-(Z)-10-heneicosenoyl-sn-glycero-3-phospho-N,N-dimethyl-N-dihydroxypropylethylammonium (n=2)
$C_{52}H_{100}NO_{10}P$ (930.34)
1575.) 1,2-di-(Z)-10-docosenoyl-sn-glycero-3-phospho-N,N-dimethyl-N-dihydroxypropylethylammonium (n=2)
$C_{54}H_{104}NO_{10}P$ (958.39)
1576.) 1,2-di-(Z)-12-docosenoyl-sn-glycero-3-phospho-N,N-dimethyl-N-dihydroxypropylethylammonium (n=2)
$C_{54}H_{104}NO_{10}P$ (958.39)
1577.) 1,2-di-(Z)-10-tricosenoyl-sn-glycero-3-phospho-N,N-dimethyl-N-dihydroxypropylethylammonium (n=2)
$C_{56}H_{108}NO_{10}P$ (986.45)
1578.) 1,2-di-(Z)-10-tetracosenoyl-sn-glycero-3-phospho-N,N-dimethyl-N-dihydroxypropylethylammonium (n=2)
$C_{58}H_{112}NO_{10}P$ (1014.50)
1579.) 1,2-di-(Z)-15-pentacosenoyl-sn-glycero-3-phospho-N,N-dimethyl-N-dihydroxypropylethylammonium (n=2)
$C_{60}H_{116}NO_{10}P$ (1042.56)
1580.) 1,2-di-(Z)-16-hexacosenoyl-sn-glycero-3-phospho-N,N-dimethyl-N-dihydroxypropylethylammonium (n=2)
$C_{62}H_{120}NO_{10}P$ (1070.61)
1581.) 1,2-di-(Z,Z)-5,11-hexadecadienoyl-sn-glycero-3-phospho-N,N-dimethyl-N-dihydroxypropylethylammonium (n=2)
$C_{42}H_{76}NO_{10}P$ (786.04)
1582.) 1,2-di-(Z,Z)-5,11-heptadecadienoyl-sn-glycero-3-phospho-N,N-dimethyl-N-dihydroxypropylethylammonium (n=2)
$C_{44}H_{80}NO_{10}P$ (814.09)
1583.) 1,2-di-(Z,Z)-5,11-octadecadienoyl-sn-glycero-3-phospho-N,N-dimethyl-N-dihydroxypropylethylammonium (n=2)
$C_{46}H_{84}NO_{10}P$ (842.15)
1584.) 1,2-di-(Z,Z)-6,12-nonadecadienoyl-sn-glycero-3-phospho-N,N-dimethyl-N-dihydroxypropylethylammonium (n=2)
$C_{48}H_{88}NO_{10}P$ (870.20)
1585.) 1,2-di-(Z,Z)-10,16-eicosadienoyl-sn-glycero-3-phospho-N,N-dimethyl-N-dihydroxypropylethylammonium (n=2)
$C_{50}H_{92}NO_{10}P$ (898.25)
1586.) 1,2-di-(Z,Z)-10,16-heneicosadienoyl-sn-glycero-3-phospho-N,N-dimethyl-N-dihydroxypropylethylammonium (n=2)
$C_{52}H_{96}NO_{10}P$ (926.31)
1587.) 1,2-di-(Z,Z)-10,16-docosadienoyl-sn-glycero-3-phospho-N,N-dimethyl-N-dihydroxypropylethylammonium (n=2)
$C_{54}H_{100}NO_{10}P$ (955.36)
1588.) 1,2-di-(Z,Z)-10,16-tricosadienoyl-sn-glycero-3-phospho-N,N-dimethyl-N-dihydroxypropylethylammonium (n=2)
$C_{56}H_{104}NO_{10}P$ (982.42)
1589.) 1,2-di-(Z,Z)-6,18-tetracosadienoyl-sn-glycero-3-phospho-N,N-dimethyl-N-dihydroxypropylethylammonium (n=2)
$C_{58}H_{108}NO_{10}P$ (1010.47)
1590.) 1,2-di-(Z,Z)-10,16-pentacosadienoyl-sn-glycero-3-phospho-N,N-dimethyl-N-dihydroxypropylethylammonium (n=2)
$C_{60}H_{112}NO_{10}P$ (1038.52)
1591.) 1,2-di-(Z,Z)-6,18-hexacosadienoyl-sn-glycero-3-phospho-N,N-dimethyl-N-dihydroxypropylethylammonium (n=2)
$C_{62}H_{116}NO_{10}P$ (1066.58)
1592.) 2-(Z)-6-hexadecenoyl-1-stearoyl-sn-glycero-3-phospho-N,N-dimethyl-N-dihydroxypropylethylammonium (n=2)
$C_{44}H_{86}NO_{10}P$ (820.14)
1593.) 2-(Z)-10-octadecenoyl-1-stearoyl-sn-glycero-3-phospho-N,N-dimethyl-N-dihydroxypropylethylammonium (n=2)
$C_{44}H_{90}NO_{10}P$ (848.20)
1594.) 2-(Z)-10-eicosenoyl-1-stearoyl-sn-glycero-3-phospho-N,N-dimethyl-N-dihydroxypropylethylammonium (n=2)
$C_{48}H_{94}NO_{10}P$ (876.25)
1595.) 1-behenyl-2-(Z)-10-docosenoyl-sn-glycero-3-phospho-N,N-dimethyl-N-dihydroxypropylethylammonium (n=2)
$C_{52}H_{102}NO_{10}P$ (932.36)
1596.) 2-(Z,Z)-6,12-hexadecadienoyl-1-stearoyl-sn-glycero-3-phospho-N,N-dimethyl-N-dihydroxypropylethylammonium (n=2)
$C_{44}H_{84}NO_{10}P$ (818.13)
1597.) 2-(Z,Z)-10,16-docosadienoyl-1-stearoyl-sn-glycero-3-phospho-N,N-dimethyl-N-dihydroxypropylethylammonium (n=2)
$C_{50}H_{96}NO_{10}P$ (902.29)
1598.) 1-stearoyl-2-(Z,Z)-6,18-tetracosadienoyl-sn-glycero-3-phospho-N,N-dimethyl-N-dihydroxypropylethylammonium (n=2)
$C_{52}H_{100}NO_{10}P$ (930.34)
1599.) 1-(Z)-10-octadecenoyl-2-stearoyl-sn-glycero-3-phospho-N,N-dimethyl-N-dihydroxypropylethylammonium (n=2)
$C_{46}H_{90}NO_{10}P$ (848.20)

1600.) 1-(Z,Z)-6,18-hexacosadienoyl-2-stearoyl-sn-glycero-3-phospho-N,N-dimethyl-N-dihydroxypropylethylammonium (n=2)
$C_{54}H_{104}NO_{10}P$ (958.39)

1601.) 1-(Z,Z)-6,18-hexacosadienoyl-2-(Z)-6-hexadecenoyl-sn-glycero-3-phospho-N,N-dimethyl-N-dihydroxypropylethylammonium (n=2)
$C_{52}H_{98}NO_{10}P$ (928.32)

1602.) 2-(Z,Z)-6,18-hexacosadienoyl-1-(Z)-6-hexadecenoyl-sn-glycero-3-phospho-N,N-dimethyl-N-dihydroxypropylethylammonium (n=2)
$C_{52}H_{98}NO_{10}P$ (928.32)

n=3

1603.) 1,2-di-(Z)-6-hexadecenoyl-sn-glycero-3-phospho-N,N-dimethyl-N-dihydroxypropylpropylammonium (n=3)
$C_{43}H_{82}NO_{10}P$ (804.10)

1604.) 1,2-di-(Z)-10-heptadecenoyl-sn-glycero-3-phospho-N,N-dimethyl-N-dihydroxypropylpropylammonium (n=3)
$C_{45}H_{86}NO_{10}P$ (832.15)

1605.) 1,2-di-(Z)-6-octadecenoyl-sn-glycero-3-phospho-N,N-dimethyl-N-dihydroxypropylpropylammonium (n=3)
$C_{47}H_{90}NO_{10}P$ (860.21)

1606.) 1,2-di-(Z)-12-eicosenoyl-sn-glycero-3-phospho-N,N-dimethyl-N-dihydroxypropylpropylammonium (n=3)
$C_{51}H_{98}NO_{10}P$ (916.31)

1607.) 1,2-di-(Z)-10-docosenoyl-sn-glycero-3-phospho-N,N-dimethyl-N-dihydroxypropylpropylammonium (n=3)
$C_{55}H_{106}NO_{10}P$ (972.42)

1608.) 1,2-di-(Z)-12-docosenoyl-sn-glycero-3-phospho-N,N-dimethyl-N-dihydroxypropylpropylammonium (n=3)
$C_{55}H_{106}NO_{10}P$ (972.42)

1609.) 1,2-di-(Z)-10-tricosenoyl-sn-glycero-3-phospho-N,N-dimethyl-N-dihydroxypropylpropylammonium (n=3)
$C_{57}H_{110}NO_{10}P$ (1000.47)

1610.) 1,2-di-(Z)-10-tetracosenoyl-sn-glycero-3-phospho-N,N-dimethyl-N-dihydroxypropylpropylammonium (n=3)
$C_{59}H_{114}NO_{10}P$ (1028.53)

1611.) 1,2-di-(Z,Z)-5,11-octadecadienoyl-sn-glycero-3-phospho-N,N-dimethyl-N-dihydroxypropylpropylammonium (n=3)
$C_{47}H_{86}NO_{10}P$ (856.17)

1612.) 1,2-di-(Z,Z)-10,16-eicosadienoyl-sn-glycero-3-phospho-N,N-dimethyl-N-dihydroxypropylpropylammonium (n=3)
$C_{51}H_{94}NO_{10}P$ (912.28)

1613.) 1,2-di-(Z,Z)-10,16-docosadienoyl-sn-glycero-3-phospho-N,N-dimethyl-N-dihydroxypropylpropylammonium (n=3)
$C_{55}H_{102}NO_{10}P$ (968.39)

1614.) 1,2-di-(Z,Z)-6,18-hexacosadienoyl-sn-glycero-3-phospho-N,N-dimethyl-N-dihydroxypropylpropylammonium (n=3)
$C_{63}H_{118}NO_{10}P$ (1080.60)

1615.) 2-(Z)-6-hexadecenoyl-1-stearoyl-sn-glycero-3-phospho-N,N-dimethyl-N-dihydroxypropylpropylammonium (n=3)
$C_{45}H_{88}NO_{10}P$ (834.17)

1616.) 2-(Z)-10-octadecenoyl-1-stearoyl-sn-glycero-3-phospho-N,N-dimethyl-N-dihydroxypropylpropylammonium (n=3)
$C_{47}H_{92}NO_{10}P$ (862.22)

1617.) 2-(Z)-10-docosenoyl-1-behenyl-sn-glycero-3-phospho-N,N-dimethyl-N-dihydroxypropylpropylammonium (n=3)
$C_{53}H_{104}NO_{10}P$ (946.38)

1618.) 2-(Z,Z)-6,12-hexadecadienoyl-1-stearoyl-sn-glycero-3-phospho-N,N-dimethyl-N-dihydroxypropylpropylammonium (n=3)
$C_{45}H_{86}NO_{10}P$ (832.15)

1619.) 1-(z)-10-octadecenoyl-2-stearoyl-sn-glycero-3-phospho-N,N-dimethyl-N-dihydroxypropylpropylammonium (n=3)
$C_{47}H_{92}NO_{10}P$ (862.22)

1620.) 1-(Z,Z)-6,18-hexacosadienoyl-2-stearoyl-sn-glycero-3-phospho-N,N-dimethyl-N-dihydroxypropylpropylammonium (n=3)
$C_{55}H_{106}NO_{10}P$ (972.42)

n=4

1621.) 1,2-di-(Z)-6-octadecenoyl-sn-glycero-3-phospho-N,N-dimethyl-N-dihydroxypropylbutylammonium (n=4)
$C_{48}H_{92}NO_{10}P$ (874.23)

1622.) 1,2-di-(Z)-10-docosenoyl-sn-glycero-3-phospho-N,N-dimethyl-N-dihydroxypropylbutylammonium (n=4)
$C_{56}H_{108}NO_{10}P$ (986.45)

1623.) 1,2-di-(Z,Z)-5,11-hexadecadienoyl-sn-glycero-3-phospho-N,N-dimethyl-N-dihydroxypropylbutylammonium (n=4)
$C_{44}H_{80}NO_{10}P$ (814.09)

1624.) 1,2-di-(Z,Z)-10,16-docosadienoyl-sn-glycero-3-phospho-N,N-dimethyl-N-dihydroxypropylbutylammonium (n=4)
$C_{56}H_{104}NO_{10}P$ (982.42)

1625.) 1,2-di-(Z,Z)-6,18-hexacosadienoyl-sn-glycero-3-phospho-N,N-dimethyl-N-dihydroxypropylbutylammonium (n=4)
$C_{64}H_{120}NO_{10}P$ (1094.63)

n=6

1626.) 1,2-di-(Z)-6-octadecenoyl-sn-glycero-3-phospho-N,N-dimethyl-N-dihydroxypropylhexylammonium (n=6)
$C_{50}H_{96}NO_{10}P$ (902.29)

1627.) 1,2-di-(z)-10-docosenoyl-sn-glycero-3-phospho-N,N-dimethyl-N-dihydroxypropylhexylammonium (n=6)
$C_{58}H_{112}NO_{10}P$ (1014.50)

1628.) 1,2-di-(Z,Z)-10,16-docosadienoyl-sn-glycero-3-phospho-N,N-dimethyl-N-dihydroxypropylhexylammonium (n=6)
$C_{58}H_{108}NO_{10}P$ (1010.47)

1629.) 1,2-di-(Z,Z)-6,18-hexacosadienoyl-sn-glycero-3-phospho-N,N-dimethyl-N-dihydroxypropylhexylammonium (n 6)
$C_{66}H_{124}NO_{10}P$ (1122.69)

2. Examples of Two-Chain glycero-phospho-N,N-dimethyl-N-(2-hydroxypropyl-3,1-O,O-dihydroxypropyl)alkylammonium Compounds

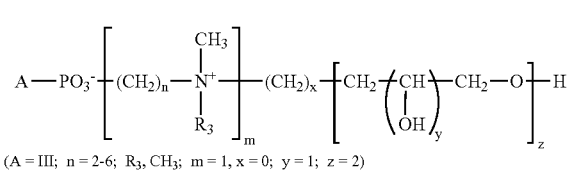

(A = III; n = 2-6; $R_3$, $CH_3$; m = 1, x = 0; y = 1; z = 2)

1630.) 1,2-di-(Z)-6-hexadecenoyl-sn-glycero-3-phospho-N,N-dimethyl-N-(2-hydroxypropyl-3,1-O,O-dihydroxypropyl)ethylammonium (n=2)
$C_{45}H_{86}NO_{12}P$ (864.15)

1631.) 1,2-di-(Z)-10-heptadecenoyl-sn-glycero-3-phospho-N,N-dimethyl-N-(2-hydroxypropyl-3,1-O,O-dihydroxypropyl)ethylammonium (n=2)
$C_{47}H_{90}NO_{12}P$ (892.20)

1632.) 1,2-di-(Z)-6-octadecenoyl-sn-glycero-3-phospho-N,N-dimethyl-N-(2-hydroxypropyl-3,1-O,O-dihydroxypropyl)ethylammonium (n=2)
$C_{49}H_{94}NO_{12}P$ (920.26)

1633.) 1,2-di-(Z)-6-nonadecenoyl-sn-glycero-3-phospho-N,N-dimethyl-N-(2-hydroxypropyl-3,1-O,O-dihydroxypropyl)ethylammonium (n=2)
$C_{51}H_{98}NO_{12}P$ (948.31)

1634.) 1,2-di-(Z)-12-eicosenoyl-sn-glycero-3-phospho-N,N-dimethyl-N-(2-hydroxypropyl-3,1-O,Odihydroxypropyl)ethylammonium (n=2)
$C_{53}H_{102}NO_{12}P$ (976.37)

1635.) 1,2-di-(Z)-10-heneicosendyl-sn-glycero-3-phospho-N,N-dimethyl-N-(2-hydroxypropyl-3,1-O,O-dihydroxypropyl)ethylammonium (n=2)
$C_{55}H_{106}NO_{12}P$ (1004.42)

1636.) 1,2-di-(Z)-10-docosenoyl-sn-glycero-3-phospho-N,N-dimethyl-N-(2-hydroxypropyl-3,1-O,O-dihydroxypropyl)ethylammonium (n=2)
$C_{57}H_{110}NO_{12}P$ (1032.47)

1637.) 1,2-di-(Z)-12-docosenoyl-sn-glycero-3-phospho-N,N-dimethyl-N-(2-hydroxypropyl-3,1-O,O-dihydroxypropyl)ethylammonium (n=2)
$C_{57}H_{110}NO_{12}P$ (1032.47)

1638.) 1,2-di-(Z)-10-tricosenoyl-sn-glycero-3-phospho-N,N-dimethyl-N-(2-hydroxypropyl-3,1-O,O-dihydroxypropyl)ethylammonium (n=2)
$C_{59}H_{114}NO_{12}P$ (1060.53)

1639.) 1,2-di-(Z)-10-tetracosenoyl-sn-glycero-3-phospho-N,N-dimethyl-N-(2-hydroxypropyl-3,1-O,O-dihydroxypropyl)ethylammonium (n=2)
$C_{61}H_{118}NO_{32}P$ (1088.58)

1640.) 1,2-di-(Z)-15-pentacosenoyl-sn-glycero-3-phospho-N,N-dimethyl-N-(2-hydroxypropyl-3,1-O,O-dihydroxypropyl)ethylammonium (n=2)
$C_{63}H_{122}NO_{12}P$ (1116.63)

1641.) 1,2-di-(Z)-16-hexacosenoyl-sn-glycero-3-phospho-N,N-dimethyl-N-(2-hydroxypropyl-3,1-O,O-dihydroxypropyl)ethylammonium (n=2)
$C_{65}H_{126}NO_{12}P$ (1144.69)

1642.) 1,2-di-(Z,Z)-5,11-hexadecadienoyl-sn-glycero-3-phospho-N,N-dimethyl-N-(2-hydroxypropyl-3,1-O,O-dihydroxypropyl)ethylammonium (n=2)
$C_{45}H_{82}NO_{12}P$ (860.12)

1643.) 1,2-di-(Z,Z)-5,11-heptadecadienoyl-sn-glycero-3-phospho-N,N-dimethyl-N-(2-hydroxypropyl-3,1-O,O-dihydroxypropyl)ethylammonium (n=2)
$C_{47}H_{86}NO_{12}P$ (888.17)

1644.) 1,2-di-(Z,Z)-5,11-octadecadienoyl-sn-glycero-3-phospho-N,N-dimethyl-N-(2-hydroxypropyl-3,1-O,O-dihydroxypropyl)ethylammonium (n=2)
$C_{49}H_{90}NO_{12}P$ (916.23)

1645.) 1,2-di-(Z,Z)-6,12-nonadecadienoyl-sn-glycero-3-phospho-N,N-dimethyl-N-(2-hydroxypropyl-3,1-O,O-dihydroxypropyl)ethylammonium (n=2)
$C_{51}H_{94}NO_{12}P$ (944.28)

1646.) 1,2-di-(Z,Z)-10,16-eicosadienoyl-sn-glycero-3-phospho-N,N-dimethyl-N-(2-hydroxypropyl-3,1-O,O-dihydroxypropyl)ethylammonium (n=2)
$C_{53}H_{98}NO_{12}P$ (972.33)

1647.) 1,2-di-(Z,Z)-10,16-heneicosadienoyl-sn-glycero-3-phospho-N,N-dimethyl-N-(2-hydroxypropyl-3,1-O,O-dihydroxypropyl)ethylammonium (n=2)
$C_{55}H_{102}NO_{12}P$ (1000.39)

1648.) 1,2-di-(Z,Z)-10,16-docosadienoyl-sn-glycero-3-phospho-N,N-dimethyl-N-(2-hydroxypropyl-3,1-O,O-dihydroxypropyl)ethylammonium (n=2)
$C_{57}H_{106}NO_{12}P$ (1028.44)

1649.) 1,2-di-(Z,Z)-10,16-tricosadienoyl-sn-glycero-3-phospho-N,N-dimethyl-N-(2-hydroxypropyl-3,1-O,O-dihydroxypropyl)ethylammonium (n=2)
$C_{59}H_{110}NO_{12}P$ (1056.50)

1650.) 1,2-di-(Z,Z)-6,18-tetracosadienoyl-sn-glycero-3-phospho-N,N-dimethyl-N-(2-hydroxypropyl-3,1-O,O-dihydroxypropyl)ethylammonium (n=2)
$C_{61}H_{114}NO_{12}P$ (1084.55).

1651.) 1,2-di-(Z,Z)-10,16-pentacosadienoyl-sn-glycero-3-phospho-N,N-dimethyl-N-(2-hydroxypropyl-3,1-O,O-dihydroxypropyl)ethylammonium (n=2)
$C_{63}H_{118}NO_{12}P$ (1112.60)

1652.) 1,2-di-(Z,Z)-6,18-hexacosadienoyl-sn-glycero-3-phospho-N,N-dimethyl-N-(2-hydroxypropyl-3,1-O,O-dihydroxypropyl)ethylammonium (n=2)
$C_{65}H_{122}NO_{12}P$ (1140.66)

1653.) 2-(Z)-6-hexadecenoyl-1-stearoyl-sn-glycero-3-phospho-N,N-dimethyl-N-(2-hydroxypropyl-3,1-O,O-dihydroxypropyl)ethylammonium (n=2)
$C_{47}H_{92}NO_{12}P$ (894.22)

1654.) 2-(Z)-10-octadecenoyl-1-stearoyl-sn-glycero-3-phospho-N,N-dimethyl-N-(2-hydroxypropyl-3,1-O,O-dihydroxypropyl)ethylammonium (n=2)
$C_{49}H_{96}NO_{12}P$ (922.27)

1655.) 2-(Z)-10-eicosenoyl-1-stearoyl-sn-glycero-3-phospho-N,N-dimethyl-N-(2-hydroxypropyl-3,1-O,O-dihydroxypropyl)ethylammonium (n 2)
$C_{51}H_{100}NO_{12}P$ (950.33)

1656.) 1-behenyl-2-(Z)-10-docosenoyl-sn-glycero-3-phospho-N,N-dimethyl-N-(2-hydroxypropyl-3,1-O,O-dihydroxypropyl)ethylammonium (n=2)
$C_{55}H_{108}NO_{12}P$ (1006.44)

1657.) 2-(Z,Z)-6,12-hexadecadienoyl-1-stearoyl-sn-glycero-3-phospho-N,N-dimethyl-N-(2-hydroxypropyl-3,1-O,O-dihydroxypropyl)ethylammonium (n=2)
$C_{47}H_{90}NO_{12}P$ (892.20)

1658.) 2-(Z,Z)-10,16-docosadienoyl-1-stearoyl-sn-glycero-3-phospho-N,N-dimethyl-N-(2-hydroxypropyl-3,1-O,O-dihydroxypropyl)ethylammonium (n=2)
$C_{53}H_{102}NO_{12}P$ (976.37)

1659.) 1-stearoyl-2-(Z,Z)-6,18-tetracosadienoyl-sn-glycero-3-phospho-N,N-dimethyl-N-(2-hydroxypropyl-3,1-O,O-dihydroxypropyl)ethylammonium (n=2)
$C_{55}H_{106}NO_{12}P$ (1004.42)

1660.) 1-(Z)-10-octadecenoyl-2-stearoyl-sn-glycero-3-phospho-N,N-dimethyl-N-(2-hydroxypropyl-3,1-O,O-dihydroxypropyl)ethylammonium (n=2)
$C_{49}H_{96}NO_{12}P$ (922.27)

1661.) 1-(Z,Z)-6,18-hexacosadienoyl-2-stearoyl-sn-glycero-3-phospho-N,N-dimethyl-N-(2-hydroxypropyl-3,1-O,O-dihydroxypropyl)ethylammonium (n=2)
$C_{57}H_{110}NO_{12}P$ (1032.47)

1662.) 1-(Z,Z)-6,18-hexacosadienoyl-2-(Z)-6-hexadecenoyl-sn-glycero-3-phospho-N,N-dimethyl-N-(2-hydroxypropyl-3,1-O,O-dihydroxypropyl)ethylammonium (n=2)
$C_{55}H_{104}NO_{12}P$ (1002.40)

1663.) 2-(Z,Z)-6,18-hexacosadienoyl-1-(Z)-6-hexadecenoyl-sn-glycero-3-phospho-N,N-dimethyl-N-(2-hydroxypropyl-3,1-O,O-dihydroxypropyl)ethylammonium (n=2)
$C_{55}H_{104}NO_{12}P$ (1002.40)

n=3

1664.) 1,2-di-(Z)-6-hexadecenoyl-sn-glycero-3-phospho-N,N-dimethyl-N-(2-hydroxypropyl-3,1-O,O-dihydroxypropyl)propylammonium (n=3)
$C_{46}H_{88}NO_{12}P$ (878.18)

1665.) 1,2-di-(Z)-10-heptadecenoyl-sn-glycero-3-phospho-N,N-dimethyl-N-(2-hydroxypropyl-3,1-O,O-dihydroxypropyl)propylammonium (n=3)
$C_{48}H_{92}NO_{12}P$ (906.23)

1666.) 1,2-di-(Z)-6-octadecenoyl-sn-glycero-3-phospho-N,N-dimethyl-N-(2-hydroxypropyl-3,1-O,O-dihydroxypropyl)propylammonium (n=3)
$C_{50}H_{96}NO_{12}P$ (934.29)

1667.) 1,2-di-(Z)-12-eicosenoyl-sn-glycero-3-phospho-N,N-dimethyl-N-(2-hydroxypropyl-3,1-O,O-dihydroxypropyl)propylammonium (n=3)
$C_{54}H_{104}NO_{12}P$ (990.39)

1668.) 1,2-di-(z)-10-docosenoyl-sn-glycero-3-phospho-N,N-dimethyl-N-(2-hydroxypropyl-3,1-O,O-dihydroxypropyl)propylammonium (n=3)
$C_{58}H_{112}NO_{12}P$ (1046.50)

1669.) 1,2-di-(Z)-12-docosenoyl-sn-glycero-3-phospho-N,N-dimethyl-N-(2-hydroxypropyl-3,1-O,O-dihydroxypropyl)propylammonium (n=3)
$C_{58}H_{112}NO_{12}P$ (1046.50)

1670.) 1,2-di-(Z)-10-tricosenoyl-sn-glycero-3-phospho-N,N-dimethyl-N-(2-hydroxypropyl-3,1-O,O-dihydroxypropyl)propylammonium (n=3)
$C_{60}H_{116}NO_{12}P$ (1074.55)

1671.) 1,2-di-(Z)-10-tetracosenoyl-sn-glycero-3-phospho-N,N-dimethyl-N-(2-hydroxypropyl-3,1-O,O-dihydroxypropyl)propylammonium (n=3)
$C_{62}H_{120}NO_{12}P$ (1102.61)

1672.) 1,2-di-(Z,Z)-5,11-octadecadienoyl-sn-glycero-3-phospho-N,N-dimethyl-N-(2-hydroxypropyl-3,1-O,O-dihydroxypropyl)propylammonium (n=3)
$C_{50}H_{92}NO_{12}P$ (930.25)

1673.) 1,2-di-(Z,Z)-10,16-eicosadienoyl-sn-glycero-3-phospho-N,N-dimethyl-N-(2-hydroxypropyl-3,1-O,O-dihydroxypropyl)propylammonium (n=3)
$C_{54}H_{100}NO_{12}P$ (986.36)

1674.) 1,2-di-(Z,Z)-10,16-docosadienoyl-sn-glycero-3-phospho-N,N-dimethyl-N-(2-hydroxypropyl-3,1-O,O-dihydroxypropyl)propylammonium (n=3)
$C_{58}H_{108}NO_{12}P$ (1042.47)

1675.) 1,2-di-(Z,Z)-6,18-hexacosadienoyl-sn-glycero-3-phospho-N,N-dimethyl-N-(2-hydroxypropyl-3,1-O,O-dihydroxypropyl)propylammonium (n=3)
$C_{66}H_{124}NO_{12}P$ (1154.68)

1676.) 2-(Z)-6-hexadecenoyl-1-stearoyl-sn-glycero-3-phospho-N,N-dimethyl-N-(2-hydroxypropyl-3,1-O,O-dihydroxypropyl)propylammonium (n=3)
$C_{48}H_{94}NO_{12}P$ (908.25)

1677.) 2-(Z)-10-octadecenoyl-1-stearoyl-sn-glycero-3-phospho-N,N-dimethyl-N-(2-hydroxypropyl-3,1-O,O-dihydroxypropyl)propylammonium (n=3)
$C_{50}H_{98}NO_{12}P$ (936.30)

1678.) 2-(Z)-10-docosenoyl-1-behenyl-sn-glycero-3-phospho-N,N-dimethyl-N-(2-hydroxypropyl-3,1-O,O-dihydroxypropyl)propylammonium (n=3)
$C_{56}H_{110}NO_{12}P$ (1020.46)

1679.) 2-(Z,Z)-6,12-hexadecadienoyl-1-stearoyl-sn-glycero-3-phospho-N,N-dimethyl-N-(2-hydroxypropyl-3,1-O,O-dihydroxypropyl)propylammonium (n=3)
$C_{48}H_{92}NO_{12}P$ (906.23)

1680.) 1-(z)-10-octadecenoyl-2-stearoyl-sn-glycero-3-phospho-N,N-dimethyl-N-(2-hydroxypropyl-3,1-O,O-dihydroxypropyl)propylammonium (n=3)
$C_{50}H_{98}NO_{12}P$ (936.30)

1681.) 2-(Z,Z)-6,18-hexacosadienoyl-2-stearoyl-sn-glycero-3-phospho-N,N-dimethyl-N-(2-hydroxypropyl-3,1-O,O-dihydroxypropyl)propylammonium (n=3)
$C_{58}H_{112}NO_{12}P$ (1046.50)

n=4

1682.) 1,2-di-(Z)-6-octadecenoyl-sn-glycero-3-phospho-N,N-dimethyl-N-(2-hydroxypropyl-3,1-O,O-dihydroxypropyl)butylammonium (n=4)
$C_{51}H_{98}NO_{12}P$ (948.31)

1683.) 1,2-di-(Z)-10-docosenoyl-sn-glycero-3-phospho-N,N-dimethyl-N-(2-hydroxypropyl-3,1-O,O-dihydroxypropyl)butylammonium (n=4)
$C_{59}H_{114}NO_{12}P$ (1060.53)

1684.) 1,2-di-(Z,Z)-5,11-hexadecadienoyl-sn-glycero-3-phospho-N,N-dimethyl-N-(2-hydroxypropyl-3,1-O,O-dihydroxypropyl)butylammonium (n=4)
$C_{47}H_{86}NO_{12}P$ (888.17)

1685.) 1,2-di-(Z,Z)-10,16-docosadienoyl-sn-glycero-3-phospho-N,N-dimethyl-N-(2-hydroxypropyl-3,1-O,O-dihydroxypropyl)butylammonium (n=4)
$C_{59}H_{110}NO_{12}P$ (1056.50)

1686.) 1,2-di-(Z,Z)-6,18-hexacosadienoyl-sn-glycero-3-phospho-N,N-dimethyl-N-(2-hydroxypropyl-3,1-O,O-dihydroxypropyl)butylammonium (n=4)
$C_{67}H_{126}NO_{12}P$ (1168.71)

n=6

1687.) 1,2-di-(Z)-6-octadecenoyl-sn-glycero-3-phospho-N,N-dimethyl-N-(2-hydroxypropyl-3,1-O,O-dihydroxypropyl)hexylammonium (n=6)
$C_{53}H_{102}NO_{12}P$ (976.37)

1688.) 1,2-di-(Z)-10-docosenoyl-sn-glycero-3-phospho-N,N-dimethyl-N-(2-hydroxypropyl-3,1-O,O-dihydroxypropyl)hexylammonium (n=6)
$C_{61}H_{118}NO_{12}P$ (1088.58)

1689.) 1,2-di-(Z,Z)-10,16-docosadienoyl-sn-glycero-3-phospho-N,N-dimethyl-N-(2-hydroxypropyl-3,1-O,O-dihydroxypropyl)hexylammonium (n=6)
$C_{61}H_{114}NO_{12}P$ (1084.55)

1690.) 1,2-di-(Z,Z)-6,18-hexacosadienoyl-sn-glycero-3-phospho-N,N-dimethyl-N-(2-hydroxypropyl-3,1-O,O-dihydroxypropyl)hexylammonium (n=6)
$C_{69}H_{130}NO_{12}P$ (1196.76)

3. Examples of Two-Chain glycero-phospho-N,N-dimethyl-N-(2-hydroxypropyl-3,1-O,O-2-hydroxypropyl-3,1-O,O-dihydroxypropyl)alkylammonium Compounds $$A-PO_3^- -[(CH_2)_n - \overset{CH_3}{\underset{R_3}{N^+}} - (CH_2)_x]_m - [CH_2 - (CH(OH))_y - CH_2 - O]_z - H$$

(A = III; n = 2-6; $R_3$, $CH_3$; m = 1, x = 0; y = 1; z = 3)

1691.) 1,2-di-(z)-6-hexadecenoyl-sn-glycero-3-phospho-N,N-dimethyl-N—($HP_1$—$HP_2$-di$HP_3$) ethylammonium (n=2)
$C_{48}H_{92}NO_{14}P$ (938.23)

1692.) 1,2-di-(Z)-10-heptadecenoyl-sn-glycero-3-phospho-N,N-dimethyl-N—(HP$_1$—HP$_2$-diHP$_3$)ethylammonium (n=2)
C$_{50}$H$_{96}$NO$_{14}$P (966.28)

1693.) 1,2-di-(z)-6-octadecenoyl-sn-glycero-3-phospho-N,N-dimethyl-N—(HP$_1$—HP$_2$-diHP$_3$) ethylammonium (n=2)
C$_{52}$H$_{100}$NO$_{14}$P (994.34)

1694.) 1,2-di-(Z)-6-nonadecenoyl-sn-glycero-3-phospho-N,N-dimethyl-N—(HP$_1$—HP$_2$-diHP$_3$) ethylammonium (n=2)
C$_{54}$H$_{104}$NO$_{14}$P (1022.39)

1695.) 1,2-di-(z)-12-eicosenoyl-sn-glycero-3-phospho-N,N-dimethyl-N—(HP$_1$—HP$_2$-diHP$_3$) ethylammonium (n=2)
C$_{56}$H$_{108}$NO$_{14}$P (1050.45)

1696.) 1,2-di-(Z)-10-heneicosenoyl-sn-glycero-3-phospho-N,N-dimethyl-N—(HP$_1$—HP$_2$-diHP$_3$) ethylammonium (n=2)
C$_{58}$H$_{112}$NO$_{14}$P (1078.50)

1697.) 1,2-di-(Z)-10-docosenoyl-sn-glycero-3-phospho-N,N-dimethyl-N—(HP$_1$—HP$_2$-diHP$_3$) ethylammonium (n=2)
C$_{60}$H$_{116}$NO$_{14}$P (1106.55)

1698.) 1,2-di-(z)-12-docosenoyl-sn-glycero-3-phospho-N,N-dimethyl-N—(HP$_1$—HP$_2$-diHP$_3$) ethylammonium (n=2)
C$_{60}$H$_{116}$NO$_{14}$P (1106.55)

1699.) 1,2-di-(Z)-10-tricosenoyl-sn-glycero-3-phospho-N,N-dimethyl-N—(HP$_1$—HP$_2$-diHP$_3$) ethylammonium (n=2)
C$_{62}$H$_{120}$NO$_{14}$P (1134.61)

1700.) 1,2-di-(Z)-10-tetracosenoyl-sn-glycero-3-phospho-N,N-dimethyl-N—(HP$_1$—HP$_2$-diHP$_3$) ethyl ammonium (n=2)
C$_{64}$H$_{124}$NO$_{14}$P (1134.61)

1701.) 1,2-di-(z)-15-pentacosenoyl-sn-glycero-3-phospho-N,N-dimethyl-N—(HP$_1$—HP$_2$-diHP$_3$) ethylammonium (n=2)
C$_{66}$H$_{128}$NO$_{14}$P (1190.71)

1702.) 1,2-di-(Z)-16-hexacosenoyl-sn-glycero-3-phospho-N,N-dimethyl-N—(HP$_1$—HP$_2$-diHP$_3$) ethylammonium (n=2)
C$_{68}$H$_{132}$NO$_{14}$P (1218.77)

1703.) 1,2-di-(Z,Z)-5,11-hexadecadienoyl-sn-glycero-3-phospho-N,N-dimethyl-N—(HP$_1$—HP$_2$-diHP$_3$) ethylammonium (n=2)
C$_{48}$H$_{88}$NO$_{14}$P (934.20)

1704.) 1,2-di-(Z,Z)-5 μl-heptadecadienoyl-sn-glycero-3-phospho-N,N-dimethyl-N—(HP$_1$—HP$_2$-diHP$_3$) ethylammonium (n=2)
C$_{50}$H$_{92}$NO$_{14}$P (962.25)

1705.) 1,2-di-(Z,Z)-5,11-octadecadienoyl-sn-glycero-3-phospho-N,N-dimethyl-N—(HP$_1$—HP$_2$-diHP$_3$) ethyl ammonium (n=2)
C$_{52}$H$_{96}$NO$_{14}$P (990.31)

1706.) 1,2-di-(Z,Z)-6,12-nonadecadienoyl-sn-glycero-3-phospho-N,N-dimethyl-N—(HP$_1$—HP$_2$-diHP$_3$) ethylammonium (n=2)
C$_{54}$H$_{100}$NO$_{14}$P (1018.36)

1707.) 1,2-di-(Z,Z)-10,16-eicosadienoyl-sn-glycero-3-phospho-N,N-dimethyl-N—(HP$_1$—HP$_2$-diHP$_3$) ethylammonium (n=2)
C$_{56}$H$_{104}$NO$_{14}$P (1046.41)

1708.) 1,2-di-(Z,Z)-10,16-heneicosadienoyl-sn-glycero-3-phospho-N,N-dimethyl-N—(HP$_1$—HP$_2$-diHP$_3$) ethylammonium (n=2)
C$_{58}$H$_{108}$NO$_{14}$P (1074.47)

1709.) 1,2-di-(Z,Z)-10,16-docosadienoyl-sn-glycero-3-phospho-N,N-dimethyl-N—(HP$_1$—HP$_2$-diHP$_3$) ethylammonium (n=2)
C$_{60}$H$_{112}$NO$_{14}$P (1102.52)

1710.) 1,2-di-(Z,Z)-10,16-tricosadienoyl-sn-glycero-3-phospho-N,N-dimethyl-N—(HP$_1$—HP$_2$-diHP$_3$)ethylammonium (n=2)
C$_{62}$H$_{116}$NO$_{14}$P (1130.58)

1711.) 1,2-di-(Z,Z)-6,18-tetracosadienoyl-sn-glycero-3-phospho-N,N-dimethyl-N—(HP$_1$—HP$_2$-diHP$_3$) ethylammonium (n=2)
C$_{64}$H$_{120}$NO$_{14}$P (1158.63)

1712.) 1,2-di-(Z,Z)-10,16-pentacosadienoyl-sn-glycero-3-phospho-N,N-dimethyl-N—(HP$_1$—HP$_2$-diHP$_3$) ethylammonium (n=2)
C$_{66}$H$_{124}$NO$_{14}$P (1186.68)

1713.) 1,2-di-(Z,Z)-6,18-hexacosadienoyl-sn-glycero-3-phospho-N,N-dimethyl-N—(HP$_1$—HP$_2$-diHP$_3$) ethylammonium (n=2)
C$_{68}$H$_{128}$NO$_{14}$P (1214.74)

1714.) 2-(Z)-6-hexadecenoyl-1-stearoyl-sn-glycero-3-phospho-N,N-dimethyl-N—(HP$_1$—HP$_2$-diHP$_3$) ethylammonium (n=2)
C$_{50}$H$_{98}$NO$_{14}$P (968.30)

1715.) 2-(Z)-10-octadecenoyl-1-stearoyl-sn-glycero-3-phospho-N,N-dimethyl-N—(HP$_1$—HP$_2$-diHP$_3$) ethylammonium (n=2)
C$_{52}$H$_{102}$NO$_{14}$P (996.35)

1716.) 2-(Z)-10-eicosenoyl-1-stearoyl-sn-glycero-3-phospho-N,N-dimethyl-N—(HP$_1$—HP$_2$-diHP$_3$) ethylammonium (n=2)
C$_{54}$H$_{106}$NO$_{14}$P (1024.41)

1717.) 1-behenyl-2-(Z)-10-docosenoyl-sn-glycero-3-phospho-N,N-dimethyl-N—(HP$_1$—HP$_2$-diHP$_3$) ethylammonium (n=2)
C$_{58}$H$_{114}$NO$_{14}$P (1080.52)

1718.) 2-(Z,Z)-6,12-hexadecadienoyl-1-stearoyl-sn-glycero-3-phospho-N,N-dimethyl-N—(HP$_1$—HP$_2$-diHP$_3$) ethylammonium (n=2)
C$_{50}$H$_{96}$NO$_{14}$P (966.28)

1719.) 2-(Z,Z)-10,16-docosadienoyl-1-stearoyl-sn-glycero-3-phospho-N,N-dimethyl-N—(HP$_1$—HP$_2$-diHP$_3$)ethylammonium (n=2)
C$_{56}$H$_{108}$NO$_{14}$P (1050.45)

1720.) 1-stearoyl-2-(Z,Z)-6,18-tetracosadienoyl-sn-glycero-3-phospho-N,N-dimethyl-N—(HP$_1$—HP$_2$-diHP$_3$)ethylammonium (n=2)
C$_{58}$H$_{112}$NO$_{14}$P (1078.50)

1721.) 1-(Z)-10-octadecenoyl-2-stearoyl-sn-glycero-3-phospho-N,N-dimethyl-N—(HP$_1$—HP$_2$-diHP$_3$) ethylammonium (n=2)
C$_{52}$H$_{102}$NO$_{14}$P (996.35)

1722.) 1-(Z,Z)-6,18-hexacosadienoyl-2-stearoyl-sn-glycero-3-phospho-N,N-dimethyl-N—(HP$_1$—HP$_2$-diHP$_3$)ethylammonium (n=2)
C$_{60}$H$_{116}$NO$_{14}$P (1106.55)

1723.) 1-(Z,Z)-6,18-hexacosadienoyl-2-(z)-6-hexadecenoyl-sn-glycero-3-phospho-N,N-dimethyl-N—(HP$_1$—HP$_2$-diHP$_3$)ethylammonium (n=2)
C$_{58}$H$_{110}$NO$_{14}$P (1076.48)

1724.) 2-(Z,Z)-6,18-hexacosadienoyl-1-(Z)-6-hexadecenoyl-sn-glycero-3-phospho-N,N-dimethyl-N—(HP$_1$—HP$_2$-diHP$_3$)ethylammonium (n=2)
C$_{58}$H$_{110}$NO$_{14}$P (1076.48)

n=3

1725.) 1,2-di-(Z)-6-hexadecenoyl-sn-glycero-3-phospho-N,N-dimethyl-N—($HP_1$—$HP_2$-diHP$_3$)propylammonium (n=3)
$C_{49}H_{94}NO_{14}P$ (952.26)
1726.) 1,2-di-(Z)-10-heptadecenoyl-sn-glycero-3-phospho-N,N-dimethyl-N—($HP_1$—$HP_2$-diHP$_3$)propylammonium (n=3)
$C_{51}H_{98}NO_{14}P$ (980.31)
1727.) 1,2-di-(z)-6-octadecenoyl-sn-glycero-3-phospho-N,N-dimethyl-N—($HP_1$—$HP_2$-diHP$_3$)propylammonium (n=3)
$C_{53}H_{102}NO_{14}P$ (1008.36)
1728.) 1,2-di-(Z)-12-eicosenoyl-sn-glycero-3-phospho-N,N-dimethyl-N—($HP_1$—$HP_2$-diHP$_3$)propylammonium (n=3)
$C_{57}H_{110}NO_{14}P$ (1064.47)
1729.) 1,2-di-(Z)-10-docosenoyl-sn-glycero-3-phospho-N,N-dimethyl-N—($HP_1$—$HP_2$-diHP$_3$) propylammonium (n=3)
$C_{61}H_{118}NO_{14}P$ (1120.58)
1730.) 1,2-di-(Z)-12-docosenoyl-sn-glycero-3-phospho-N,N-dimethyl-N—($HP_1$—$HP_2$-diHP$_3$) propylammonium (n=3)
$C_{61}H_{118}NO_{14}P$ (1120.58)
1731.) 1,2-di-(Z)-10-tricosenoyl-sn-glycero-3-phospho-N,N-dimethyl-N—($HP_1$—$HP_2$-diHP$_3$) propylammonium (n=3)
$C_{63}H_{122}NO_{14}P$ (1148.63)
1732.) 1,2-di-(Z)-10-tetracosenoyl-sn-glycero-3-phospho-N,N-dimethyl-N—($HP_1$—$HP_2$-diHP$_3$) propylammonium (n=3)
$C_{65}H_{126}NO_{14}P$ (1176.69).
1733.) 1,2-di(Z,Z)-5,11-octadecadienoyl-sn-glycero-3-phospho-N,N-dimethyl-N—($HP_1$—$HP_2$-diHP$_3$) propylammonium (n=3)
$C_{53}H_{98}NO_{14}P$ (1004.33)
1734.) 1,2-di(Z,Z)-10,16-eicosadienoyl-sn-glycero-3-phospho-N,N-dimethyl-N—($HP_1$—$HP_2$-diHP$_3$) propylammonium (n=3)
$C_{57}H_{106}NO_{14}P$ (1060.44)
1735.) 1,2-di(Z,Z)-10,16-docosadienoyl-sn-glycero-3-phospho-N,N-dimethyl-N—($HP_1$—$HP_2$-diHP$_3$) propylammonium (n=3)
$C_{61}H_{114}NO_{14}P$ (1116.55)
1736.) 1,2-di(Z,Z)-6,18-hexacosadienoyl-sn-glycero-3-phospho-N,N-dimethyl-N—($HP_1$—$HP_2$-diHP$_3$)propylammonium (n=3)
$C_{69}H_{130}NO_{14}P$ (1228.76)
1737.) 2-(Z)-6-hexadecenoyl-1-stearoyl-sn-glycero-3-phospho-N,N-dimethyl-N—($HP_1$—$HP_2$-diHP$_3$) propylammonium (n=3)
$C_{51}H_{100}NO_{14}P$ (982.33)
1738.) 2-(Z)-10-octadecenoyl-1-stearoyl-sn-glycero-3-phospho-N,N-dimethyl-N—($HP_1$—$HP_2$-diHP$_3$)propylammonium (n=3)
$C_{53}H_{104}NO_{14}P$ (1010.38)
1739.) 2-(Z)-10-docosenoyl-1-behenyl-sn-glycero-3-phospho-N,N-dimethyl-N—($HP_1$—$HP_2$-diHP$_3$)propylammonium (n=3)
$C_{59}H_{116}NO_{14}P$ (1094.54)
1740.) 2-(Z,Z)-6,12-hexadecadienoyl-1-stearoyl-sn-glycero-3-phospho-N,N-dimethyl-N—($HP_1$—$HP_2$-diHP$_3$)propylammonium (n=3)
$C_{51}H_{98}NO_{14}P$ (980.31)
1741.) 1-(Z)-10-octadecenoyl-2-stearoyl-sn-glycero-3-phospho-N,N-dimethyl-N—($HP_1$—$HP_2$-diHP$_3$)propylammonium (n=3)
$C_{53}H_{104}NO_{14}P$ (1010.38)
1742.) 1-(Z,Z)-6,18-hexacosadienoyl-2-stearoyl-sn-glycero-3-phospho-N,N-dimethyl-N—($HP_1$—$HP_2$-diHP$_3$)propylammonium (n=3)
$C_{61}H_{118}NO_{14}P$ (1120.58)
n=4
1743.) 1,2-di-(Z)-6-octadecenoyl-sn-glycero-3-phospho-N,N-dimethyl-N—($HP_1$—$HP_2$-diHP$_3$)butylammonium (n=4)
$C_{54}H_{104}NO_{14}P$ (1022.39)
1744.) 1,2-di-(Z)-10-docosenoyl-sn-glycero-3-phospho-N,N-dimethyl-N—($HP_1$—$HP_2$-diHP$_3$) butylammonium (n=4)
$C_{62}H_{120}NO_{14}P$ (1134.61)
1745.) 1,2-di-(Z,Z)-5,11-hexadecadienoyl-sn-glycero-3-phospho-N,N-dimethyl-N—($HP_1$—$HP_2$-diHP$_3$)butylammonium (n=4)
$C_{50}H_{92}NO_{14}P$ (962.25)
1746.) 1,2-di-(Z,Z)-10,16-docosadienoyl-sn-glycero-3-phospho-N,N-dimethyl-N—($HP_1$—$HP_2$-diHP$_3$) butylammonium (n=4)
$C_{62}H_{116}NO_{14}P$ (1130.58)
1747.) 1,2-di-(Z,Z)-6,18-hexacosadienoyl-sn-glycero-3-phospho-N,N-dimethyl-N—($HP_1$—$HP_2$-diHP$_3$)butylammonium (n=4)
$C_{70}H_{132}NO_{14}P$ (1242.79)
n=6
1748.) 1,2-di-(Z)-6-octadecenoyl-sn-glycero-3-phospho-N,N-dimethyl-N—($HP_1$—$HP_2$-diHP$_3$) hexylammonium (n=6)
$C_{56}H_{108}NO_{14}P$ (1050.45)
1749.) 1,2-di-(Z)-10-docosenoyl-sn-glycero-3-phospho-N,N-dimethyl-N—($HP_1$—$HP_2$-diHP$_3$) hexylammonium (n=6)
$C_{64}H_{124}NO_{14}P$ (1162.66)
1750.) 1,2-di-(Z,Z)-10,16-docosadienoyl-sn-glycero-3-phospho-N,N-dimethyl-N—($HP_1$—$HP_2$-diHP$_3$) hexylammonium (n=6)
$C_{64}H_{120}NO_{14}P$ (1158.63)
1751.) 1,2-di-(Z,Z)-6,18-hexacosadienoyl-sn-glycero-3-phospho-N,N-dimethyl-N—($HP_1$—$HP_2$-diHP$_3$)hexylammonium (n=6)
$C_{72}H_{136}NO_{14}P$ (1270.84)

4. Examples of Two-Chain glycero-phospho-N,N-dimethyl-N-(2-hydroxypropyl-3,1-O,O-2-hydroxypropyl-3,1-O,O-2-hydroxypropyl-3,1-O,O-dihydroxypropyl)alkylammonium Compounds

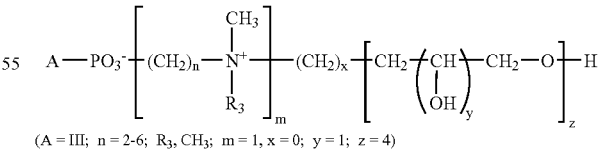

(A = III; n = 2-6; $R_3$, $CH_3$; m = 1, x = 0; y = 1; z = 4)

In the following text, N-(2-hydroxypropyl-3,1-O,O-2-hydroxypropyl-3,1-O,O-2-hydroxypropyl-3,1-O,O-dihydroxypropyl) is abbreviated to N—($HP_1$—$HP_2$—$HP_3$-diHP$_4$).
1752.) 1,2-di-(Z)-6-hexadecenoyl-sn-glycero-3-phospho-N,N-dimethyl-N—($HP_1$—$HP_2$—$HP_3$-diHP$_4$) ethylammonium (n=2)
$C_{51}H_{98}NO_{16}P$ (1012.31)

1753.) 1,2-di-(Z)-10-heptadecenoyl-sn-glycero-3-phospho-N,N-dimethyl-N—(HP$_1$—HP$_2$—HP$_3$-diHP$_4$) ethylammonium (n=2)
$C_{53}H_{102}NO_{16}P$ (1040.36)
1754.) 1,2-di-(Z)-6-octadecenoyl-sn-glycero-3-phospho-N,N-dimethyl-N—(HP$_1$—HP$_2$—HP$_3$-diHP$_4$) ethylammonium (n=2)
$C_{55}H_{106}NO_{16}P$ (1068.42)
1755.) 1,2-di-(Z)-6-nonadecenoyl-sn-glycero-3-phospho-N,N-dimethyl-N—(HP$_1$—HP$_2$—HP$_3$-diHP$_4$) ethylammonium (n=2)
$C_{57}H_{110}NO_{16}P$ (1096.47)
1756.) 1,2-di-(Z)-12-eicosenoyl-sn-glycero-3-phospho-N,N-dimethyl-N—(HP$_1$—HP$_2$—HP$_3$-diHP$_4$) ethylammonium (n=2)
$C_{59}H_{114}NO_{16}P$ (1124.53)
1757.) 1,2-di-(z)-10-heneicosenoyl-sn-glycero-3-phospho-N,N-dimethyl-N—(HP$_1$—HP$_2$—HP$_3$-diHP$_4$)ethylammonium (n=2)
$C_{61}H_{118}NO_{16}P$ (1152.58)
1758.) 1,2-di-(z)-10-docosenoyl-sn-glycero-3-phospho-N,N-dimethyl-N—(HP$_1$—HP$_2$—HP$_3$-diHP$_4$) ethylammonium (n=2)
$C_{63}H_{122}NO_{16}P$ (1180.63)
1759.) 1,2-di-(z)-12-docosenoyl-sn-glycero-3-phospho-N,N-dimethyl-N—(HP$_1$—HP$_2$—HP$_3$-diHP$_4$) ethylammonium (n=2)
$C_{63}H_{122}NO_{16}P$ (1180.63)
1760.) 1,2-di-(Z)-10-tricosenoyl-sn-glycero-3-phospho-N,N-dimethyl-N—(HP$_1$—HP$_2$—HP$_3$-diHP$_4$) ethylammonium (n=2)
$C_{63}H_{126}NO_{16}P$ (1208.69)
1761.) 1,2-di-(Z)-10-tetracosenoyl-sn-glycero-3-phospho-N,N-dimethyl-N—(HP$_1$—HP$_2$—HP$_3$-diHP$_4$)ethylammonium (n=2)
$C_{67}H_{130}NO_{16}P$ (1236.74)
1762.) 1,2-di-(Z)-15-pentacosenoyl-sn-glycero-3-phospho-N,N-dimethyl-N—(HP$_1$—HP$_2$—HP$_3$-diHP$_4$)ethylammonium (n=2)
$C_{69}H_{134}NO_{16}P$ (1264.79)
1763.) 1,2-di-(Z)-16-hexacosenoyl-sn-glycero-3-phospho-N,N-dimethyl-N—(HP$_1$—HP$_2$—HP$_3$-diHP$_4$)ethylammonium (n=2)
$C_{71}H_{138}NO_{16}P$ (1292.85)
1764.) 1,2-di-(Z,Z)-5,11-hexadecadienoyl-sn-glycero-3-phospho-N,N-dimethyl-N—(HP$_1$—HP$_2$—HP$_3$-diHP$_4$) ethylammonium (n=2)
$C_{51}H_{94}NO_{16}P$ (1008.28)
1765.) 1,2-di-(Z,Z)-5,11-heptadecadienoyl-sn-glycero-3-phospho-N,N-dimethyl-N—(HP$_1$—HP$_2$—HP$_3$-diHP$_4$) ethylammonium (n=2)
$C_{53}H_{98}NO_{16}P$ (1036.33)
1766.) 1,2-di-(Z,Z)-5,11-octadecadienoyl-sn-glycero-3-phospho-N,N-dimethyl-N—(HP$_1$—HP$_2$—HP$_3$-diHP$_4$) ethylammonium (n=2)
$C_{55}H_{102}NO_{16}P$ (1064.39)
1767.) 1,2-di-(Z,Z)-6,12-nonadecadienoyl-sn-glycero-3-phospho-N,N-dimethyl-N—(HP$_1$—HP$_2$—HP$_3$-diHP$_4$) ethylammonium (n=2)
$C_{57}H_{106}NO_{16}P$ (1092.44)
1768.) 1,2-di-(Z,Z)-10,16-eicosadienoyl-sn-glycero-3-phospho-N,N-dimethyl-N—(HP$_1$—HP$_2$—HP$_3$-diHP$_4$) ethylammonium (n=2)
$C_{59}H_{110}NO_{16}P$ (1120.49)
1769.) 1,2-di-(Z,Z)-10,16-heneicosadienoyl-sn-glycero-3-phospho-N,N-dimethyl-N—(HP$_1$—HP$_2$—HP$_3$-diHP$_4$) ethylammonium (n=2)
$C_{61}H_{114}NO_{16}P$ (1148.55)
1770.) 1,2-di-(Z,Z)-10,16-docosadienoyl-sn-glycero-3-phospho-N,N-dimethyl-N—(HP$_1$—HP$_2$—HP$_3$-diHP$_4$) ethylammonium (n=2)
$C_{63}H_{118}NO_{16}P$ (1176.60)
1771.) 1,2-di-(Z,Z)-10,16-tricosadienoyl-sn-glycero-3-phospho-N,N-dimethyl-N—(HP$_1$—HP$_2$—HP$_3$-diHP$_4$) ethylammonium (n=2)
$C_{65}H_{122}NO_{16}P$ (1204.65)
1772.) 1,2-di-(Z,Z)-6,18-tetracosadienoyl-sn-glycero-3-phospho-N,N-dimethyl-N—(HP$_1$—HP$_2$—HP$_3$-diHP$_4$) ethylammonium (n=2)
$C_{67}H_{126}NO_{16}P$ (1232.71)
1773.) 1,2-di-(Z,Z)-10,6-pentacosadienoyl-sn-glycero-3-phospho-N,N-dimethyl-N—(HP$_1$—HP$_2$—HP$_3$-diHP$_4$) ethylammonium (n=2)
$C_{69}H_{130}NO_{16}P$ (1260.76)
1774.) 1,2-di-(Z,Z)-6,18-hexacosadienoyl-sn-glycero-3-phospho-N,N-dimethyl-N—(HP$_1$—HP$_2$—HP$_3$-diHP$_4$) ethylammonium (n=2)
$C_{71}H_{134}NO_{16}P$ (1288.82)
1775.) 2-(Z)-6-hexadecenoyl-1-stearoyl-sn-glycero-3-phospho-N,N-dimethyl-N—(HP$_1$—HP$_2$—HP$_3$-diHP$_4$)ethylammonium (n=2)
$C_{53}H_{104}NO_{16}P$ (1042.38)
1776.) 2-(Z)-10-octadecenoyl-1-stearoyl-sn-glycero-3-phospho-N,N-dimethyl-N—(HP$_1$—HP$_2$—HP$_3$-diHP$_4$) ethylammonium (n=2)
$C_{55}H_{108}NO_{16}P$ (1070.43)
1777.) 2-(Z)-10-eicosenoyl-1-stearoyl-sn-glycero-3-phospho-N,N-dimethyl-N—(HP$_1$—HP$_2$—HP$_3$-diHP$_4$) ethylammonium (n=2)
$C_{57}H_{112}NO_{16}P$ (1098.49)
1778.) 1-behenyl-2-(Z)-10-docosenoyl-sn-glycero-3-phospho-N,N-dimethyl-N—(HP$_1$—HP$_2$—HP$_3$-diHP$_4$) ethylammonium (n=2)
$C_{61}H_{120}NO_{16}P$ (1154.59)
1779.) 2-(Z,Z)-6,12-hexadecadienoyl-1-stearoyl-sn-glycero-3-phospho-N,N-dimethyl-N—(HP$_1$—HP$_2$—HP$_3$-diHP$_4$)ethylammonium (n=2)
$C_{53}H_{102}NO_{16}P$ (1040.36)
1780.) 2-(Z,Z)-10,16-docosadienoyl-1-stearoyl-sn-glycero-3-phospho-N,N-dimethyl-N—(HP$_1$—HP$_2$—HP$_3$-diHP$_4$) ethylammonium (n=2)
$C_{59}H_{114}NO_{16}P$ (1124.53)
1781.) 1-stearoyl-2-(Z,Z)-6,18-tetracosadienoyl-sn-glycero-3-phospho-N,N-dimethyl-N—(HPL—HP$_2$—HP$_3$-diHP$_4$) ethylammonium (n=2)
$C_{61}H_{118}NO_{16}P$ (1152.58)
1782.) 1-(Z)-10-octadecenoyl-2-stearoyl-sn-glycero-3-phospho-N,N-dimethyl-N—(HP$_1$—HP$_2$—HP$_3$-diHP$_4$) ethylammonium (n=2)
$C_{55}H_{108}NO_{16}P$ (1070.43)
1783.) 1-(Z,Z)-6,18-hexacosadienoyl-2-stearoyl-sn-glycero-3-phospho-N,N-dimethyl-N—(HP$_1$—HP$_2$—HP$_3$-diHP$_4$) ethylanunonium (n=2)
$C_{63}H_{122}NO_{16}P$ (1180.63)
1784.) 1-(Z,Z)-6,18-hexacosadienoyl-2-(Z)-6-hexadecenoyl-sn-glycero-3-phospho-N,N-dimethyl-N—(HP$_1$—HP$_2$—HP$_3$-diHP$_4$)ethylammonium (n=2)
$C_{61}H_{116}NO_{16}P$ (1150.56)
1785.) 2-(Z,Z)-6,18-hexacosadienoyl-1-(Z)-6-hexadecenoyl-sn-glycero-3-phospho-N,N-dimethyl-N—(HP$_1$—HP$_2$—HP$_3$-diHP$_4$)ethylammonium (n=2)
$C_{61}H_{116}NO_{16}P$ (1150.56)
n=3

1786.) 1,2-di-(Z)-6-hexadecenoyl-sn-glycero-3-phospho-N,N-dimethyl-N—(HP$_1$—HP$_2$—HP$_3$-diHP$_4$) propylammonium (n=3)
$C_{52}H_{100}NO_{16}P$ (1026.34)

1787.) 1,2-di-(Z)-10-heptadecenoyl-sn-glycero-3-phospho-N,N-dimethyl-N—(HP$_1$—HP$_2$—HP$_3$-diHP$_4$)—propylammonium (n=3)
$C_{54}H_{104}NO_{16}P$ (1054.39)

1788.) 1,2-di-(Z)-6-octadecenoyl-sn-glycero-3-phospho-N,N-dimethyl-N—(HP$_1$—HP$_2$—HP$_3$-diHP$_4$)propylammonium (n=3)
$C_{56}H_{108}NO_{16}P$ (1082.44)

1789.) 1,2-di-(Z)-12-eicosenoyl-sn-glycero-3-phospho-N,N-dimethyl-N—(HP$_1$—HP$_2$—HP$_3$-diHP$_4$) propylammonium (n=3)
$C_{60}H_{116}NO_{16}P$ (1138.55)

1790.) 1,2-di-(Z)-10-docosenoyl-sn-glycero-3-phospho-N,N-dimethyl-N—(HP$_1$—HP$_2$—HP$_3$-diHP$_4$)propylammonium (n=3)
$C_{64}H_{124}NO_{16}P$ (1194.66)

1791.) 1,2-di-(z)-12-docosenoyl-sn-glycero-3-phospho-N,N-dimethyl-N—(HP$_1$—HP$_2$—HP$_3$-diHP$_4$) propylammonium (n=3)
$C_{64}H_{124}NO_{16}P$ (1194.66)

1792.) 1,2-di-(Z)-10-tricosenoyl-sn-glycero-3-phospho-N,N-dimethyl-N—(HP$_1$—HP$_2$—HP$_3$-diHP$_4$)propylammonium (n=3)
$C_{66}H_{128}NO_{16}P$ (1222.71)

1793.) 1,2-di-(Z)-10-tetracosenoyl-sn-glycero-3-phospho-N,N-dimethyl-N—(HP$_1$—HP$_2$—HP$_3$-diHP$_4$)—propylammonium (n=3)
$C_{68}H_{132}NO_{16}P$ (1250.77)

1794.) 1,2-di-(Z,Z)-5,11-octadecadienoyl-sn-glycero-3-phospho-N,N-dimethyl-N—(HP$_1$—HP$_2$—HP$_3$-diHP$_4$)—propylammonium (n=3)
$C_{56}H_{104}NO_{16}P$ (1078.41)

1795.) 1,2-di-(Z,Z)-10,16-eicosadienoyl-sn-glycero-3-phospho-N,N-dimethyl-N—(HP$_1$—HP$_2$—HP$_3$-diHP$_4$)-propylammonium (n=3)
$C_{60}H_{112}NO_{16}P$ (1134.52)

1796.) 1,2-di-(Z,Z)-10,16-docosadienoyl-sn-glycero-3-phospho-N,N-dimethyl-N—(HP$_1$—HP$_2$—HP$_3$-diHP$_4$)-propylammonium (n=3)
$C_{64}H_{120}NO_{16}P$ (1190.63)

1797.) 1,2-di-(Z,Z)-6,18-hexacosadienoyl-sn-glycero-3-phospho-N,N-dimethyl-N—(HP$_1$—HP$_2$—HP$_3$-diHP$_4$)—propylammonium (n=3)
$C_{72}H_{136}NO_{16}P$ (1302.84)

1798.) 2-(Z)-6-hexadecenoyl-1-stearoyl-sn-glycero-3-phospho-N,N-dimethyl-N—(HP$_1$—HP$_2$—HP$_3$-diHP$_4$)-propylammonium (n=3)
$C_{54}H_{106}NO_{16}P$ (1056.41)

1799.) 2-(Z)-10-octadecenoyl-1-stearoyl-sn-glycero-3-phospho-N,N-dimethyl-N—(HP$_1$—HP$_2$—HP$_3$-diHP$_4$)-propylammonium (n=3)
$C_{56}H_{110}NO_{15}P$ (1084.46)

1800.) 2-(Z)-10-docosenoyl-1-behenyl-sn-glycero-3-phospho-N,N-dimethyl-N—(HP$_1$—HP$_2$—HP$_3$-diHP$_4$)-propylammonium (n=3)
$C_{62}H_{122}NO_{16}P$ (1168.62)

1801.) 2-(Z,Z)-6,12-hexadecadienoyl-1-stearoyl-sn-glycero-3-phospho-N,N-dimethyl-N—(HP$_1$—HP$_2$—HP$_3$-diHP$_4$)propylammonium (n=3)
$C_{54}H_{104}NO_{16}P$ (1054.39)

1802.) 1-(Z)-10-octadecenoyl-2-stearoyl-sn-glycero-3-phospho-N,N-dimethyl-N—(HP$_1$—HP$_2$—HP$_3$-diHP$_4$)-propylammonium (n=3)
$C_{56}H_{110}NO_{16}P$ (1084.46)

1803.) 1-(Z,Z)-6,18-hexacosadienoyl-2-stearoyl-sn-glycero-3-phospho-N,N-dimethyl-N—(HP$_1$—HP$_2$—HP$_3$-diHP$_4$) propylammonium (n=3)
$C_{64}H_{124}NO_{16}P$ (1194.66)

n=4

1804.) 1,2-di-(Z)-6-octadecenoyl-sn-glycero-3-phospho-N,N-dimethyl-N—(HP$_1$—HP$_2$—HP$_3$-diHP$_4$)butylammonium (n=4)
$C_{57}H_{110}NO_{16}P$ (1096.47)

1805.) 1,2-di-(Z)-10-docosenoyl-sn-glycero-3-phospho-N,N-dimethyl-N—(HP$_1$—HP$_2$—HP$_3$-diHP$_4$)butylammonium (n=4)
$C_{65}H_{126}NO_{16}P$ (1208.69)

1806.) 1,2-di-(Z,Z)-5,11-hexadecadienoyl-sn-glycero-3-phospho-N,N-dimethyl-N—(HP$_1$—HP$_2$—HP$_3$-diHP$_4$) butylammonium (n=4)
$C_{53}H_{98}NO_{16}P$ (1036.33)

1807.) 1,2-di-(Z,Z)-10,16-docosadienoyl-sn-glycero-3-phospho-N,N-dimethyl-N—(HP$_1$—HP$_2$—HP$_3$-diHP$_4$) butylammonium (n=4)
$C_{65}H_{122}NO_{16}P$ (1204.65)

1808.) 1,2-di-(Z,Z)-6,18-hexacosadienoyl-sn-glycero-3-phospho-N,N-dimethyl-N—(HP$_1$—HP$_2$—HP$_3$-diHP$_4$) butylammonium (n=4)
$C_{73}H_{138}NO_{16}P$ (1316.87)

n=6

1809.) 1,2-di-(Z)-6-octadecenoyl-sn-glycero-3-phospho-N,N-dimethyl-N—(HP$_1$—HP$_2$—HP$_3$-diHP$_4$) hexylammonium (n=6)
$C_{59}H_{114}NO_{16}P$ (1124.53)

1810.) 1,2-di-(Z)-10-docosenoyl-sn-glycero-3-phospho-N,N-dimethyl-N—(HP$_1$—HP$_2$—HP$_3$-diHP$_4$)hexylammonium (n=6)
$C_{67}H_{130}NO_{16}P$ (1236.74)

1811.) 1,2-di-(Z,Z)-10,16-docosadienoyl-sn-glycero-3-phospho-N,N-dimethyl-N—(HP$_1$—HP$_2$—HP$_3$-diHP$_4$) hexylammonium (n=6)
$C_{67}H_{126}NO_{16}P$ (1232.71)

1812.) 1,2-di-(Z,Z)-6,18-hexacosadienoyl-sn-glycero-3-phospho-N,N-dimethyl-N—(HP$_1$—HP$_2$—HP$_3$-diHP$_4$) hexylammonium (n=6)
$C_{75}H_{142}NO_{16}P$ (1344.92)

5. Examples of Two-Chain glycero-phospho Compounds not Hydroxylated on the Nitrogen $$A-PO_3^- -\!\!\left[(CH_2)_n-\!\!\overset{\overset{\displaystyle CH_3}{|}}{\underset{\underset{\displaystyle R_3}{|}}{N^+}}-\!\!\right]_m\!\!(CH_2)_x-\!\!\left[CH_2\!\!\left(\overset{}{\underset{\underset{\displaystyle OH}{|}}{CH}}\right)_y\!\!CH_2-O\right]_z\!\!H$$

(A = III; n = 2-6; R$_3$, CH$_3$; m = 1, x = 1; z = 0)

1813.) 1,2-di-(Z)-6-hexadecenoyl-sn-glycero-3-phospho-N,N,N-trimethylpropylammonium (n=3)
$C_{41}H_{78}NO_8P$ (744.05)

1814.) 1,2-di-(Z)-10-heptadecenoyl-sn-glycero-3-phospho-N,N,N-trimethylpropylammonium (n=3)
$C_{43}H_{82}NO_8P$ (772.10)

1815.) 1,2-di-(Z)-6-octadecenoyl-sn-glycero-3-phospho-N,N,N-trimethylpropylammonium (n=3)
$C_{45}H_{86}NO_8P$ (800.15)

1816.) 1,2-di-(Z)-12-eicosenoyl-sn-glycero-3-phospho-N,N,N-trimethylpropylammonium (n=3)
$C_{49}H_{94}NO_8P$ (856.26)

1817.) 1,2-di-(Z)-10-docosenoyl-sn-glycero-3-phospho-N,N,N-trimethylpropylammonium (n=3)
$C_{53}H_{102}NO_8P$ (912.37)

1818.) 1,2-di-(Z)-12-docosenoyl-sn-glycero-3-phospho-N,N,N-trimethylpropylammonium (n=3)
$C_{53}H_{102}NO_8P$ (912.37)

1819.) 1,2-di-(Z)-10-tricosenoyl-sn-glycero-3-phospho-N,N,N-trimethylpropylammonium (n=3)
$C_{55}H_{106}NO_8P$ (940-42)

1820.) 1,2-di-(Z)-10-tetracosenoyl-sn-glycero-3-phospho-N,N,N-trimethylpropylammonium (n=3)
$C_{57}H_{110}NO_8P$ (968.48)

1821.) 1,2-di-(Z,Z)-5,11-octadecadienoyl-sn-glycero-3-phospho-N,N,N-trimethylpropylammonium (n=3)
$C_{45}H_{82}NO_8P$ (796.12)

1822.) 1,2-di-(Z,Z)-10,16-eicosadienoyl-sn-glycero-3-phospho-N,N,N-trimethylpropylammonium (n=3)
$C_{49}H_{10}NO_8P$ (852.23)

1823.) 1,2-di-(Z,Z)-10,16-docosadienoyl-sn-glycero-3-phospho-N,N,N-trimethylpropylammonium (n=3)
$C_{53}H_{98}NO_8P$ (908.34)

1824.) 1,2-di-(Z,Z)-6,18-hexacosadienoyl-sn-glycero-3-phospho-N,N,N-trimethylpropylammonium (n=3)
$C_{61}H_{114}NO_8P$ (1020.55)

1825.) 2-(Z)-6-hexadecenoyl-1-stearoyl-sn-glycero-3-phospho-N,N,N-trimethylpropylammonium (n=3)
$C_{43}H_{84}NO_8P$ (774.12)

1826.) 2-(Z)-10-octadecenoyl-1-stearoyl-sn-glycero-3-phospho-N,N,N-trimethylpropylammonium (n=3)
$C_{45}H_{88}NO_8P$ (802.17)

1827.) 2-(Z)-10-docosenoyl-1-behenyl-sn-glycero-3-phospho-N,N,N-trimethylpropylammonium (n 3)
$C_{51}H_{100}NO_8P$ (886.33)

1828.) 2-(Z,Z)-6,12-hexadecadienoyl-1-stearoyl-sn-glycero-3-phospho-N,N,N-trimethylpropylanmonium (n=3)
$C_{43}H_{82}NO_8P$ (772.10)

1829.) 1-(Z)-10-octadecenoyl-2-stearoyl-sn-glycero-3-phospho-N,N,N-trimethylpropylammonium (n=3)
$C_{45}H_{88}NO_8P$ (802.17)

1830.) 1-(Z,Z)-6,18-hexacosadienoyl-2-stearoyl-sn-glycero-3-phospho-N,N,N-trimethylpropylammonium (n=3)
$C_{53}H_{102}NO_8P$ (912.37)

n=4

1831.) 1,2-di-(z)-6-octadecenoyl-sn-glycero-3-phospho-N,N,N-trimethylbutylammonium (n=4)
$C_{46}H_{88}NO_8P$ (814.18)

1832.) 1,2-di-(Z)-10-docosenoyl-sn-glycero-3-phospho-N,N,N-trimethylbutylammonium (n=4)
$C_{54}H_{104}NO_8P$ (926.40)

1833.) 1,2-di-(Z,Z)-5,11-hexadecadienoyl-sn-glycero-3-phospho-N,N,N-trimethylbutylammonium (n=4)
$C_{42}H_{76}NO_8P$ (796.12)

1834.) 1,2-di-(Z,Z)-10,16-docosadienoyl-sn-glycero-3-phospho-N,N,N-trimethylbutylammonium (n=4)
$C_{54}H_{100}NO_8P$ (922.36)

1835.) 1,2-di-(Z,Z)-6,18-hexacosadienoyl-sn-glycero-3-phospho-N,N,N-trimethylbutylammonium (n=4)
$C_{62}H_{116}NO_8P$ (1034.58)

n=6

1836.) 1,2-di-(Z)-6-octadecenoyl-sn-glycero-3-phospho-N,N,N-trimethylhexylammonium (n=6)
$C_{48}H_{92}NO_8P$ (842.23)

1837.) 1,2-di-(Z)-10-docosenoyl-sn-glycero-3-phospho-N,N,N-trimethylhexylammonium (n=6)
$C_{56}H_{108}NO_8P$ (954.45)

1838.) 1,2-di-(Z,Z)-10,16-docosadienoyl-sn-glycero-3-phospho-N,N,N-trimethylhexylammonium (n=6)
$C_{56}H_{104}NO_8P$ (950.42)

1839.) 1,2-di-(Z,Z)-6,18-hexacosadienoyl-sn-glycero-3-phospho-N,N,N-trimethylhexylammonium (n 6)
$C_{64}H_{120}NO_8P$ (1062.63)

Negatively charged phospholipids: Phosphatidyloligoglycerols

6. Examples of glycero-glycerols (Na Salts of phospho-$G_1$-$G_2$ Compounds)

$$A-PO_3^- \left[-(CH_2)_n - \underset{R_3}{\underset{|}{\overset{CH_3}{\overset{|}{N^+}}}} -(CH_2)_x\right]_m \left[CH_2 - \left(\underset{OH}{\underset{|}{CH}}\right)_y - CH_2-O\right]_z H$$

(A = III; m = 0; y = 1; z = 2)

1840.) 1,2-di-(Z)-6-hexadecenoyl-sn-glycero-3-phospho-glycero-glycerol; Na salt
$C_{41}H_{76}NaO_{12}P$ (815.01)

1841.) 1,2-di-(Z)-10-heptadecenoyl-sn-glycero-3-phospho-glycero-glycerol; Na salt
$C_{43}H_{80}NaO_{12}P$ (843.06)

1842.) 1,2-di-(Z)-6-octadecenoyl-sn-glycero-3-phospho-glycero-glycerol; Na salt
$C_{45}H_{84}NaO_{12}P$ (871.12)

1843.) 1,2-di-(Z)-6-nonadecenoyl-sn-glycero-3-phospho-glycero-glycerol; Na salt
$C_{47}H_{88}NaO_{12}P$ (899.17)

1844.) 1,2-di-(Z)-12-eicosenoyl-sn-glycero-3-phospho-glycero-glycerol; Na salt
$C_{49}H_{92}NaO_{12}P$ (927.23)

1845.) 1,2-di-(Z)-10-heneicosenoyl-sn-glycero-3-phospho-glycero-glycerol; Na salt
$C_{51}H_{96}NaO_{12}P$ (955.28)

1846.) 1,2-di-(Z)-10-docosenoyl-sn-glycero-3-phospho-glycero-glycerol; Na salt
$C_{53}H_{100}NaO_{12}P$ (983.33)

1847.) 1,2-di-(Z)-12-docosenoyl-sn-glycero-3-phospho-glycero-glycerol; Na salt
$C_{53}H_{100}NaO_{12}P$ (983.33)

1848.) 1,2-di-(Z)-10-tricosenoyl-sn-glycero-3-phospho-glycero-glycerol; Na salt
$C_{55}H_{104}NaO_{12}P$ (1011.39)

1849.) 1,2-di-(Z)-10-tetracosenoyl-sn-glycero-3-phospho-glycero-glycerol; Na salt
$C_{57}H_{108}NaO_{12}P$ (1039.44)

1850.) 1,2-di-(Z)-15-pentacosenoyl-sn-glycero-3-phospho-glycero-glycerol; Na salt
$C_{59}H_{112}NaO_{12}P$ (1067.49)

1851.) 1,2-di-(Z)-16-hexacosenoyl-sn-glycero-3-phospho-glycero-glycerol; Na salt
$C_{61}H_{116}NaO_{12}P$ (1095-55)

1852.) 1,2-di-(Z,Z)-5,11-hexadecadienoyl-sn-glycero-3-phospho-glycero-glycerol; Na salt
$C_{41}H_{72}NaO_{12}P$ (810.98)

1853.) 1,2-di-(Z,Z)-5,11-octadecadienoyl-sn-glycero-3-phospho-glycero-glycerol; Na salt
$C_{45}H_{80}NaO_{12}P$ (867.09)

1854.) 1,2-di-(Z,Z)-6,12-nonadecadienoyl-sn-glycero-3-phospho-glycero-glycerol; Na salt
$C_{47}H_{84}NaO_{12}P$ (895.14)
1855.) 1,2-di-(Z,Z)-10,16-eicosadienoyl-sn-glycero-3-phospho-glycero-glycerol; Na salt
$C_{49}H_{88}NaO_{12}P$ (923.19)
1856.) 1,2-di-(Z,Z)-10,16-docosadienoyl-sn-glycero-3-phospho-glycero-glycerol; Na salt
$C_{53}H_{96}NaO_{12}P$ (979.30)
1857.) 1,2-di-(Z,Z)-6,18-tetracosadienoyl-sn-glycero-3-phospho-glycero-glycerol; Na salt
$C_{57}H_{104}NaO_{12}P$ (1035.41)
1858.) 1,2-di-(Z,Z)-10,16-pentacosadienoyl-sn-glycero-3-phospho-glycero-glycerol; Na salt
$C_{59}H_{108}NaO_{12}P$ (1063.46)
1859.) 1,2-di-(Z,Z)-6,18-hexacosadienoyl-sn-glycero-3-phospho-glycero-glycerol; Na salt
$C_{61}H_{112}NaO_{12}P$ (1091.52)
1860.) 2-(Z)-6-hexadecenoyl-1-stearoyl-sn-glycero-3-phospho-glycero-glycerol; Na salt
$C_{43}H_{82}NaO_{12}P$ (845.08)
1861.) 2-(Z)-10-octadecenoyl-1-stearoyl-sn-glycero-3-phospho-glycero-glycerol; Na salt
$C_{45}H_{86}NaO_{12}P$ (873.13)
1862.) 2-(Z)-10-eicosenoyl-1-stearoyl-sn-glycero-3-phospho-glycero-glycerol; Na salt
$C_{47}H_{90}NaO_{12}P$ (901.19)
1863.) 2-(Z,Z)-6,12-hexadecadienoyl-1-stearoyl-sn-glycero-3-phospho-glycero-glycerol; Na salt
$C_{43}H_{80}NaO_{12}P$ (843.06)
1864.) 2-(Z,Z)-10,16-docosadienoyl-1-stearoyl-sn-glycero-3-phospho-glycero-glycerol; Na salt
$C_{49}H_{92}NaO_{12}P$ (927.23)
1865.) 1-stearoyl-2-(Z,Z)-6,18-tetracosadienoyl-sn-glycero-3-phospho-glycero-glycerol; Na salt
$C_{51}H_{96}NaO_{12}P$ (955.28)
1866.) 1-(z)-10-octadecenoyl-2-stearoyl-sn-glycero-3-phospho-glycero-glycerol; Na salt
$C_{45}H_{86}NaO_{12}P$ (873.13)
1867.) 1-(Z,Z)-6,18-hexacosadienoyl-2-stearoyl-sn-glycero-3-phospho-glycero-glycerol; Na salt
$C_{53}H_{100}NaO_{12}P$ (983.33)
1868.) 1-(Z,Z)-6,18-hexacosadienoyl-2-(Z)-6-hexadecenoyl-sn-glycero-3-phospho-glycero-glycerol; Na salt
$C_{51}H_{94}NaO_{12}P$ (953.26)
1869.) 2-(Z,Z)-6,18-hexacosadienoyl-1-(z)-6-hexadecenoyl-sn-glycero-3-phospho-glycero-glycerol; Na salt
$C_{51}H_{94}NaO_{12}P$ (953.26)

7. Examples of phosphatidyl-glycero-glycero-glycerols (Na Salts of phospho-$G_1$-$G_2$-$G_3$ Compounds)

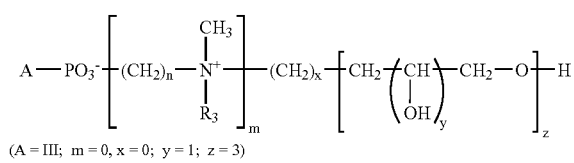

(A = III; m = 0, x = 0; y = 1; z = 3)

1870.) 1,2-di-(z)-6-hexadecenoyl-sn-glycero-3-phospho-glycero-glycero-glycerol; Na salt
$C_{44}H_{82}NaO_{14}P$ (889.09)

1871.) 1,2-di-(Z)-10-heptadecenoyl-sn-glycero-3-phospho-glycero-glycero-glycerol; Na salt
$C_{41}H_{86}NaO_{14}P$ (917.14)
1872.) 1,2-di-(Z)-6-octadecenoyl-sn-glycero-3-phospho-glycero-glycero-glycerol; Na salt
$C_{48}H_{90}NaO_{14}P$ (945.20)
1873.) 1,2-di-(Z)-6-nonadecenoyl-sn-glycero-3-phospho-glycero-glycero-glycerol; Na salt
$C_{50}H_{94}NaO_{14}P$ (973.25)
1874.) 1,2-di-(z)-12-eicosenoyl-sn-glycero-3-phospho-glycero-glycero-glycerol; Na salt
$C_{52}H_{98}NaO_{14}P$ (1001.31)
1875.) 1,2-di-(Z)-10-heneicosenoyl-sn-glycero-3-phospho-glycero-glycero-glycerol; Na salt
$C_{54}H_{102}NaO_{14}P$ (1029.36)
1876.) 1,2-di-(Z)-10-docosenoyl-sn-glycero-3-phospho-glycero-glycero-glycerol; Na salt
$C_{56}H_{106}NaO_{14}P$ (1057.41)
1877.) 1,2-di-(Z)-12-docosenoyl-sn-glycero-3-phospho-glycero-glycero-glycerol; Na salt
$C_{56}H_{106}NaO_{14}P$ (1057.41)
1878.) 1,2-di-(Z)-10-tricosenoyl-sn-glycero-3-phospho-glycero-glycero-glycerol; Na salt
$C_{58}H_{110}NaO_{14}P$ (1085.47)
1879.) 1,2-di-(Z)-10-tetracosenoyl-sn-glycero-3-phospho-glycero-glycero-glycerol; Na salt
$C_{60}H_{114}NaO_{14}P$ (1113.52)
1880.) 1,2-di-(Z)-15-pentacosenoyl-sn-glycero-3-phospho-glycero-glycero-glycerol; Na salt
$C_{62}H_{118}NaO_{14}P$ (1141.57)
1881.) 1,2-di-(Z)-16-hexacosenoyl-sn-glycero-3-phospho-glycero-glycero-glycerol; Na salt
$C_{64}H_{122}NaO_{14}P$ (1169.63)
1882.) 1,2-di-(Z,Z)-5,11-hexadecadienoyl-sn-glycero-3-phospho-glycero-glycero-glycerol; Na salt
$C_{44}H_{78}NaO_{14}P$ (885.06)
1883.) 1,2-di-(Z,Z)-5,11-octadecadienoyl-sn-glycero-3-phospho-glycero-glycero-glycerol; Na salt
$C_{48}H_{86}NaO_{14}P$ (941.17)
1884.) 1,2-di-(Z,Z)-6,12-nonadecadienoyl-sn-glycero-3-phospho-glycero-glycero-glycerol; Na salt
$C_{50}H_{90}NaO_{14}P$ (969.22)
1885.) 1,2-di-(Z,Z)-10,16-eicosadienoyl-sn-glycero-3-phospho-glycero-glycero-glycerol; Na salt
$C_{52}H_{94}NaO_{14}P$ (997.27)
1886.) 1,2-di-(Z,Z)-10,16-docosadienoyl-sn-glycero-3-phospho-glycero-glycero-glycerol; Na salt
$C_{56}H_{102}NaO_{14}P$ (1053.38)
1887.) 1,2-di-(Z,Z)-6,18-tetracosadienoyl-sn-glycero-3-phospho-glycero-glycero-glycerol; Na salt
$C_{60}H_{110}NaO_{14}P$ (1109.49)
1888.) 1,2-di-(Z,Z)-10,16-pentacosadienoyl-sn-glycero-3-phospho-glycero-glycero-glycerol; Na salt
$C_{62}H_{114}NaO_{14}P$ (1137.54)
1889.) 1,2-di-(Z,Z)-6,18-hexacosadienoyl-sn-glycero-3-phospho-glycero-glycero-glycerol; Na salt
$C_{64}H_{118}NaO_{14}P$ (1165.60)
1890.) 2-(Z)-6-hexadecenoyl-1-stearoyl-sn-glycero-3-phospho-glycero-glycero-glycerol; Na salt
$C_{46}H_{88}NaO_{14}P$ (919.16)
1891.) 2-(Z)-10-octadecenoyl-1-stearoyl-sn-glycero-3-phospho-glycero-glycero-glycerol; Na salt
$C_{48}H_{92}NaO_{14}P$ (947.21)
1892.) 2-(Z)-10-eicosenoyl-1-stearoyl-sn-glycero-3-phospho-glycero-glycero-glycerol; Na salt
$C_{50}H_{96}NaO_{14}P$ (975.27)

1893.) 2-(Z,Z)-6,12-hexadecadienoyl-1-stearoyl-sn-glycero-3-phospho-glycero-glycero-glycerol; Na salt
$C_{46}H_{86}NaO_{14}P$ (917.14)
1894.) 2-(Z,Z)-10,16-docosadienoyl-1-stearoyl-sn-glycero-3-phospho-glycero-glycero-glycerol; Na salt
$C_{52}H_{98}NaO_{14}P$ (1001.31)
1895.) 1-stearoyl-2-(Z,Z)-6,18-tetracosadienoyl-sn-glycero-3-phospho-glycero-glycero-glycerol; Na salt
$C_{54}H_{102}NaO_{14}P$ (1029.36)
1896.) 1-(Z)-10-octadecenoyl-2-stearoyl-sn-glycero-3-phospho-glycero-glycero-glycerol; Na salt
$C_{48}H_{92}NaO_{14}P$ (947.21)
1897.) 1-(Z,Z)-6,18-hexacosadienoyl-2-stearoyl-sn-glycero-3-phospho-glycero-glycero-glycerol; Na salt
$C_{56}H_{106}NaO_{14}P$ (1057.41)
1898.) 1-(Z,Z)-6,18-hexacosadienoyl-2-(Z)-6-hexadecenoyl-sn-glycero-3-phospho-glycero-glycero-glycerol; Na salt
$C_{54}H_{100}NaO_{14}P$ (1027.34)
1899.) 2-(Z,Z)-6,18-hexacosadienoyl-1-(Z)-6-hexadecenoyl-sn-glycero-3-phospho-glycero-glycero-glycerol; Na salt
$C_{54}H_{100}NaO_{14}P$ (1027.34)

8. Examples of phosphatidyl-glycero-glycero-glycero-glycerols (Na Salts of phospho-$G_1$-$G_2$-$G_3$-$G_4$ Compounds

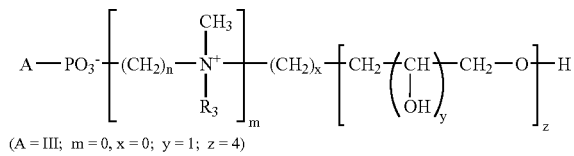

(A = III; m = 0, x = 0; y = 1; z = 4)

1900.) 1,2-di-(Z)-6-hexadecenoyl-sn-glycero-3-phospho-glycero-glycero-glycero-glycerol; Na salt
$C_{47}H_{88}NaO_{16}P$ (963.17)
1901.) 1,2-di-(Z)-10-heptadecenoyl-sn-glycero-3-phospho-glycero-glycero-glycero-glycerol; Na salt
$C_{49}H_{92}NaO_{16}P$ (991.22)
1902.) 1,2-di-(Z)-6-octadecenoyl-sn-glycero-3-phospho-glycero-glycero-glycero-glycerol; Na salt
$C_{51}H_{96}NaO_{16}P$ (1019.28)
1903.) 1,2-di-(Z)-6-nonadecenoyl-sn-glycero-3-phospho-glycero-glycero-glycero-glycerol; Na salt
$C_{53}H_{100}NaO_{16}P$ (1047.33)
1904.) 1,2-di-(Z)-12-eicosenoyl-sn-glycero-3-phospho-glycero-glycero-glycero-glycerol; Na salt
$C_{55}H_{104}NaO_{16}P$ (1075.38)
1905.) 1,2-di-(Z)-10-heneicosenoyl-sn-glycero-3-phospho-glycero-glycero-glycero-glycerol; Na salt
$C_{57}H_{108}NaO_{16}P$ (1103.44)
1906.) 1,2-di-(Z)-10-docosenoyl-sn-glycero-3-phospho-glycero-glycero-glycero-glycerol; Na salt
$C_{59}H_{112}NaO_{16}P$ (1131.49)
1907.) 1,2-di-(Z)-12-docosenoyl-sn-glycero-3-phospho-glycero-glycero-glycero-glycerol; Na salt
$C_{59}H_{112}NaO_{16}P$ (1131.49)
1908.) 1,2-di-(Z)-10-tricosenoyl-sn-glycero-3-phospho-glycero-glycero-glycero-glycerol; Na salt
$C_{61}H_{116}NaO_{16}P$ (1159.55)
1909.) 1,2-di-(Z)-10-tetracosenoyl-sn-glycero-3-phospho-glycero-glycero-glycero-glycerol; Na salt
$C_{63}H_{120}NaO_{16}P$ (1187.60)
1910.) 1,2-di-(Z)-15-pentacosenoyl-sn-glycero-3-phospho-glycero-glycero-glycero-glycerol; Na salt
$C_{65}H_{124}NaO_{16}P$ (1215.65)
1911.) 1,2-di-(Z)-16-hexacosenoyl-sn-glycero-3-phospho-glycero-glycero-glycero-glycerol; Na salt
$C_{67}H_{128}NaO_{16}P$ (1243.71)
1912.) 1,2-di-(Z,Z)-5,11-hexadecadienoyl-sn-glycero-3-phospho-glycero-glycero-glycero-glycerol; Na salt
$C_{47}H_{84}NaO_{16}P$ (959.14)
1913.) 1,2-di-(Z,Z)-5,11-octadecadienoyl-sn-glycero-3-phospho-glycero-glycero-glycero-glycerol; Na salt
$C_{51}H_{92}NaO_{16}P$ (1015.25)
1914.) 1,2-di-(Z,Z)-6,12-nonadecadienoyl-sn-glycero-3-phospho-glycero-glycero-glycero-glycerol; Na salt
$C_{53}H_{96}NaO_{16}P$ (1043.30)
1915.) 1,2-di-(Z,Z)-10,16-eicosadienoyl-sn-glycero-3-phospho-glycero-glycero-glycero-glycerol; Na salt
$C_{55}H_{100}NaO_{16}P$ (1071.35)
1916.) 1,2-di-(Z,Z)-10,16-docosadienoyl-sn-glycero-3-phospho-glycero-glycero-glycero-glycerol; Na salt
$C_{59}H_{108}NaO_{16}P$ (1127.46)
1917.) 1,2-di-(Z,Z)-6,18-tetracosadienoyl-sn-glycero-3-phospho-glycero-glycero-glycero-glycerol; Na salt
$C_{63}H_{116}NaO_{16}P$ (1183.57)
1918.) 1,2-di-(Z,Z)-10,16-pentacosadienoyl-sn-glycero-3-phospho-glycero-glycero-glycero-glycerol; Na salt
$C_{65}H_{120}NaO_{16}P$ (1211.62)
1919.) 1,2-di-(Z,Z)-6,18-hexacosadienoyl-sn-glycero-3-phospho-glycero-glycero-glycero-glycerol; Na salt
$C_{67}H_{124}NaO_{16}P$ (1239.68)
1920.) 2-(Z)-6-hexadecenoyl-1-stearoyl-sn-glycero-3-phospho-glycero-glycero-glycero-glycerol; Na salt
$C_{49}H_{94}NaO_{16}P$ (993.24)
1921.) 2-(Z)-10-octadecenoyl-1-stearoyl-sn-glycero-3-phospho-glycero-glycero-glycero-glycerol; Na salt
$C_{51}H_{98}NaO_{16}P$ (1021.29)
1922.) 2-(Z)-10-eicosenoyl-1-stearoyl-sn-glycero-3-phospho-glycero-glycero-glycero-glycerol; Na salt
$C_{53}H_{102}NaO_{16}P$ (1049.35)
1923.) 2-(Z,Z)-6,12-hexadecadienoyl-1-stearoyl-sn-glycero-3-phospho-glycero-glycero-glycero-glycerol; Na salt.
$C_{49}H_{92}NaO_{16}P$ (991.22)
1924.) 2-(Z,Z)-10,16-docosadienoyl-1-stearoyl-sn-glycero-3-phospho-glycero-glycero-glycero-glycerol; Na salt
$C_{55}H_{104}NaO_{16}P$ (1075.38)
1925.) 1-stearoyl-2-(Z,Z)-6,18-tetracosadienoyl-sn-glycero-3-phospho-glycero-glycero-glycero-glycerol; Na salt
$C_{57}H_{108}NaO_{16}P$ (1103.44)
1926.) 1-(Z)-10-octadecenoyl-2-stearoyl-sn-glycero-3-phospho-glycero-glycero-glycero-glycerol; Na salt
$C_{51}H_{98}NaO_{16}P$ (1021.29)
1927.) 1-(Z,Z)-6,18-hexacosadienoyl-2-stearoyl-sn-glycero-3-phospho-glycero-glycero-glycero-glycerol; Na salt
$C_{59}H_{112}NaO_{16}P$ (1131.49)
1928.) 1-(Z,Z)-6,18-hexacosadienoyl-2-(Z)-6-hexadecenoyl-sn-glycero-3-phospho-glycero-glycero-glycero-glycerol; Na salt
$C_{57}H_{106}NaO_{16}P$ (1101.42)

1929.) 1-(Z,Z)-6,18-hexacosadienoyl-1-(Z)-6-hexadecenoyl-sn-glycero-3-phospho-glycero-glycero-glyceroglycerol; Na salt
$C_{57}H_{106}NaO_{16}P$ (1101.42)

9. Examples of phospho-sn-$G_1$ Linkages sn-1-$G_1$-$G_2$ Compounds

1930.) 1,2-di-(Z)-6-octadecenoyl-sn-glycero-3-phospho-sn-1-glycero-glycerol; Na salt
$C_{45}H_{84}NaO_{12}P$ (871.12)
1931.) 1,2-di-(Z)-6-nonadecenoyl-sn-glycero-3-phospho-sn-1-glycero-glycerol; Na salt
$C_{47}H_{88}NaO_{12}P$ (899.17)
1932.) 1,2-di-(Z)-10-docosenoyl-sn-glycero-3-phospho-sn-1-glycero-glycerol; Na salt
$C_{53}H_{100}NaO_{12}P$ (983.33)
1933.) 1,2-di-(Z)-12-docosenoyl-sn-glycero-3-phospho-sn-1-glycero-glycerol; Na salt
$C_{53}H_{100}NaO_{12}P$ (983.33)
1934.) 1,2-di-(Z)-10-tetracosenoyl-sn-glycero-3-phospho-sn-1-glycero-glycerol; Na salt
$C_{57}H_{108}NaO_{12}P$ (1039.44)
1935.) 1,2-di-(Z)-16-hexacosenoyl-sn-glycero-3-phospho-sn-1-glycero-glycerol; Na salt
$C_{61}H_{116}NaO_{12}P$ (1095.55)
1936.) 1,2-di-(Z,Z)-5 µl-octadecadienoyl-sn-glycero-3-phospho-sn-1-glycero-glycerol; Na salt
$C_{45}H_{80}NaO_{12}P$ (867.09)
1937.) 1,2-di-(Z,Z)-10,16-docosadienoyl-sn-glycero-3-phospho-sn-1-glycero-glycerol; Na salt
$C_{53}H_{96}NaO_{12}P$ (979.30)
1938.) 1,2-di-(Z,Z)-6,18-tetracosadienoyl-sn-glycero-3-phospho-sn-1-glycero-glycerol; Na salt
$C_{57}H_{104}NaO_{12}P$ (1035.41)
1939.) 1,2-di-(Z,Z)-6,18-hexacosadienoyl-sn-glycero-3-phospho-sn-1-glycero-glycerol; Na salt
$C_{61}H_{112}NaO_{12}P$ (1091.52)
1940.) 2-(Z)-10-octadecenoyl-1-stearoyl-sn-glycero-3-phospho-sn-1-glycero-glycerol; Na salt
$C_{45}H_{86}NaO_{12}P$ (873.13)
1941.) 2-(Z)-10-eicosenoyl-1-stearoyl-sn-glycero-3-phospho-sn-1-glycero-glycerol; Na salt
$C_{47}H_{90}NaO_{12}P$ (901.19)
1942.) 2-(Z,Z)-6,12-hexadecadienoyl-1-stearoyl-sn-glycero-3-phospho-sn-1-glycero-glycerol; Na salt
$C_{43}H_{80}NaO_{12}P$ (843.06)
1943.) 2-(Z,Z)-10,16-docosadienoyl-1-stearoyl-sn-glycero-3-phospho-sn-1-glycero-glycerol; Na salt
$C_{49}H_{92}NaO_{12}P$ (927.23)
1944.) 1-(Z,Z)-6,18-hexacosadienoyl-2-stearoyl-sn-glycero-3-phospho-sn-1-glycero-glycerol; Na salt
$C_{53}H_{100}NaO_{12}P$ (983.33)

sn-1-$G_1$-$G_2$-$G_3$ Compounds

1945.) 1,2-di-(Z)-6-octadecenoyl-sn-glycero-3-phospho-sn-1-glycero-glycero-glycerol; Na salt
$C_{48}H_{90}NaO_{14}P$ (945.20)
1946.) 1,2-di-(Z)-6-nonadecenoyl-sn-glycero-3-phospho-sn-1-glycero-glycero-glycerol; Na salt
$C_{50}H_{94}NaO_{14}P$ (973.25)
1947.) 1,2-di-(Z)-10-docosenoyl-sn-glycero-3-phospho-sn-1-glycero-glycero-glycerol; Na salt
$C_{56}H_{106}NaO_{14}P$ (1057.41)
1948.) 1,2-di-(Z)-12-docosenoyl-sn-glycero-3-phospho-sn-1-glycero-glycero-glycerol; Na salt
$C_{56}H_{106}NaO_{14}P$ (1057.41)
1949.) 1,2-di-(Z)-10-tetracosenoyl-sn-glycero-3-phospho-sn-1-glycero-glycero-glycerol; Na salt
$C_{60}H_{114}NaO_{14}P$ (1113.52)
1950.) 1,2-di-(Z)-16-hexacosenoyl-sn-glycero-3-phospho-sn-1-glycero-glycero-glycerol; Na salt
$C_{64}H_{122}NaO_{14}P$ (1169.63)
1951.) 1,2-di-(Z,Z)-5,11-octadecadienoyl-sn-glycero-3-phospho-sn-1-glycero-glycero-glycerol; Na salt
$C_{48}H_{86}NaO_{14}P$ (941.17)
1952.) 1,2-di-(Z,Z)-10,16-docosadienoyl-sn-glycero-3-phospho-sn-1-glycero-glycero-glycerol; Na salt
$C_{56}H_{102}NaO_{14}P$ (1053.38)
1953.) 1,2-di-(Z,Z)-6,18-tetracosadienoyl-sn-glycero-3-phospho-sn-1-glycero-glycero-glycerol; Na salt
$C_{60}H_{110}NaO_{14}P$ (1109.49)
1954.) 1,2-di-(Z,Z)-6,18-hexacosadienoyl-sn-glycero-3-phospho-sn-1-glycero-glycero-glycerol; Na salt
$C_{64}H_{118}NaO_{14}P$ (1165.60)
1955.) 2-(Z)-10-octadecenoyl-1-stearoyl-sn-glycero-3-phospho-sn-1-glycero-glycero-glycerol; Na salt
$C_{48}H_{92}NaO_{14}P$ (947.21)
1956.) 2-(Z)-10-eicosenoyl-1-stearoyl-sn-glycero-3-phospho-sn-1-glycero-glycero-glycerol; Na salt
$C_{50}H_{96}NaO_{14}P$ (975.27)
1957.) 2-(Z,Z)-6,12-hexadecadienoyl-1-stearoyl-sn-glycero-3-phospho-sn-1-glycero-glycero-glycerol; Na salt
$C_{46}H_{86}NaO_{14}P$ (917.14)
1958.) 2-(Z,Z)-10,16-docosadienoyl-1-stearoyl-sn-glycero-3-phospho-sn-1-glycero-glycero-glycerol; Na salt
$C_{52}H_{98}NaO_{14}P$ (1001.31)
1959.) 1-(Z,Z)-6,18-hexacosadienoyl-2-stearoyl-sn-glycero-3-phospho-sn-1-glycero-glycero-glycerol; Na salt
$C_{56}H_{106}NaO_{14}P$ (1057.41)

sn-1-$G_1$-$G_2$-$G_3$-$G_4$ Compounds

1960.) 1,2-di-(Z)-6-octadecenoyl-sn-glycero-3-phospho-sn-1-glycero-glycero-glycero-glycerol; Na salt
$C_{51}H_{96}NaO_{16}P$ (1019.28)
1961.) 1,2-di-(Z)-6-nonadecenoyl-sn-glycero-3-phospho-sn-1-glycero-glycero-glycero-glycerol; Na salt
$C_{53}H_{100}NaO_{16}P$ (1047.33)
1962.) 1,2-di-(Z)-10-docosenoyl-sn-glycero-3-phospho-sn-1-glycero-glycero-glycero-glycerol; Na salt
$C_{59}H_{112}NaO_{16}P$ (1131.49)
1963.) 1,2-di-(Z)-12-docosenoyl-sn-glycero-3-phospho-sn-1-glycero-glycero-glycero-glycerol; Na salt
$C_{59}H_{112}NaO_{16}P$ (1131.49)
1964.) 1,2-di-(Z)-10-tetracosenoyl-sn-glycero-3-phospho-sn-1-glycero-glycero-glycero-glycerol; Na salt
$C_{63}H_{120}NaO_{16}P$ (1187.60)
1965.) 1,2-di-(Z)-16-hexacosenoyl-sn-glycero-3-phospho-sn-1'-glycero-glycero-glycero-glycerol; Na salt
$C_{67}H_{128}NaO_{16}P$ (1243.71)
1966.) 1,2-di-(Z,Z)-5,11-octadecadienoyl-sn-glycero-3-phospho-sn-1-glycero-glycero-glycero-glycerol; Na salt
$C_{51}H_{92}NaO_{16}P$ (1015.25)
1967.) 1,2-di-(Z,Z)-10,16-docosadienoyl-sn-glycero-3-phospho-sn-1-glycero-glycero-glycero-glycerol; Na salt
$C_{59}H_{108}NaO_{16}P$ (1127.46)
1968.) 1,2-di-(Z,Z)-16,18-tetracosadienoyl-sn-glycero-3-phospho-sn-1-glycero-glycero-glycero-glycerol; Na salt
$C_{63}H_{116}NaO_{16}P$ (1183.57)

1969.) 1,2-di-(Z,Z)-6,18-hexacosadienoyl-sn-glycero-3-phospho-sn-1-glycero-glycero-glycero-glycerol; Na salt
$C_{67}H_{124}NaO_{16}P$ (1239.68)

1970.) 2-(Z)-10-octadecenoyl-1-stearoyl-sn-glycero-3-phospho-sn-1-glycero-glycero-glycero-glycerol; Na salt
$C_{51}H_{98}NaO_{16}P$ (1021.29)

1971.) 2-(Z)-10-eicosenoyl-1-stearoyl-sn-glycero-3-phospho-sn-1-glycero-glycero-glycero-glycerol; Na salt
$C_{53}H_{102}NaO_{16}P$ (1049.35)

1972.) 2-(Z,Z)-6,12-hexadecadienoyl-1-stearoyl-sn-glycero-3-phospho-sn-1-glycero-glycero-glycero-glycerol; Na salt
$C_{49}H_{92}NaO_{16}P$ (991.22)

1973.) 2-(Z,Z)-10,16-docosadienoyl-1-stearoyl-sn-glycero-3-phospho-sn-1-glycero-glycero-glycero-glycerol; Na salt
$C_{55}H_{104}NaO_{16}P$ (1075.38)

1974.) 1-(Z,Z)-6,18-hexacosadienoyl-2-stearoyl-sn-glycero-3-phospho-sn-1-glycero-glycero-glycero-glycerol; Na salt
$C_{59}H_{112}NaO_{16}P$ (1131.49)

Linkages with Sugar Alcohols

10. Phospho-D-mannitol Compounds

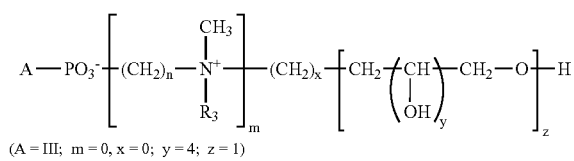

(A = III; m = 0, x = 0; y = 4; z = 1)

1975.) 1,2-di-(z)-6-hexadecenoyl-sn-glycero-3-phospho-D-mannitol; Na salt
$C_{41}H_{76}NaO_{13}P$ (831.01)

1976.) 1,2-di-(Z)-6-nonadecenoyl-sn-glycero-3-phospho-D-mannitol; Na salt
$C_{47}H_{88}NaO_{13}P$ (915.17)

1977.) 1,2-di-(Z)-12-eicosenoyl-sn-glycero-3-phospho-D-mannitol; Na salt
$C_{49}H_{92}NaO_{13}P$ (943.23)

1978.) 1,2-di-(Z)-10-docosenoyl-sn-glycero-3-phospho-D-mannitol; Na salt
$C_{53}H_{100}NaO_{13}P$ (999.33)

1979.) 1,2-di-(z)-12-docosenoyl-sn-glycero-3-phospho-D-mannitol; Na salt
$C_{53}H_{100}NaO_{13}P$ (999.33)

1980.) 1,2-di-(Z)-10-tetracosenoyl-sn-glycero-3-phospho-D-mannitol; Na salt
$C_{57}H_{108}NaO_{13}P$ (1055.44)

1981.) 1,2-di-(Z)-16-hexacosenoyl-sn-glycero-3-phospho-D-mannitol; Na salt
$C_{61}H_{116}NaO_{13}P$ (1111.55)

1982.) 1,2-di-(Z,Z)-5,11-hexadecadienoyl-sn-glycero-3-phospho-D-mannitol; Na salt
$C_{41}H_{72}NaO_{13}P$ (826.98)

1983.) 1,2-di-(Z,Z)-5,11-octadecadienoyl-sn-glycero-3-phospho-D-mannitol; Na salt
$C_{45}H_{80}NaO_{13}P$ (883.09)

1984.) 1,2-di-(Z,Z)-6,12-nonadecadienoyl-sn-glycero-3-phospho-D-mannitol; Na salt
$C_{47}H_{84}NaO_{13}P$ (911.14)

1985.) 1,2-di-(Z,Z)-10,16-docosadienoyl-sn-glycero-3-phospho-D-mannitol; Na salt
$C_{53}H_{96}NaO_{13}P$ (995.30)

1986.) 1,2-di-(Z,Z)-6,18-hexacosadienoyl-sn-glycero-3-phospho-D-mannitol; Na salt
$C_{61}H_{112}NaO_{13}P$ (1107.52)

1987.) 2-(Z)-6-hexadecenoyl-1-stearoyl-sn-glycero-3-phospho-D-mannitol; Na salt
$C_{43}H_{82}NaO_{13}P$ (861.08)

1988.) 2-(Z)-10-octadecenoyl-1-stearoyl-sn-glycero-3-phospho-D-mannitol; Na salt
$C_{45}H_{86}NaO_{13}P$ (889.13)

1989.) 2-(Z,Z)-6,12-hexadecadienoyl-1-stearoyl-sn-glycero-3-phospho-D-mannitol; Na salt
$C_{43}H_{80}NaO_{13}P$ (859.06)

1990.) 2-(Z,Z)-10,16-docosadienoyl-1-stearoyl-sn-glycero-3-phospho-D-mannitol; Na salt
$C_{49}H_{92}NaO_{13}P$ (943.23)

1991.) 1-stearoyl-2-(Z,Z)-6,18-tetracosadienoyl-sn-glycero-3-phospho-D-mannitol; Na salt
$C_{51}H_{96}NaO_{13}P$ (971.28)

1992.) 1-(Z)-10-octadecenoyl-2-stearoyl-sn-glycero-3-phospho-D-mannitol; Na salt
$C_{45}H_{86}NaO_{13}P$ (889.13)

1993.) 1-(Z,Z)-6,18-hexacosadienoyl-2-stearoyl-sn-glycero-3-phospho-D-mannitol; Na salt
$C_{53}H_{100}NaO_{13}P$ (999.33)

1994.) 1-(Z,Z)-6,18-hexacosadienoyl-2-(Z)-6-hexadecenoyl-sn-glycero-3-phospho-D-mannitol; Na salt
$C_{51}H_{94}NaO_{13}P$ (969.26)

1995.) 2-(Z,Z)-6,18-hexacosadienoyl-1-(Z)-6-hexadecenoyl-sn-glycero-3-phospho-D-mannitol; Na salt
$C_{51}H_{94}NaO_{13}P$ (969.26)

1996.) 1-(Z)-12-docosenoyl-sn-glycero-3-phospho-D-mannitol; Na salt
$C_{31}H_{60}NaO_{12}P$ (678.77)

1997.) 1-(Z,Z)-10,16-docosadienoyl-sn-glycero-3-phospho-D-mannitol; Na salt
$C_{31}H_{58}NaO_{12}P$ (676.76)

1998.) 1-(Z)-12-docosenyl-phospho-D-mannitol; Na salt
$C_{28}H_{56}NaO_9P$ (590.71)

1999.) 1-(Z,Z)-10,16-docosadienyl-phospho-D-mannitol; Na salt
$C_{28}H_{54}NaO_9P$ (588.69)

2000.) 1-O—(Z)—O-docosenyl-2-O-methyl-sn-glycero-3-phospho-D-mannitol; Na salt
$C_{32}H_{64}NaO_{11}P$ (678.82)

2001.) 1-O—(Z,Z)-10,16-docosadienyl-2-O-methyl-sn-glycero-3-phospho-D-mannitol; Na salt
$C_{32}H_{62}NaO_{11}P$ (676.80)

11. Phospho-D-lyxitol Compounds

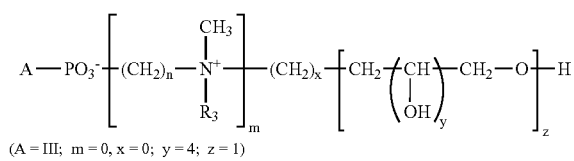

(A = III; m = 0, x = 0; y = 3; z = 1)

2002.) 1,2-di-(Z)-6-hexadecenoyl-sn-glycero-3-phospho-D-lyxitol; Na salt
$C_{40}H_{74}NaO_{12}P$ (800.98)

2003.) 1,2-di-(Z)-6-nonadecenoyl-sn-glycero-3-phospho-D-lyxitol; Na salt
$C_{46}H_{86}NaO_{12}P$ (885.15)
2004.) 1,2-di-(Z)-10-docosenoyl-sn-glycero-3-phospho-D-lyxitol; Na salt
$C_{52}H_{98}NaO_{12}P$ (969.31)
2005.) 1,2-di-(Z)-10-tetracosenoyl-sn-glycero-3-phospho-D-lyxitol; Na salt
$C_{56}H_{106}NaO_{12}P$ (1025.41)
2006.) 1,2-di-(Z)-16-hexacosenoyl-sn-glycero-3-phospho-D-lyxitol; Na salt
$C_{60}H_{114}NaO_{12}P$ (1081.52)
2007.) 1,2-di-(Z,Z)-5,11-hexadecadienoyl-sn-glycero-3-phospho-D-lyxitol; Na salt
$C_{40}H_{70}NaO_{12}P$ (796.95)
2008.) 1,2-di-(Z,Z)-5,11-octadecadienoyl-sn-glycero-3-phospho-D-lyxitol; Na salt
$C_{44}H_{78}NaO_{12}P$ (853.06)
2009.) 1,2-di-(Z,Z)-10,16-docosadienoyl-sn-glycero-3-phospho-D-lyxitol; Na salt
$C_{52}H_{94}NaO_{12}P$ (965.27)
2010.) 1,2-di-(Z,Z)-6,18-hexacosadienoyl-sn-glycero-3-phospho-D-lyxitol; Na salt
$C_{60}H_{110}NaO_{12}P$ (1077.49)
2011.) 2-(Z)-6-hexadecenoyl-1-stearoyl-sn-glycero-3-phospho-D-lyxitol; Na salt
$C_{42}H_{80}NaO_{12}P$ (831.05)
2012.) 2-(Z)-10-octadecenoyl-1-stearoyl-sn-glycero-3-phospho-D-lyxitol; Na salt
$C_{44}H_{84}NaO_{12}P$ (859.11)
2013.) 2-(Z,Z)-6,12-hexadecadienoyl-1-stearoyl-sn-glycero-3-phospho-D-lyxitol; Na salt
$C_{42}H_{78}NaO_{12}P$ (829.04)
2014.) 2-(Z,Z)-10,16-docosadienoyl-1-stearoyl-sn-glycero-3-phospho-D-lyxitol; Na salt
$C_{48}H_{90}NaO_{12}P$ (913.20)
2015.) 1-stearoyl-2-(Z,Z)-6,18-tetracosadienoyl-sn-glycero-3-phospho-D-lyxitol; Na salt
$C_{50}H_{94}NaO_{12}P$ (941.25)
2016.) 1-(Z)-10-octadecenoyl-2-stearoyl-sn-glycero-3-phospho-D-lyxitol; Na salt
$C_{44}H_{84}NaO_{12}P$ (859.11)
2017.) 1-(Z,Z)-6,18-hexacosadienoyl-2-stearoyl-sn-glycero-3-phospho-D-lyxitol; Na salt
$C_{52}H_{98}NaO_{12}P$ (969.31)
2018.) 1-(Z,Z)-6,18-hexacosadienoyl-2-(Z)-6-hexadecenoyl-sn-glycero-3-phospho-D-lyxitol; Na salt
$C_{50}H_{92}NaO_{12}P$ (939.24)
2019.) 2-(Z,Z)-6,18-hexacosadienoyl-1-(Z)-6-hexadecenoyl-sn-glycero-3-phospho-D-lyxitol; Na salt
$C_{50}H_{92}NaO_{12}P$ (939.24)

12. Phospho-D-threitol Compounds

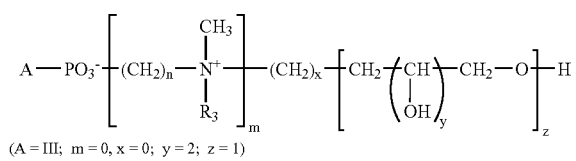

(A = III; m = 0, x = 0; y = 2; z = 1)

2020.) 1,2-di-(z)-6-hexadecenoyl-sn-glycero-3-phospho-D-threitol; Na salt
$C_{39}H_{72}NaO_{11}P$ (770.96)
2021.) 1,2-di-(Z)-6-nonadecenoyl-sn-glycero-3-phospho-D-threitol; Na salt
$C_{45}H_{84}NaO_{11}P$ (855.12)
2022.) 1,2-di-(Z)-10-docosenoyl-sn-glycero-3-phospho-D-threitol; Na salt
$C_{51}H_{96}NaO_{11}P$ (939.28)
2023.) 1,2-di-(Z)-10-tetracosenoyl-sn-glycero-3-phospho-D-threitol; Na salt
$C_{55}H_{104}NaO_{11}P$ (995.39)
2024.) 1,2-di-(Z)-16-hexacosenoyl-sn-glycero-3-phospho-D-threitol; Na salt
$C_{59}H_{112}NaO_{11}P$ (1051.50)
2025.) 1,2-di-(Z,Z)-5,11-hexadecadienoyl-sn-glycero-3-phospho-D-threitol; Na salt
$C_{39}H_{68}NaO_{11}P$ (766.93)
2026.) 1,2-di-(Z,Z)-5,11-octadecadienoyl-sn-glycero-3-phospho-D-threitol; Na salt
$C_{43}H_{76}NaO_{11}P$ (823.03)
2027.) 1,2-di-(Z,Z)-10,16-docosadienoyl-sn-glycero-3-phospho-D-threitol; Na salt
$C_{51}H_{92}NaO_{11}P$ (935.25)
2028.) 1,2-di-(Z,Z)-6,18-hexacosadienoyl-sn-glycero-3-phospho-D-threitol; Na salt
$C_{59}H_{108}NaO_{11}P$ (1047.46)
2029). 2-(Z)-6-hexadecenoyl-1-stearoyl-sn-glycero-3-phospho-D-threitol; Na salt
$C_{41}H_{78}NaO_{11}P$ (801.03)
2030). 2-(Z)-10-octadecenoyl-1-stearoyl-sn-glycero-3-phospho-D-threitol; Na salt
$C_{43}H_{82}NaO_{11}P$ (829.08)
2031). 2-(Z,Z)-6,12-hexadecadienoyl-1-stearoyl-sn-glycero-3-phospho-D-threitol; Na salt
$C_{41}H_{76}NaO_{11}P$ (799.01)
2032) 2-(Z,Z)-10,16-docosadienoyl-1-stearoyl-sn-glycero-3-phospho-D-threitol; Na salt
$C_{47}H_{88}NaO_{11}P$ (883.17)
2033) 1-stearoyl-2-(Z,Z)-6,18-tetracosadienoyl-sn-glycero-3-phospho-D-threitol; Na salt
$C_{49}H_{92}NaO_{11}P$ (911.23)
2034.) 1-(Z)-10-octadecenoyl-2-stearoyl-sn-glycero-3-phospho-D-threitol; Na salt
$C_{43}H_{82}NaO_{11}P$ (829.08)
2035.) 1-(Z,Z)-6,18-hexacosadienoyl-2-stearoyl-sn-glycero-3-phospho-D-threitol; Na salt
$C_{51}H_{96}NaO_{11}P$ (939.28)
2036.) 1-(Z,Z)-6,18-hexacosadienoyl-2-(Z)-6-hexadecenoyl-sn-glycero-3-phospho-D-threitol; Na salt
$C_{49}H_{90}NaO_{11}P$ (909.21)
2037.) 2-(Z,Z)-6,18-hexacosadienoyl-1-(Z)-6-hexadecenoyl-sn-glycero-3-phospho-D-threitol; Na salt
$C_{49}H_{90}NaO_{11}P$ (909.21)

SOURCES

[1] Kaufmann-Kolle, P., Berger M. R., Unger, C. and H. Eibl Systemic administration of alkylphosphocholines: Erucylphosphocholine and liposomal hexadecylphosphocholine *Adv. Exp. Med. Bio.* 416, 165-168 (1996)

The invention claimed is:
1. A compound of the general formula (I)

$$A\text{-}PO_3\text{-}B \quad (I)$$

in which B is a radical of the general formula (II)

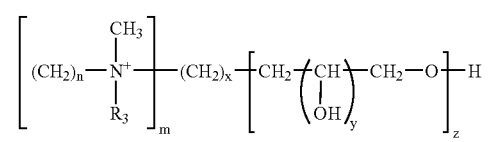

in which
n is an integer from 2 to 8;
m is 0, 1 or 2;
x is an integer from 0 to 8;
y is an integer from 1 to 4;
z is an integer from 1 to 5;
$R_3$ is an alkyl radical having 1 to 3 C atoms, which may be substituted by one or more hydroxyl groups;
and in which A is a radical selected from one of the formulae (VIII) or (IX):

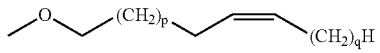

(VIII)

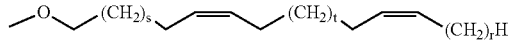

(IX)

in which
p, q, r, s, t $\leq$ 0;
12 $\leq$ p+q $\leq$ 30 and
8 $\leq$ s+t+r $\leq$ 26;
where q $\neq$ 8 for p+q=14, 16, 18 or 20, if A is a radical of the formula (VIII).

* * * * *